United States Patent
Chun

(10) Patent No.: US 7,579,154 B2
(45) Date of Patent: *Aug. 25, 2009

(54) ANNEALING CONTROL PRIMER AND ITS USES

(75) Inventor: Jong-Yoon Chun, Seoul (KR)

(73) Assignee: Seegene, Inc., Seoul (KR)

( * ) Notice: Subject to any disclaimer, the term of this patent is extended or adjusted under 35 U.S.C. 154(b) by 67 days.

This patent is subject to a terminal disclaimer.

(21) Appl. No.: 11/651,605

(22) Filed: Jan. 10, 2007

(65) Prior Publication Data

US 2007/0148683 A1 Jun. 28, 2007

Related U.S. Application Data

(63) Continuation of application No. 10/269,031, filed on Oct. 11, 2002, now abandoned, which is a continuation-in-part of application No. 10/014,496, filed on Dec. 14, 2001, now abandoned.

(30) Foreign Application Priority Data

Dec. 8, 2001 (WO) .................... PCT/KR01/02133

(51) Int. Cl.
*C12Q 1/68* (2006.01)
*C12P 19/34* (2006.01)
*C07H 21/02* (2006.01)
*C07H 21/04* (2006.01)

(52) U.S. Cl. .................... 435/6; 435/91.2; 536/23.1; 536/24.33

(58) Field of Classification Search ........................ None
See application file for complete search history.

(56) References Cited

U.S. PATENT DOCUMENTS 5,962,228 A 10/1999 Brenner

FOREIGN PATENT DOCUMENTS

WO WO 00/20630 4/2000

OTHER PUBLICATIONS

GenBank GI:895865 [online] Feb. 17, 1997 [retrieved on Aug. 16, 2008], retrieved from: http://www.ncbi.nlm.nih.gov/entrez/viewer.fcgi?895865:OLD11:1310887 (3 pages).*
Abbotts, et al., "Studies on the mechanism of *Escherichia coli* DNA polymerase I large fragment. Effect of template sequence and substrate variation on termination of synthesis," *J. Biol Chem* Oct. 15, 1988;263(29):15094-103.

(Continued)

*Primary Examiner*—Gary Benzion
*Assistant Examiner*—Samuel Woolwine
(74) *Attorney, Agent, or Firm*—Gianna Julian-Arnold; Miles & Stockbridge P.C.

(57) ABSTRACT

The present invention relates to an annealing control primer for improving annealing specificity in nucleic acid amplification and its applications to all fields of nucleic acid amplification-involved technology. The present primer comprises (a) a 3'-end portion having a hybridizing nucleotide sequence substantially complementary to a site on a template nucleic acid to hybridize therewith; (b) a 5'-end portion having a pre-selected arbitrary nucleotide sequence; and (c) a regulator portion positioned between said 3'-end portion and said 5'-end portion comprising at least one universal base or non-discriminatory base analog, whereby said regulator portion is capable of regulating an annealing portion of said primer in association with annealing temperature.

19 Claims, 34 Drawing Sheets

OTHER PUBLICATIONS

Amosova, et al., "Effect of the 1-(2'-deoxy-beta-D-ribofuranosyl)-3-nitropyrrole residue on the stability of DNA duplexes and triplexes," *Nucleic Acids Res.* May 15, 1997;25(10):1930-4.

Bartl, S. & Weissman, IL. "PCR primers containing an inosine triplet to complement a variable codon within a conserved protein-coding region," *Biotechniques* Feb. 1994;16(2):246-8, 250.

Carter, et al., "The crystal structure of an RNA oligomer incorporating tandem adenosine-inosine mismatches," *Nucleic Acids Res.* Oct. 15, 1997;25(20):4117-22.

Cornish-Bowden A., "Nomenclature for incompletely specified bases in nucleic acid sequences: recommendations," 1984. *Nucleic Acids Res.* 1985; 13(9):3021-3030.

Ehlen T. Dubeau L., "Detection of ras point mutation by polymerase chain reaction using mutation specific, inosine-containing oligonucleotide primers," *Biochem. Biophys. Res. Commun.* Apr. 28, 1989;169(2):441-7.

Noma, et al., "Structure and expression of human mitochondrial adenylate kinase targeted to the mitochondrial matrix," *Biochem J.* Aug. 15, 2001;358(Pt 1):225-32.

Ryder et al., "Sequence-specific affinity selection of mammalian splicing complexes," *Nucleic Acids Res.* Dec. 15, 1990;18(24):7373-9.

Saparbaev, et al., "Interactions of the human, rat, *Saccharomyces cerevisiae* and *Escherichia coli* 3- methyladenine-DNA glycosylases with DNA containing Dimp residues," *Nucleic Acids Res.* Mar. 15, 2000;28(6):1332-39.

General concepts for PCR Primer Design; Dieffenbach, C.W.; Lowe, TMJ; Dveksler, G.S. PCR primer: a Laboratory Manual. Cold Spring Harbor Laboratory Press,1995, 133-1 42.

Don, R.H.; Cox, P.T.; Wainwright, B.J.; Baker, K.; Mattick, J.S. Touchdown' PCR to circumvent spurious priming during gene amplification. *Nucleic Acids Res.*, 1991, vol. 19,4008.

Franz, O. ; Bruchhaus, I. ; Roeder, T. Verification of differential gene transcription using virtual northern 'blotting. *Nucleic Acids Res.*, 1999, vol. 27, 1-3.

Frohman, M.A.; Dush, M.K.; Martin, G.R. Rapid production of full-length cDNAs from rare transcripts: amplification using a single gene-specific oligonucleotide primer. *Proc. Natl. Acad. Sci. USA*, 1988, vol. 85, 8998-9002.

Fromont-Racine, M. ; Bertrand, E. ; Pictet, R. ; Grange, T. A highly sensitive method for mapping the 5' termini of mRNAs. *Nucleic Acids Res.*, 1993, vol. 21, 1683-1684.

Gottschlich, S. ; Goeoegh, T. ; Folz, B.J. ; Lippert, B.M. ; Werner, J.A. Optimized differential display and reamplification parameters for silver staining. *Res. Commun. Mol. Path. Pharm.*, 1997, vol. 97, 237-240.

Gromova, I.; Gromov, P.; Celis, J.E. Identification of true differentially expressed mRNAs in a pair of human bladder transitional cell carcinomas sing an improved differential display procedure. *Electrophoresis*, 1999, vol. 20, 241-248.

Hogan, B.; Bedding, R.; Costantini, F.; Lacy, E. Manipulating the moue embryo: a laboratory manual. Cold Spring Harbor Laboratory Press, 1994.

Hwang, LT.; Lee, Y.H.; Moon, B.C.; Ahn, K.Y.; Lee, S.W.; Chun, J.Y. Identification and characterization of a new member of the placental prolactin-like protein-C (PLP-C) subfamily, PLP-C~. *Endocrinology*, 2000, vol. 141, 3343-3352.

Henegariu, O; Hirschmann, P.; Killian, K.; Kirch, S.; Lengauer, C.; Maiwald, R.; Mielke, K.; Vogt, P. Rapid screening of the Y chromosome in idiopathic sterile men, diagnostic for deletions in AZF, a genetic Y factor expressed during spermatogenesis. *Andrologia*, 1994, vol. 26, 97-106.

Jefferies, D. ; Botman, M. F. ; Lester, D ; Whitehead, C. C. ; Thorp, B. H. Cloning differentially regulate genes from chondrocyles using agarose gel differential display. *Biochim. Biophys. Acta*, 1998, vol. 1396,237-241.

Kociok, N.; Unfried, K. ; Eser, P. ; Krott, R. ; Schraermeyer, U. ; Heimann, K. The non-radioisotopic representation of differentially expressed mRNA by a combination of RNA fingerprinting and differential display. *Mol. Biotechnol.*, 1998, vol. 9, 25-33.

Korn, B.; Sedlacek, Z.; Manca, A.; Kioschis, P.; Konecki, D.; Lehrach, H.; Poutska, A. A strategy for the selection of transcribed sequences in the Xq28 region. *Hum. Mol. Genet.*, 1992, vol. 1, 235-242.

Kulp A, D. ; Topping, R. ; Telesnitskt, A. Determination of the site of first strand transfer during Moloney murine leukemia virus reverse transcription and identification of strand transfer-associated reverse transcriptase errors. *EMBO J.*, 1997, vol. 16, 856-865.

Landegren, U.; Nilsson, M.; Kwok, P.-Y. reading bits of genetic information: methods for single-nucleotide polymorphism analysis. *Genome Res.*, 1998, vol. 8, 769-776.

Liang, P. ; Pardee, A.B. Differential display of eukaryotic messenger RNA by means of the polymerase chain reaction. *Science*, 1992, vol. 257, 967-971.

Ledbetter, S.A.; Nelson, D.L.; Warren, S.T.; Ledbetter, D.H. Rapid isolation of DNA probes within specific chromosome regions by interspersed repetitive sequence polymerase chain reaction. *Genomics*, 1990, vol. 6, 475-481.

Loakes, D.; Brown, D.M. 5-Nitroindole as an universal base analog. *Nucleic Acids Res*, 1994, vol. 22, 4039-4043.

Loakes, D. The applications of universal DNA base analogues. *Nucleic Acids Res.*, vol. 29, 2437-2447.

Matz, M.V. ; Lukyanov, S.A. Different strategies of differential display: areas of application. *Nucleic Acids Res.*, 1998, vol. 26, 5537-5543.

Matz, M.; Shagin, D.; Bogdanova, E.; Britanova, O.; Lukyanov, S.; Diatchenko, L. ; Chenchik., A. Amplification of cDNA ends based on template switching effect and step-out PCR. *Nucleic Acids Res.*, 1999, vol. 27, 1558-1560.

McPherson, M.J.; Moller, S.G. PCR. BIOS Scientific Publishers, Springer-Verlag, 2000 [0392].

Meunier, J.R.; Grimont, PA.D. Factors affecting reproducibility of amplified polymorphic DNA fingerprints. *Res. Microbial.*, 1993, vol. 144, 373-379.

Mullis, K.B. ; Faloona, FA Specific synthesis of DNA in vitro via a polymerase-catalyzed chain reaction. *Methods Enzymol.*, 1987, vol. 155,335-350.

Mutirangura, A. ; Greenberg, F. ; Butler, M.G. ; Malcolm, S. ; Nicholls, R.D.; Chakravarti, A.; Ledbetter, D.H. Multiplex PCR of three dinucleotide repeats in the Prader-Wi!-li/Angelman critical region (15q11-q13): molecular diagnosis and mechanism of uniparental disomy. *Hum. Mol. Genet.*, 1993, vol. 2, 143-151.

Nichols, R.; Andrews, P.C.; Ahang, P.; Bergstrom, D.E. A universal nucleoside for use at ambiguous sites in DNA primers. *Nature*, 1994. vol. 369, 492-493.

Ohtsuka, E.; Matsuka, S. ;Ikehara M.; Takahashi, Y.; Matsubara K. An alternative approach to deoxyoligonucleotides as hybridization probes by insertion of deoxyinosine at ambiguous codon positions. *J. Biol. Chem.*, 1985, vol. 260, 2605-2608.

Ralph, D. ; Welsh, J. ; McClelland, M. RNA fingerprinting using arbitrary primed PCR identifies differentially regulated RNAs in Mink lung (Mv1 Lu) cells growth arrested by TGF-β. *Proc. Natl. . Acad. Sci.*, 1993, vol. 90. 10710-10714.

Rompf, R.; Kahl, G. mRNA differential display in agarose gels. *BioTechniques*, 1997, vol. 23, 28-32.

Roses, A.D. Pharmacogenetics and the practice of medicine. *Nature*, 2000, vol. 405, 857-865.

Rosok, O. ; Odeberg, J. ; Rode, M. ; Stokke, T.; Funderud, 5.; Smeland, E. solid-phase method for differentially display of genes expressed in hematopoietic stem cells. *BioTechniques*, 1996, vol. 21, 114-121.

Ruano, G.; Fenton, W.; Kidd, K.K. Biphasic amplification of very dilute DNA samples via booster PCR. *Nucleic Acids Res.*, 1989, vol. 17, 5407.

Saiki, R.K. ; Scharf, S. ; Faloona, F. ; Mullis, K.B. ; Horn,G.T. j Erlich,H.A. ;Arnheim, N. Enzymatic amplification of beta-globin genomic sequences and restriction site analysis for diagnosis of sickle cell anemia. *Science*, 1985, vol. 230, 1350-1354.

Sakanari, J.A.; Staunton, C.E.; Eakin, A.E. ; Craik, C.S. Serine proteases from nematode and protozoan parasites: isolation of sequence nomologs using generic molecular probes. *Proc. Natl. Acad. Sci.*, 1989, vol. 86, 4863-4867.

Schaefer, B.C. Revolutions in rapid amplification of cDNA ends: New strategies for polymerase chain reaction cloning of full-length cDNA ends. *Anal. Biochem.*, 1995, vol. 227, 255-273.

Schmidt, W.M. ; Mueller, M.W. CapSelect: A highly sensitive method for 5' CAP-dependent rerichment of full-length cDNA in PCR-mediated analysis of mRNAs. *Nucleic Acids Res.*, 1999, vol. 27, e31.

Schramm, G. j Bruchhaus, I. ; Roeder, T. A simple and reliable 5'-RACE approach. *NucleicAcids Res.*, 2000, vol. 28, e96 [.

Shuber, A.P.; Skoletsky, J.; Stem, R.; Handelin, B.L. Efficient 12-mutation testing in the CFTR gene: a general model for complex mutation analysis. *Hum. Mol. Genet.*, 1993, vol. 2, 153-158.

Smith, N.R.; Aldersley, M.; L1, A.; High, A.S. ; Moynihan, T.P. ; Markham, A.F. ; Robinson. P.A. Automated differential display using a fluorescently labeled universal primer. *BioTechniques*, 1997, vol. 23, 274-279.

Sompayrac, L. ;Jane,S.; Burn, T.C. ;Tene, D.G.; Danna, K.J, Overcoming limitations of the mRNA differential display technique. *Nucleic Acids Res.*, 1995, vol. 23, 4738-4739.

Stone, B. ; Wharton, W. Targeted RNA fingerprtnting: the cloning of differentially-expressed cDNA fragments enriched for members of the zinc finger gene family. *Nucleic Acids Res*, 1994, vol. 22, 2612-2618.

Suzuki, Y.; Yoshitomo-Nakagawa, K.; Maruyama, K. ; Suyama, A. ; Sugano, S. Construction and characterization of a full length-enriched and a 5'-end.enriched cDNA library. *Gene*, 1997, vol. 200, 149-156.

Tagle, D.A.; Swaroop, M.; Lovett, M.; Collins, F.S. Magnetic bead capture of expressed sequences encoded within large genomic segments. *Nature*, 1993, vol. 361, 751-753.

Welsh, J.; McClelland, M. Fingerprinting genomes using PCR with arbitrary primers. *Nucleic Acids Res.*, 1990, vol. 18, 7213-7218.

Welsh, J.; McClelland, M. Genomic fingerprinting using arbitrarily primed PCR and a matrtx of pairwise combinations of primers. *Nucleic Acids Res.*, 1991, vol. 19, 5275-5279.

Williams, J.G.K. ; Kubelik, A.R. ; L1vak, K.J. ; Rafalki, J.A. ; Tingey, S.V. DNA polymorphisms amplified by arbitrary primers are useful as genetic markers. *Nucleic Acids Res.*, 1990, vol. 18, 6531-6535.

Zimmermann, K. ; Schogl, D. ; Plaimauer, B.; Mannhal Ter, J.W. Quantitative multiplex competitive PCR of HIV-1 DNA in a single reaction tube. *Bio Techniques*, 1996, vol. 21, 480-484.

Zou, S. ; Stanfield, C.; Bridge, J. Identification of new influenza B virus variants by multiplex reverse transcription-PCR and the heteroduplex mobility assay. *J. Clin. Microbiol.*, 1998, vol. 36, 1544-1548.

* cited by examiner

A

B

A

← 750 bp
← 287 bp
← 155 bp

B

A

B

C

D

E

F

```
SEQUENCE LISTING

<160> NUMBER OF SEQ ID NOS: 125

<210> SEQ ID NO 1
<211> LENGTH: 36
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (23)..(27)
<223> OTHER INFORMATION: i

<400> SEQUENCE: 1
gtctaccagg cattcgcttc atnnnnncag gagtgg                               36

<210> SEQ ID NO 2
<211> LENGTH: 37
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (23)..(27)
<223> OTHER INFORMATION: i

<400> SEQUENCE: 2
gtctaccagg cattcgcttc atnnnnnggc gacgats                              37

<210> SEQ ID NO 3
<211> LENGTH: 37
```

```
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (23)..(27)
<223> OTHER INFORMATION: i

<400> SEQUENCE: 3
gtctaccagg cattcgcttc atnnnnngcc atcgacs                                37

<210> SEQ ID NO 4
<211> LENGTH: 37
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (23)..(27)
<223> OTHER INFORMATION: i

<400> SEQUENCE: 4
gtctaccagg cattcgcttc atnnnnnaga tgcccgw                                37

<210> SEQ ID NO 5
<211> LENGTH: 37
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (23)..(27)
<223> OTHER INFORMATION: i

<400> SEQUENCE: 5
gtctaccagg cattcgcttc atnnnnnagg cgatgcs                                37

<210> SEQ ID NO 6
<211> LENGTH: 37
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (23)..(27)
<223> OTHER INFORMATION: i

<400> SEQUENCE: 6
gtctaccagg cattcgcttc atnnnnntct cccggts                                37

<210> SEQ ID NO 7
<211> LENGTH: 37
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (23)..(27)
<223> OTHER INFORMATION: i

<400> SEQUENCE: 7
gtctaccagg cattcgcttc atnnnnnttg tggcggs                                37

<210> SEQ ID NO 8
```

```
<211> LENGTH: 37
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (23)..(27)
<223> OTHER INFORMATION: i

<400> SEQUENCE: 8
gtctaccagg cattcgcttc atnnnnnctc cgatgcs                              37

<210> SEQ ID NO 9
<211> LENGTH: 37
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (23)..(27)
<223> OTHER INFORMATION: i

<400> SEQUENCE: 9
gtctaccagg cattcgcttc atnnnnncct gcgggtw                              37

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 10
gcttgactac gatactgtgc ga                                              22

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 11
tcacagaagt atgccaagcg a                                               21

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 12
gtctaccagg cattcgcttc at                                              22

<210> SEQ ID NO 13
<211> LENGTH: 37
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (23)..(27)
<223> OTHER INFORMATION: i

<400> SEQUENCE: 13
```

```
gtctaccagg cattcgcttc atnnnnngcc atcgacc                                   37

<210> SEQ ID NO 14
<211> LENGTH: 37
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (23)..(27)
<223> OTHER INFORMATION: i

<400> SEQUENCE: 14
gtctaccagg cattcgcttc atnnnnngcc atcgacg                                   37

<210> SEQ ID NO 15
<211> LENGTH: 37
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (23)..(27)
<223> OTHER INFORMATION: i

<400> SEQUENCE: 15
gtctaccagg cattcgcttc atnnnnnagg cgatgcc                                   37

<210> SEQ ID NO 16
<211> LENGTH: 37
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (23)..(27)
<223> OTHER INFORMATION: i

<400> SEQUENCE: 16
gtctaccagg cattcgcttc atnnnnnagg cgatgcg                                   37

<210> SEQ ID NO 17
<211> LENGTH: 37
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (23)..(27)
<223> OTHER INFORMATION: i

<400> SEQUENCE: 17
gtctaccagg cattcgcttc atnnnnnctc cgatgcc                                   37

<210> SEQ ID NO 18
<211> LENGTH: 37
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (23)..(27)
<223> OTHER INFORMATION: i
```

<400> SEQUENCE: 18
gtctaccagg cattcgcttc atnnnnnctc cgatgcg    37

<210> SEQ ID NO 19
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 19
gtctaccagg cattcgcttc atgccatcga cc    32

<210> SEQ ID NO 20
<211> LENGTH: 34
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (23)..(24)
<223> OTHER INFORMATION: i

<400> SEQUENCE: 20
gtctaccagg cattcgcttc atnngccatc gacc    34

<210> SEQ ID NO 21
<211> LENGTH: 36
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (23)..(26)
<223> OTHER INFORMATION: i

<400> SEQUENCE: 21
gtctaccagg cattcgcttc atnnnngcca tcgacc    36

<210> SEQ ID NO 22
<211> LENGTH: 38
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (23)..(28)
<223> OTHER INFORMATION: i

<400> SEQUENCE: 22
gtctaccagg cattcgcttc atnnnnnngc catcgacc    38

<210> SEQ ID NO 23
<211> LENGTH: 40
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (23)..(30)
<223> OTHER INFORMATION: i

<400> SEQUENCE: 23
gtctaccagg cattcgcttc atnnnnnnnn gccatcgacc    40

<210> SEQ ID NO 24
<211> LENGTH: 41
<212> TYPE: DNA
<213> ORGANISM: Artificial Sequence
<220> FEATURE:
<223> OTHER INFORMATION: Description of Artificial Sequence: Primer

<400> SEQUENCE: 24
cacagaagta tgccaagcga ctcgagtttt tttttttttt t           41

<210> SEQ ID NO 25
<211> LENGTH: 37
<212> TYPE: DNA
<213> ORGANISM: Artificial Sequence
<220> FEATURE:
<223> OTHER INFORMATION: Description of Artificial Sequence: Primer

<400> SEQUENCE: 25
gcttgactac gatactgtgc gattttttttt tttttt              37

<210> SEQ ID NO 26
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 26
cttgactacg atactgtgcg attttttttt ttttc                35

<210> SEQ ID NO 27
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 27
gcttgactac gatactgtgc gattttttttt tttttg              36

<210> SEQ ID NO 28
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 28
gcttgactac gatactgtgc gattttttttt tttta              36

<210> SEQ ID NO 29
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 29
gcttgactac gatactgtgc gattttttttt tt                32

<210> SEQ ID NO 30
<211> LENGTH: 37
<212> TYPE: DNA
<213> ORGANISM: Artificial Sequence
<220> FEATURE:

<223> OTHER INFORMATION: Description of Artificial Sequence: Primer
<220> FEATURE:
<221> NAME/KEY: modified_base
<222> LOCATION: (23)..(27)
<223> OTHER INFORMATION: i

<400> SEQUENCE: 30
gcttgactac gatactgtgc gannnnnttt tttttt    37

<210> SEQ ID NO 31
<211> LENGTH: 129
<212> TYPE: DNA
<213> ORGANISM: Mus sp.

<400> SEQUENCE: 31
ccatcgaccc gtttctctag ccccatcttc atgtgtttta atgagatgat attaattcat    60
tacattcatg gataatatgt ccctgagtac attctaatct agatttaact tcaaaaaaaa    120
aaaaaaaaa    129

<210> SEQ ID NO 32
<211> LENGTH: 207
<212> TYPE: DNA
<213> ORGANISM: Mus sp.

<400> SEQUENCE: 32
ggcgatgcgg gctgtactct gggtggctgc cacagtctca tgagaaacca agggcaaagg    60
accaaggaaa agggtctcag gcccctaaag cagtggcttt caaccatcct aatgttgtga    120 cctttttaata cagttcctca tgttgtgtga cccccccaacc ataaaatgat ttttgtttct    180
acttcaaaaa aaaaaaaaaa aaaaaaa    207

<210> SEQ ID NO 33
<211> LENGTH: 39
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (37)..(39)
<223> OTHER INFORMATION: linked to ribose

<400> SEQUENCE: 33
aagcagtggt atcaacgcag agtggccatt acggccggg    39

<210> SEQ ID NO 34
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 34
aagcagtggt atcaacgcag agt    23

<210> SEQ ID NO 35
<211> LENGTH: 59
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (59)..(59)
<223> OTHER INFORMATION: a, t, c or g

<400> SEQUENCE: 35
attctagagg ccgaggcggc cgacatgttt tttttttttt tttttttttt tttttttvn        59

<210> SEQ ID NO 36
<211> LENGTH: 32
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (23)..(27)
<223> OTHER INFORMATION: i
<220> FEATURE:
<221> NAME/KEY: modified_base
<222> LOCATION: (30)..(32)
<223> OTHER INFORMATION: linked to ribose

<400> SEQUENCE: 36
gtctaccagg cattcgcttc atnnnnnggg gg        32

<210> SEQ ID NO 37
<211> LENGTH: 32
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (23)..(27)
<223> OTHER INFORMATION: i
<220> FEATURE:
<221> NAME/KEY: modified_base
<222> LOCATION: (30)..(31)
<223> OTHER INFORMATION: linked to ribose

<400> SEQUENCE: 37
gtctaccagg cattcgcttc atnnnnnggg gg        32

<210> SEQ ID NO 38
<211> LENGTH: 32
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (23)..(27)
<223> OTHER INFORMATION: i

<400> SEQUENCE: 38
gtctaccagg cattcgcttc atnnnnnggg gg        32

<210> SEQ ID NO 39
<211> LENGTH: 45
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (23)..(27)
<223> OTHER INFORMATION: i

<400> SEQUENCE: 39
gcttgactac gatactgtgc gannnnnttt tttttttttt ttttt        45

<210> SEQ ID NO 40

```
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 40
gagaggatag tttcagggac                                               20

<210> SEQ ID NO 41
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 41
ctccgtggta cgcctgcttt ctc                                           23

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 42
tcgtcaccca cataggagtc                                               20

<210> SEQ ID NO 43
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 43
ctaagaggag gatggtcgc                                                19

<210> SEQ ID NO 44
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 44
gccggttgca gagcacc                                                  17

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 45
gaaccatgtt tctgaatgcc                                               20

<210> SEQ ID NO 46
<211> LENGTH: 44
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
```

```
<222> LOCATION: (23)..(27)
<223> OTHER INFORMATION: i

<400> SEQUENCE: 46
gtctaccagg cattcgcttc atnnnnngcc ggttgcagag cacc              44

<210> SEQ ID NO 47
<211> LENGTH: 47
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (23)..(27)
<223> OTHER INFORMATION: i

<400> SEQUENCE: 47
gcttgactac gatactgtgc gannnnngaa ccatgtttct gaatgcc           47

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 48
gaatctgaaa caactttcta                                        20

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 49
gatgcatggg acgaggcacc                                        20

<210> SEQ ID NO 50
<211> LENGTH: 47
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (23)..(27)
<223> OTHER INFORMATION: i

<400> SEQUENCE: 50
gtctaccagg cattcgcttc atnnnnngaa tctgaaacaa ctttcta           47

<210> SEQ ID NO 51
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 51
cgccgcaccc ctgcccgca                                         19

<210> SEQ ID NO 52
<211> LENGTH: 18
<212> TYPE: DNA
```

<213> ORGANISM: Artificial Sequence
<220> FEATURE:
<223> OTHER INFORMATION: Description of Artificial Sequence: Primer

<400> SEQUENCE: 52
gatgcatggg acgaggca                                                      18

<210> SEQ ID NO 53
<211> LENGTH: 46
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (23)..(27)
<223> OTHER INFORMATION: i

<400> SEQUENCE: 53
gtctaccagg cattcgcttc atnnnnncgc cgcacccctg cccgca                       46

<210> SEQ ID NO 54
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 54
tttttttttt ttttt                                                         15

<210> SEQ ID NO 55
<211> LENGTH: 47
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (23)..(27)
<223> OTHER INFORMATION: i

<400> SEQUENCE: 55
gcttgactac gatactgtgc gannnnngat gcatgggacg aggcacc                      47

<210> SEQ ID NO 56
<211> LENGTH: 45
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (23)..(27)
<223> OTHER INFORMATION: i

<400> SEQUENCE: 56
gcttgactac gatactgtgc gannnnngat gcatgggacg aggca                        45

<210> SEQ ID NO 57
<211> LENGTH: 43
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (23)..(27)
<223> OTHER INFORMATION: i

<400> SEQUENCE: 57
gcttgactac gatactgtgc gannnnnttt ttttttttt ttv                    43

<210> SEQ ID NO 58
<211> LENGTH: 33
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (23)..(27)
<223> OTHER INFORMATION: i
<220> FEATURE:
<221> NAME/KEY: modified_base
<222> LOCATION: (28)..(33)
<223> OTHER INFORMATION: a, t, c or g

<400> SEQUENCE: 58
gcttgactac gatactgtgc gannnnnnnn nnn                              33

<210> SEQ ID NO 59
<211> LENGTH: 32
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (23)..(27)
<223> OTHER INFORMATION: i
<220> FEATURE:
<221> NAME/KEY: modified_base
<222> LOCATION: (30)..(30)
<223> OTHER INFORMATION: linked to ribose

<400> SEQUENCE: 59
gtctaccagg cattcgcttc atnnnnnggg gg                               32

<210> SEQ ID NO 60
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 60
ctgtgaatgc tgcgactacg at                                          22

<210> SEQ ID NO 61
<211> LENGTH: 42
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (23)..(27)
<223> OTHER INFORMATION: i

<400> SEQUENCE: 61
ctgtgaatgc tgcgactacg atnnnnnttt ttttttttt tt                     42

<210> SEQ ID NO 62
<211> LENGTH: 43
<212> TYPE: DNA
<213> ORGANISM: Artificial Sequence
<220> FEATURE:

-continued

```
<223> OTHER INFORMATION: Description of Artificial Sequence: Primer
<220> FEATURE:
<221> NAME/KEY: modified_base
<222> LOCATION: (23)..(27)
<223> OTHER INFORMATION: i

<400> SEQUENCE: 62
ctgtgaatgc tgcgactacg atnnnnnttt ttttttttttt ttv                 43

<210> SEQ ID NO 63
<211> LENGTH: 44
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (23)..(27)
<223> OTHER INFORMATION: i
<220> FEATURE:
<221> NAME/KEY: modified_base
<222> LOCATION: (44)..(44)
<223> OTHER INFORMATION: a, t, c or g

<400> SEQUENCE: 63
ctgtgaatgc tgcgactacg atnnnnnttt ttttttttttt ttvn                44

<210> SEQ ID NO 64
<211> LENGTH: 37
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (23)..(27)
<223> OTHER INFORMATION: i

<400> SEQUENCE: 64
gtctaccagg cattcgcttc atnnnnnccg gaggatc                         37

<210> SEQ ID NO 65
<211> LENGTH: 37
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (23)..(27)
<223> OTHER INFORMATION: i

<400> SEQUENCE: 65
gtctaccagg cattcgcttc atnnnnnctg caggacg                         37

<210> SEQ ID NO 66
<211> LENGTH: 37
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (23)..(27)
<223> OTHER INFORMATION: i

<400> SEQUENCE: 66
gtctaccagg cattcgcttc atnnnnncgg agcatcc                         37
```

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 67
ttgcacactg ttgattctaa                                         20

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 68
ttattgatgg tctctacaca                                         20

<210> SEQ ID NO 69
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 69
ccactgagtc caacattc                                           18

<210> SEQ ID NO 70
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 70
ctgaaacact tcccacac                                           18

<210> SEQ ID NO 71
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 71
cctctgactg ctcttttcac                                         20

<210> SEQ ID NO 72
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 72
attgaagtct catggaagcc                                         20

<210> SEQ ID NO 73
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 73
tgcttgccac aggtctc					17

<210> SEQ ID NO 74
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 74
gcagtgctag gaaagagg					18

<210> SEQ ID NO 75
<211> LENGTH: 47
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (23)..(27)
<223> OTHER INFORMATION: i

<400> SEQUENCE: 75
gtctaccagg cattcgcttc atnnnnnttg cacactgttg attctaa					47

<210> SEQ ID NO 76
<211> LENGTH: 46
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (22)..(26)
<223> OTHER INFORMATION: i

<400> SEQUENCE: 76
tcacagaagt atgccaagcg annnnnttat tgatggtctc tacaca					46

<210> SEQ ID NO 77
<211> LENGTH: 45
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (23)..(27)
<223> OTHER INFORMATION: i

<400> SEQUENCE: 77
gtctaccagg cattcgcttc atnnnnncca ctgagtccaa cattc					45

<210> SEQ ID NO 78
<211> LENGTH: 44
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (22)..(26)
<223> OTHER INFORMATION: i

<400> SEQUENCE: 78
tcacagaagt atgccaagcg annnnnctga aacacttccc acac					44

<210> SEQ ID NO 79
<211> LENGTH: 47
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (23)..(27)
<223> OTHER INFORMATION: i

<400> SEQUENCE: 79
gtctaccagg cattcgcttc atnnnnncct ctgactgctc ttttcac                47

<210> SEQ ID NO 80
<211> LENGTH: 46
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (22)..(26)
<223> OTHER INFORMATION: i

<400> SEQUENCE: 80
tcacagaagt atgccaagcg annnnnattg aagtctcatg gaagcc                 46

<210> SEQ ID NO 81
<211> LENGTH: 44
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (23)..(27)
<223> OTHER INFORMATION: i

<400> SEQUENCE: 81
gtctaccagg cattcgcttc atnnnnntgc ttgccacagg tctc                   44

<210> SEQ ID NO 82
<211> LENGTH: 44
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (22)..(26)
<223> OTHER INFORMATION: i

<400> SEQUENCE: 82
tcacagaagt atgccaagcg annnnngcag tgctaggaaa gagg                   44

<210> SEQ ID NO 83
<211> LENGTH: 41
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (23)..(27)
<223> OTHER INFORMATION: i
<220> FEATURE:
<221> NAME/KEY: modified_base
<222> LOCATION: (30)..(30)

<223> OTHER INFORMATION: a, t, c or g

<400> SEQUENCE: 83
gcttgactac gatactgtgc gannnnngtn crrgtgtggt t         41

<210> SEQ ID NO 84
<211> LENGTH: 41
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (23)..(27)
<223> OTHER INFORMATION: i
<220> FEATURE:
<221> NAME/KEY: modified_base
<222> LOCATION: (30)..(30)
<223> OTHER INFORMATION: a, t, c or g

<400> SEQUENCE: 84
gcttgactac gatactgtgc gannnnngtn crrgtctggt t         41

<210> SEQ ID NO 85
<211> LENGTH: 41
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (23)..(27)
<223> OTHER INFORMATION: i
<220> FEATURE:
<221> NAME/KEY: modified_base
<222> LOCATION: (30)..(30)
<223> OTHER INFORMATION: a, t, c or g

<400> SEQUENCE: 85
gcttgactac gatactgtgc gannnnngtn crrgtttggt t         41

<210> SEQ ID NO 86
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 86
cctctgactg ctcttttcac         20

<210> SEQ ID NO 87
<211> LENGTH: 46
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (22)..(26)
<223> OTHER INFORMATION: i

<400> SEQUENCE: 87
tcacagaagt atgccaagcg annnnnattg aagtctcatg gaagcc         46

<210> SEQ ID NO 88
<211> LENGTH: 37
<212> TYPE: DNA
<213> ORGANISM: Artificial Sequence

```
<220> FEATURE:
<223> OTHER INFORMATION: Description of Artificial Sequence: Primer
<220> FEATURE:
<221> NAME/KEY: modified_base
<222> LOCATION: (23)..(27)
<223> OTHER INFORMATION: i

<400> SEQUENCE: 88
gtctaccagg cattcgcttc atnnnnnccc cgcgtgg                              37

<210> SEQ ID NO 89
<211> LENGTH: 37
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (23)..(27)
<223> OTHER INFORMATION: i

<400> SEQUENCE: 89
gtctaccagg cattcgcttc atnnnnnccc cccgtgg                              37

<210> SEQ ID NO 90
<211> LENGTH: 37
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (23)..(27)
<223> OTHER INFORMATION: i

<400> SEQUENCE: 90
gtctaccagg cattcgcttc atnnnnntcc ccgcgtg                              37

<210> SEQ ID NO 91
<211> LENGTH: 37
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (23)..(27)
<223> OTHER INFORMATION: i

<400> SEQUENCE: 91
gtctaccagg cattcgcttc atnnnnntcc cccgtg                               37

<210> SEQ ID NO 92
<211> LENGTH: 37
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (23)..(27)
<223> OTHER INFORMATION: i

<400> SEQUENCE: 92
gtctaccagg cattcgcttc atnnnnnctc cccgcgt                              37

<210> SEQ ID NO 93
<211> LENGTH: 37
<212> TYPE: DNA
```

```
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (23)..(27)
<223> OTHER INFORMATION: i

<400> SEQUENCE: 93
gtctaccagg cattcgcttc atnnnnnctc cccccgt                                37

<210> SEQ ID NO 94
<211> LENGTH: 37
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (23)..(27)
<223> OTHER INFORMATION: i

<400> SEQUENCE: 94
gtctaccagg cattcgcttc atnnnnngct ccccgcg                                37

<210> SEQ ID NO 95
<211> LENGTH: 37
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (23)..(27)
<223> OTHER INFORMATION: i

<400> SEQUENCE: 95
gtctaccagg cattcgcttc atnnnnngct cccccg                                 37

<210> SEQ ID NO 96
<211> LENGTH: 35
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (23)..(27)
<223> OTHER INFORMATION: i

<400> SEQUENCE: 96
gtctaccagg cattcgcttc atnnnnngct ccccg                                  35

<210> SEQ ID NO 97
<211> LENGTH: 35
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (23)..(27)
<223> OTHER INFORMATION: i

<400> SEQUENCE: 97
gtctaccagg cattcgcttc atnnnnngct ccccc                                  35

<210> SEQ ID NO 98
<211> LENGTH: 21
```

<212> TYPE: DNA
<213> ORGANISM: Artificial Sequence
<220> FEATURE:
<223> OTHER INFORMATION: Description of Artificial Sequence: Primer

<400> SEQUENCE: 98
attctgatgg tgtggattgt g                                              21

<210> SEQ ID NO 99
<211> LENGTH: 45
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (22)..(26)
<223> OTHER INFORMATION: i

<400> SEQUENCE: 99
tcacagaagt atgccaagcg annnnnaccc tggagtagac gaaga                    45

<210> SEQ ID NO 100
<211> LENGTH: 37
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (23)..(27)
<223> OTHER INFORMATION: i

<400> SEQUENCE: 100
gtctaccagg cattcgcttc atnnnnnggt acagggc                             37

<210> SEQ ID NO 101
<211> LENGTH: 37
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (23)..(27)
<223> OTHER INFORMATION: i

<400> SEQUENCE: 101
gtctaccagg cattcgcttc atnnnnnggt accgggc                             37

<210> SEQ ID NO 102
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 102
ccttctgtgc ttgatgcttt t                                              21

<210> SEQ ID NO 103
<211> LENGTH: 46
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (22)..(26)

<210> SEQ ID NO 103
<211> LENGTH: 46
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (21)..(25)
<223> OTHER INFORMATION: i

<400> SEQUENCE: 103
tcacagaagt atgccaagcg annnnncagg aaggatgagc atttag                46

<210> SEQ ID NO 104
<211> LENGTH: 37
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (23)..(27)
<223> OTHER INFORMATION: i

<400> SEQUENCE: 104
gtctaccagg cattcgcttc atnnnnntcc aaaccaa                          37

<210> SEQ ID NO 105
<211> LENGTH: 37
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (23)..(27)
<223> OTHER INFORMATION: i

<400> SEQUENCE: 105
gtctaccagg cattcgcttc atnnnnntcc aacccaa                          37

<210> SEQ ID NO 106
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 106
agaaaaacca gaggcagctt                                             20

<210> SEQ ID NO 107
<211> LENGTH: 47
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (22)..(26)
<223> OTHER INFORMATION: i

<400> SEQUENCE: 107
tcacagaagt atgccaagcg annnnnagca caaaccaaag acacagt                47

<210> SEQ ID NO 108
<211> LENGTH: 37
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (23)..(27)
<223> OTHER INFORMATION: i

<400> SEQUENCE: 108
gtctaccagg cattcgcttc atnnnnncca ttttagg        37

<210> SEQ ID NO 109
<211> LENGTH: 37
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (23)..(27)
<223> OTHER INFORMATION: i

<400> SEQUENCE: 109
gtctaccagg cattcgcttc atnnnnncca ttgtagg        37

<210> SEQ ID NO 110
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 110
ctagctgcaa gtgacatctc t        21

<210> SEQ ID NO 111
<211> LENGTH: 43
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (19)..(23)
<223> OTHER INFORMATION: i

<400> SEQUENCE: 111
tcacagagta tccaagcgnn nnntcagtaa gaagccagga gag        43

<210> SEQ ID NO 112
<211> LENGTH: 37
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (23)..(27)
<223> OTHER INFORMATION: i

<400> SEQUENCE: 112
gtctaccagg cattcgcttc atnnnnncca gaacttt        37

<210> SEQ ID NO 113
<211> LENGTH: 37
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (23)..(27)
<223> OTHER INFORMATION: i

<400> SEQUENCE: 113
gtctaccagg cattcgcttc atnnnnncca gacctttt        37

<210> SEQ ID NO 114
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 114
ttttgggtgg aggctaacat                                         20

<210> SEQ ID NO 115
<211> LENGTH: 44
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (21)..(25)
<223> OTHER INFORMATION: i

<400> SEQUENCE: 115
tcacagaagt atgccagcga nnnnnaacga tgcagacacc acca              44

<210> SEQ ID NO 116
<211> LENGTH: 37
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (23)..(27)
<223> OTHER INFORMATION: i

<400> SEQUENCE: 116
gtctaccagg cattcgcttc atnnnnngac tggtaaa                      37

<210> SEQ ID NO 117
<211> LENGTH: 37
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (23)..(27)
<223> OTHER INFORMATION: i

<400> SEQUENCE: 117
gtctaccagg cattcgcttc atnnnnngac tgataaa                      37

<210> SEQ ID NO 118
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 118
cttccaccaa tactcttttc c                                       21

<210> SEQ ID NO 119
<211> LENGTH: 45
<212> TYPE: DNA
<213> ORGANISM: Artificial Sequence
<220> FEATURE:
<223> OTHER INFORMATION: Description of Artificial Sequence: Primer

```
<220> FEATURE:
<221> NAME/KEY: modified_base
<222> LOCATION: (21)..(25)
<223> OTHER INFORMATION: i

<400> SEQUENCE: 119
tcacagaagt atgccagcga nnnnngcata cacacaagag gcaga                45

<210> SEQ ID NO 120
<211> LENGTH: 37
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (23)..(27)
<223> OTHER INFORMATION: i

<400> SEQUENCE: 120
gtctaccagg cattcgcttc atnnnnnaaa gccataa                         37

<210> SEQ ID NO 121
<211> LENGTH: 37
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (23)..(27)
<223> OTHER INFORMATION: i

<400> SEQUENCE: 121
gtctaccagg cattcgcttc atnnnnnaaa gctataa                         37

<210> SEQ ID NO 122
<211> LENGTH: 14
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (14)..(14)
<223> OTHER INFORMATION: a, t, c or g

<400> SEQUENCE: 122 ttttttttttt ttmn                                                 14

<210> SEQ ID NO 123
<211> LENGTH: 14
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (14)..(14)
<223> OTHER INFORMATION: a, t, c or g
<220> FEATURE:
<221> NAME/KEY: misc_feature
<222> LOCATION: (10)..(12)
<223> OTHER INFORMATION: nucleotide may or may not be present; this
      sequence may encompass 11-14 nucleotides according to the
      specification as filed

<400> SEQUENCE: 123 ttttttttttt ttmn                                                 14
```

```
<210> SEQ ID NO 124
<211> LENGTH: 60
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (1)..(30)
<223> OTHER INFORMATION: a, t, c or g; this range may encompass 15-30
      nucleotides according to the specification as filed
<220> FEATURE:
<221> NAME/KEY: modified_base
<222> LOCATION: (31)..(40)
<223> OTHER INFORMATION: a, t, c or g; this range may encompass 2-10
      universal bases or non-discriminatory base analogs according to
      the specification as filed
<220> FEATURE:
<221> NAME/KEY: misc_feature
<222> LOCATION: (41)..(60)
<223> OTHER INFORMATION: this range may encompass 10-20 nucleotides
      according to the specification as filed

<400> SEQUENCE: 124
nnnnnnnnnn nnnnnnnnnn nnnnnnnnnn nnnnnnnnnn tttttttttt tttttttttt       60

<210> SEQ ID NO 125
<211> LENGTH: 55
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (1)..(30)
<223> OTHER INFORMATION: a, t, c or g; this range may encompass 15-30
      nucleotides according to the specification as filed
<220> FEATURE:
<221> NAME/KEY: modified_base
<222> LOCATION: (31)..(40)
<223> OTHER INFORMATION: a, t, c or g; this range may encompass 2-10
      universal bases or non-discriminatory base analogs according to
      the specification as filed
<220> FEATURE:
<221> NAME/KEY: modified_base
<222> LOCATION: (41)..(50)
<223> OTHER INFORMATION: a, t, c or g; this range may encompass 1-10
      nucleotides according to the specification as filed
<220> FEATURE:
<221> NAME/KEY: misc_feature
<222> LOCATION: (51)..(55)
<223> OTHER INFORMATION: this range may encompass 3-5 nucleotides
      according to the specification as filed

<400> SEQUENCE: 125
nnnnnnnnnn nnnnnnnnnn nnnnnnnnnn nnnnnnnnnn nnnnnnnnnn ggggg            55
```

ANNEALING CONTROL PRIMER AND ITS USES

RELATED APPLICATIONS

This application is a continuation of U.S. application Ser. No. 10/269,031, filed Oct. 11, 2002 now abandoned, which is a continuation-in-part of U.S. application Ser. No. 10/014,496, filed Dec. 14, 2001 now abandoned and claims priority to PCT application No. PCT/KR01/02133, filed Dec. 8, 2001, all of which are herein incorporated by reference in their entirety.

DESCRIPTION OF THE FILES CONTAINED ON THE CD-R

The contents of the submission on compact discs submitted herewith are incorporated herein by reference in their entirety: A compact disc copy of the Sequence Listing (COPY 1) (filename: SEEG 001 02US SeqList.txt, date recorded: Jan. 10, 2007, file size 33 kilobytes); a duplicate compact disc copy of the Sequence Listing (COPY 2) (filename: SEEG 001 02US SeqList.txt, date recorded: Jan. 10, 2007, file size 33 kilobytes); a computer readable format copy of the Sequence Listing (CRF COPY) (filename: SEEG 001 02US SeqList.txt, date recorded: Jan. 10, 2007, file size 33 kilobytes).

BACKGROUND OF THE INVENTION

The present invention relates to an annealing control primer and its applications. More particularly, the present invention relates to an annealing control primer for improving annealing specificity in nucleic acid amplification and its applications to all fields of nucleic acid amplification-involved technology.

DESCRIPTION OF THE RELATED ART

Nucleic acid amplification is a pivotal process for a wide variety of methods in molecular biology, so that various amplification methods have been proposed. For example, Miller, H. I. et al. (WO 89/06700) disclose a nucleic acid sequence amplification based on the hybridization of a promoter/primer sequence to a target single-stranded DNA ("ss-DNA") followed by transcription of many RNA copies of the sequence. Other known nucleic acid amplification procedures include transcription-based amplification systems (Kwoh, D. et al., *Proc. Natl. Acad. Sci. U.S.A.*, 86:1173(1989); and Gingeras T. R. et al., WO 88/10315).

Schemes based on ligation of two or more oligonucleotides in the presence of nucleic acid having the sequence of the resulting "di-oligonucleotide", thereby amplifying the di-oligonucleotide, are also known (Wu, D. Y. et al., Genomics 4:560 (1989)), which are called "Ligation Chain Reaction" (LCR).

Davey, C. et al. (European Pat. Appln. Publication No. 329,822) disclose a nucleic acid amplification process involving cyclically synthesizing single-stranded RNA ("ssRNA"), ssDNA, and double-stranded DNA (dsDNA). The ssRNA is a first template for a first primer oligonucleotide, which is elongated by reverse transcriptase (RNA-dependent DNA polymerase). The RNA is then removed from resulting DNA:RNA duplex by the action of ribonuclease H. The resultant ssDNA is a second template for a second primer, which also includes the sequences of an RNA polymerase promoter. This primer is then extended by DNA polymerase, resulting as a double-stranded DNA ("dsDNA") molecule, having a sequence identical to that of the original RNA between the primers and having additionally, at one end, a promoter sequence. This promoter sequence can be used by the appropriate RNA polymerase to produce many RNA copies of the DNA. These copies can then re-enter the cycle leading to very rapid amplification.

The most predominant process for nucleic acid amplification known as polymerase chain reaction (hereinafter referred to as "PCR"), is based on repeated cycles of denaturation of double-stranded DNA, followed by oligonucleotide primer annealing to the DNA template, and primer extension by a DNA polymerase (Mullis et al. U.S. Pat. Nos. 4,683,195, 4,683,202, and 4,800,159; Saiki et al. 1985). The oligonucleotide primers used in PCR are designed to anneal to opposite strands of the DNA, and are positioned so that the DNA polymerase catalyzed extension product of one primer can serve as the template strand for the other primer. The PCR amplification process results in the exponential increase of discrete DNA fragments whose length is defined by the 5' ends of the oligonucleotide primers.

The success in the nucleic acid amplifications, in particular PCR amplification, relies on the specificity with which a primer anneals only to its target (and not non-target) sequences and therefore it is important to optimize this molecular interaction. Whether a primer can anneal only to its perfect complement or also to sequences that have one or more mismatches, depends critically upon the annealing temperature. In general, the higher the annealing temperature, the more specific annealing of the primer to its perfect matched template and so the greater the likelihood of only target sequence amplification can be accomplished. The lower the temperature, the more mismatches between template and primer can be tolerated, leading to increased amplification of non-target sequences. Adjusting the annealing temperature can alter the specificity of pairing between template and primer. For examples, if there is no product, the temperature may be too high and can be reduced. If there are products in control where only one primer is present, this indicates that the single primer is annealing to more than one region of the template. In this case, the annealing temperature should be increased. Considering such effect of annealing temperature on primer annealing specificity, there remains a strong need for an annealing control primer system which is capable of controlling primer annealing in accordance with annealing temperature to enhance primer annealing specificity regardless of primer design.

In addition to annealing temperature, several "primer search parameters" such as primer length, GC content and PCR product length (Dieffenbach et al., 1995) should be considered for primer annealing specificity. If a primer, which satisfies all such parameters, were employed, primer annealing would be specified, resulting in the significant enhancement of primer annealing specificity during target DNA amplification and the freedom from the problems such as backgrounds and non-specific products arising from primers used in the experiments. It is usual that well-designed primers can help avoid non-specific annealing and backgrounds as well as distinguish between cDNAs or genomic templates in RNA-PCR.

Many approaches have been developed to improve primer annealing specificity and therefore accomplish the amplification of the desired product. Examples are touchdown PCR (Don et al., 1991), hot start PCR (D'Aquila et al., 1991), nested PCR (Mullis and Faloona, 1987) and booster PCR (Ruano et al., 1989). Another alternative approaches have been also reported that various 'enhancer' compounds can improve the specificity of PCR. The enhancer compounds include chemicals that increase the effective annealing temperature of the reaction, DNA binding proteins and commercially available reagents. However, there is no 'magic' additive that will ensure the success in every PCR and it is very tedious to test different additives under different conditions such as annealing temperature. Although these approaches have contributed to the improvement of primer annealing specificity in some cases, they have not accessed fundamentally to a solution for the problems arising from primers used in the PCR amplification, such as non-specific products and high backgrounds.

In many cases, the primer sequence does not need to be a perfect complement to the template sequence. The region of the primer that should be perfectly matched to the template is the 3'-end because this end is the region of the primer extended by the DNA polymerase and is therefore the most important for ensuring the specificity of annealing to the correct target sequence. The 5'-end of the primer is less important in determining specificity of annealing to the target sequence and can be modified to carry additional sequence such as restriction sites and promoter sequences that are not complementary to the template (McPherson and Moller 2000). This notion is adapted to the design of the annealing control primers of this invention as described below.

PCR-based techniques have been widely used not only for amplification of a target DNA sequence but also for scientific applications or methods in the fields of biological and medical research such as Reverse transcriptase PCR (RT-PCR), Differential Display PCR (DD-PCR), Cloning of known or unknown genes by PCR, Rapid amplification of cDNA ends (RACE) and PCR-based genomic analysis (McPherson and Moller, 2000). The followings are only representatives of PCR applications.

Techniques designed to identify genes that are differentially regulated by cells under various physiological or experimental conditions (for example, differentiation, carcinogenesis, pharmacological treatment) have become pivotal in modern biology. One such method for screening differences in gene expression between various cell types or between different stages of cell development with the availability of PCR is known as Differential Display PCR (DD-PCR), described by Liang and Pardee in 1992. This method uses combinations of 10-mer arbitrary primers with anchored cDNA primers and generates fragments that originate mostly from the poly(A) tail and extend about 50-600 nucleotide upstream. By combining 3' anchored Oligo(dT) primers and short 5' arbitrary primers, the subsets of the transcriptome are amplified, the resulting cDNA fragments are generally separated on denaturing polyacrylamide gel and visualized autoradiographically.

Although this method is simple and rapid and only requires small amounts of total RNA, there are a number of disadvantages in the conventional DD-PCR methods. The differential banding patterns are often only poorly reproducible due to the use of short arbitrary primer so that many laboratories have had difficulty in obtaining reproducible results with these methods. It has been shown that at least 40% of the differentially displayed bands are not reproducible between experiments even in well-trained hands (Bauer et al., 1994). Furthermore, the pattern of differential expression often cannot be reproducible on Northern blots and the percentage of these false positives can arise up to 90% (Sompayrac et al., 1995). As a modification used for an alternative, the use of longer random primers of, e.g. 20 bases in length does not satisfactorily solve the problem of reproducibility (Ito et al., 1994). There are another factors responsible for the relatively low reproducibility of DD-PCR such as an insufficient amount of starting material and very low concentration of dNTP (2-5 µM) employed to prepare the different banding patterns (Matz and Lukyanov, 1998). It is also difficult to detect rare transcripts with these methods (Matz and Lukyanov, 1998). In addition, because the cDNA fragments obtained from DD-PCR are short (typically 100-500 bp) and correspond to the 3'-end of the gene that represent mainly the 3' untranslated region, they usually do not contain a large portion of the coding region. Therefore, the labor-intensive full-length cDNA screening is needed unless significant sequence homology, information for gene classification and prediction of function is obtained (Matz and Lukyanov, 1998).

Differential Display methods generally use radioactive detection techniques using denaturing polyacrylamide gels. The radioactive detection of the reaction products restricts the use of this technique to laboratories with the appropriate equipment. Relatively long exposure times and problems with the isolation of interesting bands from the polyacrylamide gels are additional drawbacks of Differential Display technique. Although modified non-radioactive Differential Display methods have recently been described, which include silver staining (Gottschlich et al. 1997; Kociok et al., 1998), fluorescent-labeled oligonucleotides (Bauer et al. 1993; Ito et al. 1994; Luehrsen et al., 1997; Smith et al., 1997), the use of biotinylated primers (Korn et al., 1992; Tagle et al., 1993; Rosok et al., 1996) and ethidium bromide-stained agarose gels (Rompf and Kahl, 1997; Jefferies et al., 1998; Gromova et al., 1999), these methods have met with only limited success. If the reaction products could be simply detected on ethidium bromide-stained agarose gel and the results were reproducible and reliable, it would greatly increase the speed of DD-PCR analysis and avoid the use of radioactivity.

Another PCR-based approach called targeted differential display uses an oligonucleotide primer that directs the amplification of multigene family members with conserved protein domains. Gene families are groups of genes which are often functionally characterized by a particular type of function undertaken by the gene products in a cell and which structurally have one or more conserved regions (domains) in common. Examples of gene families include the MADS-box and the homeogene family as well as further transcription factor families. The cyclin, cytokine and globin gene families are examples of medical interest. The Prosite Database provides a list of proteins that have common domains and sequence motifs. The oligonucleotide used in the PCR can either be a specific primer that is used at a low annealing temperature or, as is more often the case, a degenerate primer mixture for use at higher stringencies (Stone and Wharton, 1994). However, amplifications using degenerate primers can sometimes be problematic and may require optimization. It is important to keep the annealing temperature as high as possible to avoid extensive nonspecific amplification and a good rule of thumb is to use 55° C. as a starting temperature. In general, it is difficult to keep this rule because degenerate primers should be designed on the basis of amino acid sequences or conserved domain sequences as a precondition. In order to generate a satisfied relationship between degenerate primer and annealing temperature in this approach, it is required to use an annealing control primer which can tolerate the alternation of annealing temperature, particularly high temperature such as 68° C. regardless of primer design.

Still another PCR-based technique is arbitrary primed PCR (AP-PCR) for RNA fingerprinting. One great strength of AP-PCR methods is their simplicity (Welsh and McClelland, 1991; Williams et al., 1990). AP-PCR uses a single primer or a pair of primers, wherein the primers are 10-mers or 18-mers as longer primer. This method has previously been used to provide DNA fingerprints of hybrid cell lines (Ledbetter et al., 1990) and particular genomic regions (Welsh and McClelland, 1990; Williams et al., 1990). It provides a very useful tool for genome analysis in bacteria, fungi and plant identification and population studies, where individual isolates can be compared rapidly. For example, they can be used as a tool to identify pathogens or the occurrence of particular strains or pathotypes. Commonly, AP-PCR uses a single primer to initiate DNA synthesis from regions of a template where the primer matches imperfectly. In order for this to work, the initial cycles have to be performed at low stringency (37-50° C.), normally for the first five cycles, which allows primer annealing to imperfect sites throughout the genome. The stringency is then increased (55° C.) as for standard PCR amplification and the reaction is allowed for an additional 30-35 cycles. AP-PCR is not recommended for use in such applications as paternity testing where unequivocal results are demanded, because nonparental products are occasionally produced. Although alternative AP-PCR approaches including nested AP-PCR have been developed (McClelland et al., 1993; Ralph et al., 1993), the issue of reproducibility is still of main concern. One concern is that the patterns may vary from day to day or from lab to lab (see, e.g., Meunier and Grimont, 1993).

Still yet another PCR-based application is RACE (rapid amplification of cDNA end) technology. RACE is a procedure for amplification of cDNA regions corresponding to the 5'- or 3'-end of mRNA (Frohman et al., 1988) and it has been used to isolate rare transcripts successfully. The gene-specific primer may be derived from sequence data from a partial cDNA, genomic exon or peptide. In 3' RACE, the polyA tail of mRNA molecules is exploited as a priming site for PCR amplification. mRNAs are converted into cDNAs using reverse transcriptase and an Oligo-dT primer as known in the art. The generated cDNAs can then be directly PCR amplified using a gene-specific primer and a primer that anneals to the polyA region.

The same principle as 3' RACE applies to 5' RACE but there is no polyA tail. Thus, 5' RACE is made by tagging the 5'-end of a cDNA by means of different methods (Fromont-Racine et al., 1993; Schaefer, 1995; Franz et al., 1999). Most approaches for the 5' RACE such as homopolymeric tailing and ligation anchored tailing require a set of enzymatic reactions after completion of first strand cDNA synthesis (Schaefer, 1995). Each enzymatic step has the potential to introduce failures and to destroy the integrity of the cDNA. Recently, an alternative has been introduced, the so-called CapFinder approach (Chenchik et al., 1998; Chenchik et al. U.S. Pat. Nos. 5,962,271 and 5,962,272). The technique relies on dual functions of the reverse transcriptases: one is the terminal transferase activity to add non-templated nucleotides to the 3'-end of a cDNA and the other is the template switching activity to switch a template to a second template. This property is utilized during the retroviral life cycle (Clark, 1988; Kulpa et al., 1997). Moloney murine leukemia virus (M-MLV) reverse transcriptase (RT) often adds three to four non-template-derived cytosine residues to the 3'-end of newly synthesized cDNAs in the presence of manganese or high magnesium (Schmidt and Mueller, 1999). This approach allows the amplification of full-length cDNAs because the M-MLV RT adds C residues preferentially to the cDNA if complete (capped) mRNA serves as template.

However, the CapFinder approach for 5'-RACE experiments could not be free from background problems such as DNA smear arising from the contamination of the CapFinder and Oligo-dT primers, which are used in cDNA synthesis (Chenchik et al., 1998). Even residual amounts of these primers result in a high background because both ideally fit to all cDNAs present in the reaction mixture. In addition, 3'-RACE and full-length cDNA amplification have the same background problems due to the contamination of primers used for cDNA synthesis in which they generate non-specific products in PCR reaction (Chenchik et al., 1998). New approaches to overcome the problems above have been recently introduced. One approach is step-out PCR to suppress unwanted PCR products (Matz et al., 1999) but it has been pointed out that this approach still remains a smear of DNA rather than a single DNA (Schramm et al., 2000). Another approach which is introduced more recently is to use solid-phase cDNA synthesis and procedures to remove all contaminants used in cDNA synthesis (Schramm et al., 2000), but the major drawback of this technique is costly and time-consuming by requiring solid-phase cDNA synthesis and following procedures. Therefore, more effective, simple, rapid and inexpensive strategies are required to completely eliminate problems arising from contamination of the primers such as Oligo-dT or CapFinder primer used for cDNA synthesis.

In addition to RACE technologies, in current technologies for cDNA library construction, the 5'-ends of genes tend to be under-represented in cDNA populations, especially where a poly(dT) primer is used during first cDNA strand synthesis and the starting material is limited. Although a number of different approaches have been developed to overcome this problem, most suffer from common limitations producing full-length cDNAs or 5'-enriched cDNAs with a number of inherent problems. These approaches are complex or costly and time-consuming by requiring multiple enzymatic steps and/or are not pronounced sensitive (Carninci et al., 1997; Suzuki et al., 1997; Guegler et al. U.S. Pat. Nos. 6,083,727 and 6,326,175; Hayashizaki. U.S. Pat. No. 6,143,528). Therefore, there is continued interest in the development of improved methods for generating full-length or 5'-enriched cDNAs, particularly with the limited starting material.

Multiplex PCR is another variant of PCR in which more than one target sequence can be simultaneously amplified with more than one pair of primers in the same reaction. Since its first description in 1988 (Chamberlain et al., 1988), this method has been successfully applied in many areas of DNA testing, including analyses of gene deletion (Anonymous, 1992; Henegariu, et al., 1994), mutation and polymorphism analysis (Shuber et al., 1993; Mutirangura et al., 1993), quantitative analysis (Zimmermann et al., 1996), and RNA detection (Zou et al., 1998). In the field of infection diseases, the technique has been shown to be a valuable method for identification of viruses, bacteria, fungi, and/or parasites.

However, the results obtained with multiplex PCR are frequently complicated by the artifacts of the amplification procedure. These include "false-negative" results due to reaction failure and "false-positive" results such as the amplification of spurious products, which may be caused by annealing of the primers to sequences which are related to but distinct from the true recognition sequences. For use in multiplex PCR, a primer should be designed so that its predicted hybridization kinetics are similar to those of the other primers used in the sample multiplex reaction. While the annealing temperature and primer concentrations may be calculated to some degree, the conditions generally have to be empirically determined for each multiplex reaction. Since the possibility of non-specific priming increases with each additional primer pair, the conditions must be modified as necessary as individual primer sets are added. Moreover, the artifacts that result from competition for resources (e.g., depletion of primers) are augmented in multiplex PCR, since the differences in the yields of unequally amplified fragments are enhanced with each cycle. Thus, the optimization of the reaction conditions for multiplex PCR can become labor-intensive and time-consuming. Since the different multiplex PCRs may have unique reaction conditions, the development of new diagnostic tests can become very costly.

Therefore, there is a need in the art for primers that allow multiplex PCR reactions to be designed and carried out without elaborate optimization steps, irrespective of the potentially divergent properties of the different primers used. Furthermore, there is a need in the art for primers that allow multiplex PCR reactions that, under the same reaction conditions, simultaneously produce equivalent amounts of each of many amplification products.

Single nucleotide polymorphisms (SNPs), the most common genetic variations found in the human genome, are important markers for identifying disease-associated loci and for pharmaco-genetic studies (Landegren et al., 1998; Roses, 2000). SNPs appear in the human genome with an average of once every 1000 bp and totaling >3 million. A variety of approaches have been used to detect SNPs. However, one of the key bottlenecks is the amplification of DNA. Most current assays include a step that produces many copies of a short segment of the sample DNA spanning each target SNP. This amplification is usually necessary because only small amounts of DNA can be harvested from typical clinical samples. Also, the amplification improves the signal-to-noise ratio of the assays, increasing the reliability of detection. Most genotyping techniques accomplish this amplification using PCR. Most importantly, the specificity of PCR amplification is critical in the application of PCR in the SNP genotyping. Therefore, it would be beneficial if the methods for improving PCR specificity are available and applied to the development of SNP genotyping assay. It would also be beneficial if such methods are capable of providing multiple analyses in a single assay (multiplex assays).

As described above, all these methods and techniques involving nucleic acid amplification, in particular PCR amplification, could not be completely free from the limitations and problems resulting from the non-specificity of primers used in each method, such as false positives, poor reproducibility, high backgrounds and so on, although improved approaches to each method has been continuously introduced. Therefore, there remains a need of novel primer for improving annealing specificity and methods, which can give rise to true results.

Throughout this application, various patents and publications are referenced and citations are provided in parentheses. The disclosure of these patents and publications in their entities are hereby incorporated by references into this application in order to more fully describe this invention and the state of the art to which this invention pertains.

SUMMARY OF THE INVENTION

Endeavoring to resolve the problems of such conventional primer and various methods involving nucleic acid amplification, the present inventor has developed a novel annealing control primer that can permit nucleic acid amplification with much higher specificity and its unlimited applications in all fields of nucleic acid amplification-based technology.

Accordingly, it is an object of this invention to provide an annealing control primer for improving annealing specificity in nucleic acid amplification.

It is another object of this invention to provide a method for amplifying a nucleic acid sequence from a DNA or a mixture of nucleic acids as template.

It is still another object of this invention to provide a method for selectively amplifying a target nucleic acid sequence from a DNA or a mixture of nucleic acids as template It is further object of this invention to provide a method for selectively amplifying a target nucleic acid sequence from an mRNA.

It is still further object of this invention to provide a method for detecting DNA complementary to differentially expressed mRNA in two or more nucleic acid samples.

It is another object of this invention to provide a method for rapidly amplifying a target cDNA fragment comprising a cDNA region corresponding to the 3'-end region of an mRNA.

It is still another object of this invention to provide a method for amplifying a target cDNA fragment comprising a cDNA region corresponding to the 5'-end region of an mRNA.

It is further object of this invention to provide a method for amplifying a population of full-length double-stranded cDNAs complementary to mRNAs.

It is still further object of this invention to provide a method for amplifying 5'-enriched double-stranded cDNAs complementary to mRNAs.

It is another object of this invention to provide a method for amplifying more than one target nucleotide sequence simultaneously, It is still another object of this invention to provide a method for producing a DNA fingerprint of gDNA.

It is still another object of this invention to provide a method for producing a RNA fingerprint of an mRNA sample.

It is further object of this invention to provide a method for identifying a conserved homology segment in a multigene family.

It is still further object of this invention to provide a method for identifying a nucleotide variation in a target nucleic acid.

It is another object of this invention to provide a method for mutagenesis in a target nucleic acid.

It is still another object of this invention to provide a kit comprising an annealing control primer.

It is further object of this invention to provide kits for a variety of methods involving nucleic acid amplification.

It is still further object of this invention to provide a use of an annealing control primer for a process involving nucleic acid amplification.

Other objects and advantages of the present invention will become apparent from the detailed description to follow taken in conjugation with the appended claims and drawings.

DETAILED DESCRIPTION OF THIS INVENTION

Figure 1A:
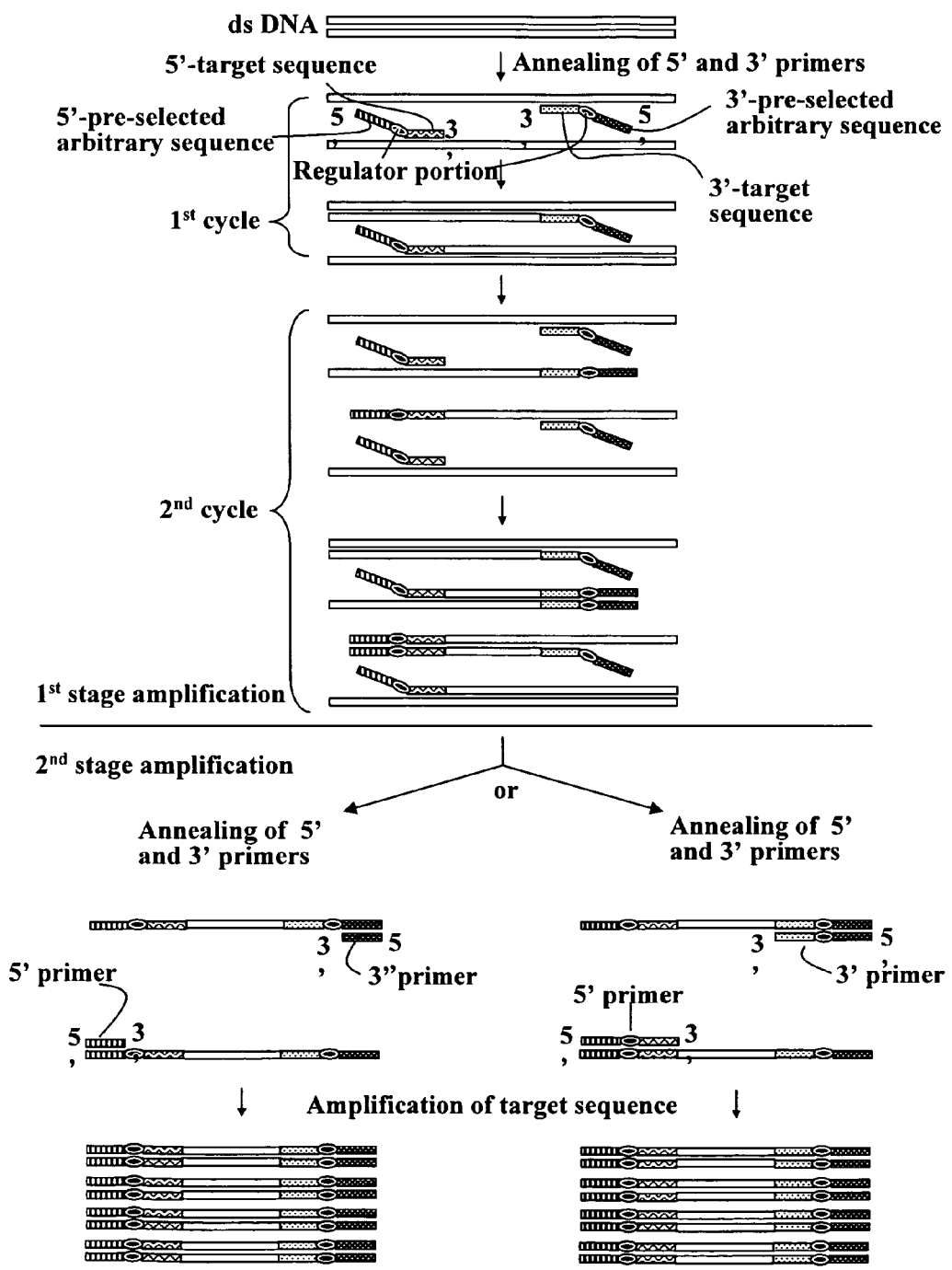
FIGS. 1A and 1B show schematic representations for selectively amplifying a target nucleic acid of double-stranded DNA (1A) or mRNA (1B) using the ACP of the present invention.

The present invention is generally directed to (a) an annealing control primer for the specificity of nucleic acid amplification and (b) its applications. The annealing control primer of this invention (hereinafter referred to as "ACP") allows primer annealing to be controlled in association with annealing temperature, such that the specificity of nucleic acid amplification (in particular, PCR) can be significantly improved. The principle of the ACP is based on the composition of an oligonucleotide primer having 3'- and 5'-ends distinct portions separated by at least one universal base or non-discriminatory base. The present inventor has discovered that the universal base or non-discriminatory base group positioned between the 3'- and 5'-end portions plays as a regulator in controlling primer annealing to a template nucleic acid in associated with annealing temperature during nucleic acid amplification. The presence of universal base or non-discriminatory base residue group positioned between the 3'- and 5'-end portions interrupts the annealing of the 5'-end portion as well as limits primer annealing to the 3'-end portion at certain annealing temperature, which results in dramatic improvement of annealing specificity. A universal base group positioned between the 3'- and 5'-end portions of ACP is designed to define each portion. For these reasons, the ACP is fundamentally different from the conventional primers in terms of the function for improving primer annealing specificity under a particular stringency conditions during nucleic acid amplification.

The ACP of this invention is significantly effective and widely accessible to nucleic acid amplification-based applications. Also, various problems related to primer annealing specificity in the conventional PCR techniques can be fundamentally solved by the ACP. The main benefits to be obtained from the use of the ACP during nucleic acid amplification (particularly PCR) are as follows:

(a) since the presence of an universal base residue group positioned between the 3'- and 5'-end portions restricts primer annealing portion to the 3'-end portion under such conditions that the 3'-end portion anneals to the template, the annealing sequence of a primer can be precisely controlled, which make it possible to design a primer with a desired number of annealing sequence. It is particularly useful when an annealing portion of a primer has to be limited (e.g., single nucleotide polymorphism (SNP) genotyping, DNA microarray screening, and detection of differentially expressed genes);

(b) since the presence of an universal base residue group positioned between the 3'- and 5'-end portions interrupts the annealing of the 5'-end portion to the template under such conditions that the 3'-end portion anneals to the template, eventually the 5'-end portion not involved in the annealing provides the 3'-end portion with primer annealing specificity;

(c) the specificity of primer annealing is highly sensitive enough to detect even a single-base mismatching. Thus, it is particularly useful for the identification of a nucleotide variation in a target nucleic acid, including, for example, single nucleotide polymorphisms and point mutations;

(d) ACP is capable of providing a primer with a high tolerance in "primer search parameters" for primer design such as primer length, annealing temperature, GC content, and PCR product length;

(e) ACP system provides two-stage PCR amplifications which allow the products to be excluded from non-specific amplification;

(f) the efficiency of PCR amplification is increased, which makes it easier to detect rare mRNAs; and (g) the reproducibility of PCR products is increased, which saves a great amount of time and cost.

Principle of ACP

In one aspect of this invention, there is provided an annealing control primer for improving annealing specificity in nucleic acid amplification, which comprises: (a) a 3'-end portion having a hybridizing nucleotide sequence substantially complementary to a site on a template nucleic acid to hybridize therewith; (b) a 5'-end portion having a pre-selected arbitrary nucleotide sequence; and (c) a regulator portion positioned between said 3'-end portion and said 5'-end portion comprising at least one universal base or non-discriminatory base analog, whereby said regulator portion is capable of regulating an annealing portion of said primer in association with annealing temperature.

The principle of ACP is based on the composition of an oligonucleotide primer having 3'- and 5'-end distinct portions separated by a regulator portion comprising at least one universal base or non-discriminatory base and the effect of the regulator portion on the 3'- and 5'-end portions in the oligonucleotide primer. The presence of the regulator portion comprising at least one universal base or non-discriminatory base between the 3'- and 5'-end portions of ACP acts as a main factor which is responsible for the improvement of primer annealing specificity.

The term "template" refers to nucleic acid. The term "nucleic acid" is a deoxyribonucleotide or ribonucleotide polymer in either single or double-stranded form, including known analogs of natural nucleotides unless otherwise indicated. Therefore, the ACP of this invention can be employed in nucleic acid amplification using single or double-stranded gDNA, cDNA or mRNA as template. The term "portion" used herein in conjunction with the primer of this invention refers to a nucleotide sequence separated by the regulator portion. The term "3'-end portion" or "5'-end portion" refers to a nucleotide sequence at the 3'-end or 5'-end of the primer of this invention, respectively, which is separated by the regulator portion.

The term "primer" as used herein refers to an oligonucleotide, whether occurring naturally or produced synthetically, which is capable of acting as a point of initiation of synthesis when placed under conditions in which synthesis of primer extension product which is complementary to a nucleic acid strand (template) is induced, i.e., in the presence of nucleotides and an agent for polymerization such as DNA polymerase and at a suitable temperature and pH. The primer is preferably single stranded for maximum efficiency in amplification. Preferably, the primer is an oligodeoxyribonucleotide. The primer of this invention can be comprised of naturally occurring dNMP (i.e., dAMP, dGM, dCMP and dTMP), modified nucleotide or non-natural nucleotide. The primer can also include ribonucleotides. The primer must be sufficiently long to prime the synthesis of extension products in the presence of the agent for polymerization. The exact length of the primers will depend on many factors, including temperature, application and source of primer. The term "annealing" or "priming" as used herein refers to the apposition of an oligodeoxynucleotide or nucleic acid to a template nucleic acid, whereby said apposition enables the polymerase to polymerize nucleotides into a nucleic acid molecule which is complementary to the template nucleic acid or a portion thereof.

The 3'-end portion of ACP has a nucleotide sequence substantially complementary to a site on a template nucleic acid molecule. The term "substantially complementary" in reference to primer is used herein to mean that the primer is sufficiently complementary to hybridize selectively to a template nucleic acid sequence under the designated annealing conditions, such that the annealed primer can be extended by polymerase to form a complementary copy of the template. Therefore, this term has a different meaning from "perfectly complementary" or related terms thereof. It will be appreciated that the 3'-end portion of ACP can have one or more mismatches to template to an extent that the ACP can serve as primer. Most preferably, the 3'-end portion of ACP has a nucleotide sequence perfectly complementary to a site on a template, i.e., no mismatches.

The 3'-end portion of ACP may have a wide variety of nucleotide sequences depending on its applications as well as template sequence. For example, where the ACP is applied to the process involving reverse transcription such as differential display PCR, RACE, amplification of full-length cDNA, fingerprinting, identification of conserved homology segment and the like, its 3'-end portion may have the nucleotide sequence which hybridizes to the polyadenosine (poly A) tail of an mRNA, preferably at least 8 deoxythymidine nucleotides, more preferably at least 10 deoxythymidine nucleotides and the most preferably, at least 10 contiguous deoxythymidine nucleotides. For the process involving reverse transcription as above, in one embodiment, the 3'-end portion of ACP has at least 10 contiguous deoxythymidine nucleotides having 3'-V at its 3'-end; in which V is one selected from the group consisting of deoxyadenosine, deoxycytidine and deoxyguanosine, in another embodiment, at least 10 contiguous deoxythymidine nucleotides having 3'-NV at its 3'-end; in which V is one selected from the group consisting of deoxyadenosine, deoxycytidine and deoxyguanosine, and N is one selected from the group consisting of deoxyadenosine, deoxythymidine, deoxycytidine and deoxyguanosine.

Furthermore, where the ACP is employed in amplification of a target nucleic acid sequence, its 3'-end portion comprises a nucleotide sequence substantially complementary to a target sequence; in differential display PCR, an arbitrary sequence substantially complementary to a site in a cDNA from an mRNA; in RACE, a gene-specific sequence substantially complementary to a site in a cDNA from an mRNA; in amplification of 5'-enriched cDNAs, a random sequence of at least six nucleotides substantially complementary to sites in mRNAs; in identification of conserved homology segment, a nucleotide sequence substantially complementary to a consensus sequence found in a gene family or degenerate sequence selected from a plurality of combinations of nucleotides encoding a predetermined amino acid sequence; in identification of a nucleotide variation (e.g., allelic site) in a target nucleic acid, a nucleotide sequence comprising a nucleotide complementary to the corresponding nucleotide of a nucleotide variation; and in mutagenesis, a nucleotide sequence comprising at least one mismatch nucleotide to a target nucleic acid.

The term "arbitrary" nucleotide sequence is used herein to mean the nucleotide sequence that is chosen without knowledge of the sequence of the target nucleic acids to be amplified. The term arbitrary should not to be confused with "random" in reference to primer which connotes a primer composed of a random population of primers each of different and random sequence. The term "degenerate" sequence in conjunction with ACP for identification of conserved homology segment refers to the nucleotide sequence that is deducted from amino acid sequence, so that the degenerate sequence can form a pool of the nucleotide sequences from one amino acid sequence due to degeneracy of genetic codon.

According to a preferred embodiment of the ACP, the pre-selected arbitrary nucleotide sequence of the 5'-end portion is substantially not complementary to any site on the template nucleic acid.

According to a preferred embodiment, the annealing control primer of this invention can be represented by a general formula (1) of 5'-Xp-Yq-Zr-3', wherein Xp represents the 5'-end portion having the pre-selected arbitrary nucleotide sequence substantially not complementary to any site on the template nucleic acid; Yq represents the regulator portion comprising at least one universal base or non-discriminatory base analog; Zr represents the 3'-end portion having a nucleotide sequence substantially complementary to a site on the template nucleic acid; wherein p, q and r represent the number of nucleotides; and wherein X, Y and Z is deoxyribonucleotide or ribonucleotide.

The regulator portion comprising at least one universal base or non-discriminatory base analog is responsible for the main function of ACP in associated with alteration of annealing temperature during nucleic acid amplification. The term "universal base or non-discriminatory base analog" used herein refers to one capable of forming base pairs with each of the natural DNA/RNA bases with little discrimination between them.

It has been widely known that nucleotides at some ambiguous positions of degenerate primers have been replaced by universal base or a non-discriminatory analogue such as deoxyinosine (Ohtsuka et al, 1985; Sakanari et al., 1989), 1-(2'-deoxy-beta-D-ribofuranosyl)-3-nitropyrrole (Nichols et al., 1994) and 5-nitroindole (Loakes and Brown, 1994) for solving the design problems associated with the degenerate primers because such universal bases are capable of non-specifically base pairing with all four conventional bases. However, there has not been any report that this universal base or a non-discriminatory analogue such as deoxyinosine, 1-(2'-deoxy-beta-D-ribofuranosyl)-3-nitropyrrole and 5-nitroindole is used to increase the specificity of primer annealing during PCR.

The presence of universal base such as deoxyinosine, 1-(2'-deoxy-beta-D-ribofuranosyl)-3-nitropyrrole and 5-nitroindole in a primer generates low annealing temperatures due to its weaker hydrogen bonding interactions in base pairing. As an extension of this theory, the present inventor has induced that the presence of the contiguous universal bases between the 3'-end and 5'-end of a primer could generate a region which has lower melting temperature, forms a boundary to each of 3'- and 5'-end portions of the primer, and affect the annealing of each portion, respectively. This theory provides the basis of the annealing control primers of this invention.

In a preferred embodiment, the ACP contains at least 2 universal base or non-discriminatory base analog residues between the 3'- and 5'-end portion sequences, more preferably, at least 3 universal bases or non-discriminatory base analogs. Advantageously, the universal base residues between the 3'- and 5'-end portion sequences can be up to 15 residues in length. According to one embodiment, the ACP contains 2-15 universal base or non-discriminatory base analog residues. Most preferably, the universal bases between the 3'- and 5'-end portion sequences are about 5 residues in length.

With reference to the optimum number of universal base, i.e., 5 residues, the minimum number of universal base residues between the 3'- and 5'-end portions of ACP is preferred in order to interrupt the annealing of the 5'-end portion to the template during nucleic acid amplification at certain annealing temperature. It is very likely that the length of universal base in the sequence (8-10 bases) does not make a significant difference on its own function in ACP.

The use of universal base residues between the 3'- and 5'-end portion sequences is considered as a key feature in the present invention because it provides each portion (3'- and 5'-end) with a distinct annealing specificity in association with an annealing temperature during nucleic acid amplification, e.g. PCR.

According to a preferred embodiment, the universal base or non-discriminatory base analog in the regulator portion includes deoxyinosine, inosine, 7-deaza-2'-deoxyinosine, 2-aza-2'-deoxyinosine, 2'-OMe inosine, 2'-F inosine, deoxy 3-nitropyrrole, 3-nitropyrrole, 2'-OMe 3-nitropyrrole, 2'-F 3-nitropyrrole, 1-(2'-deoxy-beta-D-ribofuranosyl)-3-nitropyrrole, deoxy 5-nitroindole, 5-nitroindole, 2'-OMe 5-nitroindole, 2'-F 5-nitroindole, deoxy 4-nitrobenzimidazole, 4-nitrobenzimidazole, deoxy 4-aminobenzimidazole, 4-aminobenzimidazole, deoxy nebularine, 2'-F nebularine, 2'-F 4-nitrobenzimidazole, PNA-5-introindole, PNA-nebularine, PNA-inosine, PNA-4-nitrobenzimidazole, PNA-3-nitropyrrole, morpholino-5-nitroindole, morpholino-nebularine, morpholino-inosine, morpholino-4-nitrobenzimidazole, morpholino-3-nitropyrrole, phosphoramidate-5-nitroindole, phosphoramidate-nebularine, phosphoramidate-inosine, phosphoramidate-4-nitrobenzimidazole, phosphoramidate-3-nitropyrrole, 2'-0-methoxyethyl inosine, 2'0-methoxyethyl nebularine, 2'-0-methoxyethyl 5-nitroindole, 2'-0-methoxyethyl 4-nitro-benzimidazole, 2'-0-methoxyethyl 3-nitropyrrole and combinations thereof, but not limited to. More preferably, the universal base or non-discriminatory base analog is deoxyinosine, 1-(2'-deoxy-beta-D-ribofuranosyl)-3-nitropyrrole or 5-nitroindole, most preferably, deoxyinosine.

The preferred length of an oligonucleotide primer, as used herein, is determined from desired specificity of annealing and the number of oligonucleotides having the desired specificity that are required to hybridize to the template. For example, an oligonucleotide primer of 20 nucleotides is more specific than an oligonucleotide primer of 10 nucleotides because the addition of each nucleotide to an oligonucleotide increases the annealing temperature of the primer to the template.

The lengths of the 3'- and 5'-end portion sequences of the ACP may vary and depend in part on the objective of each application using ACP. In a preferred embodiment, the 3'-end portion of ACP is at least 6 nucleotides in length, which is considered a minimal requirement of length for primer annealing. More preferably, the 3'-end portion sequence is from 10 to 25 nucleotides and can be up to 60 nucleotides in length. In another embodiment, the 3'-end portion of ACP can include ribonucleotides as well as deoxyribonucleotides.

In another preferred embodiment, the 5'-end portion of ACP contains at least 15 nucleotides in length, which is considered a minimal requirement of length for annealing under high stringent conditions. Preferably, the 5'-end portion sequence can be up to 60 nucleotides in length. More preferably, the 5'-end portion sequence is from 6 to 50 nucleotides, most preferably, from 20 to 25 nucleotides in length. The entire ACP is preferably from 35 to 50 nucleotides in length, and can be up to 100 nucleotides in length.

The 5'-end portion of ACP has a pre-selected arbitrary nucleotide sequence substantially not complementary to any site on the template nucleic acid and this nucleotide sequence can serves as a priming site for subsequent amplification. The term "pre-selected arbitrary" nucleotide sequence used herein refers as any defined or pre-selected deoxyribonucleotide, ribonucleotide, or mixed deoxyribonucleotide sequence which contains a particular sequence of natural or modified nucleotides. In some embodiment, the pre-selected arbitrary nucleotide sequence of the 5'-end portion can be composed of a universal primer sequence such as T3 promoter sequence, T7 promoter sequence, SP6 promoter sequence, and M13 forward or reverse universal sequence. Using a longer arbitrary sequence (about 25 to 60 bases) at the 5'-end portion of ACP reduces the efficiency of ACP, but shorter sequences (about 15 to 17 bases) reduce the efficiency of annealing at high stringent conditions of ACP. It is also a key feature of the present invention to use a pre-selected arbitrary nucleotide sequence at the 5'-end portion of ACP as a priming site for subsequent amplification.

According to one embodiment of the present invention, some modifications in the 5'-end portion of ACP can be made unless the modifications abolish the advantages of the ACP, i.e., improvement in annealing specificity. For example, the 5'-end portion can comprises a sequence or sequences recognized by a restriction endonuclease(s), which makes it feasible to clone the amplified product into suitable vector. In addition, the 5'-end portion can comprises at least one nucleotide with a label for detection or isolation of amplified product. Suitable labels include, but not limited to, fluorophores, chromophores, chemiluminescers, magnetic particles, radio-isotopes, mass labels, electron dense particles, enzymes, cofactors, substrates for enzymes and haptens having specific binding partners, e.g., an antibody, streptavidin, biotin, digoxigenin and chelating group. The 5'-end portion also comprises bacteriophage RNA polymerase promoter region.

According to the preferred embodiment of this invention, the ACP is applied to PCR. More preferably, the PCR is performed under a first and a second annealing temperature, i.e., under different stringent conditions. The first annealing temperature may be equal to or lower than the second annealing temperature and preferably, the second annealing temperature is higher than the first annealing temperature. In the PCR process performed under two different annealing temperatures, i.e., two-stage PCR, the 3'-end of ACP is involved in annealing at the first annealing temperature and the 5'-end of ACP incorporated into amplified product of first amplification stage serves as a priming site at the second annealing temperature. In this case, the advantages of ACP will be demonstrated in accordance with the following assumptions:

(1) since a regulator portion of ACP is composed of at least one universal base or non-discriminatory analogue which has lower Tm than other portion in ACP due to its weaker hydrogen bonding interactions in base pairing, the regulator portion of ACP is not favorable in annealing to the template nucleic acid under the conditions that the 3'-end portion of ACP anneals to a site of the template at a first annealing temperature. Consequently, the presence of a regulator portion comprising at least one universal base or non-discriminatory analogue between the 3'- and 5'-end portions of ACP restricts primer annealing portion to the 3'-end portion at first annealing temperature;

(2) the 5'-end portion which is not involved in the annealing under the first annealing temperature keeps bothering the annealing of the 3'-end portion to the template;

(3) thus, the strength in which the specific annealing of the 3'-end portion sequence occurs is relatively stronger than the strength in which non-specific annealing occurs, under the first annealing temperature, which results in the improvement of primer annealing specificity at the 3'-end portion;

(4) where the 5'-end portion comprises a pre-selected arbitrary nucleotide sequence, the portion serves as a priming site at a second annealing temperature, which is high stringency conditions and also should be higher than the first annealing temperature, for subsequent amplification of reaction product generated from annealing and extension of the 3'-end portion sequence; and (5) consequently, only the reaction product generated from annealing and extension of the 3'-end portion sequence can be amplified close to the theoretical optimum of a two-fold increase of product for each PCR cycle under the second annealing temperature.

Therefore, the 3'-end portion of ACP acts only as annealing site to the template at the first annealing temperature and the 5'-end portion of ACP is used as a priming site at the second annealing temperature for the subsequent amplification of the product generated by contacting and extending the 3'-end portion of ACP to the template.

It may be appreciated that the ACP of the present invention is very useful in a variety of primer-based nucleic acid amplification methods including the methods of Miller, H. I. (WO 89/06700) and Davey, C. et al. (EP 329,822), Ligase Chain Reaction (LCR, Wu, D. Y. et al., Genomics 4:560 (1989)), Polymerase Ligase Chain Reaction (Barany, PCR Methods and Applic., 1:5-16(1991)), Gap-LCR (WO 90/01069), Repair Chain Reaction (EP 439,182), 3SR (Kwoh et al., PNAS, USA, 86:1173(1989)) and NASBA (U.S. Pat. No. 5,130,238), but not limited to.

In another aspect of this invention, there is provided a kit comprising the annealing control primer or the annealing control primer set according to the present invention. According to one embodiment of this invention, this kit further comprises a primer or a primer pair having a nucleotide sequence corresponding to the 5'-end portion of the ACP; in case that the 5'-end portion comprises universal primer sequence, it is more preferred that the kit comprises the universal primers. The present kits may optionally include the reagents required for performing PCR reactions such as buffers, DNA polymerase, DNA polymerase cofactors, and deoxyribonucleotide-5'-triphosphates. Optionally, the kits may also include various polynucleotide molecules, reverse transcriptase, various buffers and reagents, and antibodies that inhibit DNA polymerase activity. The kits may also include reagents necessary for performing positive and negative control reactions. Optimal amounts of reagents to be used in a given reaction can be readily determined by the skilled artisan having the benefit of the current disclosure. The kits, typically, are adapted to contain in separate packaging or compartments the constituents afore-described.

The ACP of the subject invention can be applied to a variety of nucleic acid amplification-based technologies. Representative examples to prove the effect of ACP are:

I. Application to amplifying a nucleic acid sequence;
II. Application to amplifying a target nucleic acid sequence;
III. Application to multiplex DNA amplification;
IV. Application to the identification of differentially expressed genes;
V. Application to rapid amplification of cDNA ends (RACE);
VI. Application to amplifying full-length cDNA;
VII. Application to amplifying 5'-enriched cDNA;
VIII. Application to DNA or RNA fingerprinting;
IX. Application to the identification of conserved homology segments in multigene families;
X. Application to identification of a nucleotide sequence variation;
XI. Application to mutagenesis; and
XII. Other applications.

I. Application to Amplifying a (Target) Nucleic Acid Sequence

In still another of this invention, there is provided a method for amplifying a nucleic acid sequence from a DNA or a mixture of nucleic acids, comprising performing an amplification reaction using primers, characterized in that at least one primer is derived from any one of ACP described above. Preferably, the primer according to the structure of ACP is one having at its 3'end portion a hybridizing sequence substantially complementary to a region of the nucleic acid sequence to hybridize therewith.

In a specific embodiment of this method, there is provided a method using two stage amplifications for amplifying a nucleic acid sequence from a DNA or a mixture of nucleic acids, which comprises:

(a) performing a first-stage amplification of the nucleic acid sequence at a first annealing temperature comprising at least two cycles of primer annealing, primer extending and denaturing, using the primer pair of any one of the ACP described above each having at its 3'end portion a hybridizing sequence substantially complementary to a region of the nucleic acid sequence to hybridize therewith, under conditions in which each primer anneals to the region of the nucleic acid sequence, whereby the amplification product of the nucleic acid sequence is generated; and (b) performing a second-stage amplification of the amplification product generated from step (a) at a second annealing temperature, which is high stringent conditions, comprising at least one cycle of primer annealing, primer extending and denaturing, using the same primers as used in step (a) or a primer pair each comprising a pre-selected arbitrary nucleotide sequence corresponding to each 5'-end portion of the primers used in step (a), under conditions in which each primer anneals to the 3'- and 5'-ends of the amplification product, respectively, whereby the amplification product is re-amplified.

Where the method is applied to the amplification of a target nucleic acid sequence, the primer pair used has at its 3'-end portion a hybridizing sequence substantially complementary to a region of the target nucleic acid sequence to hybridize therewith. Therefore, in a further aspect of this invention, there is provided a method for selectively amplifying a target nucleic acid sequence from a DNA or a mixture of nucleic acids, wherein the method comprises performing an amplification reaction using primers, characterized in that at least one primer is derived from the ACP described above. Preferably, the primer according to the structure of ACP is one having at its 3'end portion a hybridizing sequence substantially complementary to a region of the target nucleic acid sequence to hybridize therewith.

In a specific embodiment of this method, there is provided a method using two stage amplifications for selectively amplifying a target nucleic acid sequence from a DNA or a mixture of nucleic acids, which comprises:

(a) performing a first-stage amplification of the target nucleic acid sequence at a first annealing temperature comprising at least two cycles of primer annealing, primer extending and denaturing, using the primer pair of any one of the ACP described above each having at its 3'end portion a hybridizing sequence substantially complementary to a region of the target nucleic acid sequence to hybridize therewith, under conditions in which each primer anneals to its target nucleotide sequence, whereby the amplification product of the target nucleotide sequence is generated; and (b) performing a second-stage amplification of the amplification product generated from step (a) at a second annealing temperature, which is high stringent conditions, comprising at least one cycle of primer annealing, primer extending and denaturing, using the same primers as used in step (a) or a primer pair each comprising a pre-selected arbitrary nucleotide sequence corresponding to each 5'-end portion of the primers used in step (a), under conditions in which each primer anneals to the 3'- and 5'-ends of the amplification product, respectively, whereby the amplification product is re-amplified.

Where the template for amplification is mRNA, the production of cDNA is required prior to amplification. Therefore, in still further aspect of this invention, there is provided a method for selectively amplifying a target nucleic acid sequence from an mRNA, wherein the method comprises reverse transcribing the mRNA and performing an amplification reaction using primers, characterized in that at least one primer is derived from the ACP described above. Preferably, the primer according to the structure of ACP is one having at its 3'end portion a hybridizing sequence substantially complementary to a region of the target nucleic acid sequence to hybridize therewith.

In a specific embodiment of this invention, there is provided a method using two stage amplifications for selectively amplifying a target nucleic acid sequence from an mRNA which comprises:

(a) contacting the mRNA with an oligonucleotide dT primer which is hybridized to polyA tail of the mRNA under conditions sufficient for template driven enzymatic deoxyribonucleic acid synthesis to occur;

(b) reverse transcribing the mRNA to which the oligonucleotide dT primer hybridizes to produce a first DNA strand that is complementary to the mRNA to which the oligonucleotide dT primer hybridizes;

(c) performing a first-stage amplification of the target nucleic acid sequence from the first DNA strand obtained from step (b) at a first annealing temperature comprising at least two cycles of primer annealing, primer extending and denaturing, using the primer pair of ACP described above having at its 3'end portion a hybridizing sequence substantially complementary to a region of the target nucleic acid sequence to hybridize therewith, under conditions in which each primer anneals to its target nucleotide sequence, whereby the amplification product of the target nucleotide sequence is generated; and (d) performing a second-stage amplification of the amplification product generated from step (c) at a second annealing temperature, which is high stringent conditions, comprising at least one cycle of primer annealing, primer extending and denaturing, using the same primers as used in step (c) or a primer pair each comprising a pre-selected arbitrary nucleotide sequence corresponding to each 5'-end portion of the primers used in step (c), under conditions in which each primer anneals to the 3'- and 5'-ends of the amplification product, respectively, whereby the amplification product is re-amplified.

Since the amplification methods of this invention employs the ACP of this invention, the common descriptions between them are omitted in order to avoid the complexity of this specification leading to undue multiplicity.

This application using ACP of the subject invention can provide an improved method for selectively amplifying a target nucleic acid sequence from a nucleic acid or a mixture of nucleic acids (DNA or mRNA) by performing nucleic acid amplifications, preferably, PCR. Since the effect of ACP provides the conventional primers with primer annealing specificity regardless of "primer search parameters" for primer design such as primer length, annealing temperature, GC content and product length, it is particularly recommended to use the ACP when the conventional primers used to amplify a target nucleic acid fragment are too sensitive to such parameters to generate specific nucleic acid amplification products.

Figure 1B:
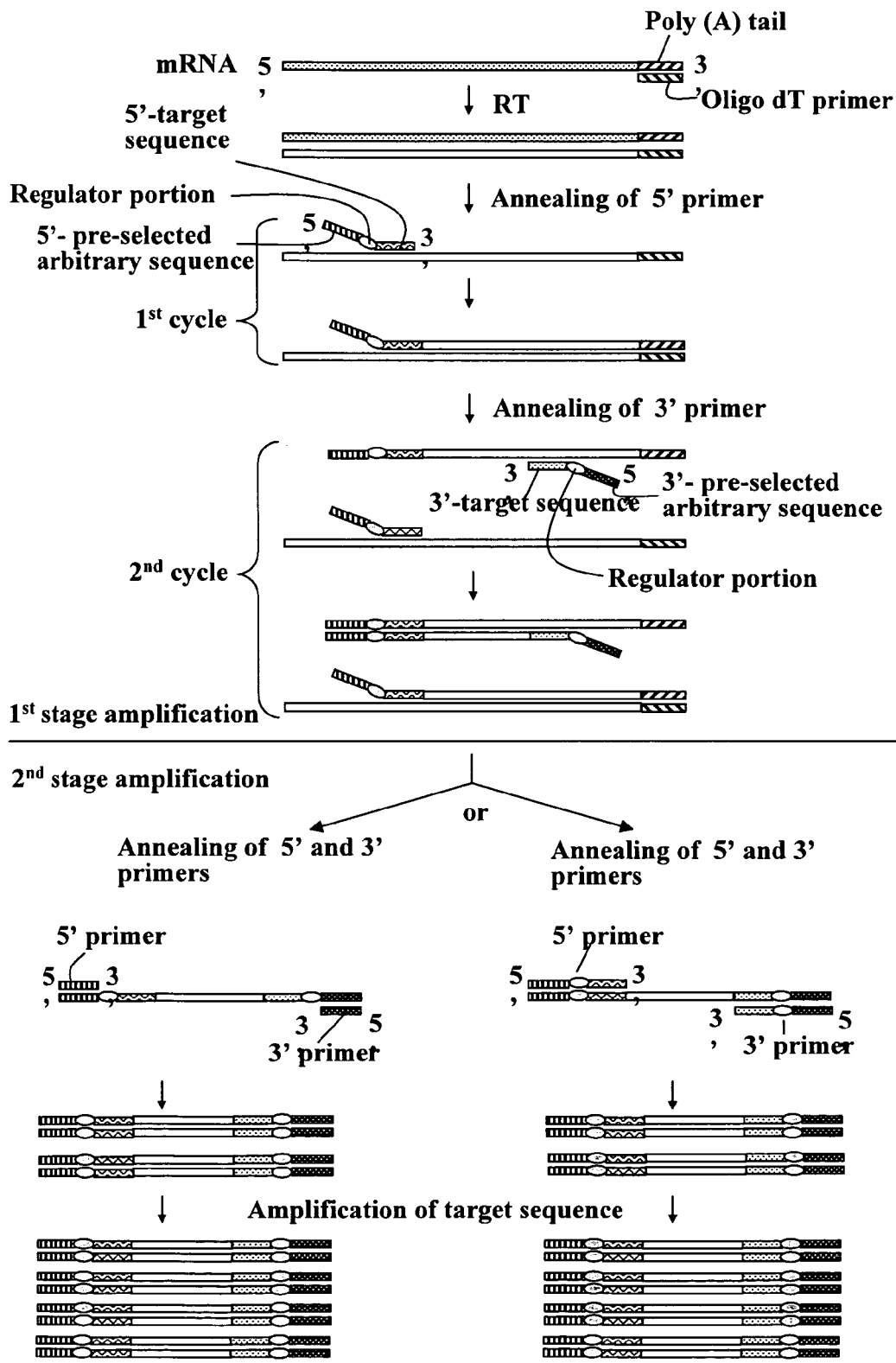

A schematic representation for selectively amplifying a target nucleic acid of double-stranded DNA using novel ACP system as described above is illustrated in FIG. 1A. FIG. 1B illustrates a schematic representation for selectively amplifying a target nucleic acid of mRNA using novel ACP system. Referring to FIGS. 1A and 1B, the present methods will be described in more detail.

The present methods for amplifying a nucleic acid sequence may be carried out in accordance with various primer-based nucleic acid amplifications known in the art. Preferably, the methods are carried out according to the two stage amplifications developed by the present inventor, more preferably, the amplification is performed by polymerase chain reaction known in the art and most preferably, hot start PCR method.

The methods of the present invention, for amplifying a nucleic acid sequence can be used to amplify any desired nucleic acid molecule. Such molecules may be either DNA or RNA. The molecule may be in either a double-stranded or single-stranded form, preferably, double-stranded. Where the nucleic acid as starting material is double-stranded, it is preferred to render the two strands into a single-stranded, or partially single-stranded, form. Methods known to separate strands includes, but not limited to, heating, alkali, formamide, urea and glycoxal treatment, enzymatic methods (e.g., helicase action) and binding proteins. For instance, strand separation can be achieved by heating at temperature ranging from 80° C. to 105° C. General methods for accomplishing this treatment are provided by Joseph Sambrook, et al., Molecular Cloning, A Laboratory Manual, Cold Spring Harbor Laboratory Press, Cold Spring Harbor, N.Y. (2001).

Where a mRNA is employed as starting material for amplification, a reverse transcription step is necessary prior to amplification, details of which are found in Joseph Sambrook, et al., Molecular Cloning, A Laboratory Manual, Cold Spring Harbor Laboratory Press, Cold Spring Harbor, N.Y. (2001); and Noonan, K. F. et al., Nucleic Acids Res. 16:10366 (1988)). For reverse transcription, an oligonucleotide dT primer hybridizable to poly A tail of mRNA is used. The oligonucleotide dT primer is comprised of dTMPs, one or more of which may be replaced with other dNMPs so long as the dT primer can serve as primer. Reverse transcription can be done with a reverse transcriptase that has RNase H activity. If one uses an enzyme having RNase H activity, it may be possible to omit a separate RNase H digestion step, by carefully choosing the reaction conditions.

The present methods do not require that the molecules to be amplified have any particular sequence or length. In particular, the molecules which may be amplified include any naturally occurring procaryotic, eukaryotic (for example, protozoans and parasites, fungi, yeast, higher plants, lower and higher animals, including mammals and humans) or viral (for example, Herpes viruses, HIV, influenza virus, Epstein-Barr virus, hepatitis virus, polio virus, etc.) or viroid nucleic acid. The nucleic acid molecule can also be any nucleic acid molecule which has been or can be chemically synthesized. Thus, the nucleic acid sequence may or may not be found in nature.

The ACP used for the present invention is hybridized or annealed to a region on template so that double-stranded structure is formed. Conditions of nucleic acid hybridization suitable for forming such double stranded structures are described by Joseph Sambrook, et al., Molecular Cloning, A Laboratory Manual, Cold Spring Harbor Laboratory Press, Cold Spring Harbor, N.Y. (2001) and Haymes, B. D., et al., Nucleic Acid Hybridization, A Practical Approach, IRL Press, Washington, D.C. (1985). The sequence of the 3'-end portion of ACP needs not to exhibit precise complementarity, but need only to be substantially complementary in sequence to be able to form a stable double-stranded structure. Thus, departures from complete complementarity are permissible, so long as such departures are not sufficient to completely preclude hybridization to form a double-stranded structure. Hybridization of ACP to a region on template nucleic acid is a prerequisite for its template-dependent polymerization with polymerases. Factors (see Joseph Sambrook, et al., Molecular Cloning, A Laboratory Manual, Cold Spring Harbor Laboratory Press, Cold Spring Harbor, N.Y. (2001); and Haymes, B. D., et. al., Nucleic Acid Hybridization, A Practical Approach, IRL Press, Washington, D.C. (1985)) which affect the base pairing of ACP to its complementary nucleic acids subsequently affect priming efficiency. The nucleotide composition of ACP can affect the temperature at which annealing is optimal and therefore can affect its priming efficiency.

A variety of DNA polymerases can be used in the amplification step of the present methods, which includes "Klenow" fragment of E. coli DNA polymerase 1, a thermostable DNA polymerase and bacteriophage T7 DNA polymerase. Preferably, the polymerase is a thermostable DNA polymerase such as may be obtained from a variety of bacterial species, including Thermus aquaticus (Taq), Thermus thermophilus (Tth), Thermus filiformis, Thermis flavus, Thermococcus literalis, and Pyrococcus furiosus (Pfu). Many of these polymerases may be isolated from bacterium itself or obtained commercially. Polymerase to be used with the subject invention can also be obtained from cells which express high levels of the cloned genes encoding the polymerase. When a polymerization reaction, is being conducted, it is preferable to provide the components required for such reaction in excess in the reaction vessel. Excess in reference to components of the amplification reaction refers to an amount of each component such that the ability to achieve the desired amplification is not substantially limited by the concentration of that component. It is desirable to provide to the reaction mixture an amount of required cofactors such as Mg2+, and dATP, dCTP, dGTP and dTTP in sufficient quantity to support the degree of amplification desired.

All of the enzymes used in this amplification reaction may be active under the same reaction conditions. Indeed, buffers exist in which all enzymes are near their optimal reaction conditions. Therefore, the amplification process of the present invention can be done in a single reaction volume without any change of conditions such as addition of reactants.

It would be understood that the 5'-end portions of a set of ACPs used in the step of the first-stage amplification could comprise identical or different sequences; if they are identical, one primer corresponding to the sequence of 5'-end portion will be used in the step of the second-stage amplification, whereas if they are different, two primers each corresponding to the sequence of each 5'-end portion of ACPs will be used in the step of the second-stage amplification.

The present invention includes an alternative process for selectively amplifying a target nucleic acid fragment from a nucleic acid or a mixture using ACP, wherein a set of primers comprising an ACP and a conventional primer can be used in the first amplification step, instead of a set of ACP. The term "conventional primer" used herein refers to any primer having a structure different from ACP, especially; in terms of the presence of the regulator portion containing universal base. In this case, the conventional primer is added only the first amplification step with the ACP and only one pre-selected arbitrary primer corresponding to the 5'-end portion sequence of the ACP is added in the second amplification step. In preferred embodiment, the alternative process can be used when each 3'-portion of a pair of ACP to be used in the first amplification step has different melting temperature (Tm). "Tm" refers to the temperature at which half the primers are annealed to the target region.

Two amplification steps of the present methods (in case of amplification from mRNA, including reverse transcriptation) are separated only in time. The first-stage amplification should be followed by the second-stage amplification. It would be understood that the first-stage amplification reaction mixture could include the primers corresponding to the 5'-end portion which will be used to anneal to the sequences of the 5'-end portions of the ACPs in the second-stage amplification, which means that the primers corresponding to the 5'-end portion can be added to the reaction mixture at the time of or after the first-stage amplification step.

As an alternative process, in the second-stage amplification step the complete sequences of the ACPs used in the first-stage amplification step, instead of the primers corresponding to the 5'-end portions of the ACPs, can be used as primers at the high stringent conditions for re-amplifying the product generated from the first-stage amplification step, wherein the 3'- and 5'-ends of the product from the first amplification step which is generated from annealing and extension of the 3'-end portion sequence of the set of ACP to the template nucleic acid at the low stringent conditions comprise the sequence or complementary sequence of ACP and also serve as perfect paring sites to the set of ACP. In this view, this alternative process is preferred because this need not further add the primers corresponding to the 5'-end portions of the ACPs to the reaction mixture at the time of or after the first-stage amplification step. FIG. 1A also illustrates a schematic representation for selectively amplifying a target nucleic acid by the alternative process stated above.

Annealing or hybridization in the present methods is performed under stringent conditions that allow for specific binding between a nucleotide sequence and ACP. Such stringent conditions for annealing will be sequence-dependent and varied depending on environmental parameters. In the present methods, the second-stage amplification is generally performed under higher stringent conditions than the first-stage amplification.

In a preferred embodiment, the first annealing temperature ranges from about 30° C. to 68° C. for the first-stage amplification step, more preferably, 40° C. to 65° C. It is preferred that the second annealing temperature ranges from about 50° C. to 72° C. for the second-stage amplification. According to a more preferred embodiment, the first annealing temperature is equal to or lower than the second annealing temperature.

The length or melting temperature (Tm) of the 3'-end portion sequence of ACP will determine the annealing temperature for the first-stage amplification. For example, in case that ACP comprises 10 arbitrary nucleotides at the 3'-end portion, preferably, the annealing temperature will be about between 45° C. and 55° C. for the first-stage amplification.

According to the present methods, the first-stage amplification under low stringent conditions is carried out for at least 2 cycles of annealing, extending and denaturing to improve the specificity of primer annealing during the first-stage amplification, and through the subsequent cycles, the second-stage amplification is processed more effectively under high stringent conditions. The first-stage amplification can be carried out up to 30 cycles. In a preferred embodiment, the first-stage amplification is carried out for 2 cycles. In another embodiment, the second-stage amplification under high stringent conditions is carried out for at least one cycle (preferably, at least 5 cycles) and up to 45 cycles to amplify the first-stage product. In a more preferred embodiment, the second-stage amplification is carried out for 25-35 cycles. High and low stringent conditions may be readily determined from the standard known in the art. "Cycle" refers to the process which results in the production of a copy of target nucleic acid. A cycle includes a denaturing step, an annealing step, and an extending step.

In the most preferable embodiment, the amplification is performed in accordance with PCR which is disclosed in U.S. Pat. Nos. 4,683,195, 4,683,202, and 4,800,159.

According to a preferred embodiment, when the first-stage amplification is carried out, the 3'-end portion of the primer pair of ACP is involved in annealing at the first annealing temperature and when the second-stage amplification is carried out, the 5'-end portion of the primer pair serves as a priming site. Such alteration of the portion to involve in annealing is mainly ascribed to the ACP itself, in particular, the regulator portion of ACP. In the present methods, the regulator portion of ACP is capable of restricting the annealing portion of ACP to its 3'-end portion at the first annealing temperature, responsible for improving annealing specificity to a target sequence.

The present methods may be combined with many other processes known in the art to achieve a specific aim. For example, the isolation (or purification) of amplified product may follow the second-stage amplification. This can be accomplished by gel electrophoresis, column chromatography, affinity chromatography or hybridization. In addition, the amplified product of this invention may be inserted into suitable vehicle for cloning. Furthermore, the amplified product of this invention may be expressed in suitable host harboring expression vector. In order to express the amplified product, one would prepare an expression vector that carries the amplified product under the control of, or operatively linked to a promoter. The promoter is originated from the vector itself or the end portion of the amplified product, which may correspond to 5'-end portion of the ACP. Many standard techniques are available to construct expression vectors containing the amplified product and transcriptional/translational/control sequences in order to achieve protein or peptide expression in a variety of host-expression systems. The promoter used for prokaryotic host includes, but not limited to, pLλ promoter, trp promoter, lac promoter and T7 promoter. The promoter used for eukaryotic host includes, but not limited to, metallothionein promoter, adenovirus late promoter, vaccinia virus 7.5K promoter and the promoters derived from polyoma, adenovirus 2, simian virus 40 and cytomegalo virus. Certain examples of prokaryotic hosts are *E. coli*, *Bacillus subtilis*, and other enterobacteriaceae such as *Salmonella typhimurium*, *Serratia marcescens*, and various *Pseudomonas* species. In addition to microorganisms, cultures of cells derived from multicellular organisms may also be used as hosts. In principle, any such cell culture is workable, whether from vertebrate or invertebrate culture. In addition to mammalian cells, these include insect cell systems infected with recombinant virus expression vectors (e.g., baculovirus); and plant cell systems infected with recombinant virus expression vectors (e.g., cauliflower mosaic virus, tobacco mosaic virus) or transformed with recombinant plasmid expression vectors (e.g., Ti plasmid) containing one or more coding sequences. The expressed polypeptide from the amplified product may be generally purified with a variety of purposes in accordance with the method known in the art.

In another aspect of this invention, there is provided a kit for nucleic acid amplification of the instant invention described previously, which comprises the annealing control primer or annealing control primer set indicated above.

In still another aspect of this invention, there is provided a kit for selective amplification of a target nucleic acid sequence from DNA described previously, which comprises the annealing control primer or annealing control primer set indicated above.

In further aspect of this invention, there is provided a kit for selective amplification of a target nucleic acid sequence from mRNA described previously, which comprises the annealing control primer or annealing control primer set indicated above.

According to one embodiment of this invention, these kits further comprises a primer or a primer pair each having a nucleotide sequence corresponding to the 5'-end portion of the ACP; in case that the 5'-end portion comprises universal primer sequence, it is more preferred that the kit comprises the universal primers. The present kits may optionally include the reagents required for performing PCR reactions such as buffers, DNA polymerase, DNA polymerase cofactors, and deoxyribonucleotide-5'-triphosphates. Optionally, the kits may also include various polynucleotide molecules, reverse transcriptase, various buffers and reagents, and antibodies that inhibit DNA polymerase activity. The kits may also include reagents necessary for performing positive and negative control reactions. Optimal amounts of reagents to be used in a given reaction can be readily determined by the skilled artisan having the benefit of the current disclosure. The kits, typically, are adapted to contain in separate packaging or compartments the constituents afore-described.

II. Application to Multiplex DNA Amplification

This application using ACP of the subject invention can also provide an improved method for amplifying more than one target sequence using more than one pair of primers in the same reaction. In general, it is extremely difficult to set up PCR conditions to amplify more than 10 targets in parallel because an optimal PCR reaction is required to amplify even one specific locus without any unspecific by-products, so that those researchers who have achieved multiplex PCR have had to work hard to optimize their systems. Since annealing needs to take place at a sufficiently high temperature to allow the perfect DNA-DNA matches to occur in the reaction, the ACP of the subject invention is ideal in the optimization of multiplex DNA amplification due to its function of improving the specificity of amplification. "Multiplex PCR" as used herein refers to the simultaneous amplification of multiplex DNA targets in a single polymerase chain reaction (PCR) mixture.

In still further aspect of this invention, there is provided a method for amplifying more than one target nucleotide sequence simultaneously using more than one pair of primers in the same reaction, wherein the method comprises performing an amplification reaction using primers, characterized in that at least one primer is derived from any one of ACP described above. Preferably, the primer according to the structure of ACP is one having at its 3'end portion a hybridizing sequence substantially complementary to a region of the target nucleic acid sequence to hybridize therewith.

In a specific embodiment of this invention, there is provided the method using two stage amplifications, which comprises:

(a) performing a first-stage amplification of more than one target nucleotide sequence at a first annealing temperature comprising at least two cycles of primer annealing, primer extending and denaturing, using the primer pairs of any one of ACP above in which its 3'end portion each of the primer pairs has a hybridizing nucleotide sequence substantially complementary to a region of the target nucleic acid sequence to hybridize therewith, under conditions in which each of each primer pair anneals to its target nucleotide sequence, whereby the amplification products of target nucleotide sequences are generated; and (b) performing a second-stage amplification of the amplification products generated from step (a) at a second annealing temperature, which is high stringent conditions, comprising at least one cycle of primer annealing, primer extending and denaturing, using the same primer pairs as used in step (a) or primer pairs each comprising a pre-selected arbitrary nucleotide sequence corresponding to each 5'-end portion of the primer pairs used in step (a), under conditions in which each of each primer pair anneals to the 3'- and 5'-end sequences of the amplification products generated from step (a), respectively, whereby the amplification products are re-amplified in the same reaction.

Since this application using the ACP of this invention is carried out in accordance with the present methods for amplification of nucleic acid sequence previously discussed, except for using more than one target nucleotide sequence and primer pairs, the common descriptions between them are omitted in order to avoid the complexity of this specification leading to undue multiplicity.

For instance, the composition and structure of ACP used and the conditions for amplification, are common between this process and the present methods for amplification of nucleic acid sequence previously discussed.

In a preferred embodiment, the amplified products from each of target nucleotide sequences are different in size for subsequent analysis.

According to a preferred embodiment, the amplification products of multiplex target nucleotide sequences may be analyzed through size separation. The size separation comparison is performed using a variety of method known in the art, such as electrophoresis through a polyacrylamide gel matrix or agarose gel matrix and nucleotide sequencing. The nucleotide sequencing may be rapidly carried out with an automatic sequencer available from various manufacturer.

As exemplified in Example below, the ACP of this invention permits the final amplified products to be free from the background problems as well as non-specificity arising from the conventional primers used in multiplex nucleic acid amplification methods known in the art.

The advantage of the multiplex amplification is that numerous diseases or specific nucleotide sequence alterations (e.g., single nucleotide polymorphism or point mutation) can be assayed in the same reaction.

The number of analyses that can be run simultaneously is unlimited; however, the upper limit is probably about 20 and is likely to be dependent on the size difference required for resolution and methods that are available to resolve the amplified product.

In another aspect of this invention, there is provided a kit for amplifying more than one target nucleotide sequence simultaneously in the same reaction, which comprises the annealing control primer or annealing control primer set described above. According to one embodiment of this invention, these kits further comprises a primer or a primer pair having a nucleotide sequence corresponding to the 5'-end portion of the ACP; in case that the 5'-end portion comprises universal primer sequence, it is more preferred that the kit comprises the universal primers. The present kits may optionally include the reagents required for performing PCR reactions such as buffers, DNA polymerase, DNA polymerase cofactors, and deoxyribonucleotide-5'-triphosphates. Optionally, the kits may also include various polynucleotide molecules, reverse transcriptase, various buffers and reagents, and antibodies that inhibit DNA polymerase activity. The kits may also include reagents necessary for performing positive and negative control reactions. Optimal amounts of reagents to be used in a given reaction can be readily determined by the skilled artisan having the benefit of the current disclosure. The kits, typically, are adapted to contain in separate packaging or compartments the constituents afore-described.

The method and kit of the present invention may be applied to the diagnosis of genetic and infectious diseases, gender determination, genetic linkage analysis, and forensic studies.

III. Application to Identification of Differentially Expressed Genes

This application using ACP of the subject invention can also provide an improved method for detecting and cloning cDNAs complementary to differentially expressed mRNAs in two or more nucleic acid samples.

In still further aspect of this invention, there is provided a method for detecting DNA complementary to differentially expressed mRNA in two or more nucleic acid samples, wherein the method comprises reverse transcribing the mRNA and performing an amplification reaction using primers, characterized in that at least one primer is derived from any one of ACP described above. Preferably, the primer according to the structure of ACP is one having at its 3'end portion a hybridizing sequence (more preferably, arbitrary sequence) substantially complementary to a region of cDNA strands generated from reverse transcription.

In a specific embodiment of this invention, there is provided the method using two stage amplifications, which comprises:

(a) providing a first sample of nucleic acids representing a first population of mRNA transcripts and a second sample of nucleic acids representing a second population of mRNA transcripts;

(b) separately contacting each of the first nucleic acid sample and the second nucleic acid sample with a first primer of any one of ACP described above, in which the 3'-end portion of the first primer comprises a hybridizing nucleotide sequence substantially complementary to a first site in the differentially expressed mRNA to hybridize therewith, under conditions sufficient for template driven enzymatic deoxyribonucleic acid synthesis to occur;

(c) reverse transcribing the differentially expressed mRNA to which the first primer hybridizes to produce a first population of first cDNA strands that are complementary to the differentially expressed mRNA in the first nucleic acid sample to which the first primer hybridizes, and a second population of first cDNA strands that are complementary to the differentially expressed mRNA in the second nucleic acid sample to which the first primer hybridizes;

(d) purifying and quantifying each of the first and second populations of first cDNA strands;

(e) performing a first-stage amplification of each of the first and second population of first DNA strands obtained from step (d) at a first annealing temperature comprising at least one cycle of primer annealing, primer extending and denaturing, using a second primer of any one of ACP described above having at its 3'end portion a hybridizing sequence substantially complementary to a second site in the first and second populations of first cDNA strands, under conditions in which the second primer anneals to the second site in each population of the first cDNA strands, whereby first and second populations of second cDNA strands are generated;

(f) performing a second-stage amplification of each second cDNA strand generated from step (e) at a second annealing temperature, which is high stringent conditions, comprising at least two cycles of primer annealing, primer extending and denaturing, using the same first and second primers as used in steps (b) and (e), respectively, or a primer pair each comprising a pre-selected arbitrary nucleotide sequence corresponding to each 5'-end portion of the first and second primers used in steps (b) and (e), respectively, under conditions in which each primer anneals to the 3'- and 5'-end sequences of each second cDNA strand, respectively, whereby amplification products of the second cDNA strands are generated, and (g) comparing the presence or level of individual amplification products in the first and second populations of amplification products obtained from step (f).

Since this application using the ACP of this invention employs the present methods for amplification of nucleic acid sequence previously discussed, the common descriptions between them are omitted in order to avoid the complexity of this specification leading to undue multiplicity.

Figure 2A:
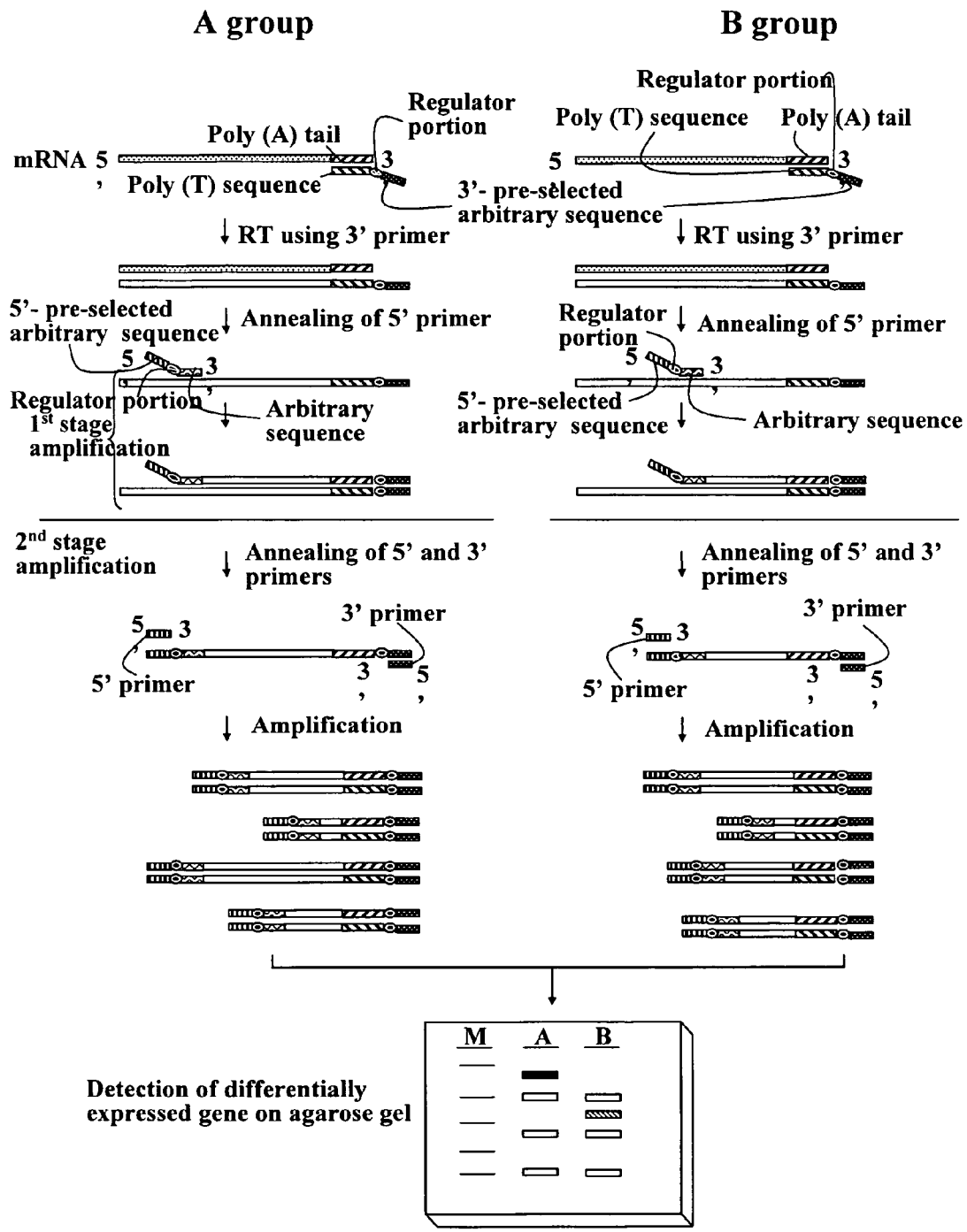
FIGS. 2A and 2B show schematic representations for identifying differentially expressed genes using the ACP of the present invention.

A schematic representation for identifying differentially expressed genes using novel ACP is illustrated in FIG. 2A.

In the present method, the nucleic acid sample representing a population of mRNA transcripts can be obtained from a wide variety of biological materials. In general, the first nucleic acid sample comprises mRNA expressed in a first cell and the second nucleic acid sample comprises mRNA expressed in a second cell. In particular, the first nucleic acid sample comprises mRNA expressed in a cell at a first developmental stage and the second nucleic acid sample comprises mRNA expressed in a cell at a second developmental stage. In addition, the first nucleic acid sample comprises mRNA expressed in a tumorigenic cell and the second nucleic acid sample comprises mRNA expressed in a normal cell.

Steps (e) and (f) of the subject application may occur in a single tube using the same reaction mixture except for primers, which means that steps (e) and (f) are separated only in time. It would be understood that the primers corresponding to the 5'-end portion could be added to the reaction mixture at the time of or after the second cDNA strand synthesis. In a preferred embodiment, the primers corresponding to the 5'-end portion are added to the reaction mixture right after step (e) is completed, followed by subsequent PCR amplification of second cDNA strands.

It would be also understood that the 5'-end portion sequences of the first and second ACPs used in steps (b) and (e), respectively, could be identical or different sequences; if they are identical, one primer corresponding to the sequence of 5'-end portion will be used in the step (f), whereas if they are different, two primers each corresponding to the sequence of each 5'-end portion of ACPs will be used in the step (f). In a preferred embodiment, the 5'-end portion sequences of the first and second ACPs used in steps (b) and (e) are different and thus, two primers each corresponding to the sequence of each 5'-end portion of ACPs are used in step (f).

Figure 2B:
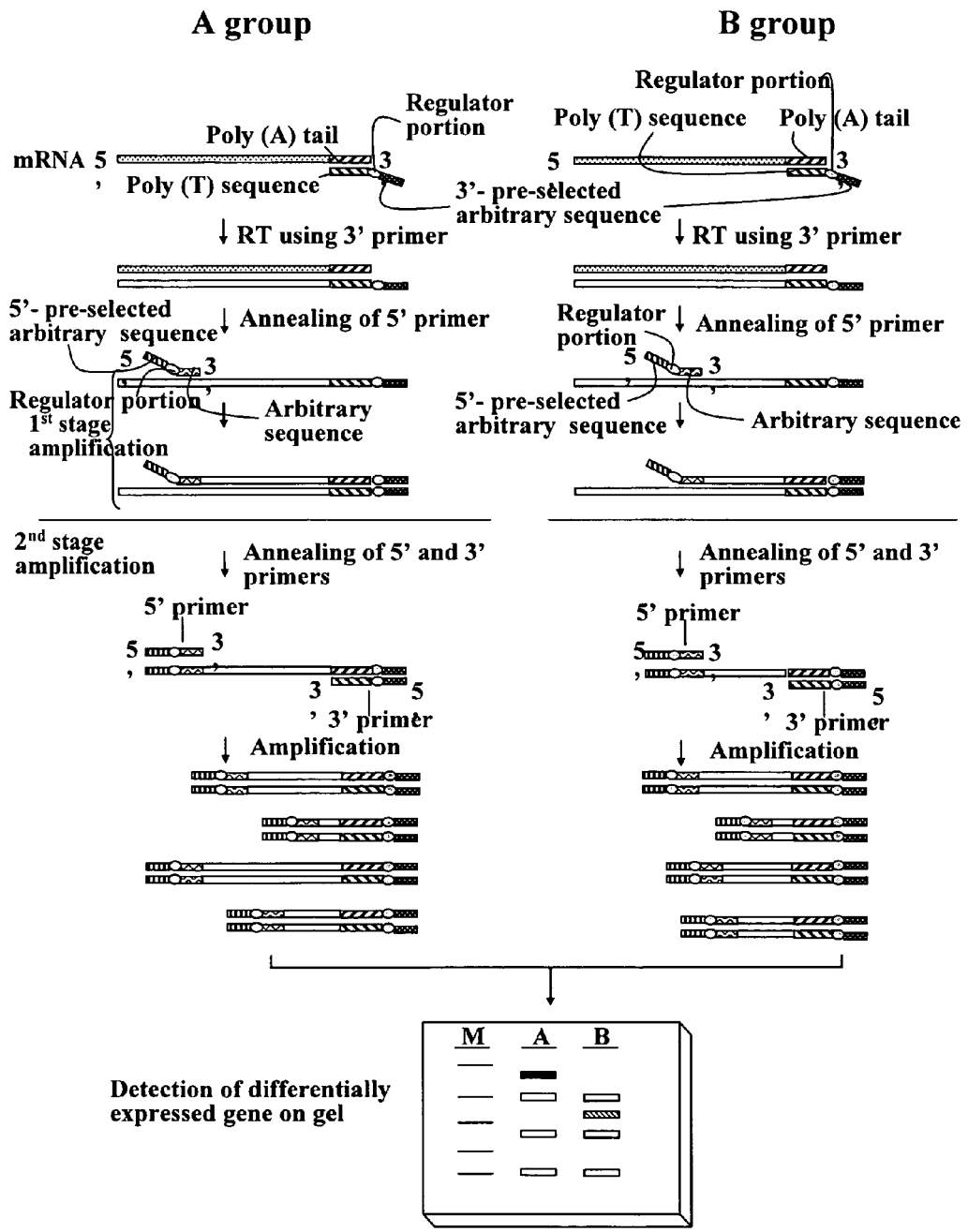

As an alternative process, in step (f) the complete sequences of the first and second ACPs used in steps (b) and (e), respectively, instead of the primers corresponding to the 5'-end portions of the ACPs, can be used as primers at the high stringent conditions for amplifying each second DNA strand obtained from step (e), wherein the 3'- and 5'-ends of the second DNA strands which are initially synthesized using the second ACP comprise the sequence of the first ACP and the complementary sequence of the second ACP, respectively, and also serve as perfect pairing sites to the first and second ACPs. In this view, this alternative process is preferred because there is no need to add the primers corresponding to the 5'-end portions of the ACPs to the reaction mixture at the time of or after first-stage PCR reaction. FIG. 2B illustrates a schematic representation for identifying differentially expressed genes by the alternative process stated above.

The method of the subject application for detecting differences in gene expression uses only a single cDNA synthesis primer (the first ACP) to react with mRNA, unlike conventional Differential Display PCR which requires multiple cDNA synthesis anchor primers. In the original differential display method outlined by Liang and Pardee in 1992, twelve anchor primers have been introduced. The anchor primers for example, having a sequence of T12 MN, where M is A, C, or G and N is A, C, G or T, produced twelve separate cDNA populations. Recently, modified anchor primers have been proposed by altering the number of nucleotides such as one or three instead of two at the 3'-end which can hybridize to a sequence that is immediately 5' to the poly A tail of mRNAs or by extending additional nucleotides at the 5'-end while retaining the Oligo (dT)9-12 MN tail resulting in at least 21 nucleotides in length (Villeponteau et al., 1996, Combates et al., 2000).

The subject invention concerns the embodiments of the ACP used in this method for the identification of differentially expressed genes, wherein the first ACP used in step (b) is represented by the following general formula (2): 5'-dXp-dYq-dTr-3' wherein dX is one of the four deoxyribonucleotides, A, C, G, or T; dY is a regulator portion comprising universal bases responsible for the main function of the ACP associated with alteration of annealing temperature during PCR; dT is a T deoxyribonucleotide; p, q, and r represent an integer, respectively; dXp represents the 5'-end portion and contains a pre-selected arbitrary nucleotide sequence; dYq contains at least 2 universal bases; dTr represents the 3'-end portion; the nucleotide sequence of the 3'-end portion should have lower Tm than that of the 5'-end portion. The formula (2) basically follows the rule of formula (1). The 3'-end portion of formula (2) consists of the sequences capable of annealing to the poly A tail of mRNA and serves as a cDNA synthesis primer for reverse transcription of mRNA.

In a preferred embodiment, the 3'-end portion of the first ACP used in step (b) contains at least 6 T nucleotides in length, which is considered a minimal requirement of length for primer annealing. More preferably, the 3'-end portion sequence is from 10 to 20 T nucleotides and can be up to 30 T nucleotides in length. Most preferably, the 3'-end portion sequence is about 15 T nucleotides in length. This primer is named dT15 annealing control primer (dT15-ACP). In a preferred embodiment, the first primer has a general formula of 5'-dX15-30-dY2-10-dT10-20-3', wherein dX represents a deoxyribonucleotide and comprises a pre-selected arbitrary nucleotide sequence not substantially complementary to the first and second populations of mRNAs; dY represents the regulator portion comprising 2-10 universal bases or non-discriminatory base analogs; and dT represents a contiguous deoxythymidine capable of annealing to the first site in the first and second populations of mRNAs.

In one embodiment, the 3'-end portion of the first ACP used in step (b) may contain at least one additional nucleotide at the 3'-end that can hybridize to an mRNA sequence which is immediately upstream of the polyA tail. The additional nucleotides at the 3' end of the first ACP may be up to 3 in length. For example, dT may further comprise 3'-V at its 3'-end; in which V is one selected from the group consisting of deoxyadenosine, deoxycytidine and deoxyguanosine. In addition, dT may further comprise 3'-NV at its 3'-end; in which V is one selected from the group consisting of deoxyadenosine, deoxycytidine and deoxyguanosine and N is one selected from the group consisting of deoxyadenosine, deoxythymidine, deoxycytidine and deoxyguanosine. Most preferably, the 3'-end portion sequence of the first ACP used in step (b) contains dT15 only.

In a preferred embodiment, the first entire ACP is about 40-45 nucleotides in length and comprises dT15 at the 3'-end portion, dX20-25 at the 5'-end portion and dY5 between the 3'- and 5'-end portions. The first entire ACP can be up to 100 nucleotides in length. The first primer is exemplified by SEQ ID NOs: 30, 39, 57 and 61-63.

The first ACP described herein is hybridized to the poly A tail of the mRNA, which is present on all mRNAs, except for a small minority of mRNA. The use of the first ACP used in this invention results in only one reaction and produces only one cDNA population, in contrast to at least 3 to 64 separate cDNA populations generated by the conventional anchor primers of Differential Display technique. This greatly increases the efficiency of the method by generating a substantially standard pool of single-stranded cDNA from each experimental mRNA population.

In the step (d), the standard pools of cDNAs synthesized by the first ACP should be purified and then quantitated by techniques well known to those of ordinary skill in the art such as spectrophotometry. This step is necessary to precisely control their inputs into the amplification step and then compare the final amplified products between two or more samples. Preferably, the amount of cDNA produced at this point in the method is measured. It is more preferred that this determination is made using ultraviolet spectroscopy, although any standard procedure known for quantifying cDNA known to those of ordinary skill in the art is acceptable for use for this purpose. When using the UV spectroscopy procedure, an absorbance of about 260 nm of UV light advantageously is used. By the measurement of cDNA quantity at this step, therefore, the cDNA quantity can be standardized between or among samples in the following amplification reaction.

After synthesis of the first cDNA strands using the first ACP, the second cDNA strands are synthesized using the second ACP primer under low stringent conditions, by at least one cycle comprising denaturing, annealing and primer extension, wherein the resultant first cDNA strands are used as templates.

The second ACP basically follows the rule of formula (1) and its 3'-end portion comprises a short arbitrary sequence, which preferably has lower Tm than that of the 5'-end portion. This primer is named an arbitrary annealing control primer (AR-ACP). In a preferred embodiment, the 3'-end portion of the second ACP can have from 8 to 15 nucleotides in length. Most preferably, the 3'-end portion of the second ACP contains about 10 nucleotides in length.

According to a preferred embodiment, the second ACP has the general formula of 5'-dX15-30-dY2-10-dZ8-15-3', wherein dX represents a deoxyribonucleotide and comprises a pre-selected arbitrary nucleotide sequence not substantially complementary to the first and second populations of the first cDNA strands; dY represents the regulator portion comprising 2-10 universal bases or non-discriminatory base analogs; dZ represents a hybridizing arbitrary nucleotide sequence capable of annealing to the second site in the first and second populations of DNA strands. More preferably, the entire second ACP is about 40-45 nucleotides in length comprising dZ10 at the 3'-end portion, dX20-25 at the 5'-end portion and dY5 between the 3'- and 5'-end portions. The second entire ACP can be up to 100 nucleotides in length. The second primer is exemplified by SEQ ID NOs: 1-9, 13-18 and 20-23.

The second ACP described herein is different from a so-called long arbitrary primer, as used in the known modified Differential Display technique. For example, the conventional long arbitrary primers as described by Villeponteau et al. (1996) and Diachenko et al. (1996), having at least 21 or 25 nucleotides in length, comprise of only arbitrary nucleotides in the entire sequences. These conventional long arbitrary primers will hybridize in a non-predictable way under the low annealing temperature (about 40° C.) which is required to achieve arbitrary priming in the early PCR cycle, such that it is impossible to design a representative set of primers rationally. Furthermore, many of the bands represent the same mRNA due to the "Stickiness" of long primers when used under such a low stringency.

The advantages of the present method for detecting differentially expressed genes are predominantly ascribed to the use of the second ACP. Since the second ACP is designed to limit the annealing of the second ACP to its 3'-end portion sequence, not to its 5'-end portion sequence, in association with annealing temperature, the resultant annealing will come out in a predictable way, such that it is possible to design a representative set of primers rationally. In addition, the use of the second ACP allows avoiding false positive problems caused by the "Stickiness" of the conventional long primers under low stringent conditions as used in the previous Differential Display technique.

The annealing temperature used for the synthesis of second DNA strands under low stringency conditions used in step (e) is preferably about between 40° C. to 65° C., more preferably, about between 45° C. and 55° C. and the most preferably, about 50° C. However, unlike Differential Display, which uses annealing temperatures between 35° C. and 45° C., the annealing temperature of low stringency conditions used in the subject application is relatively higher than those used in the known classical or enhanced Differential Display techniques with arbitrary primers.

Another unique and significant features of the subject application for detecting differentially expressed genes is to amplify only the initially synthesized second DNA strands by the subsequent amplification, wherein the 3'- and 5'-ends of the second DNA strands which have been initially synthesized using the second ACP comprise the complementary sequence of the first ACP and the sequence of the second ACP, respectively and thus, the entire sequences of the first and second ACPs, or only their 5'-end portion sequences of the first and second ACPs, are used as 3' and 5' primer sequences for the amplification of the second DNA strands.

Since the ACP in the subject application leads to the amplification of specific products, it can be possible to fundamentally eliminate the cause of major bottleneck problems, such as false products and poor reproducibility, which result from non-specific annealing of the conventional arbitrary and dT primers to first and second DNA strands as well as to amplified products during PCR in the known Differential Display methods.

In a preferred embodiment, the synthesis of second DNA strands in step (e) is carried out by at least 1 cycle of amplification under low stringent conditions to achieve arbitrary priming, and through the subsequent cycles, the amplification is processed more effectively for the amplification of the resultant second DNA strands under high stringent conditions used in step (f). Most preferably, the synthesis of second DNA strands in step (e) is carried out by one cycle of amplification under low stringent conditions.

In a preferred embodiment, the amplification of the resultant second DNA strands synthesized by the step (e) is carried out under high stringent conditions using the complete sequences of the first and second ACPs used in steps (b) and (e), respectively, as primer sequences, wherein the 3'- and 5'-ends of the resultant second DNA strands provide perfect pairing sites to the first and second ACPs. However, it is interesting that the first and second ACPs are not involved in any other annealing to the template nucleic acid, except the annealing and extension of the 3'- and 5'-ends of the second DNA strands as a reaction unit at such a high stringent condition because their 3'-end portions require relatively low annealing temperature and the high stringent conditions do not allow them to anneal to any site of the template, except the 3'- and 5'-ends of the second DNA strands. Consequently, owing to this function of ACP, which is capable of selectively annealing to the template in associated with annealing temperature, the amplified products can be free from the problems of the high false positive rate, poor reproducibility and possible under-representation of minor mRNA fractions in the analysis which are the main problems of the known Differential Display. In this view, there is a significant difference between this subject method and the conventional Differential Display methods despite the fact that they are in common to use the same primers for high stringent conditions as well as for low stringent conditions.

In a preferred embodiment, the annealing temperature of the amplification for high stringent conditions used in step (f) is preferably about between 55° C. and 72° C. Most preferably, the annealing temperature used for the high stringent conditions is about 65-68° C.

In a preferred embodiment, the amplification under high stringent conditions used step (f) is carried out by at least 10 cycles and up to 50 cycles to amplify the resultant second DNA strands synthesized by step (e) during PCR. Most preferably, the PCR amplification is carried out by 40-45 cycles.

The second-strand cDNA is preferably synthesized by PCR, more preferably, hot start PCR method in which the procedure is to set up the complete reactions without the DNA polymerase and incubate the tubes in the thermal cycler to complete the initial denaturation step at >90° C. Then, while holding the tubes at a temperature above 70° C., the appropriate amount of DNA polymerase can be pipetted into the reaction. In a preferred embodiment, the addition of the primers for the second-stage amplification into the reaction mixture after the complete reaction of the second-strand cDNA synthesis is also carried out under denaturation temperature such as >90° C. Then, while holding the tubes at a temperature about 90° C., the appropriate amount of the primers for the second-stage amplification can be pipetted into the reaction.

An example of the second DNA strand synthesis and the subsequent amplification of the resultant second DNA strands in a single tube using the pre-selected arbitrary sequence of the 5'-end portions of the first and second ACPs is conducted under the following conditions: the second DNA strands are synthesized under low stringent conditions by one cycle of the first-stage amplification comprising annealing, extending and denaturing reaction; the reaction mixture containing the first-strand cDNA, PCR reaction buffer (e.g., available from Roche), dNTP, and the second ACP is pre-heated at about 94° C., while holding the tube containing the reaction mixture at about 94° C., Taq polymerase (e.g., available from Roche) is added into the reaction mixture; the PCR reactions are as follows: one cycle of 94° C. for 1 min, 50° C. for 3 min, and 72° C. for 1 min; followed by denaturing the amplification product at 94° C.; after the complete reaction of the second DNA strand synthesis in step (e), 5' pre-selected arbitrary primer and 3'pre-selected arbitrary primer are added to the reaction mixture and then the second stage amplification is conducted as follows: 40 cycles of 94° C. for 40 sec, 68° C. for 40 sec, and 72° C. for 40 sec; followed by a 5 min final extension at 72° C.

An alternative example of the second DNA strand synthesis and the subsequent amplification of the resultant second DNA strands in a single tube using the complete sequences of the first and second ACPs used in steps (b) and (e), respectively, instead of the pre-selected arbitrary sequences of the 5'-end portions of the first and second ACPs, is conducted under the following conditions: the second DNA strands are synthesized under low stringent conditions by one cycle of the first-stage amplification comprising annealing, extending and denaturing reaction; the reaction mixture containing the first-strand cDNA, PCR reaction buffer (e.g., available from Roche), dNTP, the first ACP (dT15-ACP), and the second ACP (AR-ACP) is pre-heated at about 94° C., while holding the tube containing the reaction mixture at about 94° C., Taq polymerase (e.g., available from Roche) is added into the reaction mixture; the PCR reactions are as follows: one cycle of 94° C. for 1 min, 50° C. for 3 min, and 72° C. for 1 min; followed by the second-stage PCR amplification comprising annealing, extending and denaturing reaction; the PCR reactions are as follows: 40 cycles of 94° C. for 40 sec, 65° C. for 40 sec, and 72° C. for 40 sec; followed by a 5 min final extension at 72° C.

It should be noted that a proper concentration of arbitrary ACP (the second ACP) is used to synthesize the second-strand cDNAs by one cycle of the first-stage amplification. If the amount of the second ACP used in the step (e) is too low, the resultant amplified products are not reproducible. In contrast, the excess amount of the second ACP used in the step (e) generates backgrounds such as DNA smear during PCR. In a preferred embodiment, the concentration of the second ACP used in the step (e) is about between 0.1 μM and 1.0 μM. Most preferably, the concentration of the second ACP as well as the first ACP is about 0.2 μM. In a preferred embodiment, the concentration of the primers used in the step (f) is about between 0.1 μM and 1 μM, most preferably, about 0.4 μM.

Another significant feature of the subject application to the identification of differences in gene expression is the use of high annealing temperature in a method. High annealing temperature used in step (f) increases the specificity of primer annealing during PCR, which results in eliminating false positive products completely and increasing reproducibility. Freedom from false positives which is one major bottleneck remaining for the previous Differential Display technique is especially important in the screening step for the verification of the cDNA fragments identified by Differential Display.

The step of comparing the presence or level of amplification products obtained from step (f) may be performed in accordance with various methods known in the art. In a preferred embodiment, each of the first and second populations of amplification products of step (f) are resolved by electrophoresis to identify differentially expressed mRNAs. More preferably, the resultant PCR cDNA fragments are detected on an ethidium bromide-stained agarose gel. Another prominent feature of this subject application is the use of ethidium bromide-stained agarose gel to identify differentially expressed mRNAs. In general, the conventional Differential Display methods use radioactive detection techniques using denaturing polyacrylamide gels. However, according to the present method, the significant amount of the amplified cDNA fragments obtained through two stage amplifications allows to use an ethidium bromide-stained agarose gel to detect the amplified cDNAs, which results in increasing the speed and avoiding the use of radioactivity.

Alternatively, the resulting cDNA fragments can be also detected on a denaturing polyacrylamide gel by autoradiography or non-radioactive detection methods such as silver staining (Gottschlich et al., 1997; Kociok et al., 1998), the use of fluorescent-labelled oligonucleotides (Bauer et al. 1993; Ito et al. 1994; Luehrsen et al., 1997; Smith et al., 1997), and the use of biotinylated primers (Korn et al., 1992; Tagle et al., 1993; Rosok et al., 1996).

In another embodiment, it might be useful for diagnostic purposes to use an automatic system such as an automatic DNA sequencer together with any distinct labeling of the ACPs to detect or analyze the amplified products (Bauer, et al., 1993).

Considering the features of ACP in this subject application, the present method for detecting and cloning differentially expressed genes differs fundamentally from the previous Differential Display techniques as described above.

In conclusion, the use of the ACP in this method makes it possible to allow the amplification of only second DNA strands and the use of the sufficient amount of starting materials as well as the high concentration of dNTP, resulting in the following benefits: a) increasing primer annealing specificity, b) eliminating the problem of false positives which requires the subsequent labor-intensive work to verify true positives, c) improving reliability and reproducibility, d) detecting rare mRNAs, e) generating long-distance PCR products ranging in size from 150 bp to 2.0 kb, f) allowing the use of ethidium bromide-stained agarose gel to detect products, g) increasing the speed of analysis, h) particularly, not requiring well-trained hands to conduct this method, and i) allowing the rational design of a representative set of primers.

In further aspect of this invention, there is provided a kit for detecting DNA complementary to differentially expressed mRNA, which comprises the annealing control primer or annealing control primer set described above (the first and second primer). According to one embodiment of this invention, these kits further comprises a primer or a primer pair having a nucleotide sequence corresponding to the 5'-end portion of the ACPs; in case that the 5'-end portion comprises universal primer sequence, it is more preferred that the kit comprises the universal primers. The present kits may optionally include the reagents required for performing PCR reactions such as buffers, DNA polymerase, DNA polymerase cofactors, and deoxyribonucleotide-5'-triphosphates. Optionally, the kits may also include various polynucleotide molecules, reverse transcriptase, various buffers and reagents, and antibodies that inhibit DNA polymerase activity. The kits may also include reagents necessary for performing positive and negative control reactions. Optimal amounts of reagents to be used in a given reaction can be readily determined by the skilled artisan having the benefit of the current disclosure. The kits, typically, are adapted to contain in separate packaging or compartments the constituents afore-described.

IV. Application to Rapid Amplification of cDNA Ends (RACE)

This application using the ACP of the subject invention can provide an improved method for rapidly amplifying cDNA ends, so called RACE technologies. To be specific, the ACP of the subject application is adapted to the RACE technologies related to either of 3'- and 5'-end, and eliminates the background problems resulting from the primers used in the conventional RACE technologies.

In still further aspect of this invention, there is provided a method for rapidly amplifying a target cDNA fragment comprising a cDNA region corresponding to the 3'-end region of an mRNA, wherein the method comprises reverse transcribing said mRNA and performing an amplification reaction using primers, characterized in that at least one primer is derived from any one of ACPs described above. Preferably, the primer according to the structure of ACP is one having at its 3'-end portion a gene-specific hybridizing nucleotide sequence substantially complementary to a site in cDNA generated from reverse transcription and/or one having at its 3'-end portion a hybridizing nucleotide sequence substantially complementary to poly A tails of the mRNAs.

In a specific embodiment of this invention, there is provided the method using two stage amplifications, which comprises:

(a) contacting mRNAs with a first primer of any one of the ACP described above, in which the 3'-end portion of the primer comprises a hybridizing nucleotide sequence substantially complementary to poly A tails of the mRNAs to hybridize therewith, under conditions sufficient for template driven enzymatic deoxyribonucleic acid synthesis to occur;

(b) reverse transcribing the mRNAs to which the first primer hybridizes to produce a population of first cDNA strands that are complementary to the mRNAs to which the first primer hybridizes;

(c) performing a first-stage amplification of the first cDNA strands at a first annealing temperature comprising at least one cycle of primer annealing, primer extending and denaturing, using a second primer of any one of the ACP described above having at its 3'-end portion a gene-specific hybridizing nucleotide sequence substantially complementary to a site in one of the first cDNA strands to hybridize therewith, under conditions in which the second primer anneals to a gene-specific site on one of the first cDNA strands, whereby a gene-specific second cDNA strand is generated; and (d) performing a second-stage amplification of the gene-specific second cDNA strand generated from step (c) at a second annealing temperature, which is high stringent conditions, comprising at least two cycles of primer annealing, primer extending and denaturing, using the same first and second primers as used in steps (a) and (c), respectively, or a primer pair each comprising a pre-selected arbitrary nucleotide sequence corresponding to each 5'-end portion of the first and second primers used in steps (a) and (c), respectively, under conditions in which each primer anneals to the 3'- and 5'-end sequences of a gene-specific second cDNA strand, respectively, whereby an amplification product of a gene-specific cDNA strand is generated.

Since this application using the ACP of this invention employs the present methods for amplification of nucleic acid sequence previously discussed, the common descriptions between them are omitted in order to avoid the complexity of this specification leading to undue multiplicity.

Figure 3:
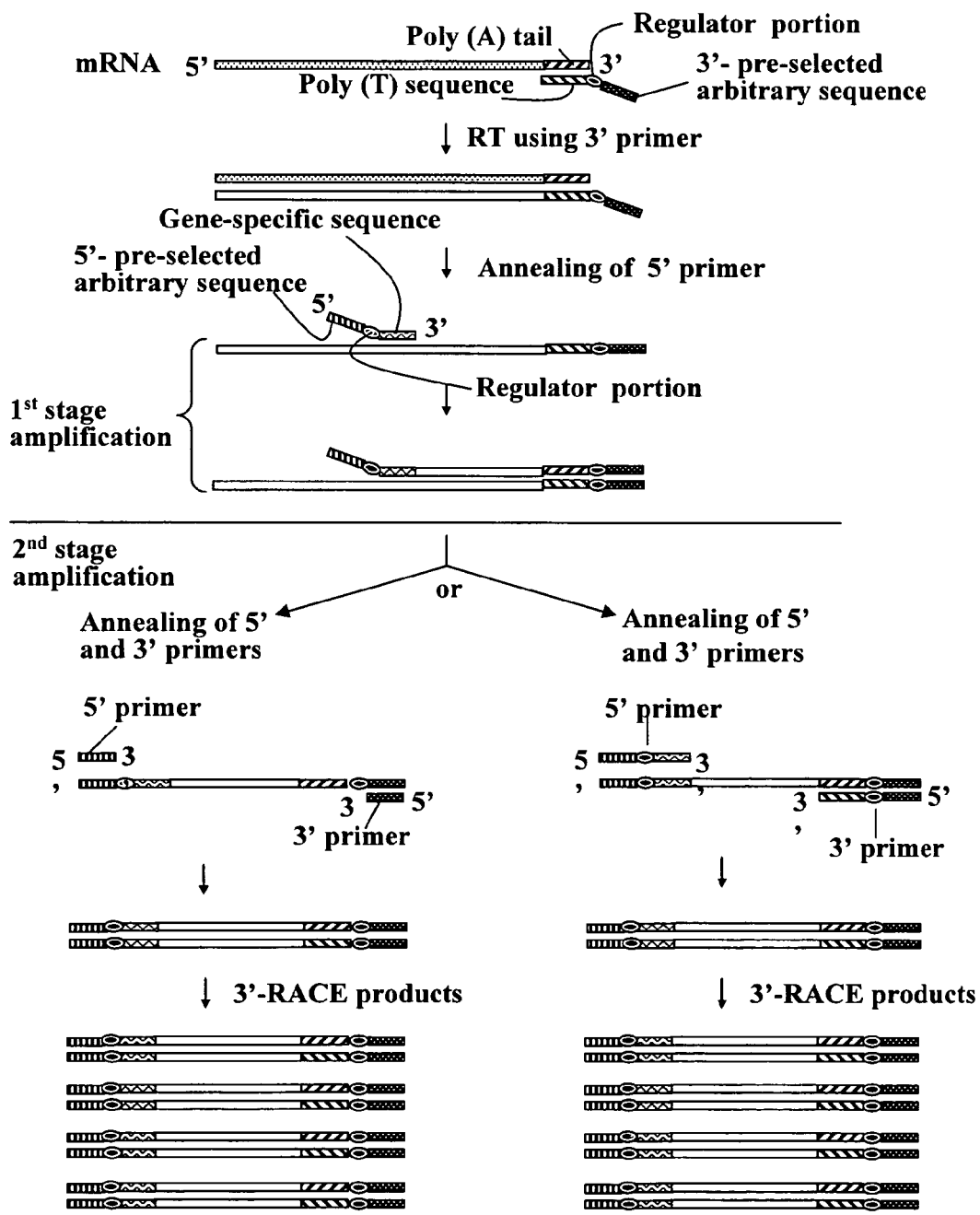
FIG. 3 shows a schematic representation for amplifying a target cDNA fragment comprising 3'-end region corresponding to the 3'-end of mRNA using the ACP of the present invention.

A schematic representation for amplifying a target cDNA fragment comprising 3'-end region corresponding to the 3'-end of mRNA using novel ACP system, called as ACP-based 3' RACE, is illustrated in FIG. 3.

Steps (c) and (d) of the subject application may occur in a single tube using the same reaction mixture except for primers, which means that steps (c) and (d) are separated only in time. It would be understood that the primers corresponding to the 5'-end portion could be added to the reaction mixture at the time of or after second cDNA strand synthesis. In a preferred embodiment, the primers corresponding to the 5'-end portion are added to the reaction mixture right after step (2) is completed, followed by subsequent amplification of second cDNA strands.

As an alternative process, in step (d) the complete sequences of the first and second ACPs, instead of the primers corresponding to the 5'-end portions of the first and second ACPs, can be used as 3' and 5' primers for amplifying the second-strand cDNA obtained from step (c), wherein the 3'- and 5'-ends of the second-strand cDNA which are initially synthesized using the second ACP comprise the complementary sequence of the first ACP and the sequence of the second ACP, respectively, and also serve as perfect pairing sites to the first and second ACPs. FIG. 3 also illustrates a schematic representation for amplifying a target cDNA fragment comprising 3'-end region corresponding to the 3'-end of mRNA by the alternative process stated above.

One of significant features of the present invention for 3'-RACE is that the first ACP comprising nucleotide sequence substantially complementary to poly A tail of mRNA is used as a cDNA synthesis primer and then the resultant cDNAs are directly used as templates for subsequent amplification without any additional purification steps to remove the cDNA synthesis primer.

The annealing of the first ACP to the templates will be interrupted during subsequent by the effect of the regulator portion on the 3'- and 5'-end portions of the ACP under relatively high stringent conditions as described in the principle of ACP. As a result, the subject application to 3'-RACE simplifies the conventional RACE methods by reducing the step of purification and also, the ACP used in the subject application does not involve the background problems because the annealing of the 3'-end portion is specified by the presence of the regulator portion positioned between the 3'- and 5'-end portions in the ACPs, whereas the conventional cDNA synthesis primers such as Oligo-dT primers for 3'-RACE generate backgrounds during PCR, which is non-specific products. According to a preferred embodiment, the formula of the first ACP for the cDNA synthesis may be identical to the formula (2).

When a gene-specific primer is used as 5' primer, the first amplification of a target cDNA fragment containing a 3'-end sequence in step (c) is carried out in accordance with conventional PCR methods as known in the art. The term "gene-specific" in reference sequence used herein refers to a partial sequence of a specific gene or complement thereof that has been generally known or available to one skilled in the art. Therefore, the gene-specific primer means one comprising the gene-specific sequence.

The generated second cDNA strand is amplified by the second-stage amplification which is used in the application of the present invention for amplifying a target nucleic acid sequence above. Since the ACP described in this invention can generate stable Tm in a primer and also tolerate "primer search parameters" for primer design such as primer length, annealing temperature, GC content, and PCR product length, it is useful when the gene-specific primer sequences have low Tm or are too sensitive to such parameters to generate specific products.

In another aspect of this invention, there is provided a method for rapidly amplifying a target DNA fragment comprising a cDNA region corresponding to the 5'-end region of an mRNA, wherein the method comprises reverse transcribing the mRNA and performing an amplification reaction using primers, characterized in that at least one primer is derived from any one of ACPs described above. Preferably, the primer according to the structure of ACP is one having at its 3'-end portion a gene-specific hybridizing nucleotide sequence substantially complementary to a site in cDNA generated from reverse transcription.

In a specific embodiment of this invention, there is provided the method using two stage amplifications, which comprises:

(a) contacting mRNAs with an oligonucleotide dT primer or random primer as a cDNA synthesis primer under conditions sufficient for template driven enzymatic deoxyribonucleic acid synthesis to occur, in which the cDNA synthesis primer comprises a hybridizing nucleotide sequence substantially complementary to a region of an mRNA to hybridize therewith;

(b) reverse transcribing the mRNAs, using a reverse transcriptase, to which the cDNA synthesis primer hybridizes to produce a population of first cDNA strands that are complementary to the mRNAs to which the cDNA synthesis primer hybridizes, whereby mRNA-cDNA intermediates are generated;

(c) permitting cytosine residues to be tailed at the 3'-ends of the first cDNA strands in the form of the mRNA-cDNA intermediates by the terminal transferase reaction of reverse transcriptase;

(d) contacting the cytosine tails at the 3'-ends of the first cDNA strands generated from step (c) with an oligonucleotide which comprises a 3'-end portion and a 5'-end portion separated by a group of universal base or non-discriminatory base analog, wherein the 3'-end portion comprises at least three guanine residues at its 3'-end to hybridize with the cytosine tails at the 3'-ends of the first cDNA strands and the 5'-end portion comprises a pre-selected arbitrary nucleotide sequence, under conditions in which the 3-end portion of the oligonucleotide is hybridized to the cytosine tails;

(e) extending the tailed 3'-ends of the first cDNA strands to generate an additional sequence complementary to the oligonucleotide using reverse transcriptase, in which the oligonucleotide serves as a template in the extension reaction, whereby full-length first cDNA strands are extended;

(f) performing a first-stage amplification of the full-length first cDNA strands obtained from step (e) at a first annealing temperature comprising (i) and (ii) as follows:

(i) at least one cycle of primer annealing, primer extending and denaturing using a first primer comprising a nucleotide sequence substantially complementary to the 3'-end sequences of the full-length first cDNA strands under conditions in which the first primer anneals to the full-length first cDNA strands, under conditions in which the first primer anneals to the 3'-ends of the full-length first cDNA strands, whereby full-length second cDNA strands are generated;

(ii) at least one cycle of primer annealing, primer extending and denaturing using a second primer of any one of claims 1-25 having at its 3'-end portion a gene-specific hybridizing sequence substantially complementary to a region on one of the full-length second cDNA strands to hybridize therewith, under conditions in which the second primer anneals to a gene-specific site on one of the full-length second cDNA strands, whereby a gene-specific cDNA strand is generated; and (g) performing a second-stage amplification of the gene-specific cDNA strand at a second annealing temperature, which is high stringent conditions, comprising at least two cycles of primer annealing, primer extending and denaturing, using the same first and second primers as used in steps (f)-(i) and (f)-(ii), respectively, or a primer pair each comprising a nucleotide sequence corresponding to each 5'-end portion of the first and second primers as used in steps (f)-(i) and (f)-(ii), respectively, under conditions in which each primer anneals to the 3'- and 5'-end sequences of a gene-specific cDNA strand, respectively, whereby an amplification product of a gene-specific cDNA strand is generated.

Figure 4A:
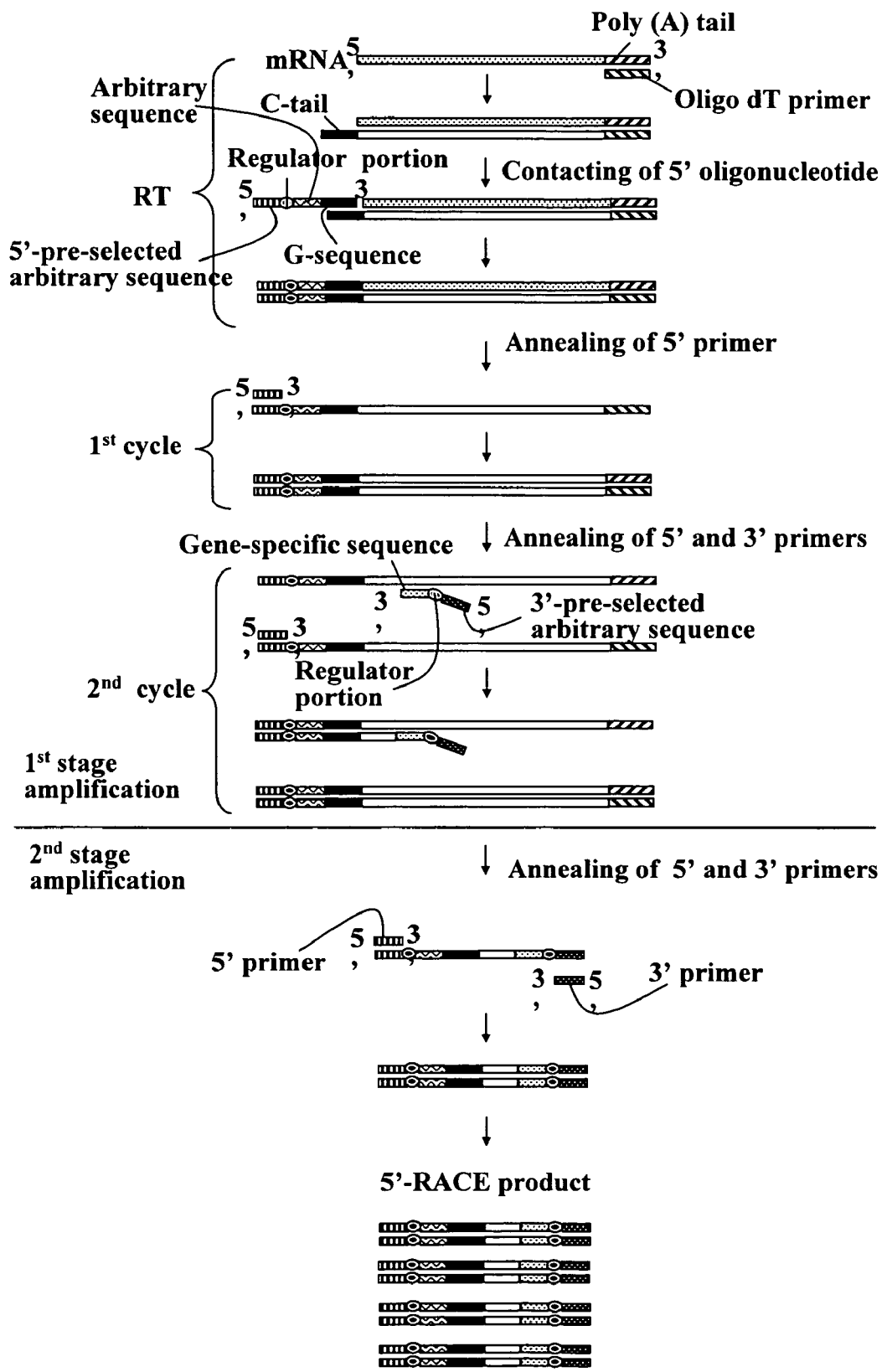
FIGS. 4A and 4B show schematic representations for amplifying a target cDNA fragment comprising 5'-end region corresponding to the 5'-end of mRNA using the ACP of the present invention. The Oligo dT (4A) or random primer (4B) is used as a first-strand cDNA synthesis primer.
Figure 4B:
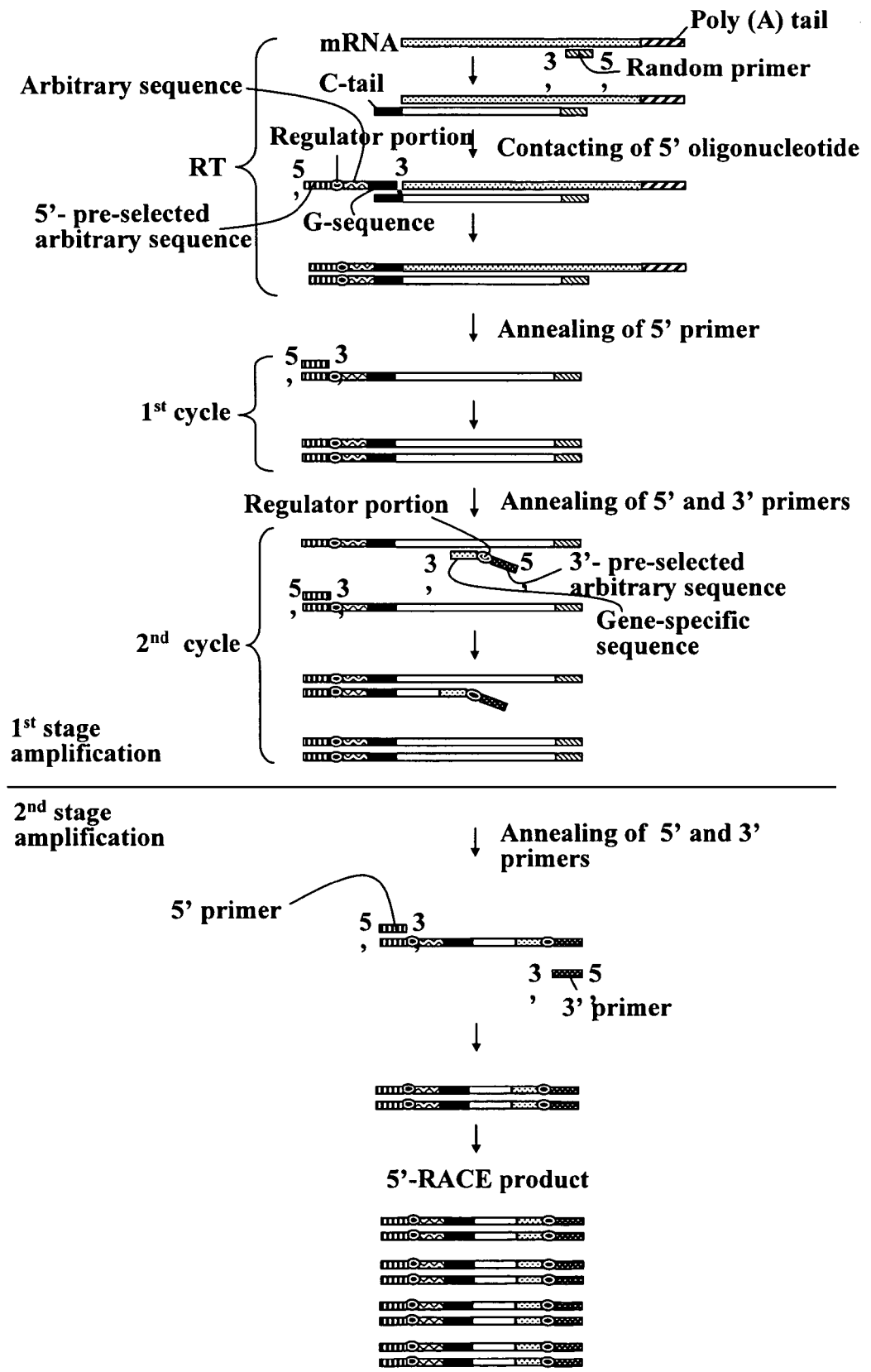

The schematic representations for amplifying a target cDNA fragment comprising 5'-end region corresponding to the 5'-end of mRNA using novel ACP system, called as ACP-based 5' RACE, is illustrated in FIG. 4A (using oligonucleotide dT primer) and 4B (using random primer).

The descriptions of the oligonucleotide dT primer used in step (a) is identical to those used in the present method for amplification of a target nucleic acid sequence from an mRNA. Alternatively, when the size of a target mRNA is so large that the reverse transcriptase falls off before reaching the 5' complete sequences, the random primer is used as cDNA synthesis primer.

According to a preferred embodiment, the step (c), permitting cytosine residues to be tailed is performed in the presence of manganese ion.

Steps (f) and (g) of the subject application may occur in a single tube using the same reaction mixture except for primers, which means that steps (f) and (g) are separated only in time. It would be understood that the primer(s) used in each step (f) and (g) can be added to the reaction mixture at the time of or after each step. In a preferred embodiment, the primer(s) is(are) added to the reaction mixture right after each step is completed, followed by subsequent PCR amplification of second cDNA strands.

When a gene-specific primer is used as 5' primer, the amplification of a target cDNA fragment containing a 5'-end sequence in step (f) is carried out under high stringent conditions in accordance with conventional PCR methods as known in the art.

In a preferred embodiment, a target cDNA fragment containing a 5'-end sequence in step (f) is amplified using a second ACP comprising a gene-specific sequence at the 3'-end portion, by two stage PCR amplifications which are used in the application of the present invention for amplifying a target nucleic acid sequence above. Since the ACP described in this invention can generate stable Tm in a primer and also tolerate "primer search parameters" such as primer design, comprising primer length, annealing temperature, GC content, and PCR product length, it is particularly useful when the gene-specific primer sequences have low Tm or are too sensitive to such parameters to generate specific products. The formula of the second ACP is identical to the formula (1) in which the 3'-end portion contains a gene-specific sequence.

The oligonucleotide for the step (d) is similar to CapFinder primer (Chenchik et al., 1998; Chenchik et al. U.S. Pat. Nos. 5,962,271 and 5,962,272) in the senses both of them comprise at least three guanine residues at its 3'-end and use them as a template switching primer for the 3'-end extension of the first cDNA strand by reverse transcriptase, whereas they are clearly different from each other in terms of the function of a switch in controlling primer annealing to a template nucleic acid in associated with annealing temperature during PCR. CapFinder primer does not comprise universal base residue group which is responsible for regulating primer annealing in ACP, so that the CapFinder PCR method for 5'-RACE (Chenchik et al., 1998) can not be free from a high background such as DNA spear arising from contamination of the primers such as the CapFinder and Oligo-dT primers used in cDNA synthesis during PCR. On the other hand, the universal base residue group of the first ACP plays a key role in regulating primer annealing, so that the subject method does not provide any cause for the background problems during subsequent PCR amplification; this is a key feature of the ACP application to 5'-RACE.

Furthermore, when the ACP of the present invention is used in 5'-RACE technology, it is unnecessary to conduct the process of physical separation such as a solid-phase cDNA synthesis and procedures which has been introduced as an alternative method to remove all contaminants used in cDNA synthesis (Schramm et al., 2000).

In a preferred embodiment, the oligonucleotide to form a base-pair(s) with the cytosine tail for 5'-RACE which has a similar structure to ACP, wherein the oligonucleotide is represented by the following general formula (3): 5'-dX15-30-dY2-10-dZ1-10-G3-5-3', in which dX represents a deoxyribonucleotide and comprises a pre-selected arbitrary sequence; dY represents a regulatory portion comprising 2-10 universal bases or non-discriminatory base analogs; dZ represents a deoxyribonucleotide and comprises a pre-selected arbitrary sequence; and G3-5 represents three to five guanines.

Most preferably, the 3'-end portion sequence dZ is about 2-3 nucleotides in length. Further, in one embodiment, the 5'-end portion dX can include a sequence that is recognized by a restriction endonuclease.

The G3-5 may be three to five riboguanines or deoxyguanines, or a combination of riboguanine and deoxyriboguanine. In more preferred embodiment, the G3-5 comprises two riboguanines and one deoxyriboguanine (r(G)-2-d(G)-3'), most preferably, three riboguanines.

When the gene-specific primer in step (f) is used as 3' primer for 5'-RACE, a target cDNA fragment containing a 5'-end sequence is amplified under high stringency conditions by conventional PCR methods as known in the art.

In a preferred embodiment, a target cDNA fragment containing a 5'-end sequence is amplified using a second ACP which comprises a gene-specific sequence at the 3'-end portion, by two stage PCR amplifications which is conducted in the application for amplifying a target nucleic acid sequence in the present invention. Since the ACP described in this invention can provide stable Tm in a primer and also tolerate "primer search parameters" for primer design such as primer length, annealing temperature, GC content, and PCR product length, it is useful when the gene-specific primer sequences have low Tm or are too sensitive to such parameters to generate specific products. The formula of the second ACP is identical to the formula (1) in which the 3'-end portion contains a gene-specific sequence.

The use of ACP in RACE technology significantly simplifies and improves the conventional RACE technologies with regard to the amplification of cDNA ends as described above. The vital feature of the subject method is to be free from the background problems arising from the primers used in conventional RACE methods. Consequently this method described herein can be more effective, easier, less labor-intensive, and more reproducible than conventional RACE methods.

In still another aspect of this invention, there is provided a kit for rapidly amplifying a target cDNA fragment comprising 3'-end region of mRNA, which comprises the annealing control primer or annealing control primer set described previously (including the first and second primer). According to one embodiment of this invention, these kits further comprises a primer or a primer pair having a nucleotide sequence corresponding to the 5'-end portion of the ACPs; in case that the 5'-end portion comprises universal primer sequence, it is more preferred that the kit comprises the universal primers. The present kits may optionally include the reagents required for performing PCR reactions such as buffers, DNA polymerase, DNA polymerase cofactors, and deoxyribonucleotide-5'-triphosphates. Optionally, the kits may also include various polynucleotide molecules, reverse transcriptase, various buffers and reagents, and antibodies that inhibit DNA polymerase activity. The kits may also include reagents necessary for performing positive and negative control reactions. Optimal amounts of reagents to be used in a given reaction can be readily determined by the skilled artisan having the benefit of the current disclosure. The kits, typically, are adapted to contain in separate packaging or compartments the constituents afore-described.

In further aspect of this invention, there is provided a kit for rapidly amplifying a target cDNA fragment comprising 5'-end region of mRNA, which comprises the annealing control primer or annealing control primer set described above (including the oligonucleotide dT primer and random primer for cDNA synthesis, the oligonucleotide to form a base-pair(s) with the cytosine tail, the first primer and the second primer). According to one embodiment of this invention, these kits further comprises a primer pair each comprising a nucleotide sequence corresponding to each 5'-end portion of the first and second primers as used in steps (f)-(i) and (f)-(ii); in case that the 5'-end portion comprises universal primer sequence, it is more preferred that the kit comprises the universal primers.

V. Application to Amplifying Full-Length cDNA

In further aspect of this invention, there is provided a method for amplifying a population of full-length double-stranded cDNAs complementary to mRNAs, wherein the method comprises reverse transcribing the mRNA and performing an amplification reaction using primers, characterized in that at least one primer is derived from any one of ACP described above. Preferably, the primer having the structure of ACP is one having a hybridizing nucleotide sequence substantially complementary to poly A tails of mRNAs.

In a specific embodiment of this invention, there is provided the method comprises:

(a) contacting the mRNAs with a first primer of any one of ACP described above, in which the 3'-end portion of the first primer has a hybridizing nucleotide sequence substantially complementary to poly A tails of the mRNAs to hybridize therewith, under conditions sufficient for template driven enzymatic deoxyribonucleic acid synthesis to occur;

(b) reverse transcribing the mRNAs, using a reverse transcriptase, to which the first primer hybridizes to produce the population of first cDNA strands that are complementary to the mRNAs to which the primer hybridizes, whereby mRNA-cDNA intermediates are generated;

(c) permitting cytosine residues to be tailed at the 3'-ends of the first cDNA strands in the form of the mRNA-cDNA intermediates by the terminal transferase reaction of reverse transcriptase;

(d) contacting the cytosine tails at the 3'-ends of the first cDNA strands generated from step (c) with an oligonucleotide which comprises a 3'-end portion and a 5'-end portion separated by a group of universal base or non-discriminatory base analog, wherein the 3'-end portion comprises at least three guanine residues at its 3'-end to hybridize with the cytosine tails at the 3'-ends of the first cDNA strands and the 5'-end portion comprises a pre-selected arbitrary nucleotide sequence, under conditions in which the 3-end portion of the oligonucleotide is hybridized to the cytosine tails;

(e) extending the tailed 3'-ends of the first cDNA strands to generate an additional sequence complementary to the oligonucleotide using reverse transcriptase, in which the oligonucleotide serves as a template in the extension reaction, whereby full-length first cDNA strands are extended; and (f) performing an amplification of the full-length first cDNA strands generated from step (e) comprising at least two cycles of primer annealing, primer extending and denaturing, using a primer pair each comprising a nucleotide sequence corresponding to the same first primer and oligonucleotide as used in steps (a) and (d), respectively, or a primer pair each comprising a nucleotide sequence corresponding to each 5'-end portion of the first primer and oligonucleotide used in steps (a) and (d), respectively, under conditions in which each primer anneals to the 3'- and 5'-end sequences of the full-length first cDNA strands, respectively, whereby amplification products of full-length cDNA strands complementary to the mRNAs are generated.

Since this application using the ACP of this invention employs in principle the present methods for amplification of nucleic acid sequence previously discussed, the common descriptions between them are omitted in order to avoid the complexity of this specification leading to undue multiplicity. In addition, the ACP described above in which the 3'-end portion has a hybridizing nucleotide sequence substantially complementary to poly A tails is in principle identical to the first primer for the present method for 3'-RACE. Furthermore, the oligonucleotide to form a base-pair(s) with the cytosine tail and the primer pair used in the step (f) are in principle identical to those for 5'-RACE of this invention discussed above.

Figure 5:
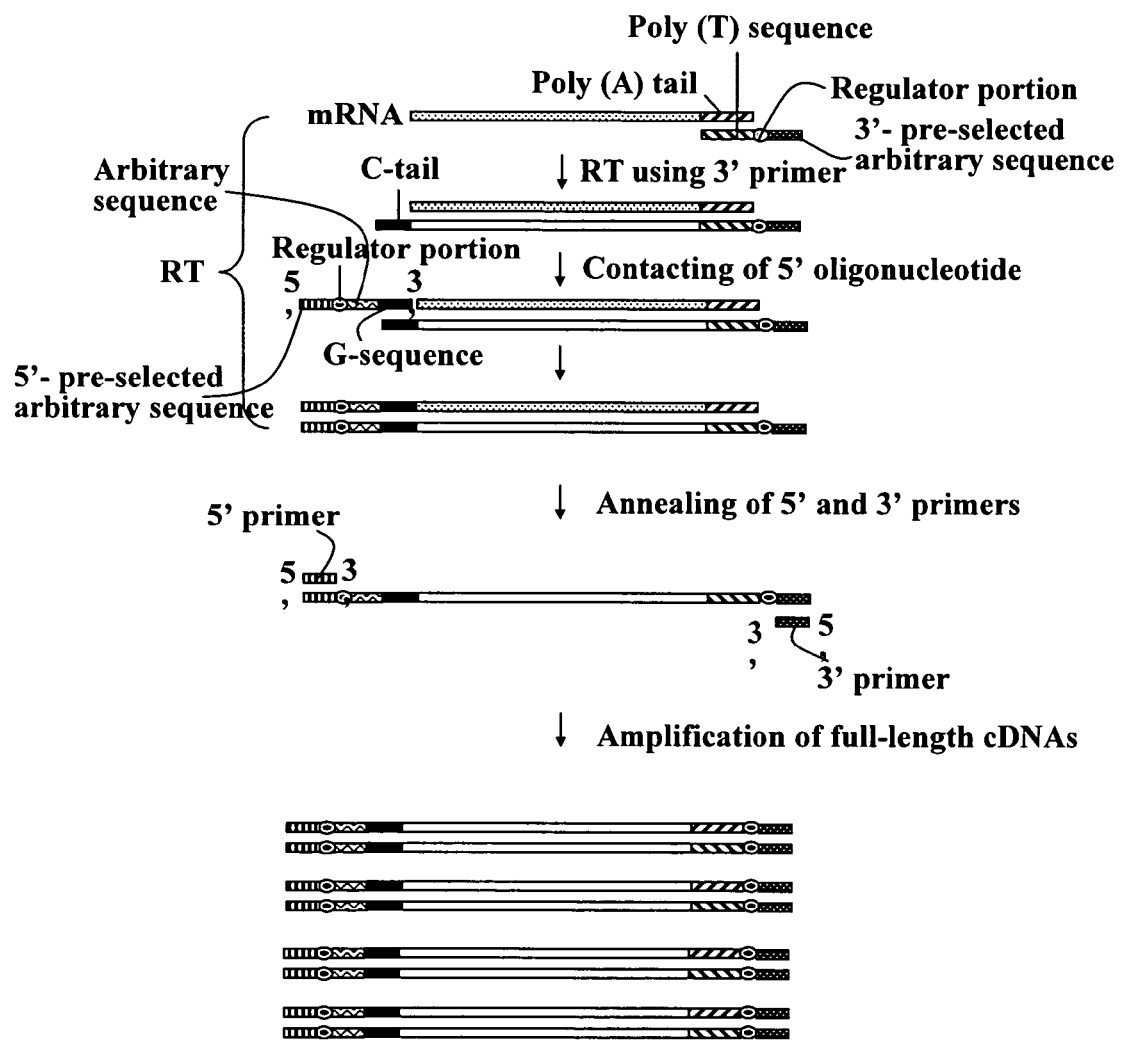
FIG. 5 shows a schematic representation for amplifying full-length cDNA molecules complementary to the mRNA molecules using the ACP of the present invention.

A schematic representation for amplifying full-length cDNA molecules of the present invention is illustrated in FIG. 5.

The use of ACP significantly simplifies and improves the conventional technologies with regard to the amplification of full-length cDNAs as described above. The vital feature of the subject method is to be free from the background problems arising from the primers used in conventional methods. Consequently this method described herein can be more effective, easier, less labor-intensive, and more reproducible than conventional methods.

In still further aspect of this invention, there is provided a kit for amplifying a full-length double stranded cDNA complementary to mRNA, which comprises the annealing control primer or the annealing control primer set described above (including the oligonucleotide dT primer, the oligonucleotide to form a base-pair(s) with the cytosine tail, the primer(s) used in the step (f)). According to one embodiment of this invention, these kits further comprises a primer pair each comprising a nucleotide sequence corresponding to each 5'-end portion of the primer and oligonucleotide used in steps (a) and (d), respectively; in case that the 5'-end portion comprises universal primer sequence, it is more preferred that the kit comprises the universal primers. The present kits may optionally include the reagents required for performing PCR reactions such as buffers, DNA polymerase, DNA polymerase cofactors, and deoxyribonucleotide-5'-triphosphates. Optionally, the kits may also include various polynucleotide molecules, reverse transcriptase, various buffers and reagents, and antibodies that inhibit DNA polymerase activity. The kits may also include reagents necessary for performing positive and negative control reactions. Optimal amounts of reagents to be used in a given reaction can be readily determined by the skilled artisan having the benefit of the current disclosure. The kits, typically, are adapted to contain in separate packaging or compartments the constituents afore-described.

VI. Application to Amplifying 5'-Enriched cDNA

In another aspect of this invention, there is provided a method for amplifying a population of 5'-enriched double-stranded cDNAs comprising cDNA regions corresponding to the 5'-end regions of mRNAs, wherein the method comprises reverse transcribing the mRNA and performing an amplification reaction using primers, characterized in that at least one primer is derived from any one of ACP described above. Preferably, the primer having the structure of ACP used for cDNA synthesis is one having at its 3'-end portion at least six random nucleotide sequences.

In a specific embodiment of this invention, there is provided the method comprises:

(a) contacting the mRNAs with a first primer of any one of ACP described above under conditions sufficient for template driven enzymatic deoxyribonucleic acid synthesis to occur, wherein the 3'-end portion of the first primer has at least six random nucleotide sequences;

(b) performing the steps (b)-(e) of the method for amplifying a population of full-length double-stranded cDNAs, whereby 5'-enriched first cDNA strands are extended;

(c) performing an amplification of the 5'-enriched first cDNA strands generated from step (b) comprising at least two cycles of primer annealing, primer extending and denaturing, using a primer pair each comprising a nucleotide sequence corresponding to each 5'-end portion of the primer and oligonucleotide used in steps (a) and (b), respectively, under conditions in which each primer anneals to the 3'- and 5'-end sequences of the 5'-enriched first cDNA strands, respectively, whereby amplification products of 5'-enriched cDNA strands are generated.

Since this application using the ACP of this invention employs in principle the present methods for amplification of nucleic acid sequence previously discussed, the common descriptions between them are omitted in order to avoid the complexity of this specification leading to undue multiplicity. In addition, the oligonucleotide to form a base-pair(s) with the cytosine tail and the primer pair used in the step (c) are in principle identical to those for 5'-RACE of this invention discussed above.

Figure 6:
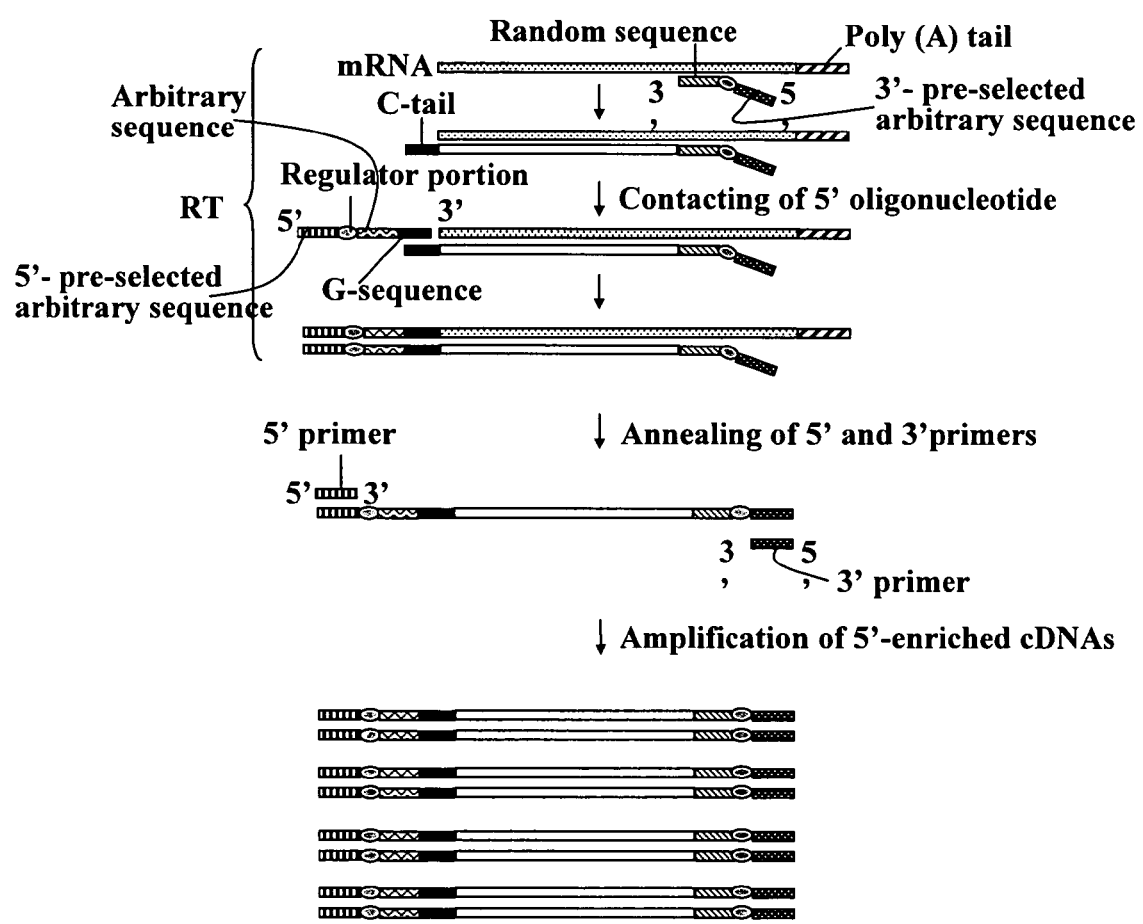
FIG. 6 shows a schematic representation for amplifying 5' enriched cDNA molecules complementary to the mRNA molecules comprising the 5'-end information using the ACP of the present invention.

A schematic representation for the method for amplifying 5'-enriched double-stranded cDNAs complementary to mRNAs is illustrated in FIG. 6.

"5' enriched cDNAs" refers to a significant portion of the cDNA constituents which contain the nucleotide sequence information of the 5'-end of the mRNAs from which the cDNAs are derived.

The formula of the first primer is identical to the formula (1) in which the 3'-end portion comprises a random nucleotide sequence. In a preferred embodiment, the 3'-end portion of the first primer used in step (a) contains at least six random deoxyribonucleotides. In a preferred embodiment, the 5'-end portion of the first primer used in step (a) can includes a sequence that is recognized by a restriction endonuclease.

The conventional methods require more steps to amplify 5'enriched cDNA molecules complementary to the mRNA molecules than the subject method because the conventional methods use the conventional primers which do not have the function of controlling primer annealing. In contrast, this subject method is considerably a simple and effective approach due to the function of regulating primer annealing generated by the effect of a universal base residue group in ACP.

In still another aspect of this invention, there is provided a kit for amplifying 5'-enriched double-stranded cDNAs complementary to mRNAs, which comprises the annealing control primer or the annealing control primer set described above (the first primer, the oligonucleotide to form a base-pair(s) with the cytosine tail). According to one embodiment of this invention, these kits further comprises a primer pair each comprising a nucleotide sequence corresponding to each 5'-end portion of the primer and oligonucleotide used in steps (a) and (b), respectively; in case that the 5'-end portion comprises universal primer sequence, it is more preferred that the kit comprises the universal primers. The present kits may optionally include the reagents required for performing PCR reactions such as buffers, DNA polymerase, DNA polymerase cofactors, and deoxyribonucleotide-5'-triphosphates. Optionally, the kits may also include various polynucleotide molecules, reverse transcriptase, various buffers and reagents, and antibodies that inhibit DNA polymerase activity. The kits may also include reagents necessary for performing positive and negative control reactions. Optimal amounts of reagents to be used in a given reaction can be readily determined by the skilled artisan having the benefit of the current disclosure. The kits, typically, are adapted to contain in separate packaging or compartments the constituents afore-described.

VII. Application to DNA or RNA Fingerprinting

This application using ACP of the subject invention can provide an improved method for detecting polymorphisms in genomic DNA (DNA fingerprinting) or for detecting differential gene expression in mRNA (RNA fingerprinting).

In further aspect of this invention, there is provided a method for producing a DNA fingerprint of gDNA, wherein the method comprises performing an amplification reaction using primers, characterized in that at least one primer is derived from any one of ACPs described above. Preferably, the primer having the structure of ACP is one having at its 3'-end portion an arbitrary nucleotide sequence substantially complementary to sites on the gDNA.

In a specific embodiment of this invention, there is provided the method using two stage amplifications, which comprises:

(a) performing a first-stage amplification of the DNA fingerprint, which is a set of discrete DNA segments characteristic of genome, from the gDNA at a first annealing temperature comprising at least two cycles of primer annealing, primer extending and denaturing, using the primer or the primer pair of any one of ACPs described above, wherein each primer has at its 3'-end portion an arbitrary nucleotide sequence substantially complementary to sites on the gDNA to hybridize therewith, under conditions in which the primer or the primer pair anneals to the gDNA, whereby the set of discrete DNA segments characterized as a DNA fingerprint is produced; and (b) performing a second-stage amplification of the set of discrete DNA segments generated from step (a) at a second annealing temperature, which is high stringent conditions, comprising at least one cycle of primer annealing, primer extending and denaturing, using the same primer or primer pair as used in step (a) or a primer or a primer pair each comprising a nucleotide sequence corresponding to each 5'-end portion of the primer or primer pair used in step (a), under conditions in which the primer or each of the primer pair anneals to the 3'- and 5'-end sequences of the set of discrete DNA segments generated from step (a), respectively, whereby the set of discrete DNA segments is re-amplified.

In still further aspect of this invention, there is provided a method for producing a RNA fingerprint of an mRNA sample, wherein the method comprises reverse transcribing and performing an amplification reaction using primers, characterized in that at least one primer is derived from any one of ACPs. Preferably, the primer according to the structure of ACP is one having at its 3'-end portion an arbitrary nucleotide sequence substantially complementary to sites on cDNA strands generated from reverse transcription and/or one having at its 3'-end portion a hybridizing nucleotide sequence substantially complementary to poly A tails of the mRNAs.

In a specific embodiment of this invention, there is provided the method using two stage amplifications, which comprises:

(a) contacting the mRNA sample with a first primer of any one of ACPs described above, in which the first primer has a hybridizing nucleotide sequence substantially complementary to poly A tails of the mRNA sample to hybridize therewith, under conditions sufficient for template driven enzymatic deoxyribonucleic acid synthesis to occur;

(b) reverse transcribing the mRNA sample to which the first primer hybridizes to produce a population of first cDNA strands that are complementary to the mRNA sample to which the first primer hybridizes;

(c) performing a first-stage amplification of the population of first cDNA strands generated from step (b) at a first annealing temperature comprising at least one cycle of primer annealing, primer extending and denaturing, using a second primer or primer pair of any one of ACPs described above, wherein each primer has at its 3'-end portion an arbitrary nucleotide sequence substantially complementary to sites on the first cDNA strands to hybridize therewith, under conditions in which the primer or primer pair anneals to the mRNA sample, whereby a set of discrete cDNA segments characterized as a RNA fingerprint is produced; and (d) performing a second stage amplification of the set of discrete cDNA segments generated from step (c) at a second annealing temperature which is high stringent conditions, comprising at least one cycle of primer annealing, primer extending and denaturing, using the same primer or primer pair as used in step (c) or a primer or primer pair each comprising a nucleotide sequence corresponding to each 5'-end portion of the primer or primer pair used in step (c), under conditions in which the primer or each of the primer pair anneals to the 3'- and 5'-end sequences of the set of discrete cDNA segments generated from step (c), respectively, whereby the set of discrete cDNA segments is re-amplified.

Since this application using the ACP of this invention employs in principle the present methods for amplification of nucleic acid sequence previously discussed, the common descriptions between them are omitted in order to avoid the complexity of this specification leading to undue multiplicity. In addition, the RNA fingerprinting in principle follows the present method for detecting DNA complementary to differentially expressed mRNA.

The term "genomic DNA" as used herein refers to a population of DNA that comprises the complete genetic component of a species. Thus genomic DNA comprises the complete set of genes present in a pre-selected species. The complete set of genes in a species is also referred to as genome. The term DNA or RNA "fingerprinting" as used herein refers to a set of discrete DNA amplification products characteristic of a genome or a set of discrete cDNA segments characteristic of a sample of mRNA, respectively.

In the previous arbitrarily primed PCR fingerprints, called AP-PCR, short or long arbitrary primers have been used under non-stringent conditions for early 2-5 cycles of PCR amplification because a low annealing temperature is required to achieve arbitrary priming, such that a significant portion of isolated fragments is not still reproducible although effective amplification proceeds in the following cycles under high stringent condition.

In contrast to AP-PCR, the ACP-based PCR for fingerprinting increases the specificity of primer annealing during PCR due to the function of a universal base residue group positioned between the 3'- and 5'-end portions of ACP, wherein the universal base residue group restricts the annealing site to the 3'-end portion of the ACP and also allows this 3'-end portion to anneal at a relatively high annealing temperature. Thus, the ACP-based PCR for fingerprinting completely eliminates false positive products and significantly increases reproducibility.

In a preferred embodiment, the ACP contains an arbitrary sequence at the 3'-end portion with at least 6 nucleotides in length. More preferably, the 3'-end portion contains 8-15 nucleotides in length, most preferably, about 10 nucleotides in length.

A single ACP or a pair of ACPs can be used for detecting polymorphisms in DNA fingerprinting. Preferably, a pair of ACPs is used for DNA fingerprinting because a pair of ACPs produces more products than a single arbitrary ACP does.

An example of the DNA fingerprinting using ACP is conducted by two stages of PCR amplifications under the following conditions: amplification reactions are performed under low stringent conditions by two cycles of the first-stage PCR comprising annealing, extending and denaturing reaction; the reaction mixture containing genomic DNA, PCR reaction buffer, MgCl2, dNTPs (dATP, dCTP, dGTP and dTTP), a pair of ACPs is pre-heated, Taq polymerase is added into the reaction mixture; the PCR reactions are performed, followed by denaturing the amplification product; after the complete reaction of the first-stage PCR, the pre-selected arbitrary primer JYC4 corresponding to the 5'-end portion of the ACPs are added to the reaction mixture and then the second stage PCR amplification is conducted.

It should be noted that a proper concentration of ACP is used to produce DNA fingerprinting. If the amount of the ACP is too low, the resultant amplified PCR products are not reproducible. In contrast, the excess amount of the ACP generates backgrounds such as DNA smear during PCR. In a preferred embodiment, the concentration of the ACP is about between 0.1 μM and 2 μM. Most preferably, the concentration of the ACP is about 1.4 μM.

In a preferred embodiment, the concentration of the primer corresponding to the 5'-end portion of the ACPs is about between 0.1 μM and 2 μM, most preferably, about 0.8 μM.

The genomic DNA and mRNA samples may be obtained from a wide variety of biomaterials and conditions. For example, they may be obtained from plants, animal (human) and microbes and from different individual organisms.

The amplified products can be analyzed by gel electrophoresis. In one embodiment, the resulting PCR products can be also detected on a denaturing polyacrylamide gel by autoradiography or non-radioactive detection methods such as silver staining (Gottschlich et al., 1997; Kociok et al., 1998), the use of fluorescent-labelled oligonucleotides (Bauer et al. 1993; Ito et al. 1994; Luehrsen et al., 1997; Smith et al., 1997), and the use of biotinylated primers (Korn et al., 1992; Tagle et al., 1993; Rosok et al., 1996).

In still further aspect of this invention, there is provided a kit for producing a DNA fingerprint by use of gDNA or mRNA, which comprises the annealing control primer or annealing control primer set described above. The descriptions of the kits for the amplification of nucleic acid sequence and for detecting DNA complementary to differentially expressed mRNA of this invention can be applied to the present kit.

VIII. Application to Identification of Conserved Homology Segments in Multigene Families This application using ACP of the subject invention can also provide an improved method for the identification of conserved homology segments in multigene families.

In another aspect of this invention, there is provided a method for identifying conserved homology segments in a multigene family from an mRNA sample, wherein the method comprises reverse transcribing and performing an amplification reaction using primers, characterized in that at least one primer is derived from any one of ACPs described above. Preferably, the primer having the structure of ACP is one having at its 3'-end portion a hybridizing sequence substantially complementary to a consensus sequence or a degenerate sequence encoding amino acid sequence of a conserved homology segment on cDNA strands generated from reverse transcription and/or one having at its 3'-end portion a hybridizing nucleotide sequence substantially complementary to poly A tails of the mRNAs.

In a specific embodiment of this invention, there is provided the method using two stage amplifications, which comprises:

(a) contacting the mRNA sample with a first primer of any one of claims 1-29, in which the first primer has a hybridizing nucleotide sequence substantially complementary to poly A tails of the mRNA sample to hybridize therewith, under conditions sufficient for template driven enzymatic deoxyribonucleic acid synthesis to occur;

(b) reverse transcribing the mRNA sample to which the first primer hybridizes to produce a population of first cDNA strands that are complementary to the mRNA sample to which the first primer hybridizes;

(c) performing a first-stage amplification of the population of first cDNA strands generated from step (b) at a first annealing temperature comprising at least one cycle of primer annealing, primer extending and denaturing, using a second primer of any one of claims 1-25 having at its 3'end portion a hybridizing sequence substantially complementary to a consensus sequence or a degenerate sequence encoding amino acid sequence of a conserved homology segment on the first cDNA strands to hybridize therewith, under conditions in which the second primer anneals to the consensus sequence or degenerate sequence of first cDNA strands, whereby 3'-end cDNA segments having the consensus sequence or degenerate sequence are generated; and (d) performing a second stage amplification of the 3'-end cDNA segments generated from step (c) at a second annealing temperature which is high stringent conditions, comprising at least two cycles of primer annealing, primer extending and denaturing, using the same first and second primers as used in steps (a) and (c) or a primer pair each comprising a nucleotide sequence corresponding to each 5'-end portion of the first and second primers used in steps (a) and (c), respectively, under conditions in which each primer anneals to the 3'- and 5'-end sequences of the 3'-end cDNA segments, respectively, whereby the 3'-end conserved homology cDNA segments are amplified.

This specific embodiment follows in principle, the present method for 3' RACE as discussed previously except for the second primer used.

In another specific embodiment of this invention, there is provided the method using two stage amplifications, which comprises:

(a) performing steps of (a)-(e) of the method for amplifying a population of full-length double-stranded cDNA, whereby full-length cDNA strands are generated;

(b) performing a first-stage amplification of the full-length first cDNA strands obtained from step (a) at a first annealing temperature, which comprises the steps of:

(i) at least one cycle of primer annealing, primer extending and denaturing using a first primer comprising a nucleotide sequence substantially complementary to the 3'-end sequences of the full-length first cDNA strands under conditions in which the first primer anneals to the full-length first cDNA strands, under conditions in which the first primer anneals to the 3'-ends of the full-length first cDNA strands, whereby full-length second cDNA strands are generated; and (ii) at least one cycle of primer annealing, primer extending and denaturing using a second primer of any one of claims 1-25 having at its 3'end portion a hybridizing sequence substantially complementary to a consensus sequence or a degenerate sequence encoding amino acid sequence of a conserved homology segment on the full-length second cDNA strands to hybridize therewith, under conditions in which the second primer anneals to the consensus sequence or degenerate sequence of full-length second cDNA strands, whereby 5'-end cDNA segments having the consensus sequence or degenerate sequence are generated; and (c) performing a second stage amplification of the 5'-end cDNA segments generated from step (b) at a second annealing temperature which is high stringent conditions, comprising at least two cycles of primer annealing, primer extending and denaturing, using the same first and second primers as used in steps (b)-(i) and (b)-(ii), respectively, or a primer pair each comprising a nucleotide sequence corresponding to each 5'-end portion of the first and second primers used in steps (b)-(i) and (b)-(ii), respectively, under conditions in which each primer anneals to the 3'- and 5'-end sequences of the 5'-end cDNA segments, respectively, whereby the 5'-end conserved homology cDNA segments are amplified.

This specific embodiment follows in principle, the present method for 5' RACE as discussed previously except for the second primer used.

In further aspect of this invention, there is provided a method for identifying conserved homology segments in a multigene family from gDNA, wherein the method comprises performing an amplification reaction using primers, characterized in that at least one primer is derived from any one of ACPs described above. Preferably, the primer having the structure of ACP is one having at its 3'-end portion a hybridizing sequence substantially complementary to a consensus sequence or a degenerate sequence encoding amino acid sequence of a conserved homology segment on the gDNA.

In a specific embodiment of this invention, there is provided the method using two stage amplifications, which comprises:

(a) performing a first-stage amplification of the conserved homology segments from the gDNA at a first annealing temperature comprising at least two cycles of primer annealing, primer extending and denaturing, using the primer or the primer pair of any one of ACPs described above, wherein each primer has at its 3'end portion a hybridizing sequence substantially complementary to a consensus sequence or a degenerate sequence encoding amino acid sequence of a conserved homology segment on the gDNA to hybridize therewith, under conditions in which the primer or the primer pair anneals to the consensus sequence or degenerate sequence of gDNA, whereby genomic DNA segments having the consensus sequence or degenerate sequence are generated; and (b) performing a second-stage amplification of the genomic DNA segments generated from step (a) at a second annealing temperature, which is high stringent conditions, comprising at least one cycle of primer annealing, primer extending and denaturing, using the same primer or primer pair as used in step (a) or a primer or a primer pair each comprising a nucleotide sequence corresponding to each 5'-end portion of the primer or primer pair used in step (a), under conditions in which the primer or each of the primer pair anneals to the 3'- and 5'-end sequences of the genomic DNA segments generated from step (a), respectively, whereby the conserved homology genomic segments are amplified.

The present method follows in principle, the present method for amplifying a target nucleic acid sequence from a DNA as discussed previously except for the primer used.

Since this application using the ACP of this invention employs in principle the present methods for amplification of nucleic acid sequence previously discussed, the common descriptions between them are omitted in order to avoid the complexity of this specification leading to undue multiplicity. In addition, where an mRNA is used as starting material, the present methods for 3' or 5' RACE are in principle applied to the present methods for the identification of conserved homology segments in multigene families.

The formula of ACP for the identification of conserved homology segments in multigene families is identical to the formula (1) in which the 3'-end portion of ACP has a hybridizing sequence substantially complementary to a consensus sequence in a gene family or a degenerate sequence encoding amino acid sequence of a conserved homology.

There are two principle approaches to the design of degenerate primer: (a) using peptide sequence data obtained from a purified protein; and (b) using consensus protein sequence data from alignments of gene families. If orthologs of the gene of interest have been cloned from other organisms, or if the gene is a member of a gene family, it will be possible to generate protein sequence alignments.

These may reveal appropriate regions for the design of degenerate primers, for example, from consensus sequence of highly conserved regions. Amplifications using degenerate primers can sometimes be problematic and may require optimization. The first parameter is annealing temperature. It is important to keep the annealing temperature as high as possible to avoid extensive nonspecific amplification and a good rule of thumb is to use 55° C. as a starting temperature. In general, it is difficult to keep this rule because degenerate primers should be designed based on amino acid sequences as a precondition. However, the ACP of the present invention does not have to satisfy this requirement because it allows a high annealing temperature such as 65° C. at the second stage of PCR amplification regardless of primer design.

According to a preferred embodiment, the second primer is a pool of primers each comprising a degenerate sequence selected from a plurality of the nucleotides coding for amino acid sequence of the consensus sequence.

The term "conserved region" and more specifically "conserved region of a gene in a multigene family" as used herein refers to a segment of nucleotide sequence of a gene or amino acid sequence of a protein that is significantly similar between members of gene families. The degree of similarity can vary. In some cases the conserved regions will be identical between family members. In some cases the nucleotide sequence may vary significantly but still encode for amino acid segments that are conserved between family members. The term "consensus sequence" as used herein refers to the bases most often found at any given position when comparing a large number of similar nucleotide sequences.

Alternatively, the present methods for the identification of conserved homology segments can be also combined with that for detecting differentially expressed mRNAs.

In still further aspect of this invention, there is provided a kit for identifying a conserved homology segment in a multigene family by use of mRNA or gDNA, which comprises the annealing control primer or annealing control primer set described above. The descriptions of the kits for the amplification of nucleic acid sequence, 3' RACE and 5' RACE of this invention can be applied to the present kit.

IX. Application to Identification of a Nucleotide Variation

This application using ACP system of the subject invention can also provide an improved method for identifying a nucleotide variation in a target nucleic acid.

In another aspect of this invention, there is provided a method for identifying a nucleotide variation in a target nucleic acid, wherein the method comprises performing an amplification reaction using primers, characterized in that at least one primer is derived from any one of ACPs described above. Preferably, the primer having the structure of ACP is (a) a first primer one having at its 3'-end portion a hybridizing sequence substantially complementary to a pre-selected sequence at a first site of target nucleic acid, wherein each of the first primer and the first site comprises an interrogation position corresponding to the nucleotide variation, and/or (b) a second primer having a hybridizing sequence substantially complementary to a pre-selected sequence at a second site of target nucleic acid.

In a specific embodiment of this invention, there is provided the method using two stage amplifications, which comprises:

(a) performing a first-stage amplification to produce a first DNA strand complementary to the target nucleic acid including the nucleotide variation at a first annealing temperature comprising at least one cycle of primer annealing, primer extending and denaturing, using a first primer of any one of ACPs described above having at its 3'-end portion a hybridizing sequence substantially complementary to a pre-selected sequence at a first site of the target nucleic acid to hybridize therewith, wherein each of the first primer and the first site comprises an interrogation position corresponding to the nucleotide variation, whereby the first DNA strand complementary to the target nucleic acid including the nucleotide variation is generated when the interrogation position is occupied by the complementary nucleotide of the first primer to its corresponding nucleotide of the first site; and (b) performing a second-stage amplification of the first DNA strand generated from step (a) at a second annealing temperature, which is high stringent conditions, comprising the steps:

(i) at least one cycle of primer annealing, primer extending and denaturing using a second primer of any one of ACPs described above having at its 3'-end portion a hybridizing sequence substantially complementary to a pre-selected sequence at a second site of the target nucleic acid to hybridize therewith under conditions in which the second primer anneals to the second site of the target nucleic acid, whereby a second DNA strand complementary to the first DNA strand including the nucleotide variation is generated; and (ii) at least one cycle of primer annealing, primer extending and denaturing using the same first and second primers as used in steps (a) and (b)-(i) or a primer pair each having a hybridizing sequence complementary or corresponding to the 3'- and 5'-ends of the second DNA strand generated from step (b)-(i) to hybridize therewith, under conditions in which each primer anneals to the 3'- and 5'-end sequences of the second DNA strand, respectively, whereby the second DNA strand which comprises the first and second sites of the target nucleic acid at its 3'- and 5'-ends is amplified so that a short target nucleotide segment corresponding to the second DNA strand containing the nucleotide variation is generated.

Since this application using the ACP of this invention employs in principle the present methods for amplification of nucleic acid sequence previously discussed, the common descriptions between them are omitted in order to avoid the complexity of this specification leading to undue multiplicity.

Figure 7A:
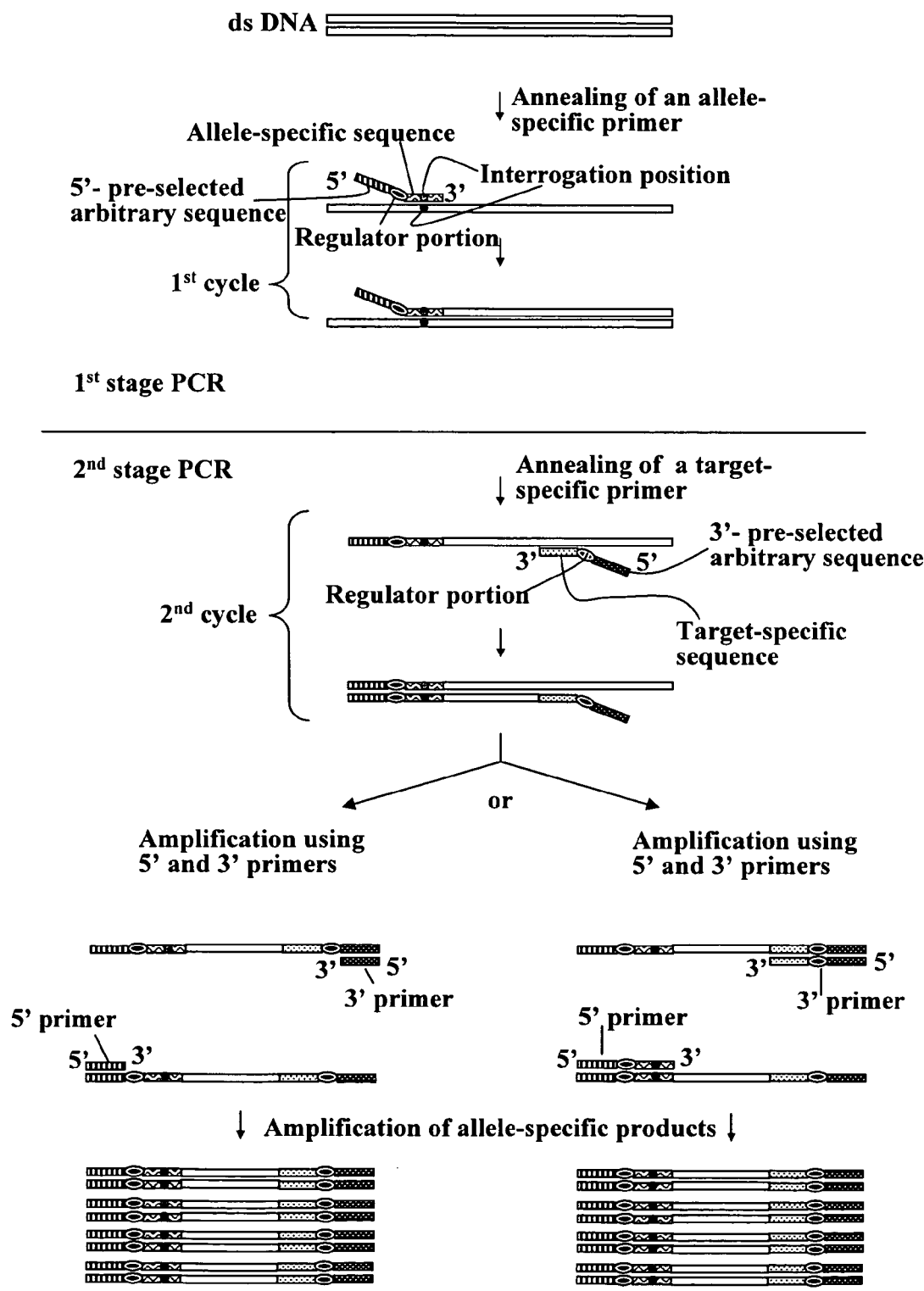
FIG. 7A shows a schematic representation for detecting single nucleotide polymorphism (SNP) using the ACP of the present invention.

A schematic representation of this specific embodiment for single nucleotide polymorphism (SNP) genotyping using novel ACP is illustrated in FIG. 7A.

The formula of ACP for the detection of a nucleotide variation, is identical to the formula (1) in which its 3'-end portion comprises a hybridizing sequence substantially complementary to a pre-selected sequence at a site of the target nucleic acid to hybridize therewith which contains the nucleotide variation, wherein the nucleotide corresponding to the nucleotide variation and its complementary nucleotide of the ACP occupy an interrogation position. The process for this application is carried out by two stage PCR amplifications using the genomic DNA obtained from samples such as patient blood or a short segment of the sample DNA, which includes a target nucleotide variation. The interesting nucleotide sample may be obtained from human nucleic acid and an organism that can cause an infectious disease.

The method using two-stage PCR amplifications for detecting single nucleotide polymorphism (SNP) genotyping basically follows the process used for amplifying a target nucleic acid sequence using genomic DNA as a starting material. In addition, the process for multiplex DNA amplification can be adapted to this application.

To use a short segment of the sample DNA including a target nucleotide variation as a starting material for the above process, it is preferable that the target short segment is pre-amplified prior to step (a) using a primer pair in which each has a hybridizing sequence substantially complementary to the sample DNA to hybridize therewith. Furthermore, more than one target nucleotide segment each including a SNP can be prepared by the multiplex DNA amplification as described in Application II to be used as a starting material in the subject invention for multiple SNP screening.

The first ACP used in step (a) for the detection of a polymorphic base is an allele-specific ACP which contains an interrogation position within its 3'-end portion occupied by a complementary nucleotide to the corresponding nucleotide of the nucleotide variation in a target nucleic acid. Preferably, the interrogation position of the first primer is in the middle of its 3'-end portion. In a more preferred embodiment, the interrogation position of the allele-specific ACP is within about 10 bases of the 3'-end nucleotide. More advantageously, the interrogation position of the allele-specific ACP is within about 6 bases of the 3'-end nucleotide of the allele-specific ACP. In another preferred embodiment, the interrogation position of the allele-specific ACP is located within positions 4 and 6 from the 3'-end nucleotide. Most preferably, the interrogation position of the allele-specific ACP is located in position 5 from the 3'-end nucleotide. The term "3'-end nucleotide" used herein refers to a nucleotide which is positioned at the 3'-end of ACP.

In another embodiment, the 3'-end portion of the allele-specific ACP used in step (a) contains at least 6 nucleotides in length, which is a minimal requirement of length for primer annealing. Preferably, the 3'-end portion sequence is about 8 to 20 nucleotides in length. Most preferably, the 3'-end portion sequence is about 10 nucleotides in length including an interrogation position.

In one embodiment, at least one artificial mismatch can be also placed within the 3'-end portion of ACP using universal base or non-discriminatory analog that hydrogen-bonds minimally with all four bases without steric disruption of the DNA duplex. Although the position of the artificial mismatch can vary depending on experimental designs, it is preferred that the mismatch nucleotide is substantially adjacent the interrogation position of the first primer.

In a preferred embodiment, the first or second primers comprise at least one nucleotide with a label for detection or isolation.

According to a preferred embodiment, the first DNA strand including nucleotide variation in step (a) is generated by one cycle of primer annealing, primer extending, and denaturing. It is preferred that the second DNA strand including nucleotide variation in step (b)-(i) is generated by one cycle of primer annealing, primer extending, and denaturing. Preferably, the second DNA strand including nucleotide variation in step (b)-(ii) is amplified by at least 5 cycles of primer annealing, primer extending, and denaturing.

In another specific embodiment of this invention using amplified short DNA strand fragment containing the nucleotide variation, there is provided the method using two individual amplifications of a first and a second amplifications in which the second amplification is performed using two stage amplifications, which comprises:

(a) performing the first amplification to produce a short DNA strand fragment containing the nucleotide variation between its ends comprising at least two cycles of primer annealing, primer extending and denaturing, using a primer pair each primer comprising a hybridizing sequence substantially complementary to a pre-selected sequence at a site of the target nucleic acid under conditions that the nucleotide variation is positioned between the pre-selected sequences, in which at least one primer of the primer set is any one of ACPs described above having at its 3'-end portion the hybridizing sequence, whereby the short DNA strand fragment containing the nucleotide variation between its ends is amplified;

(b) performing a first-stage amplification of the second amplification to produce a first DNA strand complementary to the short DNA strand fragment including the nucleotide variation at a first annealing temperature comprising at least one cycle of primer annealing, primer extending and denaturing, using a first primer of any one of ACPs described above having at its 3'-end portion a hybridizing sequence substantially complementary to a pre-selected sequence at a first site of the target nucleic acid to hybridize therewith, wherein each of the first primer and the first site comprises an interrogation position corresponding to the nucleotide variation, whereby the first DNA strand complementary to the target nucleic acid including the nucleotide variation is generated when the interrogation position is occupied by the complementary nucleotide of the first primer to its corresponding nucleotide of the first site; and (c) performing a second-stage amplification of the second amplification of the first DNA strand generated from step (a) at a second annealing temperature, which is high stringent conditions, comprising at least one cycle of primer annealing, primer extending and denaturing using a primer pair in which amongst the primer pair one is the same as the primer of any one of ACPs used in step (a) the other is the same as the first primer used in step (b), or a primer pair each having a hybridizing sequence complementary or corresponding to the 3'- and 5'-ends of the first DNA strand generated from step (b) to hybridize therewith, under conditions in which each primer anneals to the 3'- and 5'-end sequences of the first DNA strand, respectively, whereby the first DNA strand is amplified so that a short target nucleotide segment corresponding to the first DNA strand containing the nucleotide variation is generated.

Figure 7B:
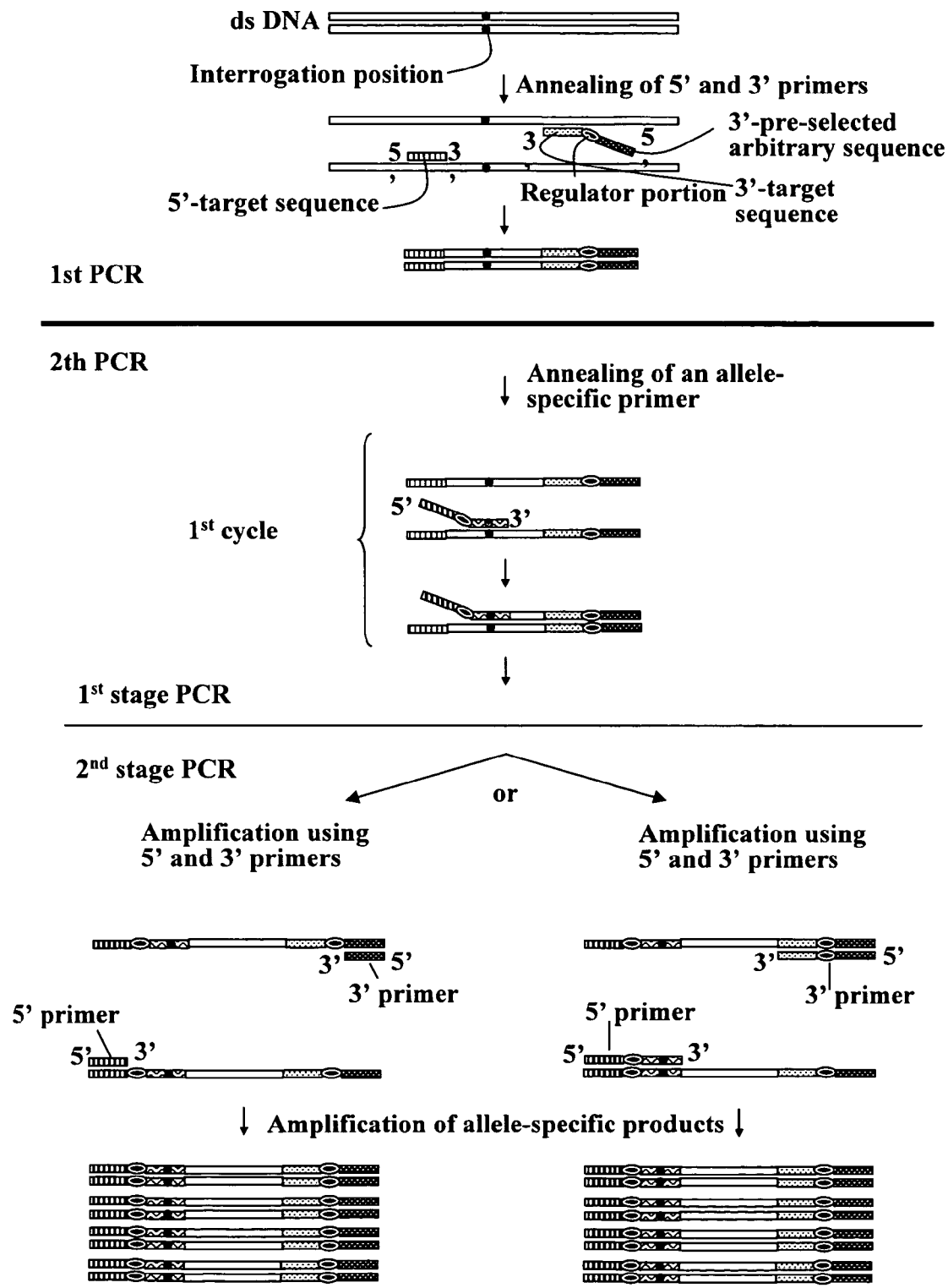
FIG. 7B shows another schematic representation for detecting single nucleotide polymorphism (SNP) using the ACP of the present invention.

A schematic representation of another specific embodiment for single nucleotide polymorphism (SNP) genotyping using novel ACP is illustrated in FIG. 7B. Since this specific embodiment is carried out in a similar manner to above embodiment, the common descriptions between them are omitted in order to avoid the complexity of this specification leading to undue multiplicity.

The present method can be applied to a variety of nucleotide variations including single nucleotide polymorphism and point mutation (substitution, deletion and insertion).

The amplified products can be analyzed by gel electrophoresis. In one embodiment, the resulting PCR products can be also detected on a denaturing polyacrylamide gel by autoradiography or non-radioactive detection methods such as silver staining (Gottschlich et al., 1997; Kociok et al., 1998), the use of fluorescent-labelled oligonucleotides (Bauer et al. 1993; Ito et al. 1994; Luehrsen et al., 1997; Smith et al., 1997), and the use of biotinylated primers (Korn et al., 1992; Tagle et al., 1993; Rosok et al., 1996).

The amplified products generated by multiplex DNA amplification for multiple SNP screening can be compared through the size separation of the products. The size separation comparison is also performed by electrophoresis through an agarose gel matrix or polyacrylamide gel matrix or sequencing. The products can be also detected by the use of fluorescent-labelled oligonucleotide primers for automatic analysis.

The term "interrogation position" as used herein refers to the location of a specific nucleotide base of interest within a target nucleic acid. For example, in the analysis of SNPs, the "interrogation position" in the target nucleic acid is in position what would be different from wild type. The interrogation position also includes the location of nucleotide sequence of a primer which is complementary to an interrogation position of the target nucleic acid. The interrogation position of the target nucleic acid is opposite the interrogation position of the primer, when the primer is hybridized with the target nucleic acid.

The term "polymorphism" as used herein refers to the presence of two or more alternative genomic sequences or alleles between or among different genomes or individuals. "Polymorphic" refers to the condition in which two or more variants of a specific genomic sequence can be found in a population. A "polymorphic site" is the locus at which the variation occurs. A single nucleotide polymorphism, or SNP, is a single base-pair variant, typically the substitution of one nucleotide by another nucleotide at the polymorphic site. Deletion of a single nucleotide or insertion of a single nucleotide, also give rise to single nucleotide polymorphisms. Typically, between different genomes or between different individuals, the polymorphic site may be occupied by two different nucleotides. The term "allele" as used herein refers a specific member of a collection of naturally occurring sequence variants (detectable within a population of individuals) at a specific genomic locus or marker.

In still another aspect of this invention, there is provided a kit for identifying a nucleotide variation in a target nucleic acid, which comprises the annealing control primer or annealing control primer set (including the first and second primers) described above. The descriptions of the kits for the amplification of nucleic acid sequence of this invention can be applied to the present kit.

X. Application to Mutagenesis

This application using ACP of the subject invention can also provide an improved method for mutagenesis. The ACP-based PCR provides an excellent tool for mutagenesis, including deletion, or insertion of sequences, the alteration of one or a few specific nucleotides, and the random mutation of nucleotide sequence.

In further aspect of this invention, there is provided a method for mutagenesis in a target nucleic acid, comprising performing an amplification reaction using primers, characterized in that at least one primer is derived from any one of ACPs described above. Preferably, the primer having the structure of ACP is one having at its 3'-end portion a hybridizing sequence substantially complementary to a region of target nucleic acid sequence, wherein the hybridizing sequence has a nucleotide sequence responsible for mutagenesis.

In a specific embodiment of this invention, there is provided the method using two stage amplifications, which comprises:

(a) performing a first-stage amplification of the target nucleic acid sequence at a first annealing temperature comprising at least two cycles of primer annealing, primer extending and denaturing, using a primer pair of any one of ACPs described above each having at its 3'end portion a hybridizing sequence substantially complementary to a region of the target nucleic acid sequence to hybridize therewith, wherein the hybridizing sequence has at least one mismatch nucleotide to generate site-directed mutation, under conditions in which the primer or primer pair anneals to its target nucleotide sequence, whereby an amplification product containing site-directed mutation site is generated; and (b) performing a second-stage amplification of the amplification product generated from step (a) at a second annealing temperature, which is high stringent conditions, comprising at least one cycle of primer annealing, primer extending and denaturing, using the same primers as used in step (a) or a primer pair each comprising a pre-selected arbitrary nucleotide sequence corresponding to each 5'-end portion of the primers used in step (a), under conditions in which each primer anneals to the 3'- and 5'-ends of the amplification product, respectively, whereby the amplification product containing site-directed mutation site is re-amplified.

This specific embodiment relates to site-directed mutagenesis.

Since this application using the ACP of this invention employs in principle the present methods for amplification of nucleic acid sequence previously discussed, the common descriptions between them are omitted in order to avoid the complexity of this specification leading to undue multiplicity.

The formula of ACP for PCR mutagenesis is identical to the formula (1) in which the 3'-end portion comprises a sequence for site-directed mutagenesis or for random mutation.

In still further aspect of this invention, there is provided a kit for mutagenesis in a target nucleic acid, which comprises the annealing control primer or annealing control primer set described above. The descriptions of the kits for the amplification of nucleic acid sequence of this invention can be applied to the present kit.

XI. Other Applications

The ACP of the subject invention can be also useful in a variety of processes involving nucleic acid amplifications, particularly, PCR. For example, the processes include mixed oligonucleotide-primed amplification of cDNA, long-range PCR, linear PCR, inverse PCR, quantitative PCR, touchdown PCR, sequencing, in situ PCR, vectorette PCR and thermal asymmetric interlaced PCR. The general procedures for these methods can be found in Joseph Sambrook, et al., Molecular Cloning, A Laboratory Manual, Cold Spring Harbor Laboratory Press, Cold Spring Harbor, N.Y. (2001) and M.J. McPherson, et al., PCR, Springer-Verlag New York Inc., N.Y. (2000).

Therefore, the present invention encompasses all uses of the primer according to ACP for process involving nucleic acid amplification, particularly PCR.

The ACP of this invention is significantly effective and widely accessible to nucleic acid amplification-based applications. Also, various problems related to primer annealing specificity remained in the previous nucleic acid amplification techniques can be fundamentally solved by the ACP and the methods of the present invention. The main benefits to be obtained from the use of the ACP during nucleic acid amplification are as follows:

(a) since the presence of a regulator portion positioned between the 3'- and 5'-end portions restricts primer annealing portion to the 3'-end portion under such conditions that the 3'-end portion anneals to the template, the annealing sequence of a primer can be precisely controlled, which makes it possible to design a primer capable of having only a desired number of sequence annealed (or possible to design a primer capable of controlling an annealing portion thereof). It is particularly useful when an annealing portion of a primer has to be limited (e.g., SNP genotyping, DNA microarray screening, and detection of differentially expressed genes);

(b) since the presence of a regulator portion positioned between the 3'- and 5'-end portions interrupts the annealing of the 5'-end portion to the template under such conditions that the 3'-end portion anneals to the template, eventually the 5'-end portion not involved in the annealing provides the 3'-end portion with primer annealing specificity;

(c) the specificity of primer annealing is highly sensitive enough to detect even a single-base mismatching. It is particularly useful for single nucleotide polymorphisms (SNPs) genotyping;

(d) the ACP is capable of providing a primer with a high tolerance in "primer search parameters" for primer design such as primer length, annealing temperature, GC content, and PCR product length;

(e) the ACP provides two-stage nucleic acid amplifications which allow the amplified products to be excluded from non-specific amplification;

(f) the efficiency of nucleic acid amplification is increased, which makes it easier to detect rare mRNAs; and (g) the reproducibility of nucleic acid amplification products is increased, which saves a great amount of time and cost.

As much as the nucleic acid amplification technology such as PCR has influenced the biotechnological field, the use of ACP fundamentally alter the principles of the current existing nucleic acid amplification methods, as mentioned above, by exhibiting unlimited applicability, and have them significantly upgraded at one time. In consequence, the ACP and its various applications described herein provide a turning point to open a new biotechnological era since the introduction of nucleic acid amplification technology.

The following specific examples are intended to be illustrative of the invention and should not be construed as limiting the scope of the invention as defined by appended claims.

EXAMPLES

In the experimental disclosure which follows, the following abbreviations apply to: M (molar), mM (millimolar), µM (micromolar), g (gram), µg (micrograms), ng (nanograms), l (liters), ml (milliliters), µl (microliters), ° C. (degree Centigrade); Promega (Promega Co., Madison, USA); Clontech (CLONTECH Laboratories, Palo Alto, USA); Roche (Roche Diagnostics, Mannheim, Germany); QIAGEN (QIAGEN GmbH, Hilden, Germany).

The primers used in the subject invention are shown in Table 1.

Example 1

Evaluation of Universal Base Effect in ACP

The effect of universal base residues positioned between the 3'- and 5'-end portions of ACP was evaluated by RT-PCR using mouse conceptus tissues.

Total RNA was isolated from the entire conceptuses of mouse strain ICR at the day of 4.5, 11.5 and 18.5 during gestation period using either Tri-reagent (Sigma), or the LiCl/Urea method (Hogan et al., 1994) as previously described (Chun et al., 1999; Hwang et al., 2000). Two individual experiments of cDNA amplifications using ACP were performed to examine the effect of universal base, particularly, deoxyinosine residues positioned between the 3'- and 5'-end portions of ACP as follows: A. The effect of deoxyinosine residues positioned between the 3'- and 5'-end portions of ACP in comparison with ACP and the conventional primer not containing a dexoyinosine group; B. The effect of deoxyinosine residues positioned between the 3'- and 5'-end portions of ACP in association with the alteration of number of dexoyinosine.

These experiments were conducted based on the following assumptions:

(i) the presence of universal base residues which have lower $T_m$ than other portions in ACP due to their weaker hydrogen bonding interactions in base pairing would not be involved in annealing to the template nucleic acid under the conditions that the 3'-end portion of ACP anneals to a site of the template at a first annealing temperature.

(ii) the presence of at least one universal base residue between the 3'- and 5'-end portions of ACP would be capable of interrupting the annealing of the 5'-end portion and restricting a primer annealing portion to the 3'-end.

(iii) the 3'-end portion of ACP would act only as a annealing portion to the template during PCR.

(iv) the 3'-end portion of dT-ACP which is $dT_{10}$ comprising 10 T nucleotides also has too low $T_m$ to bind the template nucleic acid.

(v) consequently, the $dT_{10}$-ACP does not produce any PCR products under high annealing temperature.

A. The Effect of Deoxyinosine Residues Positioned Between the 3'- and 5'-End Portions of ACP in Comparison with ACP with the Primer not Containing a Dexoyinosine Group (a) First-Strand cDNA Synthesis $dT_{10}$-JYC2     5'-GCTTGACTACGATACTGTGC-GATTTTTTTTT-3' (SEQ ID NO:29) or $dT_{10}$-ACP1 5'-GCT- TGACTACGATACTGTGCGAIIIIITTTTTTTTTT-3' (SEQ ID NO:30) was used as a cDNA synthesis primer.

Three micrograms of total RNA and 2 µl of 10 µM dT10-JYC2 or 10 µM dT10-ACP1 were combined in a 20 µl final volume. The solution was heated at 65° C. for 10 minutes, quenched on ice, and microcentrifuged to collect solvent at the bottom. The following components were added sequentially to the annealed primer/template on ice: 0.5 µl (40 units/µl) of RNasin ribonuclease inhibitor (Promega), 4 µl of 5× reaction buffer (250 mM Tris-HCl, pH 8.3, 375 mM KCl, 15 mM MgCl2, 50 mM DTT; Promega), 5 µl of 2 mM each deoxynucleotide mix (dATP, dCTP, dGTP, dTTP), and 1 µl of Moloney-murine leukemia virus (M-MLV) reverse transcriptase (200 units/µl; Promega). The 20 µl of reaction mixture was incubated at 37° C. for 90 min, microcentrifuged, and placed on ice for 2 min. The reaction was stopped by incubation at 94° C. for 2 min.

(b) cDNA Amplification Using ACPs

The $dT_{10}$-ACP1 was used to examine the effect of a deoxyinosine group positioned between the 3'- and 5'-end portions during PCR. The $dT_{10}$-JYC2 not containing a deoxyinosine group was used as a control.

The ACP10 5'-GTCTACCAGGCATTCGCTTCATII-IIIGCCATCGACC-3' (SEQ ID NO:13) was used as 5' primer for this experiment.

The PCR amplification was conducted in a 50 µl volume containing 50 ng of the first-strand cDNA, 5 µl of 10×PCR buffer, 1 µl of 10 µM 5'primer (ACP10), 1 µl of 10 µM 3'primer (dT10-JYC2 or dT10-ACP1), 3 µl of 25 mM MgCl2, 5 µl of 2 mM dNTP, 0.5 µl of Taq polymerase (5 units/µl). The PCR reactions were conducted under the following conditions: 5 min at 94° C. followed by 30 cycles of 94° C. for 1 min, 54° C. for 1 min, and 72° C. for 1 min; followed by a 5 min final extension at 72° C. Amplified products were analyzed by electrophoresis in a 2% agarose gel followed by ethidium bromide staining.

Figure 8:
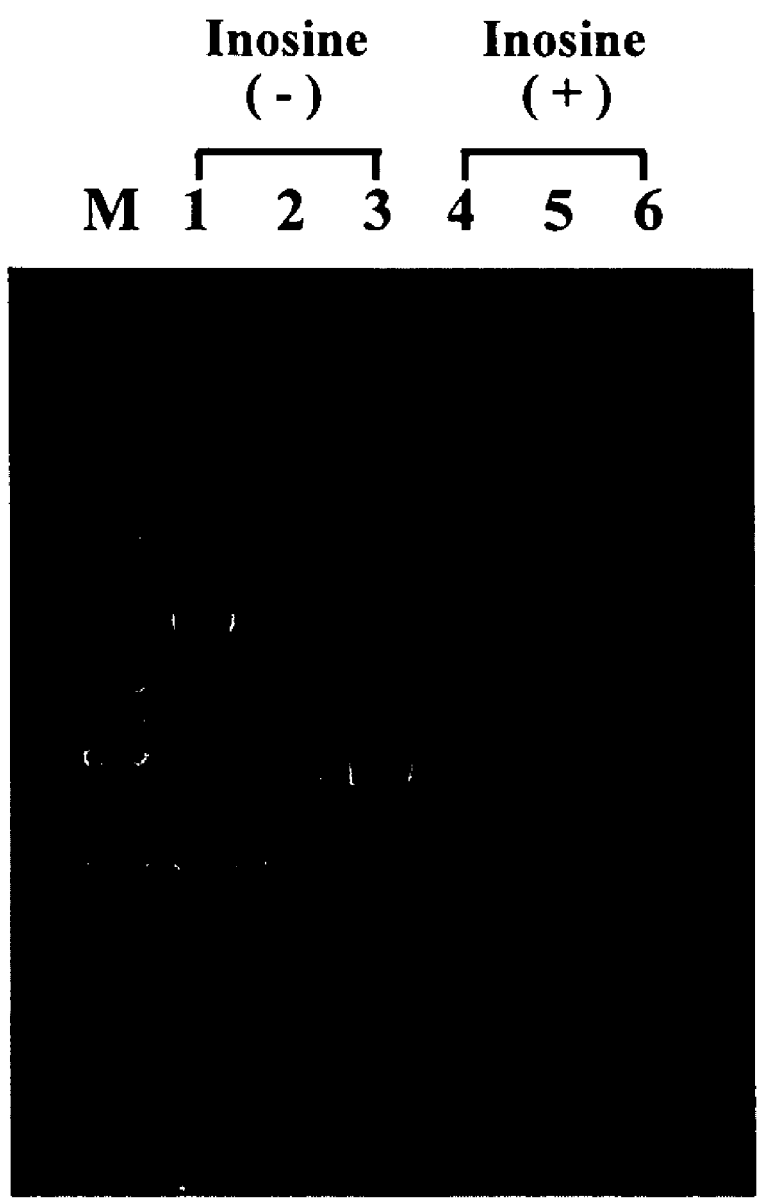
FIG. 8 is an agarose gel photograph to show the effect of a deoxyinosine group positioned between the 3'- and 5'-end portions of ACP. The cDNA was amplified using total RNA isolated from conceptus tissues at E4.5 (lanes 1 and 4), E11.5 (lanes 2 and 5), and E18.5 (lanes 3 and 6), with a set of the dT10-JYC2 (SEQ ID NO. 29) and ACP10 (lanes 1-3) (SEQ ID NO. 13), and a set of the dT10-ACP1 (SEQ ID NO. 30) and ACP10 (lanes 4-6), respectively.

As a result, FIG. 8 shows that the dT10-ACP1 containing a deoxyinosine group produced almost no products (lanes 4-6), whereas the dT10-JYC2 not containing a deoxyinosine group produced a plurality of amplified cDNA products (lanes 1-3). Consistent with our assumption, the results clearly indicate that the deoxyinosine group positioned between the 3'- and 5'-end portions affects the annealing of the 3'- and 5'-end portions of the dT10-ACP to the template cDNA under such high annealing temperature, resulting in no product as stated in the above assumption.

B. The Effect of Deoxyinosine Residues Positioned Between the 3'- and 5'-End Portions of ACP in Association with the Alteration of Number of Dexoyinosine (a) First-Strand cDNA Synthesis The first-strand cDNA was synthesized from total RNA of mouse concentues using $dT_{10}$-JYC2 as a cDNA synthesis primer as the above.

(b) cDNA Amplification Using ACPs

This experiment used four ACPs each comprising different number of deoxyinosine residues as follows, to examine the effect of deoxyinosine residues positioned between the 3'- and 5'-end portions in association with the alteration of number of deoxyinosine, under a particular stringency conditions.

ACP16    5'-GTCTACCAGGCATTCGCTTCATIIGC-CATCGACC-3' (SEQ ID NO:20);

ACP17    5'-GTCTACCAGGCATTCGCTTCATIIIGC-CATCGACC-3' (SEQ ID NO:21);

ACP18    5'-GTCTACCAGGCATTCGCTTCATII-IIIIGCCATCGACC-3' (SEQ ID NO:22);

ACP19    5'-GTCTACCAGGCATTCGCTTCATII-IIIIIGCCATCGACC-3' (SEQ ID NO:23); and

CRP2I0   5'-GTCTACCAGGCATTCGCTTCATGCCATC-GACC-3' (SEQ ID NO:19) not containing a deoxyinosine group was used as a control.

The resultant first-strand cDNA generated from step (A), which comprises the pre-selected arbitrary sequence of the dT10-ACP at its 5'-end, was used as a template and the primer JYC2 5'-GCTTGACTACGATACTGTGCGA-3' (SEQ ID NO:10) corresponding to the 5'-end portion of the dT10-ACP was used as 3' primer.

The PCR amplification was conducted in a 50 µl volume containing 50 ng of the first-strand cDNA, 5 µl of 10×PCR buffer, 1 µl of 10 µM 5'primer (ACP16, 17, 18, 19, or CRP2I0), 1 µl of 10 µM 3'primer (JYC2), 3 µl of 25 mM MgCl2, 5 µl of 2 mM dNTP, 0.5 µl of Taq polymerase (5 units/µl). The PCR reactions were comprised of: 5 min at 94° C., followed by 30 cycles of 94° C. for 1 min, 57° C. for 1 min, and 72° C. for 1 min; followed by a 5 min final extension at 72° C. Amplified products were analyzed by electrophoresis in a 2% agarose gel followed by ethidium bromide staining.

Figure 9:
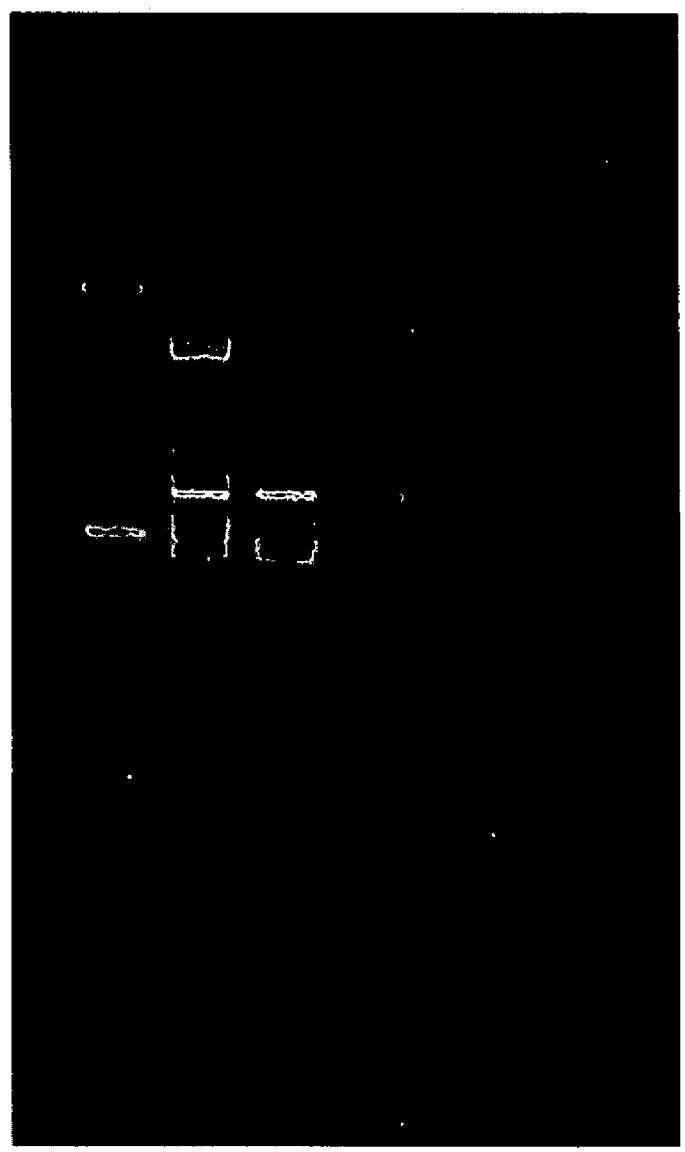
FIG. 9 is an agarose gel photograph to show the effect of deoxyinosine residues positioned between the 3'- and 5'-end portions of ACP in association with the alteration of number of deoxyinosine during PCR. The lanes 0, 2, 4, 6, and 8 represent the number of deoxyinosine residues, respectively.

As a result, FIG. 9 shows that the CRP2I0 not containing any deoxyinosine residues produced a plurality of amplified cDNA products, whereas the ACPs containing at least two deoxyinosine residues generated the significant reduction of amplified cDNA products, and even more, the ACP containing eight deoxyinosine residues produced almost no products. Consistent with our assumption, the results clearly indicates that the annealing of the 3'-end portion of ACP to the template could be separated from the 5'-portion since a group of contiguous deoxyinosine residues separates the annealing of the 3'-end and 5'-end portions under high stringent conditions due to the property of deoxyinosine such as its weaker hydrogen bonding interaction in base pairing.

Example 2

Method for Amplifying a Target Nucleic Acid Sequence Using ACP

The ACP of the subject invention was applied to amplify target nucleotide sequences of mouse placenta-specific homeobox gene Esx1 cDNA. The process and results for the amplification of the target nucleotide sequences of Esx1 cDNA using ACPs are described herein. Total RNA (3 µg) obtained from mouse 18.5-day-old placenta was used as a starting material. First-strand cDNAs were prepared under the same conditions as used in the cDNA synthesis of Example 1, except that Oligo-dT15 was used as the first-strand cDNA synthesis primer.

```
Oligo-dT15
  5'-TTTTTTTTTTTTTTT-3'       (SEQ ID NO:54)
```

The resultant first-strand cDNAs were used as templates to amplify target cDNA fragments of Esx1 using ACPs. These experiments conducted two stage PCR amplifications, which is one of unique features of the present invention.

The conventional primers of Esx1 used in the Example are:

```
EsxN7
5'-GCCGGTTGCAGAAGCACC-3';     (SEQ ID NO:44)

EsxC6
5'-GAACCATGTTTCTGAATGCC-3';   (SEQ ID NO:45)
```

-continued

```
EsxN1
5'-GAATCTGAAACAACTTTCTA-3';      (SEQ ID NO:48)

EsxC2
5'-GATGCATGGGACGAGGCACC-3';      (SEQ ID NO:49)

EsxN3
5'-CGCCGCAACCCCTGCCCGCA-3';      (SEQ ID NO:51)
and

EsxC5
5'-GATGCATGGGACGAGGGA-3'.        (SEQ ID NO:52)
```

Three primer sets, EsxN7 and EsxC6, EsxN1 and EsxC2, and EsxN3 and EsxC5, were used in the Example because they are known as the primer sets which generate high backgrounds as well as non-specific products in conventional PCR methods as known in the art.

According to single-target PCR systems, primers with similar melting temperatures (Tm) should be chosen. However, a primer set of EsxN1 (Tm 50.7° C.) and EsxC2 (Tm 71.9° C.) shows about 20° C. of different melting temperatures between them, and a primer set of EsxN3 (Tm 86.9° C.) and EsxC5 (Tm 66.2° C.) both has high melting temperatures. Also, a primer set of EsxN7 (Tm 68.2° C.) and EsxC6 (Tm 61.2° C.), which has relatively similar melting temperature, are selected to observe the effect of ACP.

The ACP of the subject invention was applied to these three conventional primer sets to demonstrate if the ACP system can overcome the main problems arising from these conventional primer sets, such as background and non-specific products.

The following ACPs comprise the sequences of the above conventional primers at their 3'-end portions and were used as Esx1 gene-specific primers for the first-stage PCR amplification:

```
EsxN7-ACP 5' primer
5'-GTCTACCAGGCATTCGCTTCATIIIIIGCCGGT (SEQ ID NO:46)
TGCAGAAGC ACC-3';

EsxC6-ACP 3' primer
5'-GCTTGACTACGATACTGTGCGAIIIIIGAACCA (SEQ ID NO:47)
TGTTTCTGAATGCC-3';

EsxN1-ACP 5' primer
5'-GTCTACCAGGCATTCGCTTCATIIIIIGAATCT (SEQ ID NO:50)
GAAACAACT TTCTA-3';

EsxC2-ACP 3' primer
5'-GCTTGACTACGATACTGTGCGAIIIIIGATGCA (SEQ ID NO:55)
TGGGACGAG GCACC-3';

EsxN3-ACP 5' primer
5'-GTCTACCAGGCATTCGCTTCATIIIIICGCCGC (SEQ ID NO:53)
AACCCCTG CCCGCA-3';
and EsxC5-ACP 3' primer
5'-GCTTGACTACGATACTGTGCGAIIIIIGATGCA (SEQ ID NO:56)
TGGGACGA GGCA-3'.
```

The 5'-end portion sequences of the ACPs were served as pre-selected arbitrary primer sequences only for the second-stage PCR amplification: JYC2 and JYC4 5'-GTCTACCAG-GCATTCGCTTCAT-3' (SEQ ID NO:12).

During the first-stage PCR amplification, the primer set of EsxN7-ACP and EsxC6-ACP was used as 5' and 3' primers, respectively, to generate the 520-bp fragment of the Esx1 cDNA, the primer set of EsxN1-ACP and EsxC2-ACP was used as 5' and 3' primers, respectively, to generate the 784-bp fragment of the Esx1 cDNA, and the primer set of EsxN3-ACP and EsxC5-ACP was used as 5' and 3' primers, respectively, to generate the 483-bp fragment of the Esx1 cDNA.

During the second-stage PCR amplification, JYC4 and JYC2 were used as pre-selected arbitrary 5' and 3' primers, respectively (PROTOCOL A). As an alternative, the complete sequences of the ACPs, instead of the pre-selected arbitrary primers such as JYC4 and JYC2, can be used as 5' and 3' primers for the second-stage PCR amplification at the high stringent conditions. In this case, it is not necessary to add the pre-selected arbitrary primers to the reaction mixture at the time of or after the first-stage PCR reaction (PROTOCOL B).

PROTOCOL A: One-Stop Two-Stage PCR Amplifications (A) First-Stage PCR Amplification The first-stage PCR amplification was performed by hot start PCR method in which the procedure is to set up the complete reactions without the DNA polymerase and incubate the tubes in the thermal cycler to complete the initial denaturation step at >90° C. Then, while holding the tubes at a temperature above 70° C., the appropriate amount of DNA polymerase can be pipetted into the reaction.

The first-stage PCR amplification was conducted by two cycles of PCR consisting of annealing, extending and denaturing reaction; the reaction mixture in a final volume of 49.5 μl containing 50 ng of the first-strand cDNA, 5 μl of 10×PCR reaction buffer (Promega), 5 μl of 25 mM MgCl2, 5 μl of dNTP (2 mM each dATP, dCTP, dGTP, dTTP), 1.35 μl of 5' ACP (1 μM) and 1.35 μl of 3' ACP (1 μM) is pre-heated at 94° C., while holding the tube containing the reaction mixture at the 94° C., 0.5 μl of Taq polymerase (5 units/μl; Promega) is added into the reaction mixture; the PCR reactions comprise two cycles of 94° C. for 40 sec, 60° C. for 40 sec, and 72° C. for 40 sec; followed by denaturing the amplification product at 94° C.

(B) Second-Stage PCR Amplification

The resultant cDNA product generated by the first-stage PCR amplification using Esx1 gene-specific ACPs was then amplified by the following second-stage PCR amplification under higher annealing temperature. After the completion of the first-stage PCR amplification, each 1 μl of 10 μM pre-selected arbitrary primers, JYC4 and JYC2, was added into the reaction mixture obtained from the first-stage PCR amplification, under denaturing temperature such as at 94° C. The second stage-PCR reaction was as follows: 35 cycles of 94° C. for 40 sec, 68° C. for 40 sec, and 72° C. for 40 sec; followed by a 5 min final extension at 72° C.

The amplified products were analyzed by electrophoresis in a 2% agarose gel and detected by staining with ethidium bromide. The resulting PCR products can be also detected on a denaturing polyacrylamide gel by autoradiography or non-radioactive detection methods such as silver staining (Gottschlich et al., 1997; Kociok et al., 1998), the use of fluorescent-labelled oligonucleotides (Bauer et al. 1993; Ito et al. 1994; Luehrsen et al., 1997; Smith et al., 1997), and the use of biotinylated primers (Korn et al., 1992; Tagle et al., 1993; Rosok et al., 1996).

Figure 10A:
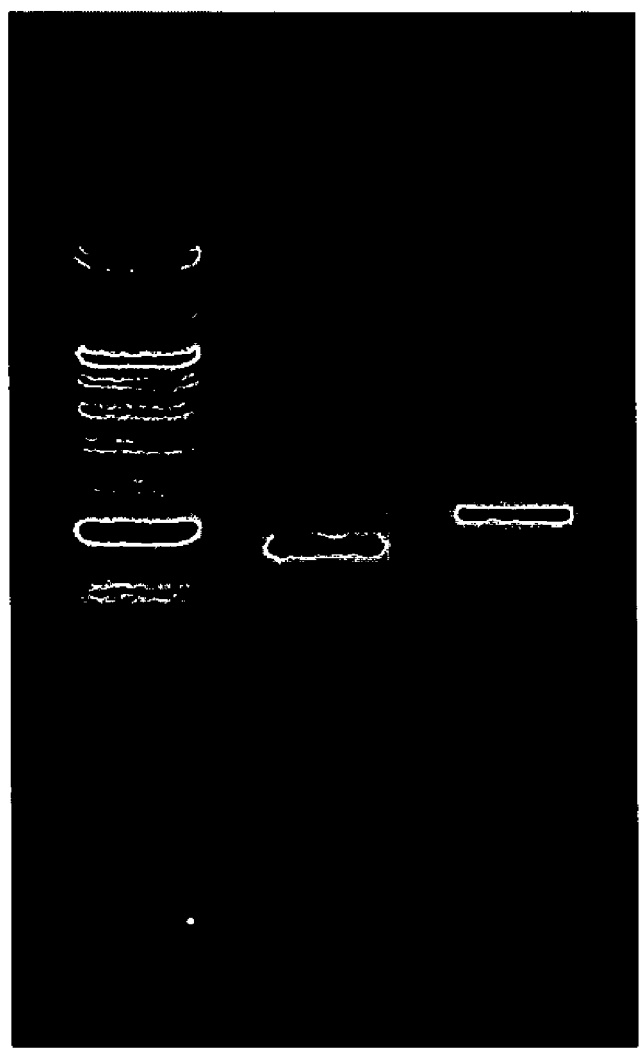
FIG. 10A is an agarose gel photograph to show the results of two stage PCR amplifications for Esx1 using a set of EsxN7 and EsxC6 primers (lane 1) and a set of EsxN7-ACP and EsxC6-ACP primers (lane 2).
Figure 10B:
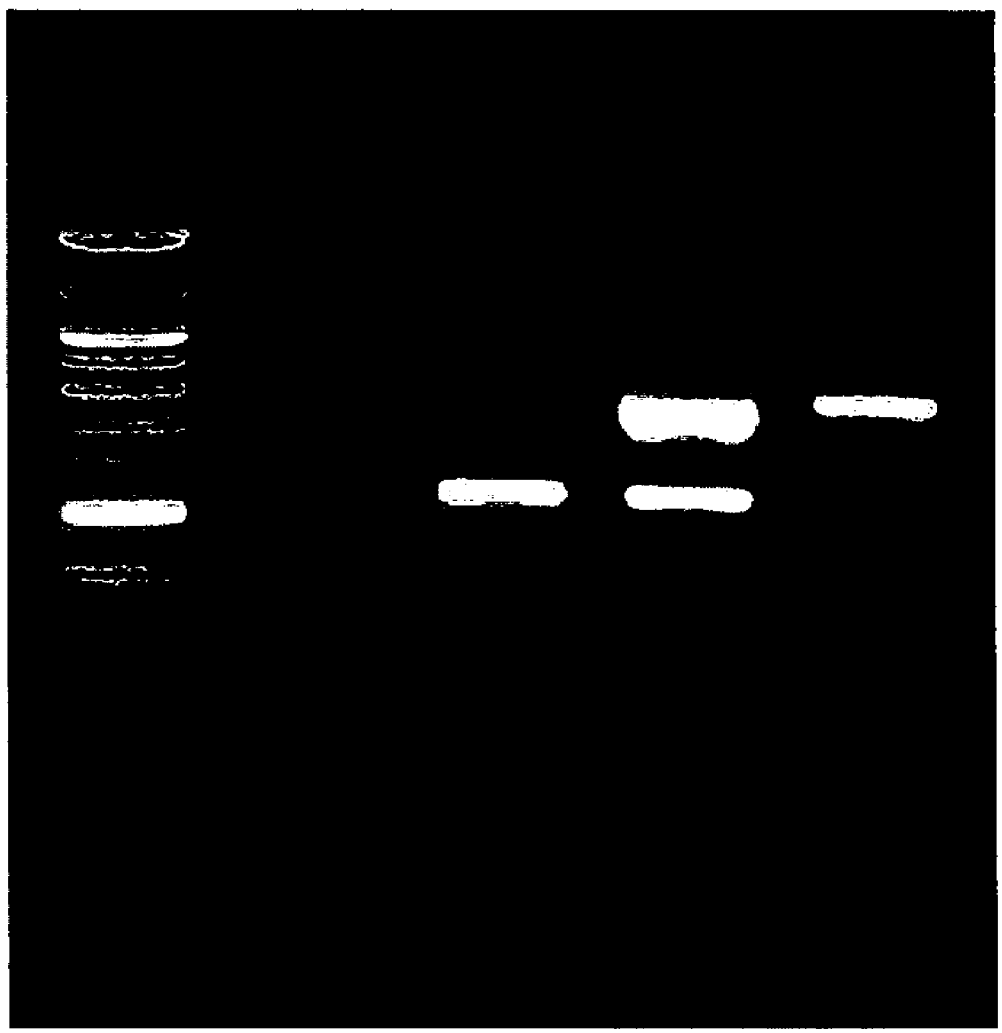
FIG. 10B is an agarose gel photograph to show the results of two stage PCR amplifications for Esx1 using EsxN1 (lane 1), EsxC2 (lane 2), a set of EsxN1-ACP and EsxC2 (lane 3), and a set of EsxN1-ACP and EsxC2-ACP (lane 4).
Figure 10C:
FIG. 10C is an agarose gel photograph to show the results of two stage PCR amplifications for Esx1 using a set of EsxN3 and EsxC5 (lanes 1 and 2) and a set of EsxN3-ACP and EsxC5-ACP (lane 3).

As shown in FIGS. 10A-C, the one-stop two-stage PCR amplifications for Esx1 using each primer set of EsxN7-ACP and EsxC6-ACP, EsxN1-ACP and EsxC2-ACP, and EsxN3-ACP and EsxC5-ACP generated a single band which corresponds to the expected size, 520-bp (FIG. 10A, lane 2), 784-bp (FIG. 10B, lane 4), and 483-bp (FIG. 10C, lane 3) of Esx1 cDNA fragments, respectively. Subsequent cloning and sequence analysis of the clones confirm that the band is Esx1 cDNA fragments. In contrast, the conventional primer sets, which contain the sequences corresponding only to the 3'-end portions of each ACP sets, produced non-specific products as well as high backgrounds such as DNA smear (FIG. 10A, lane 1; FIG. 10B, lane 3; FIG. 10C, lanes 1 and 2). Since the PCR products using a ACP set comprise the pre-selected arbitrary sequences at their 5'- and 3'-ends, additional 54-bp sequences corresponding to the pre-selected arbitrary sequences and deoxyinosine residues were found.

FIG. 10A shows the amplified cDNA products generated by the following sets of primers; a set of EsxN7 and EsxC6 (lane 1), and a set of EsxN7-ACP and EsxC6-ACP (lane 2). PCR reactions using the conventional primer set EsxN7 and EsxC6 were as follows: 5 min at 94° C. followed by 30 cycles of 94° C. for 40 sec, 60° C. for 40 sec, and 72° C. for 40 sec; followed by a 5 min final extension at 72° C.

FIG. 10B shows the amplified cDNA products generated by a single primer or a primer pair as follows: the primers, EsxN1 and EsxC2, were used in lanes 1 and 2, respectively; a combination of EsxN1-ACP and conventional primer EsxC2 was used in lanes 3; two ACPs EsxN1-ACP and EsxC2-ACP were used in lane 4. When a conventional primer set, EsxN1 and EsxC2, was used under high annealing temperature of 60° C., no specific-target product was produced. When a primer set comprising one ACP EsxN1-ACP and a conventional primer of EsxC2 was used, a target-specific product as well as non-specific products were amplified due to the non-specific binding of the conventional primer EsxC2 (lane 3). However, when a ACP set was used, only a single target-specific product was amplified (lane 4), which indicates that the ACP of the subject invention provides primers with tolerance to "primer design parameter" related to melting temperatures of general primers requested for single-target PCR systems.

FIG. 10C shows the amplified cDNA products generated by using the following primer sets: a set of EsxN3 and EsxC5 was used in lanes 1 and 2, and a set of EsxN3-ACP and EsxC5-ACP was used in lane 3. PCR reactions using the conventional primer set of EsxN3 and EsxC5 were as follows: 5 min at 94° C. followed by 30 cycles of 94° C. for 40 sec, 58° C. for 40 sec, and 72° C. for 40 sec; followed by a 5 min final extension at 72° C. (lane 1). The conventional primer set was also compared with the ACP set by conducting the same two stage PCR amplifications as used in the ACP, such that its annealing temperature is increased from 60° C. to 68° C. (lane 2). These results also indicate that although the conventional primers including ones having high Tm are used in the same two stage PCR amplification, they could not be free from the problems of non-specific products and background, whereas the ACP of the subject invention can help overcome such problems arising from these conventional primers.

PROTOCOL B: Non-Stop Two-Stage PCR Amplifications

Alternatively, the complete sequences of the ACPs, instead of the pre-selected arbitrary primers such as JYC4 and JYC2, can be used as primers for the second-stage PCR amplification at the high stringent conditions. In this case, it is not necessary to add the pre-selected arbitrary primers to the reaction mixture at the time of or after the first-stage PCR reaction.

The process of the non-stop two-stage PCR amplifications is basically identical to Protocol A, except that the ACPs, 1 μl of 5' ACP (10 μM) and 1 μl of 3' ACP (10 μM), are added at the first stage PCR amplification and the second stage PCR amplification immediately follows the first stage PCR amplification without any delay because there is no step of adding pre-selected arbitrary primers.

The amplified products were analyzed by electrophoresis in a 2% agarose gel and detected by staining with ethidium bromide. The resulting PCR products can be also detected on a denaturing polyacrylamide gel by autoradiography or non-radioactive detection methods such as silver staining (Gottschlich et al., 1997; Kociok et al., 1998), the use of fluorescent-labelled oligonucleotides (Bauer et al. 1993; Ito et al. 1994; Luehrsen et al., 1997; Smith et al., 1997), and the use of biotinylated primers (Korn et al., 1992; Tagle et al., 1993; Rosok et al., 1996).

Figure 10D:
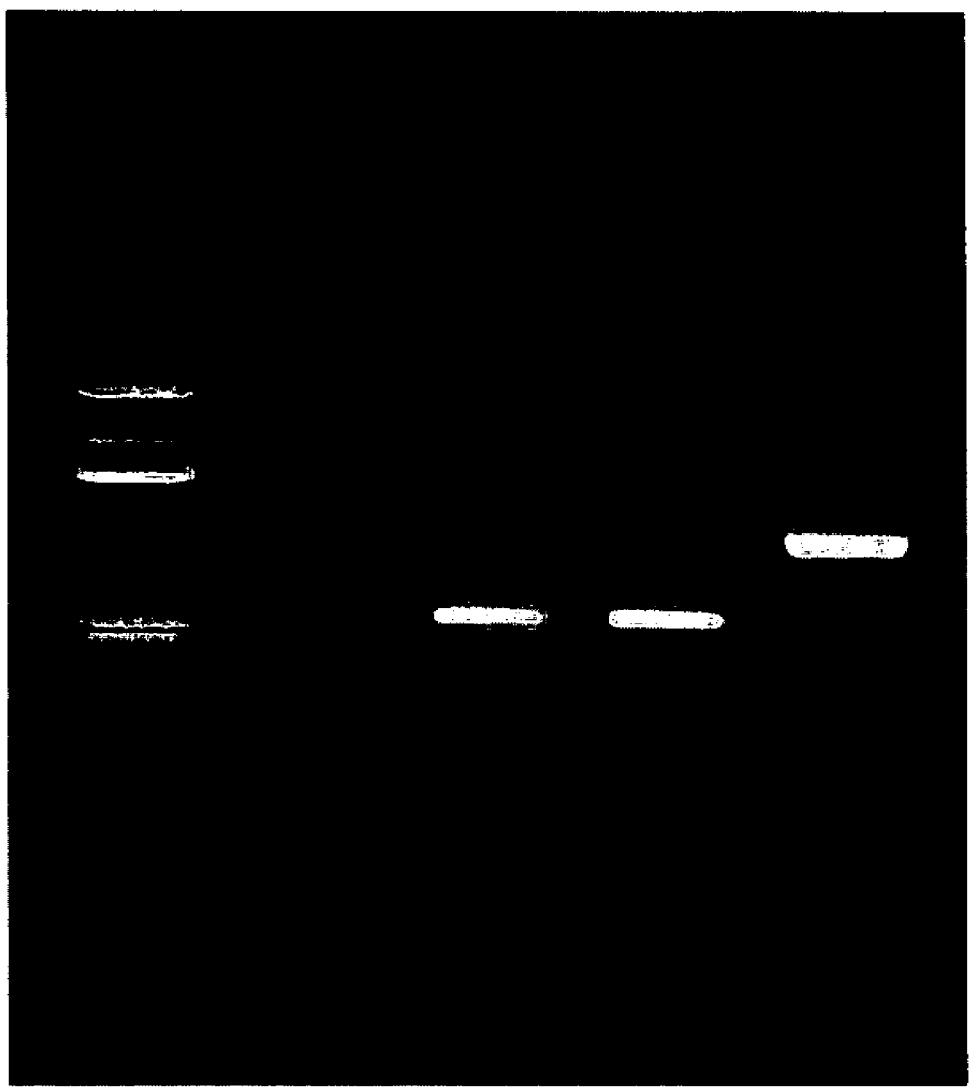
FIG. 10D is an agrasoe gel photograph to show the results of non-stop two stage PCR amplifications for Esx1 using the primer EsxN1 (lane 1), EsxC2 (lane 2), a pair of EsxN1 and EsxC2 (lane 3) and a pair of EsxN1-ACP and EsxC2-ACP (lane 4).

FIG. 10D shows the amplified cDNA products generated by the non-stop two-stage PCR Amplifications using the following single primer or a primer pair; the primers EsxN1 and EsxC2 were used in lane 1 and 2, respectively; a pair of EsxN1 and EsxC2 was used in lane 3; and a pair of EsxN1-ACP and EsxC2-ACP was used in lane 4. When a conventional primer set, EsxN1 and EsxC2, was used, no specific-target product was produced. However, when a ACP set was used in non-stop two-stage PCR amplifications, only a single target-specific product was amplified (lane 4), which is consistent with the results of one-stop two-stage PCR Amplifications (FIG. 10B).

These examples illustrate that the ACP permits the products to be free from the background problems as well as non-specificity arising from the conventional primers used in PCR methods as described in the art. It could be also understood that the ACP allows the generation of the specific products regardless of the design of gene-specific primers.

Example 3

Identification and Characterization of Differentially Expressed mRNAs During Mouse Embryonic Development Using ACP The ACP of the subject invention has been applied to detect differentially expressed mRNAs in embryonic developments. Specifically, three different procedures and results using different stages of conceptus total RNAs as starting materials are described herein. The primers used in the subject invention are shown in Table 1.

A1. PROCEDURE 1

Step (1): First-Strand cDNA Synthesis

The first-strand cDNAs were prepared under the same conditions as used in the cDNA synthesis of Example 1 using the dT10-ACP1 or JYC5-T15-ACP as a cDNA synthesis primer. The resultant cDNAs were purified by a spin column (PCR purification Kit, QIAGEN) to remove primers, dNTP, and the above reagents. It is necessary to perform the purification step prior to the determination of the cDNAs concentration using the UV spectroscopy at an absorbance of 260 nm. The same amount of cDNAs from each sample was used for comparing their amplification patterns using the ACP system described herein.

Step (2): First-Stage PCR Amplification Using ACP

The following ACPs were used as arbitrary ACPs (AR-ACPs) for the first PCR amplification:

```
ACP3
5'-GTCTACCAGGCATTCGCTTCATIIIIIGCCATC (SEQ ID NO:3)
GACS-3';

ACP5
5'-GTCTACCAGGCATTCGCTTCATIIIIIAGGCGA (SEQ ID NO:5)
TGCS-3';

ACP8
5'-GTCTACCAGGCATTCGCTTCATIIIIICTCCGA (SEQ ID NO:8)
TGCS-3';
```

-continued

```
ACP10
5'-GTCTACCAGGCATTCGCTTCATIIIIIGCCATC  (SEQ ID NO:13)
GACC-3';

ACP13
5'-GTCTACCAGGCATTCGCTTCATIIIIIAGGCGA  (SEQ ID NO:16)
TGCG-3';
and

ACP14
5'-GTCTACCAGGCATTCGCTTCATIIIIICTCCGA  (SEQ ID NO:17)
TGCC-3'.
```

The 5'-end portion sequences of the dT10-ACP1 and AR-ACPs serve as pre-selected arbitrary primer sequences only for the second-PCR amplification. The pre-selected arbitrary primers are JYC2 and JYC4.

The first-strand cDNAs produced from step (1) were amplified by the following first-stage PCR amplification using one of AR-ACPs (ACP3, ACP5, ACP8, ACP10, ACP13, or ACP14) and the dT10-ACP1 as 5' and 3' primers, respectively. The first-stage PCR amplification was conducted in a 50 µl volume containing 50 ng of the first-strand cDNA, 5 µl of 10×PCR reaction buffer (Promega), 3 µl of 25 mM MgCl2, 5 µl of dNTP (0.2 mM each dATP, dCTP, dGTP, dTTP), 5 µl of 5' primer (1 µM), 5 µl of 3' primer (1 µM), and 0.5 µl of Taq polymerase (5 units/µl; Promega). The PCR reactions were as follows: 5 min at 94° C. followed by 20 cycles of 94° C. for 1 min, 50° C. for 1 min, and 72° C. for 1 min; followed by a 5 min final extension at 72° C.

The cycle of the first-stage PCR amplification can be varied depending on the types of samples. For example, the 20 cycles of the first PCR amplification were used for mouse conceptus samples.

Step (3): Second-Stage PCR Amplification Using Pre-Selected Arbitrary Primers Corresponding to the 5'-End Portion Sequences of ACPs The amplified cDNA products produced from step (2) are re-amplified by the following second-stage PCR amplification using two pre-selected arbitrary primers, JYC4 and JYC2, each corresponding to the 5'-end portion sequences of AR-ACP and dT10-ACP1, respectively. The second-stage PCR amplification was conducted in a 50 µl volume containing 5 µl of the first amplified cDNA products (50 µl), 5 µl of 10×PCR reaction buffer (Promega), 3 µl of 25 mM MgCl2, 5 µl of 2 mM dNTP, 1 µl of 5' primer (10 µM), 1 µl of 3' primer (10 µM), and 0.5 µl of Taq polymerase (5 units/µl). The PCR reactions were as follows: 5 min at 94° C. followed by 30 cycles of 94° C. for 1 min, 65° C. for 1 min, and 72° C. for 1 min; followed by a 5 min final extension at 72° C.

A2. PROCEDURE 2

The alternative procedure comprises the following steps of:

(a) providing a first sample of nucleic acids representing a first population of mRNA transcripts and a second sample of nucleic acids representing a second population of mRNA transcripts;

(b) contacting each of the first nucleic acid sample and the second nucleic acid sample with a first ACP, wherein the first ACP has a hybridizing sequence substantially complementary to a region of the first and second population of mRNA transcripts to hybridize therewith;

(c) reverse transcribing the mRNA to which the first ACP hybridizes to produce a first population of DNA strands that are complementary to the mRNAs in the first nucleic acid sample to which the first ACP hybridizes, and a second population of DNA strands that are complementary to the mRNA in the second nucleic acid sample to which the first ACP hybridizes;

(d) purifying and quantifying the complementary DNA strands produced as a result of the reverse transcription step (c);

(e) synthesizing a second DNA strand complementary to each of the first and second populations of DNA strands using a second ACP under low stringent conditions, by at least one PCR cycle comprising denaturing, annealing and primer extension, wherein the second ACP has a hybridizing sequence substantially complementary to the first and second populations of DNA strands;

(f) amplifying each second DNA strand obtained from step (e) under high stringent conditions, by at least one PCR cycle comprising denaturing, annealing and primer extension to generate first and second populations of amplification products using two pre-selected arbitrary primers each comprising a sequence corresponding to each 5'-end portion of the first and second annealing control primers; and (g) comparing the amount of individual amplification products in the first and second populations of amplification products.

The first-strand cDNAs are synthesized using JYC5-T15-ACP 5'-CTGTGAATGCTGC GACTACGATII-IIIITTTTTTTTTTTTTTT-3' (SEQ ID NO:61).

The 5'-end portion sequence of the JYC5-T15-ACP serves as a 3' pre-selected arbitrary primer sequence to be used only for the second stage of PCR amplification:

```
JYC5
5'-CTGTGAATGCTGCGACTACGAT-3'.   (SEQ ID NO:60)
```

Step (1): First-Strand cDNA Synthesis

1. Combine 3 µg total RNA and 2 µl of 10 µM JYC5-T15-ACP in a sterile 0.2 ml microcentrifuge tube.

2. Add sterile H2O to a final volume of 9.5 µl. Mix contents and spin the tube briefly in a microcentrifuge.

3. Incubate the tube at 80° C. for 3 minutes or use a thermocycler for the same purpose.

4. Cool the tube on ice for 2 minutes. Spin down the contents of the tube briefly in a microcentrifuge.

5. To the same reaction tube add the following reagents: 4 µl 5× First-strand buffer (Promega), 5 µl dNTP (2 mM each dATP, dCTP, dGTP, dTTP), 0.5 µl RNasin inhibitor (40 units/µl, Promega) and 1 µl M-MLV reverse transcriptase (200 U/µl).

6. Mix contents and spin the tube briefly in a microcentrifuge.

7. Incubate the tube at 42° C. for 90 min.

8. Incubate the tube at 94° C. for 2 minutes to terminate first-strand synthesis.

9. Place the tube on ice for 2 min.

10. Purify the resultant cDNAs by a spin column (PCR purification Kit, QIAGEN) to remove primers, dNTP, and the above reagents.

11. Next, measure the concentration of the cDNAs using the UV spectroscopy at an absorbance of 260 nm.

12. Process to step 2.

Step (2): Second-Strand cDNA Synthesis Using ACP

The same amount of cDNAs from each sample was used for the comparison of their amplification patterns using the ACPs described herein. The second-strand cDNA was synthesized using arbitrary ACP10 by hot start PCR method in which the procedure is to set up the complete reactions without the DNA polymerase and incubate the tubes in the thermal cycler to complete the initial denaturation step at >90° C. Then, while holding the tubes at a temperature above 90° C., the appropriate amount of DNA polymerase can be pipetted into the reaction.

1. Combine the following reagents in a sterile 0.2 ml microcentrifuge tube: 49.5 µl of the total volume containing 1 µl of first-strand cDNA (50 ng/µl) prepared by step 1, 5 µl of 10×PCR buffer (Roche), 5 µl of 2 mM dNTP, 1 µl of 10 µM arbitrary ACP (5' primer) and 37.5 µl of sterile dH2O.

2. Mix contents and spin the tube briefly in a microcentrifuge.

3. Place the tube in the preheated thermal cycler at 94° C.

4. Add the 0.5 µl of Taq polymerase (5 units/µl; Roche) into the reaction, while holding the tube at the temperature 94° C.

5. Conduct PCR reaction under the following conditions: one cycle of 94° C. for 5 min, 50° C. for 3 min, and 72° C. for 1 min; followed by denaturing the first amplification product at 94° C.

Step (3): PCR Amplification of the second-strand cDNAs using pre-selected arbitrary primers corresponding to the 5'-end portion sequences of ACPs 1. After the completion of the first stage PCR amplification, while holding the tubes at a temperature above 94° C., add 2 µl of 10 µM JYC4 and 2 µl of 10 µM JYC5, in which each corresponds to the 5'-end portion sequences of both 5' and 3' ACPs, respectively, into the reaction mixture used in step (2).

2. Conduct second stage PCR reactions under the following conditions: 40 cycles of 94° C. for 40 sec, 68° C. for 40 sec, and 72° C. for 40 sec; followed by a 5 min final extension at 72° C.

A3. PROCEDURE 3

As an alternative process, in the step (f) of PROCEDURE 2 the complete sequences of the first and second ACPs used in the steps (b) and (e) of PROCEDURE 2, instead of the preselected arbitrary sequences of the 5'-end portions of the first and second ACPs, can be used as 3' and 5' primers, respectively, at the high stringent conditions for amplifying each second DNA strand obtained from the step (e) of PROCEDURE 2, wherein the 3'- and 5'-ends of the second DNA strands which were initially synthesized using the second ACP comprise the sequence of the first ACP and the complementary sequence of the second ACP, respectively, and also serve as perfect pairing sites to the first and second ACPs. In this case, it is not necessary to add the pre-selected arbitrary primers to the reaction mixture at the time of or after first-stage PCR reaction.

Step (1): First-Strand cDNA Synthesis

The first-strand cDNAs were prepared under the same conditions as used in the cDNA synthesis of PROCEDURE 2 using the JYC5-T15-ACP as a cDNA synthesis primer.

Step (2): Second-Strand cDNA Synthesis and Amplification Using Non-Stop Two-Stage PCR The same amount of cDNAs from each sample was used for the comparison of their amplification patterns using the ACPs described herein. The second-strand cDNA was synthesized using arbitrary ACP10 by hot start PCR method in which the procedure is to set up the complete reactions without the DNA polymerase and incubate the tubes in the thermal cycler to complete the initial denaturation step at >90° C. Then, while holding the tubes at a temperature above 90° C., the appropriate amount of DNA polymerase can be pipetted into the reaction.

1. Combine the following reagents in a sterile 0.2 ml microcentrifuge tube: 49.5 µl of the total volume containing 1 µl of first-strand cDNA (50 ng/µl) prepared by step 1, 5 µl of 10×PCR buffer (Roche), 5 µl of 2 mM dNTP, 1 µl of 10 µM arbitrary ACP10 (5' primer), 1 µl of 10 µM JYC5-T15-ACP (3' primer) and 36.5 µl of sterile dH2O.

2. Mix contents and spin the tube briefly in a microcentrifuge.

3. Place the tube in the preheated thermal cycler at 94° C.

4. Add the 0.5 µl of Taq polymerase (5 units/µl; Roche) into the reaction, while holding the tube at the temperature 94° C.

5. Conduct PCR reaction under the following conditions: one cycle of 94° C. for 1 min, 50° C. for 3 min, and 72° C. for 1 min; followed by 40 cycles of 94° C. for 40 sec, 65° C. for 40 sec, and 72° C. for 40 sec; and followed by a 5 min final extension at 72° C.

B. Separation of Amplified PCR Products by Electrophoresis Analysis and Recovery of the Differentially Displayed Bands The amplified products were analyzed by electrophoresis in a 2% agarose gel and detected by staining with ethidium bromide. Several major bands differentially expressed during embryonic development (E4.5, E11.5, and E18.5) were selected, excised and extracted from the gels using GENECLEAN II Kit (BIO 101). The resulting PCR products can be also detected on a denaturing polyacrylamide gel by autoradiography or non-radioactive detection methods such as silver staining (Gottschlich et al., 1997; Kociok et al., 1998), the use of fluorescent-labelled oligonucleotides (Bauer et al. 1993; Ito et al. 1994; Luehrsen et al., 1997; Smith et al., 1997), and the use of biotinylated primers (Korn et al., 1992; Tagle et al., 1993; Rosok et al., 1996).

C. Re-Amplification of the Recovered Bands

The bands obtained from step B were re-amplified using the same pre-selected arbitrary primers and PCR conditions as used in PROCEDURE 1, 2 and 3.

D. Cloning and Sequencing of the Re-Amplified Fragments

Each amplified fragment was cloned into the pGEM-T Easy vector (Promega) and sequenced with the ABI PRISM 310 Genetic Analyzer (Perkin Elmer Biosystem) using Big-Dye Terminator cycle sequencing kit (Perkin Elmer). Computer-assisted sequence analysis was carried out using the BLAST search program (Basic Local Alignment Search Tool).

E. Northern Analysis

Twenty micrograms of total RNA from conceptus tissues were resolved on denaturing 1% agarose gels containing formaldehyde, transferred onto nylon membranes (Hybond-N, Amersham, USA), and hybridized with a 32P-labeled subcloned PCR product in QuikHyb solution (Stratagene, USA) overnight at 58° C. as previously described (Chun et al., 1999; Hwang et al., 2000). Blots were washed at 65° C. twice for 20 min in 2×SSC, 0.1% SDS, twice for 20 min in 1×SSC, 0.1% SDS, and twice for 20 min in 0.1×SSC, 0.1% SDS. The membranes were exposed to Kodak X-Omat XK-1 film with a Fuji intensifying screen at −80° C.

Figure 11A:
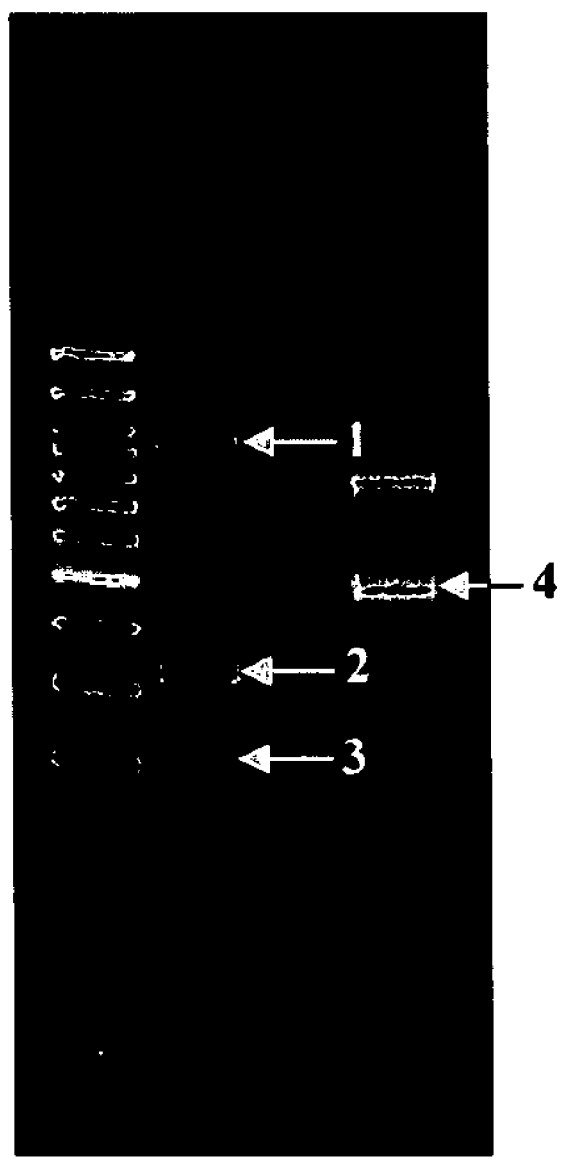
FIG. 11A is a photograph of agarose gels to show examples of the ACP used for detecting differentially expressed mRNAs during embryonic development using different stages of mouse conceptus tissues. The cDNAs were amplified using total RNA isolated from conceptus tissues at E4.5 (lane 1), E11.5 (lane 2), and E18.5 (lane 3), with a set of ACP3 (SEQ ID NO. 3) and dT10-ACP1. The bands indicated by arrows represent the cDNA fragments amplified from differentially expressed mRNAs. The numbers of the arrows indicate the cDNA fragments used as probes in the Northern blot analysis of FIG. 13.
Figure 11B:
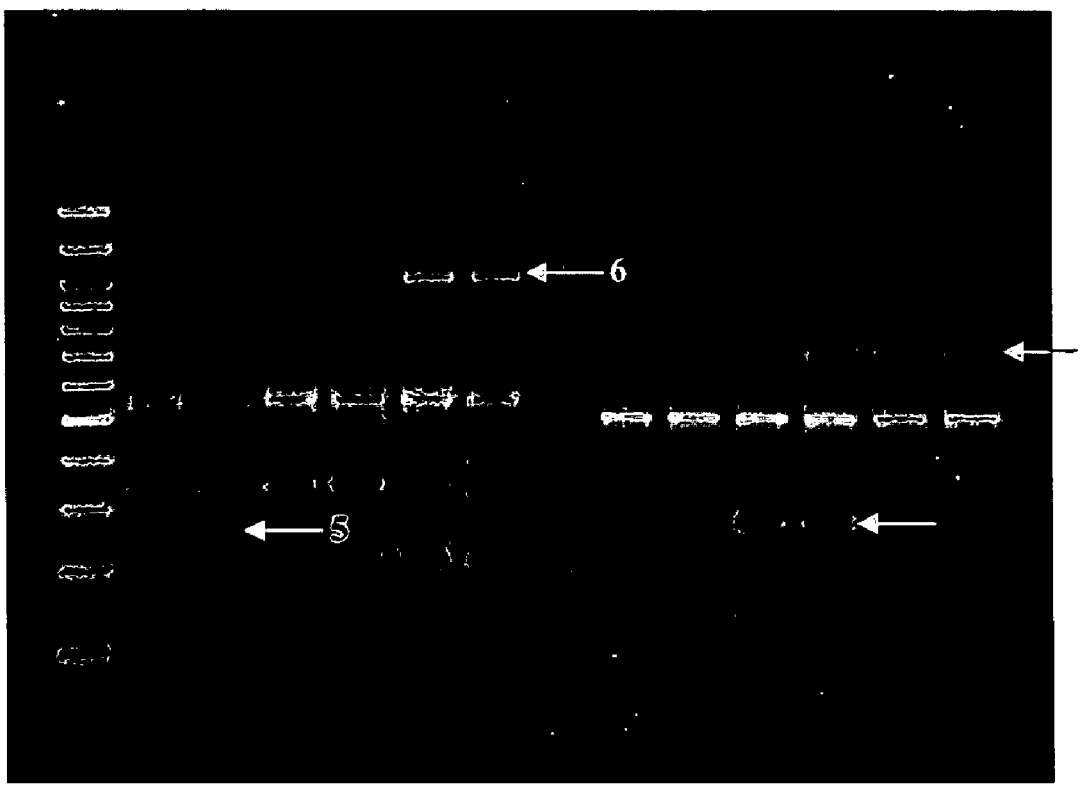
FIG. 11B is a photograph of agarose gels to show examples of the ACP used for detecting differentially expressed mRNAs during embryonic development using different stages of mouse conceptus tissues. The cDNAs were amplified using total RNA isolated from conceptus tissues at E4.5 (lanes 1-2 and 7-8), E11.5 (lanes 3-4 and 9-10), and E18.5 (lanes 5-6 and 11-12), with a set of ACP5 (SEQ ID NO. 5) and dT10-ACP1 (the lanes 1-6), and a set of ACP8 (SEQ ID NO. 8) and dT10-ACP1 (lanes 7-12), respectively. The bands indicated by arrows represent the cDNA fragments amplified from differentially expressed mRNAs. The numbers of the arrows indicate the cDNA fragments used as probes in the Northern blot analysis of FIG. 13.
Figure 11C:
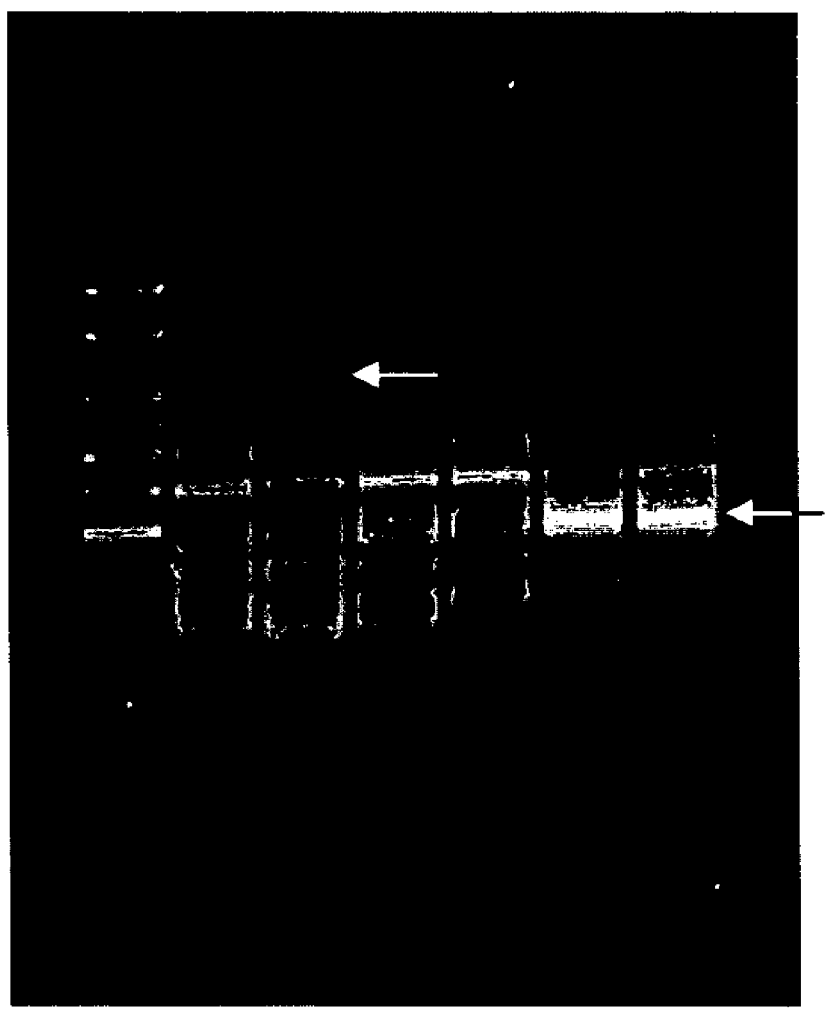
FIG. 11C is an agarose gel photograph to show the amplified cDNA products obtained from different stages of mouse conceptus samples (E4.5: lanes 1 and 2; E11.5: lanes 3 and 4; E18.5: lanes 5 and 6) using a set of ACP10 and dT10-ACP primers.
Figure 11D:
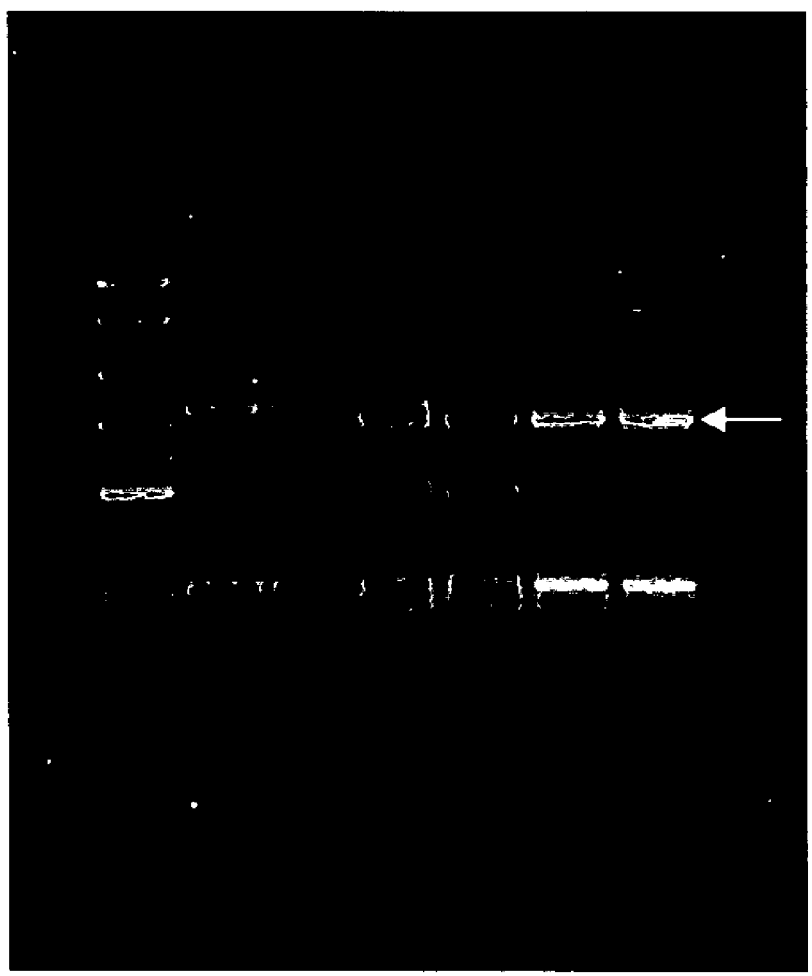
FIG. 11D is an agarose gel photograph to show the amplified cDNA products obtained from different stages of mouse conceptus samples (E4.5: lanes 1 and 2; E11.5: lanes 3 and 4; E18.5: lanes 5 and 6) using a set of ACP14 and T10-ACP1 primers.

FIGS. 11A-D shows the amplified cDNA products, wherein mouse conceptus samples obtained from different stages were amplified by PROCEDURE 1 using the primer sets as follows; a set of ACP3 and dT10-ACP1 for the lanes 1-3 of FIG. 11A; a set of ACP5 and dT10-ACP1 for the lanes 1-6 and of FIG. 11B and a set of ACP8 and dT10-ACP1 for the lanes 7-12 of FIG. 10B, respectively. FIG. 1B also shows additional results of the amplified cDNA products generated by using another ACP sets. FIGS. 11C-D shows the amplified products generated by using two primer sets of the ACP10 and dT10-ACP1 (FIG. 11C), and ACP14 and dT10-ACP1 (FIG. 11D), respectively. Many differentially expressed bands in a specific stage were obtained, subcloned into the pGEM-T Easy vector (Promega), and sequenced. Sequence analysis reveals that all of the clones are known genes except two novel genes (Table 2). The expression patterns were confirmed by Northern blot analysis using mouse conceptus stage blot (Seegene, Inc., Seoul, Korea).

Figure 12A:
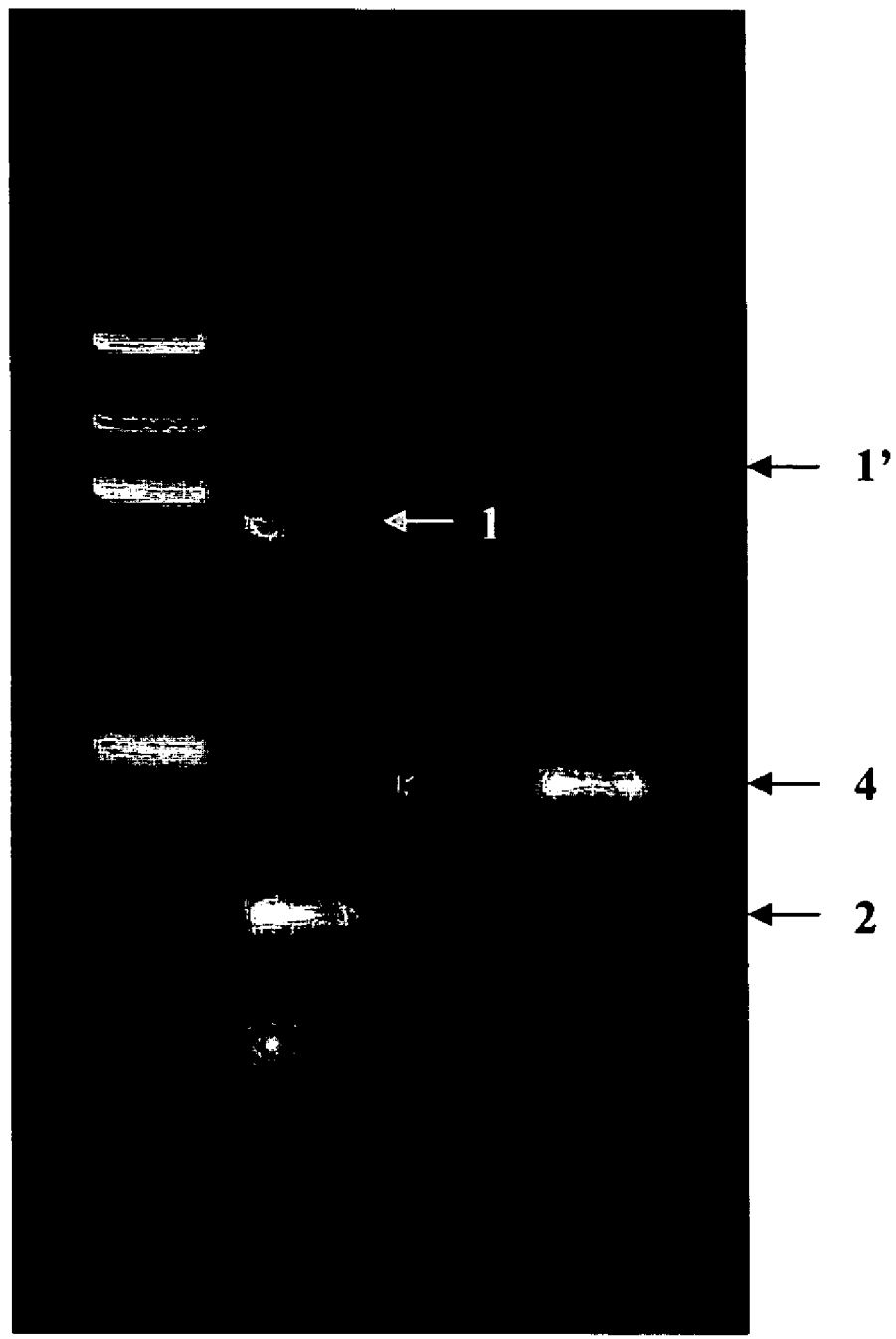
FIG. 12A is an agarose gel photograph to show the amplified cDNA products obtained from different stages of mouse conceptus samples (E4.5: lane 1; E11.5: lane 2; E18.5: lane 3) by one-stop two-stage PCR amplification using a set of ACP10 and JYC5-T15-ACP primers.

FIG. 12A shows the amplified cDNA products, wherein mouse conceptus samples (E4.5: lane 1; E11.5: lane 2; E18.5: lane 3) obtained from different stages were amplified by PROCEDURE 2 using a set of ACP10 and JYC5-T15-ACP. Many differentially expressed bands in a specific stage were obtained, subcloned into the pGEM-T Easy vector (Promega), and sequenced. Sequence analysis reveals that all of the clones are known genes except one DEG 2 (Table 2). The expression patterns were confirmed by Northern blot analysis using mouse conceptus stage blot (Seegene, Inc., Seoul, Korea).

Figure 12B:
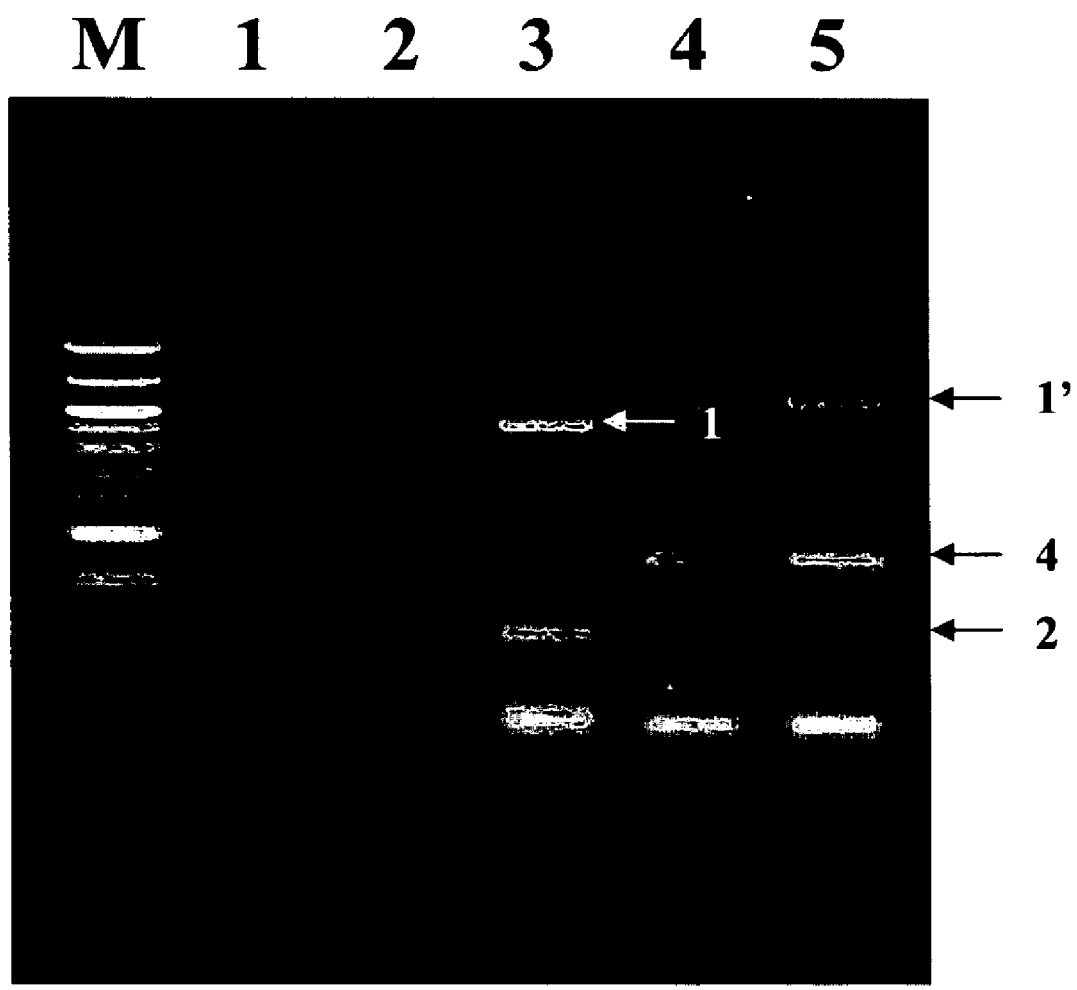
FIG. 12B is an agarose gel photograph to show the amplified cDNA products obtained from different stages of mouse conceptus samples (E4.5: lane 1; E11.5: lane 2; E18.5: lane 3) by non-stop two-stage PCR amplification using a set of ACP10 and JYC5-T15-ACP primers.

FIG. 12B shows the amplified cDNA products, wherein mouse conceptus samples at the different stages of (E4.5: lane 3; E11.5: lane 4; E18.5: lane 5) were amplified by non-stop two-stage PCR amplifications using a set of ACP10 and JYC5-T15-ACP as above mentioned in PROCEDURE 3. When a set of ACP10 and JYC5-T15-ACP (lanes 3-5) was used, the resultant bands were identical to the bands which were obtained by PROCEDURE 2 comprising one-stop two-stage PCR amplifications (FIG. 12A). However, no products were generated when a single primer, ACP10 (lane 1) or JYC5-T15-ACP (lane 2) was used, which indicates that the amplified products were generated only when both ACP10 and JYC5-T15-ACP as a set were used for their specific bindings.

Figure 13:
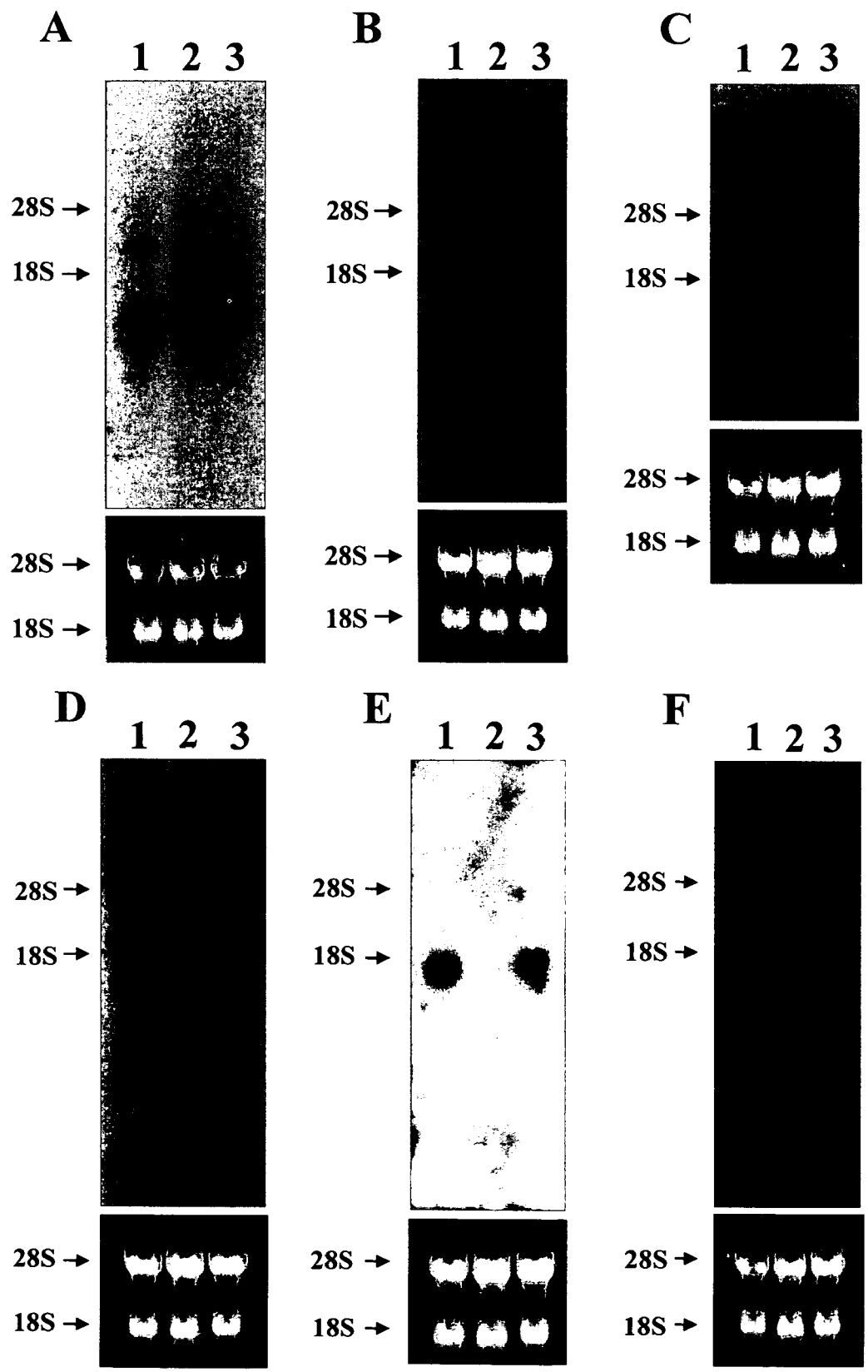
FIG. 13 shows Northern blot analysis of six cDNA fragments amplified from differentially expressed mRNAs during embryonic development. The six 32P-labeled fragments indicated by arrows in FIG. 11 were used as probes for Northern blot analysis. The arrows 1, 2, 3, 4, 5, and 6 are DEG1 (FIG. 13A), DEG3 (FIG. 13B), DEG2 (FIG. 13C), DEG8 (FIG. 13D), DEG5 (FIG. 13E), and DEG7 (FIG. 13F), respectively, wherein the results of the DEG sequence analysis are shown in Table 1. DEG2 (SEQ ID NO. 31) and DEG5 (SEQ ID NO. 32) are turned out as novel genes (Table 2). The control panels (the lower part of each panel) show each gel before blotting, stained with ethidium bromide and photographed under UV light, demonstrating similar levels of 18S and 28S rRNA as a loading control.

FIG. 13 shows the results of Northern blot hybridization for representing six different clones using DEG1 (A; arrow 1 of FIG. 10A, FIG. 11, and FIG. 12), DEG2 (C), DEG3 (B; arrow 2 of FIG. 10A, FIG. 11, and FIG. 12), DEG5 (E), DEG7 (F), and DEG8 (D; arrow 4 of FIG. 10A, FIG. 11, and FIG. 12) as probes. The DEG1 probe was also hybridized to the alternative isoform of Tropomyosin 2 (arrow 1' of FIG. 11, and FIG. 12), which was discovered by this present invention. Consistent with the results of agarose gel analysis, Northern blot analysis showed that the expression patterns of the clones are identical to the original bands on the agarose gels, indicating that all of the clones are true positive products. Thus, the ACP produces only positive products without any false positives, which means that the ACP eliminates the problem of false positives.

Figure 14:
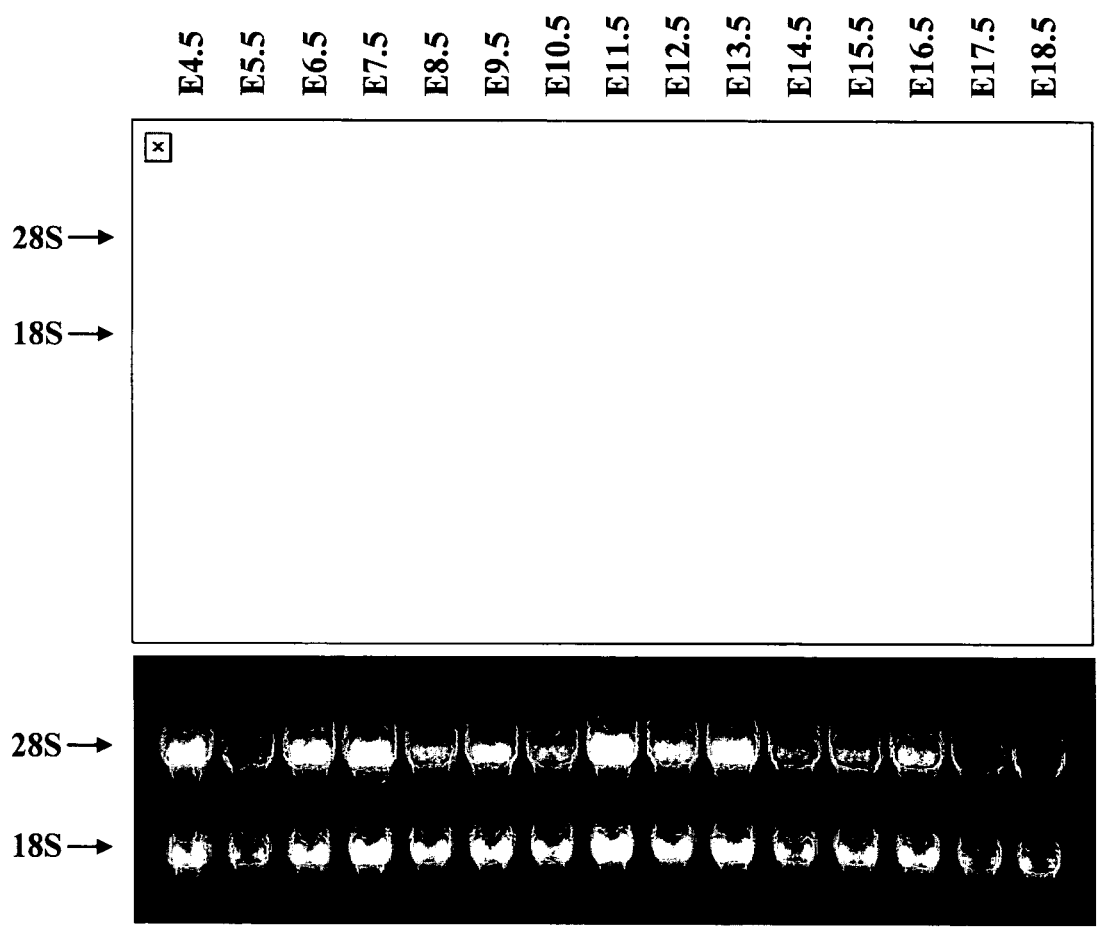
FIG. 14 shows the expression patterns of a novel gene, DEG5, in a full stage of mouse conceptus. Northern blot analysis was performed using the radio-labeled DEG5 cDNA fragment as a probe. Total RNA (20 µg/lane) was prepared from mouse conceptuses at the gestation times as indicated. The control panel at the lower part shows a gel before blotting, stained with ethidium bromide and photographed under UV light, demonstrating similar levels of 18S and 28S rRNA as a loading control.

FIG. 14 shows the results of Northern blot hybridization for the expression of DEG5 during mouse embryonic development. DEG5, which is turned out as a novel gene by sequence analysis, shows an interesting expression patterns: after a strong expression appeared in the early pregnancy stage (E4.5), its expression was gradually reduced in the middle stages and gradually increased again in the late development stage (E17.5 and E18.5).

These results indicate that the method using ACP for isolating differentially expressed genes produces only real PCR products and completely eliminates false positive products. Freedom from false positives which have been one major bottleneck remaining for the previous Differential Display technique allows avoiding the subsequent labor-intensive work required for the verification of the cDNA fragments identified by Differential Display.

Example 5

Method for Rapid Amplification of 3'-Ends of cDNA (3'-RACE) Using ACP

The present example compares the ACP-based 3'-RACE and the conventional 3'-RACE in order to demonstrate if the ACP of the present invention can exclude such background problems arising from conventional oligo-dT primers used in cDNA synthesis.

In the conventional 3'-RACE, the poly(A) tail of mRNA molecules is exploited as a priming site for PCR amplification and thus the oligo-dT primer is used as a 3' primer for the conventional 3'-RACE. In contrast, the ACP of the present invention uses the poly(A) tail of mRNA as a priming site only for the cDNA synthesis but not for the subsequent PCR amplification.

Mouse first-strand cDNAs were prepared under the same conditions as used in the cDNA synthesis of Example 1 using Oligo VdT15-ACP 5'-GCTTGACTACGATACTGTGC-GAIIIII TTTTTTTTTTTTTTTV-3' (SEQ ID NO:57) (V is A, C or G) as a cDNA synthesis primer and then, directly used as templates for the subsequent PCR amplification without the purification step for the removal of the cDNA synthesis primer.

For the conventional 3'-RACE, the first-strand cDNAs were synthesized using the following cDNA synthesis primer;

CDS III/3' 5'-ATTCTAGAGGCCGAGGCGGCCGA-CATG-(dT)30-VN-3' (SEQ ID NO:35) (V is A, C or G; and N is A, C, T or G).

This cDNA synthesis primer, CDS III/3', was used as 3' primer for subsequent PCR amplification.

The PCR amplification was conducted in a 50 µl volume containing 50 ng of the first-strand cDNA, 5 µl of 10×PCR buffer (Promega), 1 µl of a gene-specific 5'primer (10 µM), 1 µl of pre-selected arbitrary 3' primer JYC2 (10 µM) or CDS III/3' (10 µM), 3 µl of 25 mM MgCl2, 5 µl of 2 mM dNTP, 0.5 µl Taq polymerase (5 units/µl; Promega). The PCR reactions were conducted under the following conditions: 5 min at 94° C. followed by 30 cycles of 94° C. for 1 min, 65° C. for 1 min, and 72° C. for 1 min; followed by a 5 min final extension at 72° C. Amplified products were analyzed by electrophoresis in a 2% agarose gel followed by ethidium bromide staining. The resulting PCR products can be also detected on a denaturing polyacrylamide gel by autoradiography or non-radioactive detection methods such as silver staining (Gottschlich et al., 1997; Kociok et al., 1998), the use of fluorescent-labelled oligonucleotides (Bauer et al. 1993; Ito et al. 1994; Luehrsen et al., 1997; Smith et al., 1997), and the use of biotinylated primers (Korn et al., 1992; Tagle et al., 1993; Rosok et al., 1996).

Figure 15:
FIG. 15 is an agarose gel photograph to show the difference between the conventional 3'-RACE (lane 1) and the ACP-based 3'-RACE (lane 2) with regard to beta-actin 3'-RACE.

FIG. 15 shows the results of beta-actin 3'-RACE. The conventional 3'-RACE (lane 1) was compared with ACP-based 3'-RACE (lane 2). The conventional 3'-RACE method produced non-specific products as well as DNA smear background, whereas the ACP-based 3'-RACE produced only a single band, which is the expected size of 348-bp. These results indicate that the ACP-based 3'-RACE can exclude the background problems such as DNA smear and non-specific products.

Example 6

Method for Rapid Amplification of 5'-End (5'-RACE) and Full-Length cDNAs Using ACP The ACP of the subject invention was also used to amplify the 5'-ends of cDNA fragments. The first-strand cDNAs were synthesized using Oligo VdT15-ACP, or Random dN6-ACP:

```
Oligo VdT15-ACP
5'-GCTTGACTACGATACTGTGCGAIIIIITTTTTT  (SEQ ID NO:57)
TTTTTTTTV-3',
wherein V can be A, C, or G;

Random dN6-ACP
5'-GCTTGACTACGATACTGTGCGAIIIIINNNNN  (SEQ ID NO:58)
N-3',
wherein N can be A, C, G, or T.
```

After the complete synthesis of the first strand cDNA sequences present in the form of mRNA-cDNA intermediates, cytosine residues are tailed at the 3'-end of the first strand cDNA sequences by the terminal transferase reaction of reverse transcriptase in the presence of manganese. The 3'-ends of the first strand cDNAs were extended using the first strand cDNA 3'-end extending ACP (rG3-ACP, rG2-ACP, or dG3-ACP) and then, directly used as templates for the subsequent PCR amplification without a purification step for the removal of the first strand cDNA 3'-end extending ACP as well as the cDNA synthesis primer.

The sequences of the first-strand cDNA 3'-end extending ACPs are:

```
rG3-ACP
5'-GTCTACCAGGCATTCGCTTCATIIIIIGGr   (SEQ ID NO:36)
(GGG)-3';

rG2-ACP
5'-GTCTACCAGGCATTCGCTTCATIIIIIGGr   (SEQ ID NO:37)
(GG)-dG-3';

rG1-ACP
5'-GTCTACCAGGCATTCGCTTCATIIIIIGGr   (SEQ ID NO:59)
(G)-d(GG)-3';
or dG3-ACP
5'-GTCTACCAGGCATTCGCTTCATIIIIIGGd   (SEQ ID NO:38)
(GGG)-3'
(wherein r and d represent ribo-
nucleotide and
deoxyribonucleotide, respectively).
```

A. First-Strand Full-Length cDNA Synthesis

PROTOCOL A: First-strand cDNA synthesis using the ACP of the subject invention

1. Combine the followings in a sterile 0.2 ml microcentrifuge tube: 3 μg of total RNA and 2 μl of 10 μM of Oligo VdT15-ACP or random dN6-ACP.
2. Add sterile H2O to a final volume of 10 μl. Mix contents and spin the tube briefly in a microcentrifuge.
3. Incubate the tube in a 65° C. water bath for 15 minutes or use a thermocycler for the same purpose.
4. Cool the tube on ice for at least 2 minutes. Spin down the contents of the tube briefly in a microcentrifuge.
5. Add the following reagents to the same reaction tube: 4 μl of 5× first-strand buffer (Invitrogen), 1 μl of 0.1 M DTT, 2 μl of BSA (1 mg/ml), 2 μl of dNTP (10 mM each dATP, dCTP, dGTP, dTTP), 0.4 μl of 100 mM MnCl2 and 0.5 μl of RNasin inhibitor (40 units/μl, Promega).
6. Mix contents and spin the tube briefly in a microcentrifuge.
7. Incubate the tube at 42° C. for 2 minutes in an incubator or thermocycler.
8. Add 1 μl of SuperScript II reverse transcriptase (200 units/μl; Invitrogen).
9. Incubate the tube at 42° C. for 1 hour in an incubator or thermocycler.
10. Add 1 μl of 10 μM first strand cDNA 3'-end extending ACP (rG3-ACP, rG2-ACP, or dG3-ACP).
11. Add 0.3 μl of SuperScript II reverse transcriptase (200 units/μl; Invitrogen).
12. Incubate the tube at 42° C. for 30 minutes in an incubator or thermocycler.
13. Incubate the tube at 70° C. for 15 minutes in an incubator or thermocycler to terminate first-strand synthesis.
14. Place the tube on ice or can be stored at −20° C.

PROTOCOL B: First-Strand Full-Length cDNA Synthesis by CapFinder Method

The following primers are used in the CapFinder method (Clontech):

```
SMART IV ™ Oligonucleotide
5'-AAGCAGTGGTATCAACGCAGAGTGGCCATTACG  (SEQ ID NO:33)
GCCr(GGG)-3';
and 5' PCR primer
5'-AAGCAGTGGTATCAACGCAGAGT-3',          (SEQ ID NO:34)
and CDS III/3' PCR primer.
```

1. Combine the followings in a sterile 0.2 ml microcentrifuge tube: 3 μg of total RNA, 1 μl of 10 μM CDS III/3' PCR primer (Clontech) and 1 μl of 10 μM SMART IV Oligonucleotide (Clontech).
2. Add sterile H2O to a final volume of 5 μl. Mix contents and spin the tube briefly in a microcentrifuge.
3. Incubate the tube at 72° C. for 2 minutes.
4. Cool the tube on ice for 2 minutes. Spin down the contents of the tube briefly in a microcentrifuge.
5. Add the following reagents to the same reaction tube: 10 μl of the total volume containing 2 μl of 5× first-strand buffer (Clontech), 1 μl of 20 mM DTT, 1 μl of dNTP (10 mM each dATP, dCTP, dGTP, dTTP) and 1 μl of PowerScript Reverse Transcriptase (Clontech).
6. Mix contents and spin the tube briefly in a microcentrifuge.
7. Incubate the tube at 42° C. for 1 hour
8. Place the tube on ice or can be stored at −20° C.

B. PCR Amplification

PROTOCOL C: Amplification of a Target 5'-End cDNA Fragment Using ACP System or Conventional 5'-RACE Method The present example compares the current CapFinder 5'-RACE technology and ACP-based 5' RACE method, wherein the current CapFinder 5'-RACE technology could not exclude the high background due to residual amount of the primers during the process. In order to demonstrate if the ACP of the present invention can eliminate such background problems arising from primers such as the CapFinder primer, SMART IV Oligonucleotide (Clontech), and cDNA synthesis primer, CDS III/3' PCR primer (Clontech), used in cDNA synthesis, both the ACP-based 5'-RACE and the CapFinder 5'-RACE for the amplification of 5'-ends of mouse JunB and beta-actin cDNAs were conducted in the same conditions.

The mouse JunB mRNA is a relatively rare transcript in mouse 18.5-day-old placenta RNA, whereas mouse beta-actin is a relatively abundant.

1. Combine the following reagents in a sterile 0.2 ml microcentrifuge tube: 50 µl of the total volume containing 1 µl of first-strand cDNA prepared from Protocol A or B, 5 µl of 10×PCR buffer (Promega), 5 µl of 25 mM MgCl2, 5 µl of 2 mM dNTP, 1 µl of 10 µM gene-specific 5'-RACE primer, 1 µl of 10 µM JYC2 or 5' PCR primer (Clontech), 0.5 µl of Taq Polymerase (5 units/µl; Promega) and 31.5 µl of sterile dH2O.

2. Mix contents and spin the tube briefly in a microcentrifuge.

3. Conduct PCR reaction under the following conditions: 5 min at 94° C., followed by 30 cycles of 94° C. for 40 seconds, 58° C. for 40 seconds, and 72° C. for 1 min 30 sec; followed by a 5 min final extension at 72° C.

4. Analyze the amplified products by electrophoresis in a 2% agarose gel followed by ethidium bromide staining.

The resulting PCR products can be also detected on a denaturing polyacrylamide gel by autoradiography or non-radioactive detection methods such as silver staining (Gottschlich et al., 1997; Kociok et al., 1998), the use of fluorescent-labelled oligonucleotides (Bauer et al. 1993; Ito et al. 1994; Luehrsen et al., 1997; Smith et al., 1997), and the use of biotinylated primers (Korn et al., 1992; Tagle et al., 1993; Rosok et al., 1996).

Figure 16:
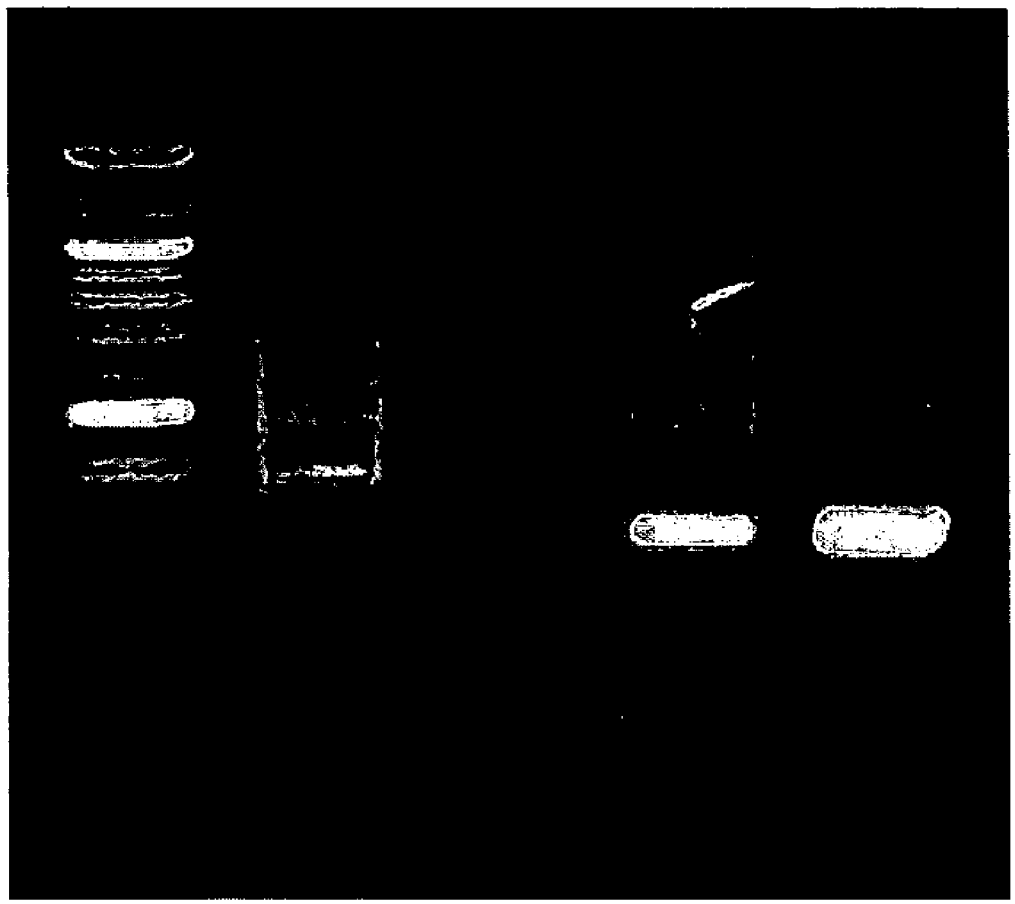
FIG. 16 is an agarose gel photograph to show the difference between CapFinder methods and ACP-based methods for mouse JunB (lanes 1 and 2) and beta-actin 5'-RACE (lanes 3 and 4) using the conventional primer (lanes 1 and 3) and ACP (lanes 2 and 4), respectively

As shown in FIG. 16, the CapFinder methods for mouse JunB and beta-actin 5'-RACE using the 5' PCR primer (Clontech) and the gene-specific primer produced high backgrounds such as DNA smear (lanes 1 and 3) as described by many researchers (Chenchik et al., 1998; Matz et al., 1999; Schramm et al., 2000), whereas the ACP-based 5'-RACE of the present invention generated only a single band which corresponds each to the expected size 155-bp or 319-bp of mouse JunB (lane 2) or mouse beta-actin (lane 4) 5'-end cDNA fragment, respectively. These examples illustrate that the ACP can be used to fundamentally eliminate such background problems arising from contamination of primers used during cDNA synthesis, without the purification step for the removal of primers used in the cDNA synthesis.

Figure 17:
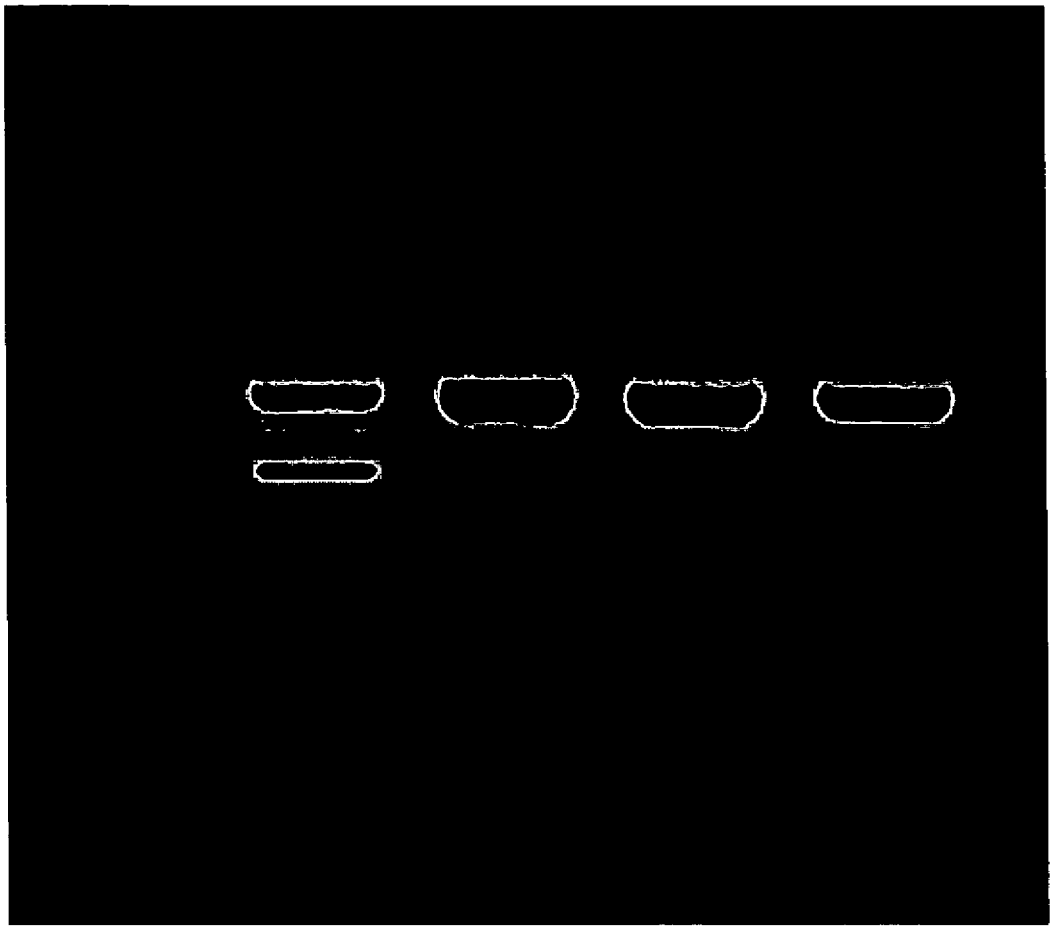
FIG. 17 is an agarose gel photograph to show the difference between CapFinder methods and ACP-based methods for mouse PLP-C alpha 5'-RACE using the conventional primer (lane 1) and ACP (lanes 2, 3, and 4), respectively.

FIG. 17 also shows that the ACP of the subject invention permits the non-specific products not to be formed, which are generated by the CapFinder method (lane 1). The first-strand cDNA was synthesized either by CapFinder method (lane 1) or ACP method (lanes 2, 3, and 4) and then, directly used as template in the subsequent PCR amplification for mouse prolactin-like protein PLP-C alpha 5'-RACE. The PLP-C alpha-specific 5'-RACE primer is: PLP-C alpha 5'-GAGAGGAT-AGTTTCAGGGAC-3' (SEQ ID NO:40). The first-strand cDNA 3'-end extending ACPs comprising either three riboguanines (rG3-ACP; lane 2), three deoxyriboguanines (dG3-ACP; lane 4), or a combination of two riboguanines and one deoxyriboguanine (rG2-ACP; lane 3) at the 3'-end generated 5'-end cDNAs so that a single band which corresponds to the expected size 506-bp of mouse PLP-C alpha 5'-end cDNA fragment was produced from the ACP-based PCR for PLP-C alpha 5'-RACE.

PROTOCOL D: Amplification of 5' Enriched cDNA Fragments Using ACP

The first-strand cDNAs are synthesized using Random dN6-ACP in Protocol A. The PCR amplification was performed by hot start PCR method in which the procedure is to set up the complete reactions without the DNA polymerase and incubate the tubes in the thermal cycler to complete the initial denaturation step at >90° C. Then, while holding the tubes at a temperature above 70° C., the appropriate amount of DNA polymerase can be pipetted into the reaction.

1. Combine the following reagents in a sterile 0.2 ml microcentrifuge tube: 49.5 µl of the total volume containing 1 µl of first-strand cDNA prepared by Random dN6-ACP in Protocol A, 5 µl of 10×PCR buffer (Promega), 5 µl of 25 mM MgCl2, 5 µl of 2 mM dNTP, 1 µl of 10 µM JYC2 (3' primer), 1 µl of 10 µM JYC4 (5' primer) and 31.5 µl sterile dH2O.

2. Mix contents and spin the tube briefly in a microcentrifuge.

3. Place the tube in the preheated thermal cycler at 94° C.

4. Add the 0.5 µl of Taq polymerase (5 units/µl; Promega) into the reaction, while holding the tube at the temperature 94° C.

5. Conduct PCR reaction under the following conditions: 5 min at 94° C. followed by 30 cycles of 94° C. for 40 seconds, 68° C. for 40 seconds, and 72° C. for 1 min 30 sec; followed by a 5 min final extension at 72° C.

6. Analyze the amplified products by electrophoresis in a 2% agarose gel followed by ethidium bromide staining.

The resulting PCR products can be also detected on a denaturing polyacrylamide gel by autoradiography or non-radioactive detection methods such as silver staining (Gottschlich et al., 1997; Kociok et al., 1998), the use of fluorescent-labelled oligonucleotides (Bauer et al. 1993; Ito et al. 1994; Luehrsen et al., 1997; Smith et al., 1997), and the use of biotinylated primers (Korn et al., 1992; Tagle et al., 1993; Rosok et al., 1996).

PROTOCOL E: Amplification of Full-Length Enriched cDNAs Using ACP

The first-strand cDNAs are synthesized using Oligo VdT15-ACP in Protocol A. The PCR amplification was performed by hot start PCR method as in Protocol D.

1. Combine the following reagents in a sterile 0.2 ml microcentrifuge tube: 49.5 µl of the total volume containing 1 µl of first-strand cDNA prepared by Oligo VdT15-ACP in Protocol A, 5 µl of 10×PCR buffer (Promega), 5 µl of 25 mM MgCl2, 5 µl of 2 mM dNTP, 1 µl of 10 µM JYC2 (3' primer), 1 µl of 10 µM JYC4 (5' primer) and 31.5 µl of sterile dH2O.

2. Mix contents and spin the tube briefly in a microcentrifuge.

3. Place the tube in the preheated thermal cycler at 94° C.

4. Add the 0.5 µl of Taq polymerase (5 units/µl; Promega, Madison, USA) into the reaction, while holding the tube at the temperature 94° C.

5. Conduct PCR reaction under the following conditions: 5 min at 94° C. followed by 30 cycles of 94° C. for 40 seconds, 68° C. for 40 seconds, and 72° C. for 1 min 30 sec; followed by a 5 min final extension at 72° C.

6. Analyze the amplified products by electrophoresis in a 2% agarose gel followed by ethidium bromide staining.

The resulting PCR products can be also detected on a denaturing polyacrylamide gel by autoradiography or non-radioactive detection methods such as silver staining (Gottschlich et al., 1997; Kociok et al., 1998), the use of fluorescent-labelled oligonucleotides (Bauer et al. 1993; Ito et al. 1994; Luehrsen et al., 1997; Smith et al., 1997), and the use of biotinylated primers (Korn et al., 1992; Tagle et al., 1993; Rosok et al., 1996).

To evaluate the efficiency of the method using ACP in the amplification of full-length cDNAs, the full-length cDNAs amplified by either the above procedures of ACP method or the current CapFinder method were blotted to a Hybond-N membrane (Amersham/United States Biochemical). The mouse glyceraldehydes-3-phosphate dehydrogenase (GAPDH) cDNA was labeled with [alpha-32P]dCTP using a random labeling kit (Roche Diagnostics Co, Indianapolis, USA) and used as a probe.

Figure 18:
FIG. 18 shows the results of virtual Northern analysis by the CapFinder methods or ACP-based methods for the amplification of mouse full-length GAPDH cDNA.

As shown in FIG. 18, the GAPDH cDNA probe detected a single band which corresponds to the expected size 1.3-kb of full-length GAPDH cDNA. As expected, the signals of the PCR products generated by the above ACP method (lane 2) were several fold stronger than the ones by the CapFinder method (lane 1). This example illustrates that the ACP method of the present invention much more effectively amplifies full-length cDNAs than the CapFinder method does.

Example 7

Genomic Fingerprinting Using ACP-Based Arbitrarily Primed PCR

The ACP of the subject invention has been applied to detect polymorphisms in mouse. The genomic DNAs of mouse strains C57BL/6J, CBA, BALB/cJ, NOR, SPRETUS, PANCEVO, and Korean Wild Mouse were used starting materials. Genomic DNA was prepared from the liver of mice using the QIAamp Tissue Kit (QIAGEN, Hilden, Germany). The arbitrary ACPs used in the subject invention are:

```
ACP101
5'-GTCTACCAGGCATTCGCTTCATIIIIICCGGAG (SEQ ID NO:64)
GATC-3';

ACP109
5'-GTCTACCAGGCATTCGCTTCATIIIIICTGCAG (SEQ ID NO:65)
GACG-3';
and

ACP116
5'-GTCTACCAGGCATTCGCTTCATIIIIICGGAGC (SEQ ID NO:66)
ATCC-3'.
```

A set of arbitrary ACPs, ACP101 and ACP109 (FIG. 19A), or ACP101 and ACP116 (FIG. 19B), was used as primers for mouse genomic fingerprinting. The PCR amplification was performed by hot start PCR method as described in Example 2. The genomic fingerprinting using ACP is conducted by two stages of PCR amplifications under the following conditions: amplification reactions are performed under low stringent conditions by two cycles of the first-stage PCR comprising annealing, extending and denaturing reaction; the reaction mixture in the final volume of 49.5 μl containing 50 ng of the genomic DNA, 5 μl of 10×PCR reaction buffer (Promega), 5 μl of 25 mM MgCl2, 5 μl of dNTP (2 mM each dATP, dCTP, dGTP, dTTP), each 7 μl of a pair of ACPs (each 10 μM) is pre-heated at 94° C., while holding the tube containing the reaction mixture at the 94° C., 0.5 μl of Taq polymerase (5 units/μl; Promega) is added into the reaction mixture; the PCR reactions are as follows: two cycles of 94° C. for 40 sec, 52° C. for 3 min, and 72° C. for 1 min; followed by denaturing the amplification product at 94° C.; after the complete reaction of the first-stage PCR, 4 μl of the pre-selected arbitrary primer JYC4 (10 μM) corresponding to the 5'-end portion of the ACPs are added to the reaction mixture and then the second stage PCR amplification is conducted as follows: 40 cycles of 94° C. for 40 sec, 68° C. for 40 sec, and 72° C. for 40 sec; followed by a 5 min final extension at 72° C.

Amplification products were resolved and analyzed by electrophoresis in a 2.0 agarose gel which was stained with ethidium bromide and photographed. The resulting PCR products can be also detected on a denaturing polyacrylamide gel by autoradiography or non-radioactive detection methods such as silver staining (Gottschlich et al., 1997; Kociok et al., 1998), the use of fluorescent-labelled oligonucleotides (Bauer et al. 1993; Ito et al. 1994; Luehrsen et al., 1997; Smith et al., 1997), and the use of biotinylated primers (Korn et al., 1992; Tagle et al., 1993; Rosok et al., 1996).

Figure 19:
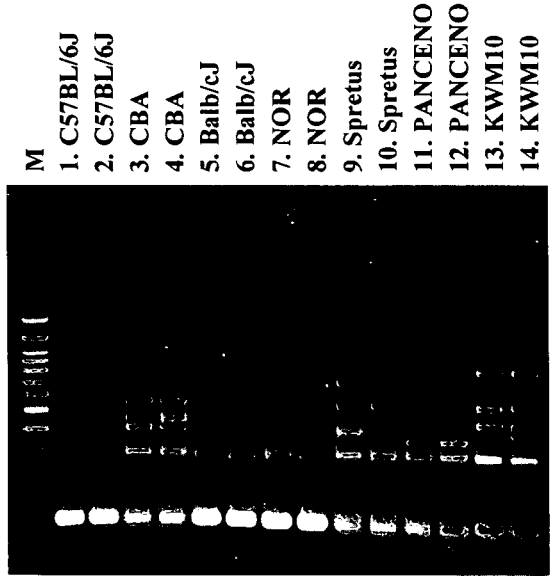
FIG. 19 shows agarose gel photographs to show the results of genomic fingerprintings of 7 mouse stains using two different sets of arbitrary ACPs.
Figure 19:
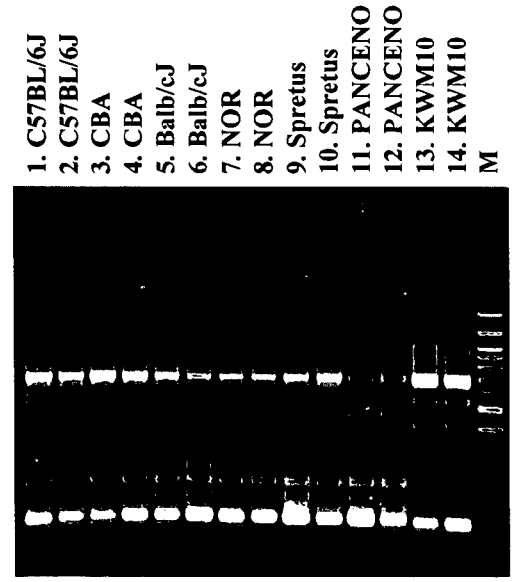

FIG. 19 shows the results of an experiment in which a pair of arbitrary ACPs were used to amplify segments of genomic DNA from a variety of mouse strains. To examine the reproducibility of genomic fingerprinting, the fingerprinting of each mouse strain was duplicated using two different sets of ACPs. The ACP-based PCR amplification produced several DNA segments from each set of primers and the results were reproducible. The polymorphisms were apparent between mice stains, indicating that mice stains can be distinguished through polymorphisms in genomic fingerprintings generated by ACP-based arbitrarily primed PCR. Thus, the ACP of the subject invention is useful to detect polymorphisms and construct genetic maps.

Example 8

Multiplex PCR Using ACP-Based PCR

To demonstrate the application of ACP in multiplex PCR, the portions containing single nucleotide polymorphisms of human leukocyte adhesion molecule I (ELAM1) and human p53 (TP53) genes were amplified with either conventional primers or ACP. The process and results for the multiplex PCR amplification using ACPs are described herein. DNA template was obtained from human placenta.

The conventional primers for exon3 of ELAM1 (155 bp) used in the Example are:

```
ELAM1N1
5'-TTGCACACTGTTGATTCTAA-3';    (SEQ ID NO:67)
and

ELAM1C1
5'-TTATTGATGGTCTCTACACA-3'.    (SEQ ID NO:68)
```

The conventional primers for exon10 of ELAM1 (287 bp) used in the Example are:

```
ELAM1N2  5'-CCACTGAGTCCAACATTC-3';    (SEQ ID NO:69)
and

ELAM1C2  5'-CTGAAACACTTCCCACAC-3'.    (SEQ ID NO:70)
```

The conventional primers for exon4 of TP53 (349 bp) used in the Example are:

```
P53N1  5'-CCTCTGACTGCTCTTTTCAC-3';    (SEQ ID NO:71)
and

P53C1  5'-ATTGAAGTCTCATGGAAGCC-3'.    (SEQ ID NO:72)
```

The conventional primers for exons7-8 of TP53 (750 bp) used in the Example are:

```
P53N2    5'-TGCTTGCCACAGGTCTC-3';      (SEQ ID NO:73)
and

P53C2    5'-GCAGTGCTAGGAAAGAGG-3'.     (SEQ ID NO:74)
```

These conventional primers used in the Example are known as the primers that generate non-specific products in conventional multiplex PCR methods as known in the art.

The ACPs of the subject invention were applied to these four conventional primer sets to demonstrate if the ACP can overcome the problems such as non-specific products resulting from the use of these conventional primer sets for multiplex PCR.

The 3'-end portions of the ACPs comprise the sequences of the above conventional primers as follows and thus the size of ACPs is 26 bp or 27 bp bigger than that of the conventional primers:

```
ELAM1N1-ACP 5'-GTCTACCAGGCATTCGCTTCA    (SEQ ID NO:75)
            TIIIIITTGCACACTGTTGATTCT
            A A-3';

ELAM1C1-ACP 5'-TCACAGAAGTATGCCAAGCGA    (SEQ ID NO:76)
            IIIIITTATTGATGGTCTCTACAC
            A-3';

ELAM1N2-ACP 5'-GTCTACCAGGCATTCGCTTCA    (SEQ ID NO:77)
            TIIIIICCACTGAGTCCAACATT
            C-3';

ELAM1C2-ACP 5'-TCACAGAAGTATGCCAAGCGA    (SEQ ID NO:78)
            IIIIICTGAAACACTTCCCACAC-
            3';

P53N1-ACP   5'-GTCTACCAGGCATTCGCTTCA    (SEQ ID NO:79)
            TIIIIICCTCTGACTGCTCTTTTC
            AC-3';

P53C1-ACP   5'-TCACAGAAGTATGCCAAGCGA    (SEQ ID NO:80)
            IIIIIATTGAAGTCTCATGGAAGC
            C-3';

P53N2-ACP   5'-GTCTACCAGGCATTCGCTTCA    (SEQ ID NO:81)
            TIIIIITGCTTGCCACAGGTCTC-
            3';
and P53C2-ACP   5'-TCACAGAAGTATGCCAAGCGA    (SEQ ID NO:82)
            IIIIIGCAGTGCTAGGAAAGAGG-
            3'.
```

The 5'-end portion sequences of the ACPs comprise and serve as pre-selected arbitrary primer sequences only for the second-stage PCR amplification:

```
JYC3 5'-TCACAGAAGTATGCCAAGCGA-3'      (SEQ ID NO:11)
and

JYC4 5'-GTCTACCAGGCATTCGCTTCAT-3'.    (SEQ ID NO:12)
```

Multiplex PCR amplifications were conducted by one-stop or non-stop two-stage PCR amplifications, which is a unique feature of the present invention. The PCR amplification was performed by hot start PCR method as described in Example 2.

PROTOCOL A: One-Stop Two-Stage PCR Amplifications (A) First-Stage PCR Amplification The first-stage PCR amplification was conducted by two cycles of PCR comprising of annealing, extending and denaturing reaction; the reaction mixture in the final volume of 49.5 μl containing 50 ng of human genomic DNA, 8 μl of 10×PCR reaction buffer (Promega), 7 μl of 25 mM MgCl2, 5 μl of dNTP (2 mM each dATP, dCTP, dGTP, dTTP), each 0.5 μl of each 5' ACP (10 μM) and 3' ACP (10 μM) set is preheated at 94° C., while holding the tube containing the reaction mixture at the 94° C., 0.5 μl of Taq polymerase (5 units/μl; Promega) is added into the reaction mixture; the PCR reactions are as follows: two cycles of 94° C. for 40 sec, 60° C. for 40 sec, and 72° C. for 40 sec; followed by denaturing the amplification product at 94° C.

(B) Second-Stage PCR Amplification

The resultant products generated by the first-stage PCR amplification using multiple sets of the ACPs were then amplified by the following second-stage PCR amplification under higher annealing temperature. After the completion of the first-stage PCR amplification, each 2 μl of 10 μM preselected arbitrary primers, JYC3 and JYC4, was added into the reaction mixture obtained from the first-stage PCR amplification, under denaturing temperature such as at 94° C. The second stage-PCR reaction was as follows: 40 cycles of 94° C. for 40 sec, 68° C. for 40 sec, and 72° C. for 1 min; followed by a 5 min final extension at 72° C.

The amplified products were analyzed by electrophoresis in a 2% agarose gel and detected by staining with ethidium bromide. The resulting PCR products can be also detected on a denaturing polyacrylamide gel by autoradiography or non-radioactive detection methods such as silver staining (Gottschlich et al., 1997; Kociok et al., 1998), the use of fluorescent-labelled oligonucleotides (Bauer et al. 1993; Ito et al. 1994; Luehrsen et al., 1997; Smith et al., 1997), and the use of biotinylated primers (Korn et al., 1992; Tagle et al., 1993; Rosok et al., 1996).

Figure 20:
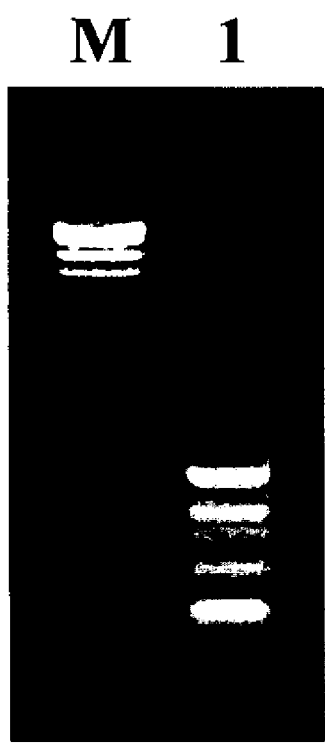
FIG. 20 shows agarose gel photographs to show the amplified products of multiplex PCR by the conventional methods (A) or ACP-based methods (B) for the amplification of three target nucleic acids.
Figure 20:
Figure 21:
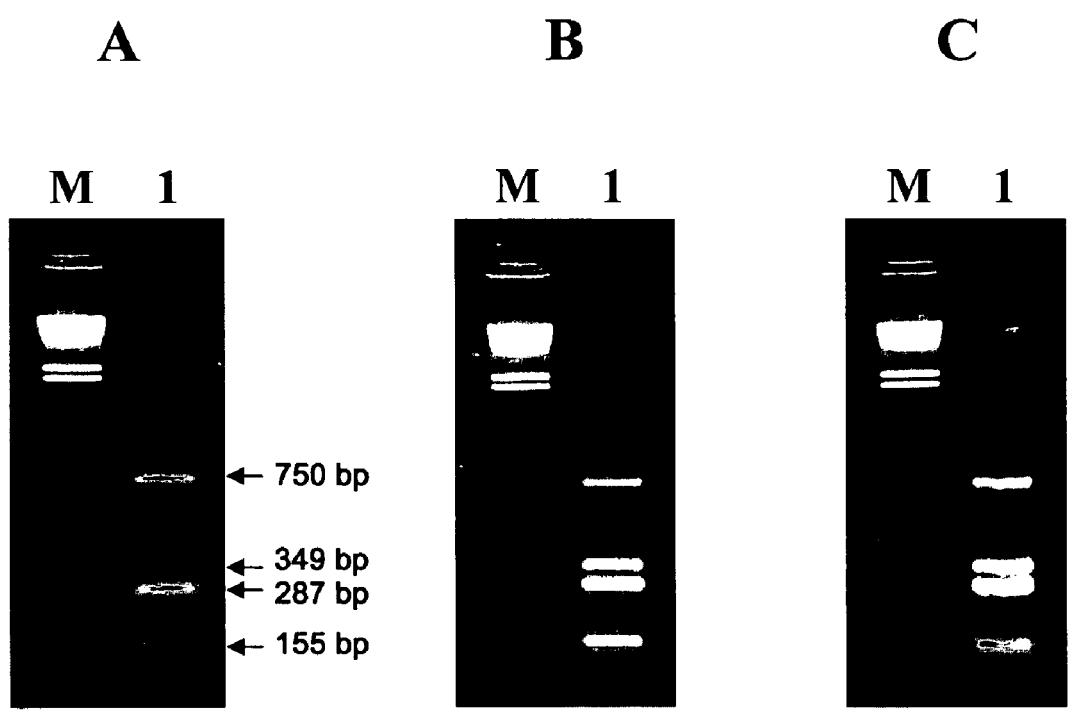
FIG. 21 shows agarose gel photographs to show the amplified products of multiplex PCR by the conventional methods (A) or ACP-based methods (B and C) for the amplification of four target nucleic acids. The ACP-based multiplex was conducted by one-stop (B) or non-stop (C) two-stage PCR amplification.

FIGS. 20 and 21 show the results of experiments in which three or four sets of primers were used to amplify multiplex segments of genomic DNA at one reaction. The conventional primer sets generated non-specific products as well as specific-target products from three sets (FIG. 20A) or four sets (FIG. 21A) of primers. In contrast, the three sets (FIG. 20B) or four sets (FIG. 21B) of ACPs produced only multiplex target products. Thus, the ACP of the subject invention can be used for the application of multiplex PCR.

PROTOCOL B: Non-Stop Two-Stage PCR Amplifications

Alternatively, the complete sequences of each ACP set, instead of the pre-selected arbitrary primers such as JYC3 and JYC4, can be used as primers for the second-stage PCR amplification at the high stringent conditions. In this case, it is not necessary to add the pre-selected arbitrary primers to the reaction mixture at the time of or after the first-stage PCR reaction.

The process of the non-stop two-stage PCR amplifications is basically identical to Protocol A, except that the second stage PCR amplification should immediately follow first stage PCR amplification without any delay because there is no step of adding pre-selected arbitrary primers and that the concentration of each ACP set, each 1 μl of 5' ACP (10 μM) and 3' ACP (10 μM) set, is added at the first stage PCR amplification.

The amplified products were analyzed by electrophoresis in a 2% agarose gel and detected by staining with ethidium bromide. The resulting PCR products can be also detected on a denaturing polyacrylamide gel by autoradiography or non-radioactive detection methods such as silver staining (Gottschlich et al., 1997; Kociok et al., 1998), the use of fluorescent-labelled oligonucleotides (Bauer et al. 1993; Ito et al. 1994; Luehrsen et al., 1997; Smith et al., 1997), and the use of biotinylated primers (Korn et al., 1992; Tagle et al., 1993; Rosok et al., 1996).

Consistent with the results of one-stop two-stage PCR amplifications (FIG. 21B), non-stop two-stage PCR amplification also produced only target multiplex specific products (FIG. 21C). These examples illustrate that ACP permits the products to be free from the background problems as well as non-specificity arising from the conventional primers used in multiplex PCR methods as known in the art.

Example 9

Identification of Conserved Homology Segments in Multigene Families Using ACP

The ACP of the subject invention was applied to detect and clone conserved homology segments in multigene families. In the present example, degenerate primers were designed to detect homeobox sequences. The homeobox genes are characterized by a conserved 180-bp nucleotide sequence known as the homeobox, which encodes a 60-aa DNA binding homeodomain. To isolate homeobox genes involved in mouse embryo development, total RNA obtained from three different stages of conceptus development, mouse 4.5-, 11.5-, and 18.5-day-old conceptuses, was used as a starting material. First-strand cDNAs were prepared under the same conditions as used in the cDNA synthesis of Example 3, wherein JYC5-T15-ACP was used as the first-strand cDNA synthesis primer.

The following ACPs comprise the degenerate sequences for homeobox sequence at their 3'-end portions and were used as degenerate homeobox-specific primers for the first-stage PCR amplification:

```
JYC2-HD1 5'-GCTTGACTACGATACTGTGCGAII  (SEQ ID NO:83)
        IIIGTNCRRGTGTGGTT-3';

JYC2-HD2 5'-GCTTGACTACGATACTGTGCGAII  (SEQ ID NO:84)
        IIIGTNCRRGTCTGGTT-3';
and JYC2-HD3 5'-GCTTGACTACGATACTGTGCGAII  (SEQ ID NO:85)
        IIIGTNCRRGTTTGGTT-3'.
```

The PCR amplification was performed by hot start PCR method as described in Example 2 and conducted by one-stop or non-stop two-stage PCR amplifications. The following is an example of the process of one-stop two-stage PCR amplifications.

1. Combine the following reagents in a sterile 0.2 ml microcentrifuge tube: 49.5 μl of the total volume containing 1 μl of first-strand cDNA (50 ng/μl), 5 μl of 10×PCR buffer (Roche), 5 μl of 2 mM dNTP, 1 μl of one of 10 μM JYC2-HD1, JYC2-HD2, or JYC2-HD3 (5' primer), 1 μl of 10 μM JYC5-T15-ACP (3' primer) and 36.5 μl of sterile dH2O.

2. Mix contents and spin the tube briefly in a microcentrifuge.

3. Place the tube in the preheated thermal cycler at 94° C.

4. Add 0.5 μl of Taq polymerase (5 units/μl; Roche) into the reaction while holding the tube at the temperature 94° C.

5. Conduct PCR reaction under the following conditions: one cycle of 94° C. for 1 min, 52° C. for 3 min, and 72° C. for 1 min; followed by 40 cycles of 94° C. for 40 sec, 65° C. for 40 sec, and 72° C. for 40 sec; and followed by a 5 min final extension at 72° C.

The amplified products were analyzed by electrophoresis in a 2% agarose gel and detected by staining with ethidium bromide. The resulting PCR products can be also detected on a denaturing polyacrylamide gel by autoradiography or non-radioactive detection methods such as silver staining (Gottschlich et al., 1997; Kociok et al., 1998), the use of fluorescent-labelled oligonucleotides (Bauer et al. 1993; Ito et al. 1994; Luehrsen et al., 1997; Smith et al., 1997), and the use of biotinylated primers (Korn et al., 1992; Tagle et al., 1993; Rosok et al., 1996).

Many differentially expressed bands in a specific stage were obtained, subcloned into the pGEM-T Easy vector (Promega), and sequenced. Sequence analysis reveals that some of the clones contain homeobox sequences. Northern blot or RT-PCR analysis shows that the clones are identical to the results of the expression patterns observed by the electrophoresis. These results indicate that the method using the ACP of the present invention for isolating conserved homology segments in multigene families produces only real PCR products. Freedom from false positives, which is one major bottleneck remaining in the previous PCR-based techniques for isolating conserved homology segments in multigene families, allows avoiding the subsequent labor-intensive work required for the verification of the amplified cDNA fragments.

Example 10

Single Nucleotide Polymorphism Genotyping Using ACP-Based PCR

To demonstrate the application of ACP in single nucleotide polymorphism genotyping, a portion containing a single nucleotide polymorphism (SNP) of human p53 (TP53) gene was amplified with either conventional primer or ACP. The process and results for the SNP genotyping using ACPs are described herein. DNA templates were obtained from human blood samples which have a SNP in exon 4 of the TP53 gene. This polymorphism is expressed as an Arg→Pro substitution at amino acid position 72 by replacing G with C. A 349 nt sequence between nucleotide 11991 and 12339 of the TP53 gene was amplified from each type of template by a set of the following primers:

```
P53N     5'-CCTCTGACTGCTCTTTTCAC-3'    (SEQ ID NO:86)
and

P53C-ACP 5'-TCACAGAAGTATGCCAAGCGAIII  (SEQ ID NO:87)
         IIATTGAAGTCTCATGGAAGCC-3'.
```

The amplified products containing the SNP between their ends were used as templates for detecting the SNP using allele-specific ACPs as follows:

```
P53N1A-ACP  5'-GTCTACCAGGCATTCGCTTCA  (SEQ ID NO:88)
              TIIIIICCCCGCGTGG-3',

P53N1B-ACP  5'-GTCTACCAGGCATTCGCTTCA  (SEQ ID NO:89)
              TIIIIICCCCCCGTGG-3',

P53N2A-ACP  5'-GTCTACCAGGCATTCGCTTCA  (SEQ ID NO:90)
              TIIIIITCCCCGCGTG-3',

P53N2B-ACP  5'-GTCTACCAGGCATTCGCTTCA  (SEQ ID NO:91)
              TIIIIITCCCCCCGTG-3',

P53N3A-ACP  5'-GTCTACCAGGCATTCGCTTCA  (SEQ ID NO:92)
              TIIIIICTCCCCGCGT-3',

P53N3B-ACP  5'-GTCTACCAGGCATTCGCTTCA  (SEQ ID NO:93)
              TIIIIICTCCCCCCGT-3',

P53N4A-ACP  5'-GTCTACCAGGCATTCGCTTCA  (SEQ ID NO:94)
              TIIIIIGCTCCCCGCG-3',

P53N4B-ACP  5'-GTCTACCAGGCATTCGCTTCA  (SEQ ID NO:95)
              TIIIIIGCTCCCCCCG-3',

P53N5A-ACP  5'-GTCTACCAGGCATTCGCTTCA  (SEQ ID NO:96)
              TIIIIIGCTCCCCG-3',
```

```
and

P53N5B-ACP  5'-GTCTACCAGGCATTCGCTTCA  (SEQ ID NO:97)
            TIIIIIGCTCCCCC-3'.
```

The polymorphic base is underlined at the 3'-end portion of each allele-specific ACP and the position of the polymorphic base is considered an interrogation position. The interrogation position is placed at several different positions from the 3'-end of allele-specific ACPs in order to determine the most critical position in annealing specificity for detecting the SNP.

The allele-specific ACPs were used as 5' primers. P53C-ACP and one of P53N1A-ACP, P53N2A-ACP, P53N3A-ACP, P53N4A-ACP and P53N5A-ACP were used for wild-type A genotyping. P53C-ACP and one of P53NIB-ACP, P53N2B-ACP, P53N3B-ACP, P53N4B-ACP and P53N5B-ACP were used for variant-type B genotyping. The 5'-end portion sequences of the ACPs were served as pre-selected arbitrary primer sequences for the second-stage PCR amplification:

```
JYC3  5'-TCACAGAAGTATGCCAAGCGA-3'      (SEQ ID NO:11)
and

JYC4  5'-GTCTACCAGGCATTCGCTTCAT-3'.    (SEQ ID NO:12)
```

(A) First-Stage PCR Amplification

The first-stage PCR amplification was conducted by one cycle of PCR consisting of annealing, extending and denaturing reaction; the reaction mixture in a final volume of 49.5 μl containing 1 μl of the amplified target genomic segment containing the SNP in exon 4 of the TP53 gene, 5 μl of 10×PCR reaction buffer (Promega), 5 μl of 25 mM MgCl2, 5 μl of dNTP (2 mM each dATP, dCTP, dGTP, dTTP), and 1 μl of one of allele-specific ACPs (10 μM) is pre-heated at 94° C., while holding the tube containing the reaction mixture at the 94° C., 0.5 μl of Taq polymerase (5 units/μl; Promega) is added into the reaction mixture; for the allele-specific ACPs having 10 nucleotides at its 3'-end portion, the PCR reactions are as follows: one cycle of 94° C. for 40 sec, 55° C. for 40 sec, and 72° C. for 40 sec; followed by denaturing the amplification product at 94° C.; for the allele-specific ACPs having 8 nucleotides at its 3'-end portion, the PCR reactions are as follows: one cycle of 94° C. for 40 sec, 50° C. for 40 sec, and 72° C. for 40 sec; followed by denaturing the amplification product at 94° C. The resultant product is a first DNA strand complementary to the target genomic segment.

(B) Second-Stage PCR Amplification

The resultant product generated by the first-stage PCR amplification was then amplified by the following second-stage PCR amplification at a higher annealing temperature than the first annealing temperature. After the completion of the first-stage PCR amplification, 1 μl of 10 μM pre-selected arbitrary primer, JYC3, was added into the reaction mixture obtained from the first-stage PCR amplification, under denaturing temperature such as at 94° C. The second stage-PCR reaction was performed as follows: 30 cycles of 94° C. for 40 sec, 68° C. for 40 sec, and 72° C. for 40 sec; followed by a 5 min final extension at 72° C.

The amplified products were analyzed by electrophoresis in a 2% agarose gel and detected by staining with ethidium bromide. The resulting PCR products can be also detected on a denaturing polyacrylamide gel by autoradiography or non-radioactive detection methods such as silver staining (Gottschlich et al., 1997; Kociok et al., 1998), the use of fluorescent-labelled oligonucleotides (Bauer et al. 1993; Ito et al. 1994; Luehrsen et al., 1997; Smith et al., 1997), and the use of biotinylated primers (Korn et al., 1992; Tagle et al., 1993; Rosok et al., 1996).

Figure 22:
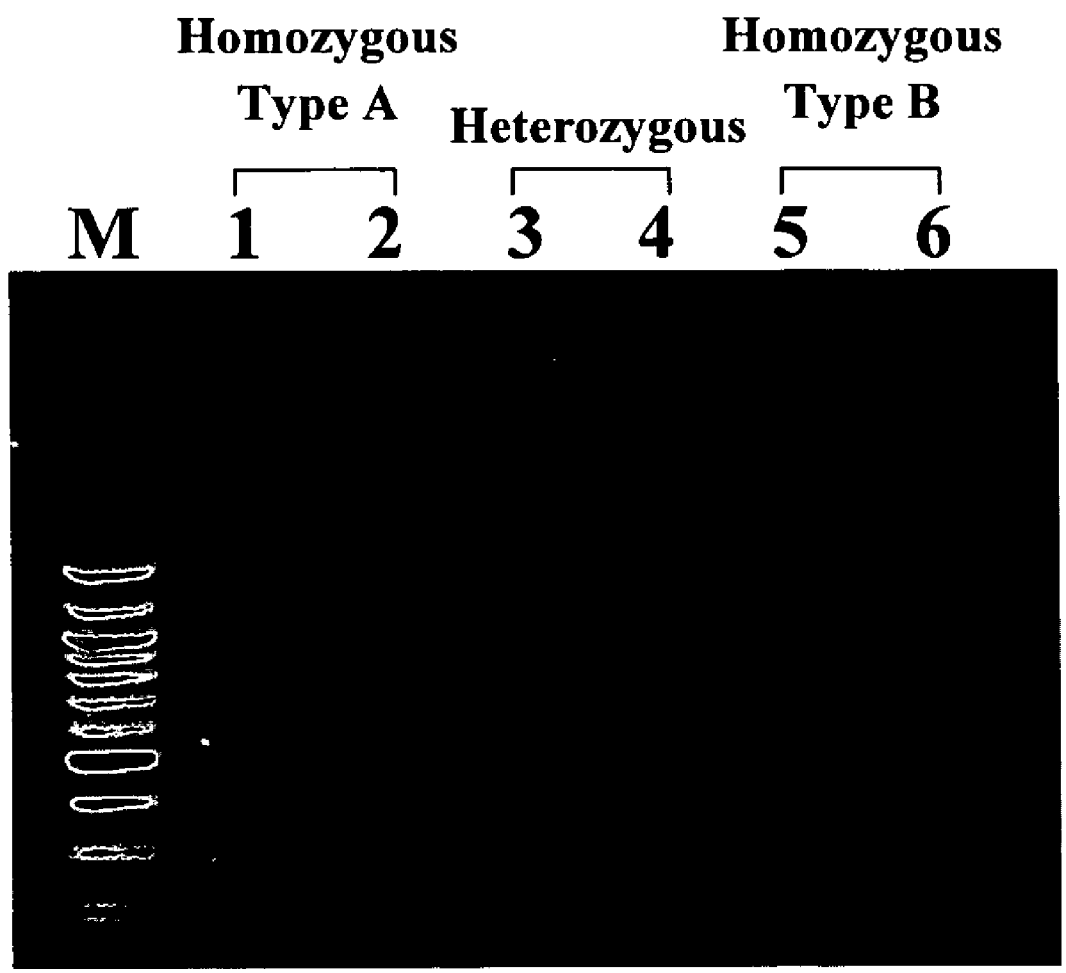
FIG. 22 shows an agarose gel photograph to show the results of allele-specific amplification for a SNP in exon 4 of the human TP53 gene using ACP.

FIG. 22 shows the results of allele-specific amplification using ACP. The pair of wild-type A-specific ACPs (P53N2A-ACP and P53C-ACP) generated a specific target product only from the samples having homozygous wild-type A (lane 1) or heterozygous genotyping (lane 3), but not from the samples having homozygous variant-type B genotyping (lane 5). The pair of variant-type B-specific ACPs (P53N2B-ACP and P53C-ACP) generated a specific target product only from the samples having homozygous variant-type B (lane 6) or heterozygous genotyping (lane 4), but not from the samples having homozygous wild-type A genotyping (lane 2). These results indicate that the ACP of the subject invention can be applied as an easy and economic method for detecting the genotype of SNPs since the use of fluorescent DNA probe nor post-PCR processing is not required in this approach. The allele-specific ACPs each having an interrogation position at its 3'-end portion showed improvement of annealing specificity. Moreover, when the allele-specific ACP has an interrogation position at the position 5 from the 3'-end (e.g., P53N2A-ACP and P53N2B-ACP), the annealing specificity is most critically accomplished.

In order to verify if the position 5 from the actual 3'-end of the allele-specific ACP is the most appropriate for the interrogation position, additional six experiments were conducted using the same process as used in FIG. 22. DNA templates were obtained from human blood samples which have a SNP. Six short genomic fragments containing SNPs were amplified using each different primer set as follows:

```
703N
5'-ATTCTGATGGTGTGGATTGTG-3'                              (SEQ ID NO:98)
and SM703C
5'-TCACAGAAGTATGCCAAGCGAIIIIIACCCTGGAGTAGACGAAGA-3'      (SEQ ID NO:99)
for Beta-2 adrenergic receptor (ADRB2), 028N
5'-CCTTCTGTGCTTGATGCTTTT-3'                              (SEQ ID NO:102)
and SM028C
5'-TCACAGAAGTATGCCAAGCGAIIIIICAGGAAGGATGAGCATTTAG-3'     (SEQ ID NO:103)
for Chemokine (c-c motif) receptor 5 (CCR5),
```

-continued

```
695N:
5'-AGAAAAACCAGAGGCAGCTT-3'                                      (SEQ ID NO:106)
and SM695C
5'-TCACAGAAGTATGCCAAGCGAIIIIIAGCACAAACCAAAGACACAGT-3'           (SEQ ID NO:107)
for Interleukin 13 receptor, 679N
5'-CTAGCTGCAAGTGACATCTCT-3'                                     (SEQ ID NO:110)
and SM679C
5'-TCACAGAGTATCCAAGCGIIIIITCAGTAAGAAGCCAGGAGAG-3'               (SEQ ID NO:111)
for Leukocyte adhesion molecule-1 (LAM-1), 832N
5'-TTTTGGGTGGAGGCTAACAT-3'                                      (SEQ ID NO:114)
and SM832C:
5'-TCACAGAAGTATGCCAGCGAIIIIIAACGATGCAGACACCACCA-3'              (SEQ ID NO:115)
for Tachykinin receptor 3 (TACR3),
and 880N
5'-CTTCCACCAATACTCTTTTCC-3'                                     (SEQ ID NO:118)
and SM880C:
5'-TCACAGAAGTATGCCAGCGAIIIIII GCATACACACAAGAGGCAGA-3'           (SEQ ID NO:119)
for Interleukin 1, beta (IL1B).
```

The amplified products containing the SNP between their ends were used as templates for detecting the SNPs wherein allele-specific ACPs were applied as follows:

```
SM703-A
5'-GTCTACCAGGCATTCGCTTCATIIIIIIGGTACAGGGC-3'                    (SEQ ID NO:100)
and SM703-B
5'-GTCTACCAGGCATTCGCTTCATIIIIIIGGTACCGGGC-3'                    (SEQ ID NO:101)
for Beta-2 adrenergic receptor (ADRB2), SM028-A
5'-GTCTACCAGGCATTCGCTTCATIIIIIITCCAAACCAA-3'                    (SEQ ID NO:104)
and SM028-B
5'-GTCTACCAGGCATTCGCTTCATIIIIIITCCAACCCAA-3'                    (SEQ ID NO:105)
for Chemokine (c-c motif) receptor 5 (CCR5), SM695-A
5'-GTCTACCAGGCATTCGCTTCATIIIIII CCATTTTAGG-3'                   (SEQ ID NO:108)
and SM695-B
5'-GTCTACCAGGCATTCGCTTCATIIIIII CCATTGTAGG-3'                   (SEQ ID NO:109)
for Interleukin 13 receptor, SM679-A
5'-GTCTACCAGGCATTCGCTTCATIIIIIICCAGAACTTT-3'                    (SEQ ID NO:112)
and SM679-B
5'-GTCTACCAGGCATTCGCTTCATIIIIIICCAGACCTTT-3'                    (SEQ ID NO:113)
for Leukocyte adhesion molecule-1 (LAM-1), SM832-A
5'-GTCTACCAGGCATTCGCTTCATIIIIIGACTGGTAAA-3'                     (SEQ ID NO:116)
and
```

-continued

```
SM832-B
5'-GTCTACCAGGCATTCGCTTCATIIIIIGACTGATAAA-3'   (SEQ ID NO:117)
for Tachykinin receptor 3 (TACR3),
and SM880-A
5'-GTCTACCAGGCATTCGCTTCATIIIIIAAAGCCATAA-3'   (SEQ ID NO:120)
and SM880-B
5'-GTCTACCAGGCATTCGCTTCATIIIIIAAAGCTATAA-3'   (SEQ ID NO:121)
for Interleukin 1, beta (IL1B).
```

Figure 23:
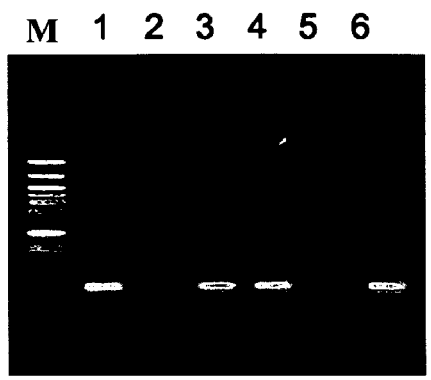
FIG. 23 shows six agarose gel photographs which show the results of allele-specific amplifications using ACPs for six additional SNPs each present in different gene such as Beta-2 adrenergic receptor (ADRB2) (A), Chemokine (c-c motif) receptor 5 (CCR5) (B), Interleukin 13 receptor (C), Leukocyte adhesion molecule-1 (LAM-1) (D), Tachykinin receptor 3 (TACR3) (E), and Interleukin 1, beta (IL1B) (F).
Figure 23:
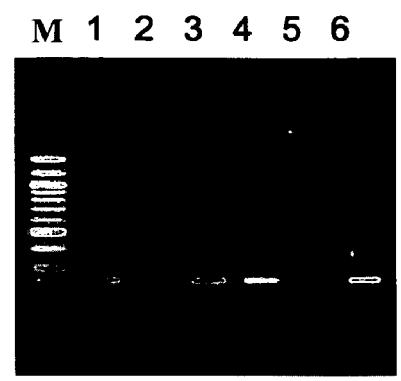
Figure 23:
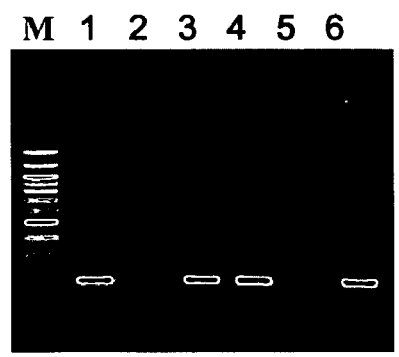
Figure 23:
Figure 23:
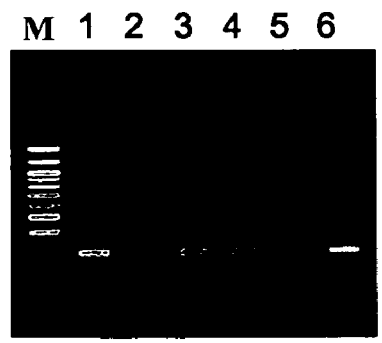
Figure 23:

FIG. 23 shows the results of allele-specific amplifications for six additional SNPs each present in different gene such as Beta-2 adrenergic receptor (ADRB2) (A), Chemokine (c-c motif) receptor 5 (CCR5) (B), Interleukin 13 receptor (C), Leukocyte adhesion molecule-1 (LAM-1) (D), Tachykinin receptor 3 (TACR3) (E), and Interleukin 1, beta (IL1B) (F). Consistent with the results of FIG. 22, the annealing specificity is critically accomplished when the allele-specific ACP has an interrogation position at the position 5 from the 3'-end. The pair of wild-type A-specific ACPs generated a specific target product only from the samples having homozygous wild-type A (lane 1) or heterozygous genotyping (lane 3), but not from the samples having homozygous variant-type B genotyping (lane 5). The pair of variant-type B-specific ACPs generated a specific target product only from the samples having homozygous variant-type B (lane 6) or heterozygous genotyping (lane 4), but not from the samples having homozygous wild-type A genotyping (lane 2).

Having described a preferred embodiment of the present invention, it is to be understood that variants and modifications thereof falling within the spirit of the invention may become apparent to those skilled in this art, and the scope of this invention is to be determined by appended claims and their equivalents.

TABLE 1

| SEQ ID NO | Designation | Sequence Information |
|---|---|---|
| 1 | ACP1 | 5'-GTCTACCAGGCATTCGCTTCATIIIIICAGGAGTGG-3' |
| 2 | ACP2 | 5'-GTCTACCAGGCATTCGCTTCATIIIIIGGCGACGATS-3' |
| 3 | ACP3 | 5'-GTCTACCAGGCATTCGCTTCATIIIIIGCCATCGACS-3' |
| 4 | ACP4 | 5'-GTCTACCAGGCATTCGCTTCATIIIIIAGATGCCCGW-3' |
| 5 | ACP5 | 5'-GTCTACCAGGCATTCGCTTCATIIIIIAGGCGATGCS-3' |
| 6 | ACP6 | 5'-GTCTACCAGGCATTCGCTTCATIIIIITCTCCCGGTS-3' |
| 7 | ACP7 | 5'-GTCTACCAGGCATTCGCTTCATIIIIITTGTGGCGGS-3' |
| 8 | ACP8 | 5'-GTCTACCAGGCATTCGCTTCATIIIIICTCCGATGCS-3' |
| 9 | ACP9 | 5'-GTCTACCAGGCATTCGCTTCATIIIIICCTGCGGGTW-3' |
| 10 | JYC2 | 5'-GCTTGACTACGATACTGTGCGA-3' |
| 11 | JYC3 | 5'-TCACAGAAGTATGCCAAGCGA-3' |
| 12 | JYC4 | 5'-GTCTACCAGGCATTCGCTTCAT-3' |
| 13 | ACP10 | 5'-GTCTACCAGGCATTCGCTTCATIIIIIGCCATCGACC-3' |
| 14 | ACP11 | 5'-GTCTACCAGGCATTCGCTTCATIIIIIGCCATCGACG-3' |
| 15 | ACP12 | 5'-GTCTACCAGGCATTCGCTTCATIIIIIAGGCGATGCC-3' |
| 16 | ACP13 | 5'-GTCTACCAGGCATTCGCTTCATIIIIIAGGCGATGCG-3' |
| 17 | ACP14 | 5'-GTCTACCAGGCATTCGCTTCATIIIIICTCCGATGCC-3' |
| 18 | ACP15 | 5'-GTCTACCAGGCATTCGCTTCATIIIIICTCCGATGCG-3' |
| 19 | CRP2I0 | 5'-GTCTACCAGGCATTCGCTTCATGCCATCGACC-3' |
| 20 | ACP16 | 5'-GTCTACCAGGCATTCGCTTCATIIGCCATCGACC-3' |
| 21 | ACP17 | 5'-GTCTACCAGGCATTCGCTTCATIIIIGCCATCGACC-3' |
| 22 | ACP18 | 5'-GTCTACCAGGCATTCGCTTCATIIIIIIGCCATCGACC-3' |

TABLE 1-continued

| SEQ ID NO | Designation | Sequence Information |
|---|---|---|
| 23 | ACP19 | 5'-GTCTACCAGGCATTCGCTTCATIIIIIIIIGCCATCGACC-3' |
| 24 | dT-JYC3 | 5'-CACAGAAGTATGCCAAGCGACTCGAGTTTTTTTTTTTTTT-3' |
| 25 | dT-JYC2 | 5'-GCTTGACTACGATACTGTGCGATTTTTTTTTTTTTT-3' |
| 26 | JYC2-T13C | 5'-CTTGACTACGATACTGTGCGATTTTTTTTTTTTC-3' |
| 27 | JYC2-T13G | 5'-GCTTGACTACGATACTGTGCGATTTTTTTTTTTTG-3' |
| 28 | JYC2-T13A | 5'-GCTTGACTACGATACTGTGCGATTTTTTTTTTTTA-3' |
| 29 | dT$_{10}$-JYC2 | 5'-GCTTGACTACGATACTGTGCGATTTTTTTTTT-3' |
| 30 | dT$_{10}$-ACP1 | 5'-GCTTGACTACGATACTGTGCGAIIIIITTTTTTTTTT-3' |
| 31 | DEG 2 | GCCATCGACCCGTTTCTCTAGCCCCATCTTCATGTGT TTTAATGAGATGATATTAATTCATTACATTCATGGAT AATATGTCCCTGAGTACATTCTAATCTAGATTTAACT TCAAAAAAAAAAAAAAAAA |
| 32 | DEG 5 | AGGCGATGCGGGCTGTACTCTGGGTGGCTGCCACAGT CTCATGAGAAACCAAGGGCAAAGGACCAAGGAAAAG GGTCTCAGGCCCCTAAAGCAGTGGCTTTCAACCATCCTA ATGTTGTGACCTTTTAATACAGTTCCTCATGTTGTG TGACCCCCCAACCATAAAATGATTTTTGTTTCTACTTC AAAAAAAAAAAAAAAAAAAAA |
| 33 | SMART IV | 5'-AAGCAGTGGTATCAACGCAGAGTGGCCATTACG GCCr(GGG)-3' |
| 34 | 5' PCR Primer | 5'-AAGCAGTGGTATCAACGCAGAGT-3' |
| 35 | CDS III/3' | 5'-ATTCTAGAGGCCGAGGCGGCCGACATG-(dT)$_{30}$VN-3' |
| 36 | rG3-ACP | 5'-GTCTACCAGGCATTCGCTTCATIIIIIGGr(GGG)-3' |
| 37 | rG2-AGP | 5'-GTCTACCAGGCATTCGCTTCATIIIIIGGr(GG)d(G)-3' |
| 38 | dG3-ACP | 5'-GTCTACCAGGCATTCGCTTCATIIIIIGGd(GGG)-3' |
| 39 | Oligo dT$_{18}$-ACP | 5'-GCTTGACTACGATACTGTGCGAIIIIITTTTTTTTTTTTTTTTTT-3' |
| 40 | PLP-Cα | 5'-GAGAGGATAGTTTCAGGGAC-3' |
| 41 | JunB3 | 5'-CTCCGTGGTACGCCTGCTTTCTC-3' |
| 42 | β-actin 1 | 5'-TCGTCACCCACATAGGAGTC-3' |
| 43 | β-actin 2 | 5'-CTAAGAGGAGGATGGTCGC-3' |
| 44 | EsxN7 | 5'-GCCGGTTGCAGAGCACC-3' |
| 45 | EsxC6 | 5'-GAACCATGTTTCTGAATGCC-3' |
| 46 | EsxN7-ACP | 5'-GTCTACCAGGCATTCGCTTCATIIIIIGCCGGT TGCAGAGCACC-3' |
| 47 | EsxC6-ACP | 5'-GCTTGACTACGATACTGTGCGAIIIIIGAACCAT GTTTCTGAATGCC-3' |
| 48 | EsxN1 | 5'-GAATCTGAAACAACTTTCTA-3' |
| 49 | EsxC2 | 5'-GATGCATGGGACGAGGCACC-3' |
| 50 | EsxN1-ACP | 5'-GTCTACCAGGCATTCGCTTCATIIIIIGAATCT GAAACAACTTTCTA-3' |
| 51 | EsxN3 | 5'-CGCCGCACCCCTGCCCGCA-3' |
| 52 | EsxC5 | 5'-GATGCATGGGACGAGGCA-3' |

TABLE 1-continued

| SEQ ID NO | Designation | Sequence Information |
|---|---|---|
| 53 | EsxN3-ACP | 5'-GTCTACCAGGCATTCGCTTCATIIIIICGCCGCACCCCTGCCCGCA-3' |
| 54 | Oligo-dT$_{15}$ | 5'-TTTTTTTTTTTTTTT-3' |
| 55 | EsxC2-ACP | 5'-GCTTGACTACGATACTGTGCGAIIIIIGATGCATGGGACGAGGCACC-3' |
| 56 | EsxC5-ACP | 5'-GCTTGACTACGATACTGTGCGAIIIIIGATGCATGGGACGAGGCA-3' |
| 57 | OligoVdT$_{15}$-ACP | 5'-GCTTGACTACGATACTGTGCGAIIIIITTTTTTTTTTTTTTTV-3' |
| 58 | dN$_6$-ACP | 5'-GCTTGACTACGATACTGTGCGAIIIIINNNNNN-3' |
| 59 | rG1-ACP | 5'-GTCTACCAGGCATTCGCTTCATIIIIIGGr(G)d(GG)-3' |
| 60 | JYC5 | 5'-CTGTGAATGCTGCGACTACGAT-3' |
| 61 | JYC5-T$_{15}$-ACP | 5'-CTGTGAATGCTGCGACTACGATIIIIITTTTTTTTTTTTTTT-3' |
| 62 | JYC5-T$_{15}$V-ACP | 5'-CTGTGAATGCTGCGACTACGATIIIIITTTTTTTTTTTTTTTV-3' |
| 63 | JYC5-T$_{15}$VN-ACP | 5'-CTGTGAATGCTGCGACTACGATIIIIITTTTTTTTTTTTTTTVN-3' |
| 64 | ACP101 | 5'-GTCTACCAGGCATTCGCTTCATIIIIICCGGAGGATC-3' |
| 65 | ACP109 | 5'-GTCTACCAGGCATTCGCTTCATIIIIICTGCAGGACG-3' |
| 66 | ACP116 | 5'-GTCTACCAGGCATTCGCTTCATIIIIICGGAGCATCC-3' |
| 67 | ELAM1N1 | 5'-TTGCACACTGTTGATTCTAA-3' |
| 68 | ELAM1C1 | 5'-TTATTGATGGTCTCTACACA-3' |
| 69 | ELAM1N2 | 5'-CCACTGAGTCCAACATTC-3' |
| 70 | ELAM1C2 | 5'-CTGAAACACTTCCCACAC-3' |
| 71 | P53N1 | 5'-CCTCTGACTGCTCTTTTCAC-3' |
| 72 | P53C1 | 5'-ATTGAAGTCTCATGGAAGCC-3' |
| 73 | P53N2 | 5'-TGCTTGCCACAGGTCTC-3' |
| 74 | P53C2 | 5'-GCAGTGCTAGGAAAGAGG-3' |
| 75 | ELAM1N1-ACP | 5'-GTCTACCAGGCATTCGCTTCATIIIIITTGCACACTGTTGATTCTAA-3' |
| 76 | ELAM1C1-ACP | 5'-TCACAGAAGTATGCCAAGCGAIIIIITTATTGATGGTCTCTACACA-3' |
| 77 | ELAM1N2-ACP | 5'-GTCTACCAGGCATTCGCTTCATIIIIICCACTGAGTCCAACATTC-3' |
| 78 | ELAM1C2-ACP | 5'-TCACAGAAGTATGCCAAGCGAIIIIICTGAAACACTTCCCACAC-3' |
| 79 | P53N1-ACP | 5'-GTCTACCAGGCATTCGCTTCATIIIIICCTCTGACTGCTCTTTTCAC-3' |
| 80 | P53C1-ACP | 5'-TCACAGAAGTATGCCAAGCGAIIIIIATTGAAGTCTCATGGAAGCC-3' |
| 81 | P53N2-ACP | 5'-GTCTACCAGGCATTCGCTTCATIIIIITGCTTGCCACAGGTCTC-3' |
| 82 | P53C2-ACP | 5'-TCACAGAAGTATGCCAAGCGAIIIIIGCAGTGCTAGGAAAGAGG-3' |

TABLE 1-continued

| SEQ ID NO | Designation | Sequence Information |
|---|---|---|
| 83 | JYC2-HD1 | 5'-GCTTGACTACGATACTGTGCGAIIIIIGTNCRRGTGTGGTT-3' |
| 84 | JYC2-HD2 | 5'-GCTTGACTACGATACTGTGCGAIIIIIGTNCRRGTCTGGTT-3' |
| 85 | JYC2-HD3 | 5'-GCTTGACTACGATACTGTGCGAIIIIIGTNCRRGTTTGGTT-3' |
| 86 | P53N | 5'-CCTCTGACTGCTCTTTTCAC-3' |
| 87 | P53C-ACP | 5'-TCACAGAAGTATGCCAAGCGAIIIIIATTGAAGTCTCATGGAAGCC-3' |
| 88 | P53N1A-ACP | 5'-GTCTACCAGGCATTCGCTTCATIIIIICCCCGCGTGG-3' |
| 89 | P53N1B-ACP | 5'-GTCTACCAGGCATTCGCTTCATIIIIICCCCCCGTGG-3' |
| 90 | P53N2A-ACP | 5'-GTCTACCAGGCATTCGCTTCATIIIIITCCCCGCGTG-3' |
| 91 | P53N2B-ACP | 5'-GTCTACCAGGCATTCGCTTCATIIIIITCCCCCCGTG-3' |
| 92 | P53N3A-ACP | 5'-GTCTACCAGGCATTCGCTTCATIIIIICTCCCCGCGT-3' |
| 93 | P53N3B-ACP | 5'-GTCTACCAGGCATTCGCTTCATIIIIICTCCCCCCGT-3' |
| 94 | P53N4A-ACP | 5'-GTCTACCAGGCATTCGCTTCATIIIIIGCTCCCCGCG-3' |
| 95 | P53N4B-ACP | 5'-GTCTACCAGGCATTCGCTTCATIIIIIGCTCCCCCCG-3' |
| 96 | P53N5A-ACP | 5'-GTCTACCAGGCATTCGCTTCATIIIIIGCTCCCCG-3' |
| 97 | P53N5B-ACP | 5'-GTCTACCAGGCATTCGCTTCATIIIIIGCTCCCCC-3' |
| 98 | 703N | 5'-ATTCTGATGGTGTGGATTGTG-3' |
| 99 | SM703C | 5'-TCACAGAAGTATGCCAAGCGAIIIIIACCCTGGAGTAGACGAAGA-3' |
| 100 | SM703-A | 5'-GTCTACCAGGCATTCGCTTCATIIIIIGGTACAGGGC-3' |
| 101 | SM703-B | 5'-GTCTACCAGGCATTCGCTTCATIIIIIGGTACCGGGC-3' |
| 102 | 028N | 5'-CCTTCTGTGCTTGATGCTTTT-3' |
| 103 | SM028C | 5'-TCACAGAAGTATGCCAAGCGAIIIIICAGGAAGGATGAGCATTTAG-3' |
| 104 | SM028-A | 5'-GTCTACCAGGCATTCGCTTCATIIIIITCCAAACCAA-3' |
| 105 | SM028-B | 5'-GTCTACCAGGCATTCGCTTCATIIIIITCCAACCCAA-3' |
| 106 | 695N | 5'-AGAAAAACCAGAGGCAGCTT-3' |
| 107 | SM695C | 5'-TCACAGAAGTATGCCAAGCGAIIIIIAGCACAAACCAAAGACACAGT-3' |
| 108 | SM695-A | 5'-GTCTACCAGGCATTCGCTTCATIIIII CCATTTTAGG-3' |
| 109 | SM695-B | 5'-GTCTACCAGGCATTCGCTTCATIIIII CCATTGTAGG-3' |
| 110 | 679N | 5'-CTAGCTGCAAGTGACATCTCT-3' |
| 111 | SM679C | 5'-TCACAGAGTATCCAAGCGIIIIITCAGTAAGAAGCCAGGAGAG-3' |
| 112 | SM679-A | 5'-GTCTACCAGGCATTCGCTTCATIIIIICCAGAACTTT-3' |
| 113 | SM679-B | 5'-GTCTACCAGGCATTCGCTTCATIIIIICCAGACCTTT-3' |
| 114 | 832N | 5'-TTTTGGGTGGAGGCTAACAT-3' |
| 115 | SM832C | 5'-TCACAGAAGTATGCCAGCGAIIIIIAACGATGCAGACACCACCA-3' |
| 116 | SM832-A | 5'-GTCTACCAGGCATTCGCTTCATIIIIIGACTGGGTAAA-3' |

TABLE 1-continued

| SEQ ID NO | Designation | Sequence Information |
|---|---|---|
| 117 | SM832-B | 5'-GTCTACCAGGCATTCGCTTCATIIIIIGACTGATAAA-3' |
| 118 | 880N | 5'-CTTCCACCAATACTCTTTTCC-3' |
| 119 | SM880C | 5'-TCACAGAAGTATGCCAGCGAIIIIGCATACACACA AGAGGCAGA-3' |
| 120 | SM880-A | 5'-GTCTACCAGGCATTCGCTTCATIIIIIAAAGCCATAA-3' |
| 121 | SM880-B | 5'-GTCTACCAGGCATTCGCTTCATIIIIIAAAGCTATAA-3' |

S = G or C
W = A or T
V = A, G, or C
N = A, G, C, or T
I is deoxyinosine
r is ribose
d is deoxyribose

TABLE 2

Differentially Expressed cDNA Fragments
Cloned by the ACP of the Present Invention

| Nomenclature | Identity | Homology |
|---|---|---|
| DEG 1 | Tropomyosin 2 (beta) | Mouse 92% |
| DEG 2 | Novel | Novel |
| DEG 3 | Hypothetical protein (Tes gene) | Mouse 99% |
| DEG 4 | Protease-6 | Mouse 92% |
| DEG 5 | Novel | Novel |
| DEG 6 | Cytochrome c oxidase, subunit Vb | Mouse 99% |
| DEG 7 | Hydroxylacyl-Coenzyme A dehydrogense (Hadh) | Mouse 98% |
| DEG 8 | Troponin T2, cardiac (Tnnt2) | Mouse 94% |
| DEG 9 | RNA binding motif protein, X chromosome | Mouse 96% |
| DEG 10 | Peroxiredoxin 6 (Prdx6) | Mouse 89% |
| DEG 11 | 11 days or 13 days embryo cDNA | Mouse 98% |

REFERENCES

Anonymous (1992) Diagnosis of Duchenne and Becker muscular dystrophies by polymerase chain reaction. A multi-center study. JAMA 267, 2609-2615.

Bauer, D., Muller, H., Reich, J., Ahrenkiel, V., Warthoe, P., Strauss, M. (1993) Identification of differentially expressed mRNA species by an improved display technique (DDRT-PCR). Nucleic Acids Res. 21, 4272-4280.

Bauer, D., Warthoe, P., Rohde, M., Struss, M. (1994) PCR Methods & App: Manual Supplement., pp. S97-S108. Cold Spring Harbor Laboratory, Cold Spring Harbor, N.Y.

Carninci, P., Westover, A., Nishiyama, Y., Ohsumi, T., Itoh, M., Nagaoka, S., Sasaki, N., Okazaki, Y., Muramatsu, M., Hayashizaki, Y. (1997) High efficiency selection of full-length cDNA by improved biotinylated cap trapper. DNA Res. 4, 61-66.

Chamberlain, J. S., Gibbs, R. A., Ranier, J. E., Nguyen, P. N., Caskey, C. T. (1988) Deletion screening of the Duchenne muscular dystrophy locus via multiplex DNA amplification. Nucleic Acids Res. 16, 11141-11156.

Chenchik, A., Zhu, Y., Diatchenko, L., Li, R., Hill, J., Siebert, P. (1998) Generation and use of high-quality cDNA from small amounts of total RNA by Smart™ PCR. In Siebert, P. and Larrick, J. (eds), Gene Cloning and analysis by RT-PCR. Biotechniques Books, Natick, Mass., pp. 305-319.

Chenchik, A., Zhu, Y., Diatchenko, L., Siebert, P. Methods and compositions for generating full-length cDNA having arbitrary nucleotide sequence at the 3'-end. U.S. Pat. No. 5,962,271. Date of patent: Oct. 5, 1999.

Chenchik, A., Zhu, Y., Diatchenko, L., Siebert, P. Methods and compositions for full-length cDNA cloning using a template-switching oligonucleotide. U.S. Pat. No. 5,962,272. Date of patent: Oct. 5, 1999.

Chun, J. Y., Han, Y. J., Ahn, K. Y. (1999) Psx homeobox gene is X-linked and specifically expressed in trophoblast cells o mouse placenta. Dev. Dyn. 216, 257-266

Clark, J. M. (1988) Novel non-templated nucleotide addition reactions catalyzed by prokaryotic and eucaryotic DNA polymerases. Nucleic Acids Res. 16, 9677-9686.

Combates, N., Pardinas, J. R., Parimoo, S., Prouty, S. M., Stenn, K. S. Technique for differential display. U.S. Pat. No. 6,045,998. Date of patent: Apr. 4, 2000.

D'Aquila, R. T., Bechtel, L. J., Videler, J. A., Eron, J. J., Gorczyca, P., Kaplan, J. C. (1991) Maximizing sensitivity and specificity of PCR by pre-amplification heating. Nucleic Acids Res., 19, 3749.

Diachenko, L. B., Ledesma, J., Chenchik, A. A., Siebert, P. D. (1996) Combining the technique of RNA fingerprinting and differential display to obtain differentially expressed mRNA. Biochem. Biophys. Res. Commun. 219, 824-828.

Dieffenbach, C. W., Lowe, T. M. J, Dveksler, G. S. (1995) General concepts for PCR primer design. PCR primer: a Laboratory Manual., pp. 133-142, Cold Spring Harbor Laboratory Press, Cold Spring Harbor. NY.

Don, R. H., Cox, P. T., Wainwright, B. J., Baker, K., Mattick, J. S. (1991) 'Touchdown' PCR to circumvent spurious priming during gene amplification. Nucleic Acids Res., 19, 4008.

Franz, O., Bruchhaus, I., Roeder, T. (1999) Verification of differential gene transcription using virtual northern blotting. Nucleic Acids Res., 27, 1-3.

Frohman, M. A., Dush, M. K., Martin, G. R. (1988) Rapid production of full-length cDNAs from rare transcripts: amplification using a single gene-specific oligonucleotide primer. Proc. Natl. Acad. Sci. USA 85, 8998-9002.

Fromont-Racine, M., Bertrand, E., Pictet, R., Grange, T. (1993) A highly sensitive method for mapping the 5' termini of mRNAs. Nucleic Acids Res., 21, 1683-1684.

Gottschlich, S., Goeoegh, t., Folz, B. J., Lippert, B. M., Werner, J. A. (1997) Optimized differential display and reamplification parameters for silver staining. Res. Commun. Mol. Path. Pharm. 97, 237-240.

Gromova, I., Gromov, P., Celis, J. E. (1999) Identification of true differentially expressed mRNAs in a pair of human bladder transitional cell carcinomas sing an improved differential display procedure. Electrophoresis 20, 241-248.

Guegler, K., Tan, R., Rose, M. J. Methods and compositions for producing 5' enriched cDNA libraries. U.S. Pat. No. 6,083,727. Date of patent: Jul. 4, 2000.

Guegler, K., Tan, R., Rose, M. J. Methods and compositions for producing full length cDNA libraries. U.S. Pat. No. 6,326,175. Date of patent: Dec. 4, 2001.

Hogan, B., Bedding, R., Costantini, F., Lacy, E. (1994) Manipulating the moue embryo: a laboratory manual. Cold Spring Harbor Laboratory Press, Cold Spring Harbor, N.Y.

Hwang, I. T., Lee, Y. H., Moon, B. C., Ahn, K. Y., Lee, S. W., Chun, J. Y. (2000) Identification and characterization of a new member of the placental prolactin-like protein-C (PLP-C) subfamily, PLP-Cβ. Endocrinology 141, 3343-3352.

Hayashizaki, Y. Method for forming full length cDNA libraries. U.S. Pat. No. 6,143,528. Date of patent: Nov. 7, 2000.

Henegariu, O, Hirschmann, P., Killian, K., Kirch, S., Lengauer, C., Maiwald, R., Mielke, K., Vogt, P. (1994) Rapid screening of the Y chromosome in idiopathic sterile men, diagnostic for deletions in AZF, a genetic Y factor expressed during spermatogenesis. Andrologia, 26, 97-106.

Ito, T., Kito, K., Adati, N., Mitsui, Y., Hagiwara, H., Sakaki, Y. (1994) Fluorescent differential display: arbitrarily primed RT-PCR fingerprinting on an automated DNA sequencer. FEBS Lett. 351, 231-236.

Jefferies, D., Botman, M. F., Lester, D, Whitehead, C. C., Thorp, B. H. (1998) Cloning differentially regulate genes from chondrocytes using agarose gel differential display. Biochim. Biophys. Acta 1396, 237-241.

Kociok, N., Unfried, K., Eser, P., Krott, R., Schraermeyer, U., Heimann, K. (1998) The nonradioisotopic representation of differentially expressed mRNA by a combination of RNA fingerprinting and differential display. Mol. Biotechnol. 9, 25-33.

Korn, B., Sedlacek, Z., Manca, A., Kioschis, P., Konecki, D., Lehrach, H., Poutska, A. (1992) A strategy for the selection of transcribed sequences in the Xq28 region. Hum. Mol. Genet. 1, 235-242.

Kulpa, D., Topping, R., Telesnitskt, A. (1997) Determination of the site of first strand transfer during Moloney murine leukemia virus reverse transcription and identification of strand transfer-associated reverse transcriptase errors. EMBO J. 16, 856-865.

Landegren, U., Nilsson, M., Kwok, P.-Y. (1998) reading bits of genetic information: methods for single-nucleotide polymorphism analysis. Genome Res. 8, 769-776.

Liang, P., Pardee, A. B. (1992) Differential display of eukaryotic messenger RNA by means of the polymerase chain reaction. Science 257, 967-971.

Ledbetter, S. A., Nelson, D. L., Warren, S. T., Ledbetter, D. H. (1990) Rapid isolation of DNA probes within specific chromosome regions by interspersed repetitive sequence polymerase chain reaction. Genomics 6,475-481.

Loakes, D., Brown, D. M. (1994) 5-Nitroindole as an universal base analog. Nucleic Acids Res. 22, 4039-4043.

Loakes, D. The applications of universal DNA base analogues. Nucleic Acids Res. 29, 2437-2447.

Luehrsen, K. R., Marr, L. L., Van Der Knaap, E., Cumberledge, S. (1997) Analysis of differential display RT-PCR products using fluorescent primers and genescan software. BioTechniques 22, 168-174.

Matz, M. V., Lukyanov, S. A. (1998) Different strategies of differential display: areas of application. Nucleic Acids Res. 26, 5537-5543.

Matz, M., Shagin, D., Bogdanova, E., Britanova, O., Lukyanov, S., Diatchenko, L., Chenchik., A. (1999) Amplification of cDNA ends based on templateswitching effect and step-out PCR. Nucleic Acids Res. 27, 1558-1560.

McClelland, M., Chada, K., Welsh, J., Ralph, D. (1993). Arbitrary primed PCR fingerprinting of RNA applied to mapping differentially expressed genes. In Symposium on DNA fingerprinting: State of the science, November, 1992 (ed. S. D. Pena et al.). Birkhauser Verlag, Basel, Switzerland.

McPherson, M. J., Moller, S. G. (2000) PCR. BIOS Scientific Publishers, Springer-Verlag New York Berlin Heidelberg, N.Y.

Meunier, J. R., Grimont, PA. D. (1993) Factors affecting reproducibility of amplified polymorphic DNA fingerprints. Res. Microbiol. 144, 373-379.

Mullis, K. B., Faloona, F. A. (1987) Specific synthesis of DNA in vitro via a polymerase-catalyzed chain reaction. Methods Enzymol. 155, 335-350.

Mullis, K. B., Erlich, H. A, Arnheim, N., Horn, G. T., Saiki, R. K., Scharf, S. J. Process for amplifying, detecting, and/or cloning nucleic acid sequences. U.S. Pat. No. 4,683,195. Date of patent: Jul. 28, 1987.

Mullis, K. B. Process for amplifying nucleic acid sequences. U.S. Pat. No. 4,683,202. Date of patent: Jul. 28, 1987.

Mullis, K. B., Erlich, H. A, Arnheim, N., Horn, G. T., Saiki, R. K., Scharf, S. J. Process for amplifying, detecting, and/or cloning nucleic acid sequences. U.S. Pat. No. 4,800,159. Date of patent: Jan. 24, 1989.

Mutirangura, A., Greenberg, F., Butler, M. G., Malcolm, S., Nicholls, R. D., Chakravarti, A., Ledbetter, D. H. (1993) Multiplex PCR of three dinucleotide repeats in the Prader-Willi/Angelman critical region (15q11-q13): molecular diagnosis and mechanism of uniparental disomy. Hum. Mol. Genet., 2, 143-151.

Nichols, R., Andrews, P. C., Ahang, P., Bergstrom, D. E. (1994) A universal nucleoside for use at ambiguous sites in DNA primers. Nature 369, 492-493.

Ohtsuka, E., Matsuka, S., Ikehara M., Takahashi, Y., Matsubara K. (1985) An alternative approach to deoxyoligonucleotides as hybridization probes by insertion of deoxyinosine at ambiguous codon positions. J. Biol. Chem. 260, 2605-2608.

Ralph, D., Welsh, J., McClelland, M. (1993) RNA fingerprinting using arbitrary primed PCR identifies differentially regulated RNAs in Mink lung (Mv1Lu) cells growth arrested by TGF-β. Proc. Natl. Acad. Sci. 90, 10710-10714.

Rompf, R., Kahl, G. (1997) mRNA differential display in agarose gels. BioTechniques 23, 28-32.

Roses, A. D. (2000) Pharmacogenetics and the practice of medicine. Nature, 405, 857-865.

Rosok, O., Odeberg, J., Rode, M., Stokke, T., Funderud, S., Smeland, E. (1996) solid-phase method for differentially display of genes expressed in hematopoietic stem cells. BioTechniques 21, 114-121.

Ruano, G., Fenton, W., Kidd, K. K. (1989) Biphasic amplification of very dilute DNA samples via "booster PCR". Nucleic Acids Res. 17, 5407.

Saiki, R. K., Scharf, S., Faloona, F., Mullis, K. B., Horn, G. T., Erlich, H. A., Arnheim, N. (1985) Enzymatic amplification of beta-globin genomic sequences and restriction site analysis for diagnosis of sickle cell anemia. Science 230, 1350-1354.

Sakanari, J. A., Staunton, C. E., Eakin, A. E., Craik, C. S. (1989) Serine proteases from nematode and protozoan parasites: Isolation of sequence homologs using generic molecular probes. Proc. Natl. Acad. Sci. 86, 4863-4867.

Schaefer, B. C. (1995) Revolutions in rapid amplification of cDNA ends: New strategies for polymerase chain reaction cloning of full-length cDNA ends. Anal. Biochem. 227, 255-273.

Schmidt W. M., Mueller, M. W. (1999) CapSelect: A highly sensitive method for 5'CAP-dependent rerichment of full-length cDNA in PCR-mediated analysis of mRNAs. Nucleic Acids Res. 27, e31.

Schramm, G., Bruchhaus, I., Roeder, T. (2000) A simple and reliable 5'-RACE approach. Nucleic Acids Res. 28, e96.

Shuber, A. P., Skoletsky, J., Stern, R., Handelin, B. L. (1993) Efficient 12-mutation testing in the CFTR gene: a general model for complex mutation analysis. Hum. Mol. Genet., 2, 153-158.

Smith, N. R., Aldersley, M., Li, A., High, A. S., Moynihan, T. P., Markham, A. F., Robinson. P. A. (1997) Automated differential display using a fluorescently labeled universal primer. BioTechniques 23, 274-279.

Sompayrac, L., Jane, S., Burn, T. C., Tene, D. G., Danna, K. J. (1995) Overcoming limitations of the mRNA differential display technique. Nucleic Acids Res. 23, 4738-4739.

Stone, B., Wharton, W. (1994) Targeted RNA fingerprinting: the cloning of differentially-expressed cDNA fragments enriched for members of the zinc finger gene family. Nucleic Acids Res. 22, 2612-2618.

Suzuki, Y., Yoshitomo-Nakagawa, K., Maruyama, K., Suyama, A., Sugano, S. (1997) Construction and characterization of a full length-enriched and a 5'-end-enriched cDNA library. Gene 200, 149-156.

Tagle, D. A., Swaroop, M., Lovett, M., Collins, F. S. (1993) Magnetic bead capture of expressed sequences encoded within large genomic segments. Nature 361. 751-753.

Villeponteau, B., Feng, J., Funk, W., Linskens, M. H. K. Method and kit for enhanced differential display. U.S. Pat. No. 5,580,726. Date of patent: Dec. 3, 1996.

Welsh, J., McClelland, M. (1990) Fingerprinting genomes using PCR with arbitrary primers. Nucleic Acids Res. 18, 7213-7218.

Welsh, J., McClelland, M. (1991) Genomic fingerprinting using arbitrarily primed PCR and a matrix of pairwise combinations of primers. Nucleic Acids Res. 19, 5275-5279.

Williams, J. G. K., Kubelik, A. R., Livak, K. J., Rafalki, J. A., Tingey, S. V. (1990) DNA polymorphisms amplified by arbitrary primers are useful as genetic markers. Nucleic Acids Res. 18, 6531-6535.

Zimmermann, K., Schogl, D., Plaimauer, B., Mannhalter, J. W. (1996) Quantitative multiplex competitive PCR of HIV-1 DNA in a single reaction tube. BioTechniques 21, 480-484.

Zou, S., Stanfield, C., Bridge, J. (1998) Identification of new influenza B virus variants by multiplex reverse transcription-PCR and the heteroduplex mobility assay. J. Clin. Microbiol. 36, 1544-1548.

What is claimed is:

1. A method for improving the annealing specificity of a primer in nucleic acid amplification, comprising the steps of:
   (a) preparing a 3'-end portion of the primer having a hybridizing nucleotide sequence substantially complementary to a site on a template nucleic acid to hybridize therewith;
   (b) forming at the 5'-end of the 3'-end portion a regulator portion comprising at least three contiguous universal bases to have the lowest Tm in the three portions of the primer, wherein the regulator portion restricts a primer annealing site to the 3'-end portion to improve the annealing specificity of the 3'-end portion; and
   (c) forming at the 5'-end of the regulator portion a 5'-end portion having a pre-selected arbitrary nucleotide sequence substantially not complementary to any site on the template nucleic acid,
   whereby the primer has three distinct portions and the annealing specificity of the primer is improved by the presence of the regulator portion and the 5'-end portion, and
   wherein the primer has a general formula of 5'-$X_p$-$Y_q$-$Z_r$-3', wherein $X_p$ represents said 5'-end portion having said pre-selected arbitrary nucleotide sequence substantially not complementary to any site on the template nucleic acid; $Y_q$ represents said regulator portion comprising at least three contiguous universal base; $Z_r$ represents said 3'-end portion having a hybridizing nucleotide sequence substantially complementary to a site on the template nucleic acid to hybridize therewith; wherein p, q and r represent the number of nucleotides; and wherein X, Y and Z is deoxyribonucleotide or ribonucleotide, and wherein $Z_r$ comprises at least 10 contiguous deoxythymidine nucleotides.

2. The method according to claim 1, wherein $Z_r$ comprises at least 10 contiguous deoxythymidine nucleotides having 3'-V at its 3'-end; in which V is one selected from the group consisting of deoxyadenosine, deoxycytidine and deoxyguanosine.

3. The method according to claim 2, wherein $Z_r$ comprises at least 10 contiguous deoxythymidine nucleotides having 3'-NV at its 3'-end; in which V is one selected from the group consisting of deoxyadenosine, deoxycytidine and deoxyguanosine, and N is one selected from the group consisting of deoxyadenosine, deoxythymidine, deoxycytidine and deoxyguanosine.

4. A method for improving the annealing specificity of a first primer in nucleic acid amplification, which comprises the steps of:
    (a) preparing a 3'-end portion of the first primer having a hybridizing nucleotide sequence substantially complementary to a site on a template nucleic acid to hybridize therewith at a first annealing temperature in said amplification;
    (b) forming at the 5'-end of the 3'-end portion a regulator portion comprising at least three contiguous universal bases to have the lowest Tm in the three portions of the primer, wherein the regulator portion restricts a primer annealing site to the 3'-end portion to improve the annealing specificity of the 3'-end portion at a first annealing temperature in said amplification; and
    (c) forming at the 5'-end of the regulator portion a 5'-end portion having a pre-selected arbitrary nucleotide sequence that serves as a priming site at a second annealing temperature in said amplification and is substantially not complementary to any site on the template nucleic acid,
    (d) annealing the first primer to a target at the first annealing temperature and extending the first primer to form a first primer extension product;
    (e) synthesizing a polynucleotide complementary to the first primer extension product;
    (f) annealing a second primer to the portion of said complementary polynucleotide that is complementary to the pre-selected arbitrary nucleotide sequence at the second annealing temperature, and extending the second primer to form a second primer extension product;
    whereby the first primer has three distinct portions and the annealing specificity of the first primer is improved by the presence of the regulator portion and the 5'-end portion, and
    wherein the first annealing temperature and the second annealing temperature are different.

5. The method according to claim 4, wherein said universal base is selected from the group consisting of deoxyinosine, inosine, 7-deaza-2'-deoxyinosine, 2-aza-2'-deoxyinosine, 2'-OMe inosine, 2'-F inosine, deoxy 3-nitropyrrole, 3-nitropyrrole, 2'-OMe 3-nitropyrrole, 2'-F 3-nitropyrrole, 1-(2'-deoxy-beta-D-nbofuranosyl)-3-nitropyrrole, deoxy 5-nitroindole, 5-nitroindole, 2'-OMe 5-nitroindole, 2'-F 5-nitroindole, deoxy 4-nitrobenzimidazole, 4-nitrobenzimidazole, deoxy 4-aminobenzimidazole, 4-nitrobenzimidazole, 4-nitrobenzimidazole, deoxy 4-aminobenzimidazole, 4-aminobenzimidazole, deoxy nebularine, 2'-F nebularine, 2'-F 4-nitrobenzimidazole, PNA-5-introindole, PNA-nebularine, PNA-inosine, PNA-4-nitrobenzimidazole, PNA-3-nitropyrrole, morpholino-5-nitroindole, morpholino-nebularine, morpholino-inosine, morpholino-4-nitrobenzimidazole, morpholino-3-nitropyrrole, phosphoramidate-5-nitroindole, phosphoramidate-nebularine, phosphoramidate-inosine, phosphoramidate-4-nitrobenzimidazole, phosphoramidate-3-nitropyrrole, 2'-O-methoxyethyl inosine, 2'0-methoxyethyl nebularine, 2'-O-methoxyethyl 5-nitroindole, 2'-O-methoxyethyl 4-nitrobenzimidazole, 2'-O-methoxyethyl 3-nitropyrrole, and combinations thereof.

6. The method according to claim 5, wherein said universal base is deoxyinosine, 1-(2'-deoxy-beta-D-ribofuranosyl)-3-nitropyrrole or 5-nitroindole.

7. The method according to claim 6, wherein said universal base is deoxyinosine.

8. The method according to claim 4, wherein said regulator portion comprises more than three contiguous nucleotides having universal base or non-discriminatory base analog.

9. The method according to claim 4, wherein the second annealing temperature is higher than the first annealing temperature.

10. The method according to claim 4, wherein said first annealing temperature is approximately equal to the Tm of said 3'-end portion of said primer.

11. The method according to claim 4, wherein said second annealing temperature is approximately equal to the Tm of said 5'-end portion of said primer.

12. The method according to claim 4, wherein the primer has a general formula of 5'-$X_p$-$Y_q$-$Z_r$-3', wherein $X_p$ represents said 5'-end portion having said pre-selected arbitrary nucleotide sequence substantially not complementary to any site on the template nucleic acid; $Y_q$ represents said regulator portion comprising at least three contiguous universal base; $Z_r$ represents said 3'-end portion having a hybridizing nucleotide sequence substantially complementary to a site on the template nucleic acid to hybridize therewith; wherein p, q and r represent the number of nucleotides; and wherein X, Y and Z is deoxynbonucleotide or ribonucleotide.

13. The method according to claim 12, wherein $Z_r$ comprises at least 10 contiguous deoxythymidine nucleotides.

14. The method according to claim 13, wherein $Z_r$ comprises at least 10 contiguous deoxythymidine nucleotides having 3'-V at its 3'-end; in which V is one selected from the group consisting of deoxyadenosine, deoxycytidine and deoxyguanosine.

15. The method according to claim 14, wherein $Z_r$ comprises at least 10 contiguous deoxythymidine nucleotides having 3'-NV at its 3'-end; in which V is one selected from the group consisting of deoxyadenosine, deoxycytidine and deoxyguanosine, and N is one selected from the group consisting of deoxyadenosine, deoxythymidine, deoxycytidine and deoxyguanosine.

16. The method according to claim 12, wherein p represents an integer of 15 to 60.

17. The method according to claim 12, wherein q represents an integer of 3 to 15.

18. The method according to claim 12, wherein r represents an integer of 6 to 50.

19. The method according to claim 12, wherein p is an integer of 15 to 60, q is an integer of 3 to 15 and r is an integer of 6 to 30.

* * * * *